US008338138B2

(12) United States Patent

Ostermeier et al.

(10) Patent No.: US 8,338,138 B2

(45) Date of Patent: Dec. 25, 2012

(54) METHODS FOR MAKING AND USING MOLECULAR SWITCHES INVOLVING CIRCULAR PERMUTATION

(75) Inventors: Marc A. Ostermeier, Baltimore, MD (US); Gurkan Guntas, Baltimore, MD (US)

(73) Assignee: The John Hopkins University, Baltimore, MD (US)

( * ) Notice: Subject to any disclaimer, the term of this patent is extended or adjusted under 35 U.S.C. 154(b) by 940 days.

(21) Appl. No.: 10/588,114

(22) PCT Filed: Jan. 28, 2005

(86) PCT No.: PCT/US2005/002633

§ 371 (c)(1),
(2), (4) Date: Aug. 1, 2007

(87) PCT Pub. No.: WO2005/072392

PCT Pub. Date: Aug. 11, 2005

(65) Prior Publication Data

US 2009/0005266 A1 Jan. 1, 2009

Related U.S. Application Data

(60) Provisional application No. 60/539,774, filed on Jan. 28, 2004, provisional application No. 60/557,152, filed on Mar. 26, 2004, provisional application No. 60/607,684, filed on Sep. 7, 2004, provisional application No. 60/628,997, filed on Nov. 18, 2004.

(51) Int. Cl.
*C12N 15/66* (2006.01)

(52) U.S. Cl. ...................... 435/91.41; 435/462; 435/463

(58) Field of Classification Search ........................ None
See application file for complete search history.

(56) References Cited

U.S. PATENT DOCUMENTS

| | | | | |
|---|---|---|---|---|
| 6,469,154 | B1 * | 10/2002 | Tsien et al. | 536/23.5 |
| 6,485,912 | B1 | 11/2002 | Heintz et al. | |
| 6,596,485 | B2 | 7/2003 | Anderson et al. | |
| 6,867,035 | B2 | 3/2005 | Ong | |
| 7,135,176 | B2 | 11/2006 | Norris et al. | |

FOREIGN PATENT DOCUMENTS

WO WO-03/078575 A2 9/2003

OTHER PUBLICATIONS

Ostermeier, Current Opinion in Structural Biology (2009) vol. 19, pp. 442-448.*

G.S. Baird et al., "Circular permutation and receptor insertion within green fluorescent proteins", *Proceedings of the National Academy of Sciences of USA*, vol. 96, pp. 11241-11246 (Sep. 1999).

R. Graf et al., "Random circular permutation of genes and expressed polypeptide chains: Application of the method to the catalytic chains of aspartate transcarbamoylase", *Proceedings of the National Academy of Sciences of USA*, vol. 93, pp. 11591-11596 (Oct. 1996).

C.A. McWherter et al., "Circular permutation of the granulocyte colony-stimulating factor receptor agonist domain of myelopoietin", *Biochemistry*, vol. 38, pp. 4564-4571 (1999).

JM. Betton et al., "Creating a bifunctional protein by insertion of β-lactamase into the maltodextrin-binding protein", *Nature Biotechnology*, vol. 15, pp. 1276-1279 (Nov. 1997).

G. Guntas et al., "Creation of an allosteric enzyme by domain insertion", *Journal of Molecular Biology*, vol. 336, pp. 263-273 (2004).

R.J. Kreltman et al., "Incrased antitumor activity of a circularly permuted interleukin 4-toxin in mice with interleukin 4 receptor-bearing human carcinoma", *Cancer Research*, vol. 55, pp. 3357-3363 (Aug. 1995).

J. Osuna et al., "Improving a circularly permuted TEM-1 β-lactamase by directed evolution", *Protein Engineering*, 15(6), pp. 463-470 (2002).

M. Ostermeier et al., "Evolution of protein function by domain swapping", *Advances in Protein Chemsitry*, vol. 55, pp. 29-77 (Jan. 2000).

Guntas, Chemistry & Biology, 11:1483-1487 (2004).

U.S. Appl. No. 10/507,466, filed Aug. 18, 2005, Marc Ostermeier.

Lacatena RM, et al. "Topological analysis of the human b2-adrenergic receptor expressed in *Escherichia coli*" Proc Natl Acad Sci U S A. Oct. 25, 1994; 91(22): 10521-10525.

Manoil C., et al. "Alkaline phosphatase fusions: sensors of subcellular location." *J Bacteriol.* Feb. 1990;172 (2):515-518.

Mountford PS., et al. "Internal ribosome entry sites and dicistronic RNAs in mammalian transgenesis." Trends Genet. May 1995;11(5):179-184.

* cited by examiner

*Primary Examiner* — Jim Ketter

(74) *Attorney, Agent, or Firm* — Edwards Wildman Palmer LLP; Peter F. Corless; Melissa Hunter-Ensor, Esq.

(57) ABSTRACT

The invention provides molecular switches which couple external signals to functionality, and combinatorial methods of making and using the same involving circular permutation of nucleic acid and amino acid sequences. The switches according to the invention can be used, for example, to regulate gene transcription, target drug delivery to specific cells, transport drugs intracellularly, control drug release, provide conditionally active proteins, perform metabolic engineering, and modulate cell signaling pathways. Libraries comprising the switches, expression vectors and host cells for expressing the switches are also provided.

12 Claims, 18 Drawing Sheets

METHODS FOR MAKING AND USING MOLECULAR SWITCHES INVOLVING CIRCULAR PERMUTATION

CROSS REFERENCE TO RELATED APPLICATIONS

This application claims the priority of U.S. Provisional Patent Application Ser. Nos. 60/539,774, 60/557,152, 60/607,684, and 60/628,997, filed Jan. 28, 2004, Mar. 26, 2004, Sep. 7, 2004, and Nov. 18, 2004, respectively, the entire disclosures of which are incorporated herein by reference in their entirety.

STATEMENT AS TO FEDERALLY SUPPORTED RESEARCH

The present invention was made with United States government support under grant number R01 GM066972-01A1 from the National Institutes of Health. Accordingly, the United States government may have certain rights in the invention.

FIELD OF THE INVENTION

The invention relates to fusion molecules which function as molecular switches and to methods for making and using the same. More particularly, combinatorial methods involving circular permutation of DNA are used.

BACKGROUND OF THE INVENTION

A hallmark of biological systems is the high degree of interactions among their constituent components. Cells can be described as complex circuits consisting of a network of interacting molecules. Key component of these networks are proteins that serve to couple cellular functions. A protein that couples functions can be described as a “molecular switch.” In most general terms, a molecular switch recognizes an effector (input) signal (e.g., ligand concentration, pH, covalent modification) with resultant modification of its output signal (e.g., enzymatic activity, ligand affinity, oligomeric state). Examples of natural molecular switches include allosteric enzymes that couple concentration of effector molecules with level of enzymatic activity, and ligand-dependent transcription factors that couple ligand concentration to output level of gene expression. Molecular switches can be “ON/OFF” in nature or can exhibit a graded response to a signal.

There is recognition that there is great potential to design fusion proteins that act as molecular switches to modulate or report on biological functions for a variety of applications including biosensors (Siegel and Isacoff 1997; Baird, Zacharias et al. 1999; Doi and Yanagawa 1999; de Lorimier, Smith et al. 2002; Fehr, Frommer et al. 2002) modulators of gene transcription and cell signaling pathways (Rivera 1998; Guo, Zhou et al. 2000; Picard 2000), and novel biomaterials (Stayton, Shimoboji et al. 1995). Despite its great potential, however, molecular switch technology has not been extensively exploited, in part due to technical challenges in engineering effective molecular switches. In general, existing approaches to creating protein molecular switches include: control of oligomerization or proximity using chemical inducers of dimerization (CID); chemical rescue; fusion of the target protein to a steroid binding domain (SBD); coupling of proteins to nonbiological materials such as ‘smart’ polymers (Stayton, Shimoboji et al. 1995; Ding, Fong et al. 2001; Kyriakides, Cheung et al. 2002) or metal nanocrystals (Hamad-Schifferli, Schwartz et al. 2002); and domain insertion.

The approach of control using a chemical inducer of dimerization (CID) utilizes a synthetic ligand as the CID that controls the oligomeric or proximity of two proteins (Rivera 1998). CIDs are small molecules that have two binding surfaces that facilitate the dimerization of domains fused to target proteins. This approach was first developed using the immunosupressant FK506 to facilitate dimerization of target proteins fused to the FK506-binding protein, FKBP12 (Spencer, Wandless et al. 1993). Several variations on this system have since appeared as well as a system using the antibiotic coumermycin to dimerize proteins fused to B subunit of bacterial DNA gyrase (GyrB) (Farrar, Olson et al. 2000). CIDs have been used to initiate signaling pathways by dimerizing receptors on the cell surface, to translocate cytosolic proteins to the plasma membrane, to import and export proteins from the nucleus, to induce apoptosis and to regulate gene transcription (Bishop, Buzko et al. 2000; Farrar, Olson et al. 2000). However, CIDs have only been applied to those functions that require changes in the oligomeric state or proximity of the two proteins. As described in the literature however, this approach cannot be readily applied to a single protein.

Chemical rescue has recently been applied as a strategy for control, in the case of dimerization (Guo, Zhou et al. 2000). Chemical rescue aims to restore activity to a mutant, catalytically defective enzyme by the introduction of a small molecule that has the requisite properties of the mutated residues. Since first described for subtilisin (Carter and Wells 1987), chemical rescue has been demonstrated for a number of different mutated protein-small molecule pairs (Williams, Wang et al. 2000). The vast majority of these rescues required >5 mM concentrations to show detectable rescue, and the maximum fold improvement in activity of the mutant was generally less than 100-fold and required >100 mM concentrations of the rescuing molecule.

For the strategy of fusion to a steroid binding domain, the protein to be controlled is fused end-to-end to a SBD (Picard 2000). In the absence of the steroid that binds to the SBD, it is believed that a Hsp90-SBD complex sterically interferes with the activity of the protein fused to the SBD. The disassembly of the complex upon steroid binding restores activity to the protein. This strategy has been successfully applied principally to transcription factors and kinases (Picard 2000). Artificial transcription factors (such as GeneSwitch™) have been developed using this strategy and have promise for tissue-specific gene expression in transgenic animals and human gene therapy (Burcin, B W et al. 1998; Burcin, Schiedner et al. 1999).

For approaches involving coupling to non-biological materials, the protein to be controlled is coupled to a non-biological material that responds to an external signal and thereby affects the protein coupled to it. ‘Smart’ polymers that change their conformation upon a change in pH or temperature have been conjugated to proteins near ligand binding sites, to create switches that sterically block access to the binding site at, for example, higher temperatures, but not at lower temperatures (Stayton, Shimoboji et al. 1995; Ding, Fong et al. 2001). Inductive coupling of a magnetic field to metal nanocrystals attached to biomolecules resulting in an increase in local temperature thereby inducing denaturation, has so far only been applied to DNA (Hamad-Schifferli, Schwartz et al. 2002).

Relatively few studies have attempted to create a molecular switch using the approach of insertional fusion, in which one gene is inserted into another gene. Insertions result in a continuous domain being split into a discontinuous domain. The first example of successful insertion of one protein into another was of alkaline phosphatase (AP) into the *E. Coli* outer membrane protein MalF, constructed as a tool for studying membrane topology (Ehrmann, Boyd et al. 1990). High levels of alkaline phosphatase activity were obtained in the fusions despite the fact that alkaline phosphatase requires dimerization for activity. Other examples of proteins that have been inserted into other proteins include green fluorescent protein GFP) (Siegel and Isacoff 1997; Biondi, Baehler et al. 1998; Kratz, Bottcher et al. 1999; Siegel and Isacoff 2000), TEM1 β-lactamase (Betton, Jacob et al. 1997; Doi and Yanagawa 1999; Collinet, Herve et al. 2000), thioredoxin (Lu, Murray et al. 1995), dihydrofolate reductase (Collinet, Herve et al. 2000), FKBP12 (Tucker and Fields 2001), estrogen receptor-α (Tucker and Fields 2001) and β-xylanase (Ay, Gotz et al. 1998).

In studies of insertions into GFP, molecular sensors were created by inserting β-lactamase into GFP by random mutagenesis, to create a protein whose fluorescence increased 60% upon binding of the β-lactamase inhibitory protein. Insertions of calmodulin (a $Ca^{2+}$ binding protein) into GFP resulted in a fusion whose fluorescence changed up to 40% upon increases in $Ca^{2+}$ concentration (Baird, Zacharias et al. 1999). In a related strategy, the gene for a circularly permuted GFP was sandwiched between the gene for calmodulin and its target peptide M13 to create a series of sensors whose fluorescence intensity increased, decreased or showed an excitation wavelength change upon binding $Ca^{2+}$ (Nagai, Sawano et al. 2001).

With the exception of the domain insertion strategy, all of the above-described approaches to engineering a molecular switch are limited in the sorts of signals that can be employed or the types of proteins that can be controlled. CIDs have only been applied to those functions that require changes in the oligomeric state or proximity of the two proteins and thus cannot be used to control a single protein. The chemical rescue approach is limited by the inability to apply the method to any desired signal and by the lack of sensitivity (high concentrations of the signal are required for a small change in activity). The SBD strategy appears to be limited as a general method for controlling any protein due to the apparent requirement for end-to-end fusion.

The domain insertion strategy is a promising and generally applicable approach to engineering a molecular switch. However existing domain insertion strategies are limited by the number of possible insertional fusions between the two domains. Generally, methods for generating molecular switches have not provided a systematic way to generate very large numbers of fusions of different geometries that would be ideal for generating and optimizing functional coupling of protein domains in molecular switches.

SUMMARY OF THE INVENTION

The invention provides improved molecular switches, for example with switching activity greater than previously demonstrated, or with altered ligand recognition and binding, and methods of making these molecules involving circular permutation of nucleic acid or amino acid sequences. Molecular switches have been created by recombining nonhomologous genes in vitro and subjecting the genes to evolutionary pressure using combinatorial techniques. The approach may be envisioned as "rolling" two proteins across each other's surfaces and fusing them at points where their surfaces meet. The approach allows for recombination and testing of maximal numbers of geometric configurations between the two domains. Libraries comprising vast numbers of such fused molecules are provided from which molecular switches with optimal characteristics can be isolated.

Preferred switches are fusion molecules comprising an insertion sequence and an acceptor sequence for receiving the insertion sequence, wherein the state of the insertion sequence is coupled to the state of the acceptor sequence. For example, the activity of the insertion sequence can be coupled to the activity/state of the acceptor sequence.

The "state" of a molecule can comprise its ability or latent ability to emit or absorb light, its ability or latent ability to change conformation, its ability or latent ability to bind to a ligand, to catalyze a substrate, transfer electrons, and the like. Preferably, molecular switches according to the invention are multistable, i.e., able to switch between at least two states. In one aspect, the fusion molecule is bistable, i.e., a state is either "ON" or "OFF," for example, able to emit light or not, able to bind or not, able to catalyze or not, able to transfer electrons or not, and so forth. In another aspect, the fusion molecule is able to switch between more than two states. For example, in response to a particular threshold state exhibited by an insertion sequence or acceptor sequence, the respective other sequence of the fusion may exhibit a range of states (e.g., a range of binding activity, a range of enzyme catalysis, etc.). Thus, rather than switching from "ON" or "OFF," the fusion molecule can exhibit a graded response to a stimulus. More generally, a molecular switch is one which generates a measurable change in state in response to a signal.

Accordingly, and in one aspect, the invention provides a method for assembling a fusion molecule, comprising: generating an insertion sequence by circular permutation; and inserting the insertion sequence into an acceptor sequence.

In one variation of the method, the insertion sequence is inserted at a selected site in the acceptor sequence. In another variation, the insertion sequence is inserted at a random site in the acceptor sequence.

Another aspect of the invention is a method for assembling a modulatable fusion molecule, comprising: generating an insertion sequence by circular permutation; inserting the insertion sequence into an acceptor sequence, wherein the insertion sequence and the acceptor sequence each comprise a state; and selecting a fusion molecule, wherein the state of the insertion sequence and the state of the acceptor sequence are coupled. As in the above method, variations are provided wherein the insertion sequence is inserted at a selected site in the acceptor sequence or at a random site in the acceptor sequence.

In some embodiments of the method, the state of the insertion sequence generated by circular permutation is modulated. The state of the insertion sequence can be modulated in response to a change in the state of the acceptor sequence, or modulated in response to a change in the state of the insertion sequence. The fusion molecule can further comprise a new state.

In yet another aspect is provided a method for assembling a multistable fusion molecule which can switch between at least an active state and a less active state, comprising: generating an insertion sequence by circular permutation; inserting the insertion sequence into an acceptor sequence, wherein either the insertion sequence or the acceptor sequence comprises a state; and wherein the respective other sequence is responsive to a signal; and selecting a fusion molecule, wherein the state is coupled to the signal, such that the fusion molecule switches state in response to the signal.

In some versions of the methods of making fusion molecules the insertion sequence and acceptor sequence can comprise nucleic acids. In these methods, insertion includes obtaining a first nucleic acid fragment encoding an insertion polypeptide and a second nucleic acid fragment encoding an acceptor polypeptide and inserting the first nucleic acid fragment into the second nucleic acid fragment. In some aspects this method is used to provide libraries of fusion nucleic acids encoding fusion polypeptides comprising insertion polypeptides inserted into acceptor polypeptide sequences. Preferred fusion polypeptides are selected from these libraries in which the states of the insertion and acceptor polypeptides are coupled.

The invention also provides a method for modulating a cellular activity, comprising: providing a fusion molecule generated according to the above-described methods involving circular permutation of DNA, wherein a change in state of at least the insertion sequence or the acceptor sequence modulates a cellular activity, and wherein the change in state which modulates the cellular activity is coupled to a change in state of the respective other portion of the fusion molecule. Changing the state of the respective other portion of the fusion molecule thereby modulates the cellular activity.

Yet a further aspect is a method for delivering a bio-effective molecule to a cell, comprising: providing to the cell a fusion molecule associated with a bio-effective molecule generated according to any of the above methods, the fusion molecule comprising an insertion sequence and an acceptor sequence, wherein either the insertion sequence or the acceptor sequence binds to a cellular marker of a pathological condition and wherein upon binding to the marker, the fusion molecule dissociates from the bio-effective molecule, thereby delivering the molecule to the cell.

Further provided is a method for delivering a bio-effective molecule intracellularly, comprising: providing to a cell a fusion molecule associated with a bio-effective molecule generated according to any of the above-described methods involving circular permutation, the fusion molecule comprising an insertion sequence and an acceptor sequence, wherein either the insertion sequence or acceptor sequence comprises a transport sequence for transporting the fusion molecule intracellularly, and wherein release of the bio-effective molecule from the fusion molecule is coupled to transport of the fusion molecule intracellularly.

Another aspect of the invention is a method for modulating a molecular pathway in a cell, comprising: providing to a cell a fusion molecule generated according to any of the above-described methods, the fusion molecule comprising an insertion sequence and an acceptor sequence, wherein the activities of the insertion sequence and acceptor sequence are coupled, and responsive to a signal, and wherein the activity of either the insertion sequence or the acceptor sequence modulates the activity or expression of a molecular pathway molecule in the cell; and exposing the fusion molecule to the signal.

Also provided is a method for controlling the activity of a nucleic acid regulatory sequence, comprising: providing a fusion molecule generated by circular permutation according to any of the above methods, the fusion molecule comprising an insertion sequence and an acceptor sequence, wherein either the insertion sequence or the acceptor sequence responds to a signal, and wherein the respective other sequence of the fusion molecule binds to the nucleic acid regulatory sequence when the signal is responded to; and exposing the fusion molecule to the signal.

The invention further provides in another aspect a sensor molecule for detecting a target analyte. The sensor molecule comprises an insertion sequence and an acceptor sequence generated according to any of the above methods. Either the insertion sequence or the acceptor sequence binds the analyte, and binding of the analyte is coupled to production of a signal from the sensor molecule.

In yet another aspect, the invention provides a fusion molecule comprising: an insertion sequence and an acceptor sequence, generated according to the above-described methods. In one embodiment, either the insertion sequence or the acceptor sequence transports the fusion molecule intracellularly, wherein intracellular transport of the fusion molecule is coupled to binding of the fusion molecule to a bio-effective molecule.

Further provided is a fusion molecule generated as described, comprising: an insertion sequence and an acceptor sequence generated by circular permutation, wherein either the insertion sequence or the acceptor sequence binds to a nucleic acid molecule, and wherein nucleic acid binding activity is coupled to the response of the respective other sequence of the fusion molecule to a signal.

Yet another embodiment is a fusion molecule generated as described wherein either the insertion sequence or the acceptor sequence associates with a bio-effective molecule, and disassociates from the bio-effective molecule, when the respective other sequence of the fusion molecule binds to a cellular marker of a pathological condition.

Another variation is a fusion molecule capable of switching from a non-toxic to a toxic state, comprising: an insertion sequence and an acceptor sequence generated according to any of the above methods wherein either the insertion sequence or the acceptor sequence binds to a cellular marker of a pathology, and wherein binding of the marker to the fusion molecule switches the fusion molecule from a non-toxic state to a toxic state. Other fusion molecules of this type are capable of switching from a toxic state to a less toxic state.

The invention further provides "modified" molecular switches generated according to the above methods, wherein as a result of modification, for example by mutagenesis, the switch is responsive to at least one ligand that differs from a ligand recognized by an unmodified form of the same switch.

Yet a further aspect of the invention is a molecular switch for controlling a cellular pathway, comprising: a fusion molecule comprising an insertion sequence and an acceptor sequence generated according to any of the above methods, wherein the states of the insertion and acceptor sequences are coupled, and responsive to a signal, and wherein the state of either the insertion sequence or the acceptor sequence modulates the activity or expression of a molecular pathway molecule in a cell.

Further provided are libraries of molecular switches made according to the methods of the invention by generating insertion and/or acceptor sequences by circular permutation. The step of insertion can be repeated a plurality of times with a plurality of first and second nucleic acid molecules, to generate a library of acceptor sequences comprising circularized sequences. Preferred library members comprise a first nucleic acid sequence encoding a first polypeptide having a first state, the first nucleic acid sequence having been circularly permuted and inserted into a second nucleic acid sequence encoding a second polypeptide having a second state.

Some versions of the libraries can be produced by iterative processing of at least one existing library, generated according to any of the above-described methods. In one variation, a selected circularly permuted insert sequence generated from a first library is inserted into an acceptor sequence, to generate a second library having a plurality of members, each of which comprise the selected circularly permuted insert sequence. In one embodiment of such a library, the selected circularly permuted insert sequence is inserted at a random site in the acceptor sequence. In another embodiment, the selected circularly permuted insert sequence is inserted at a non-random site in the acceptor sequence.

The invention further provides isolated nucleic acids encoding molecular switch proteins. Preferred nucleic acids comprise nucleotide sequences selected from any of SEQ ID NOS: 35, 37, 39, 41, 43, 45, 47, 49, 51, 53, 56, 58, 60, 62, 64, 66, 68, 70, 72, and 74, or an effective fragment thereof.

Yet another aspect of the invention are molecular switch proteins comprising an amino acid sequence selected from any of SEQ ID NOS: 36, 38, 40, 42, 44, 46, 48, 50, 52, 54, 55, 57, 59, 61, 63, 65, 67, 69, 71, 73, and 75, or an effective fragment thereof.

BRIEF DESCRIPTION OF THE DRAWINGS

The objects and features of the invention can be better understood with reference to the following detailed description and accompanying drawings.

FIG. 6A shows the steps involved in creating the fusion molecule. FIG. 6B is a schematic diagram illustrating the amino acid sequence of the fusion protein, termed RG13. FIG. 6C is a drawing illustrating the structure of the RG13 fusion protein (GSGGG linker disclosed as SEQ ID NO: 1).

FIG. 7A shows that enzyme activity (nitrocefin hydrolysis) is specific to ligands of MBP. FIG. 7B shows reversible switching using competing ligand. FIG. 7C shows reversible switching after dialysis.

FIG. 9A shows dissociation constants for maltose as a function of apo MBP closure angle. FIGS. 9B-D show steady-state kinetic parameters of nitrocefin hydrolysis of the molecular switches.

DETAILED DESCRIPTION

Figure 1:
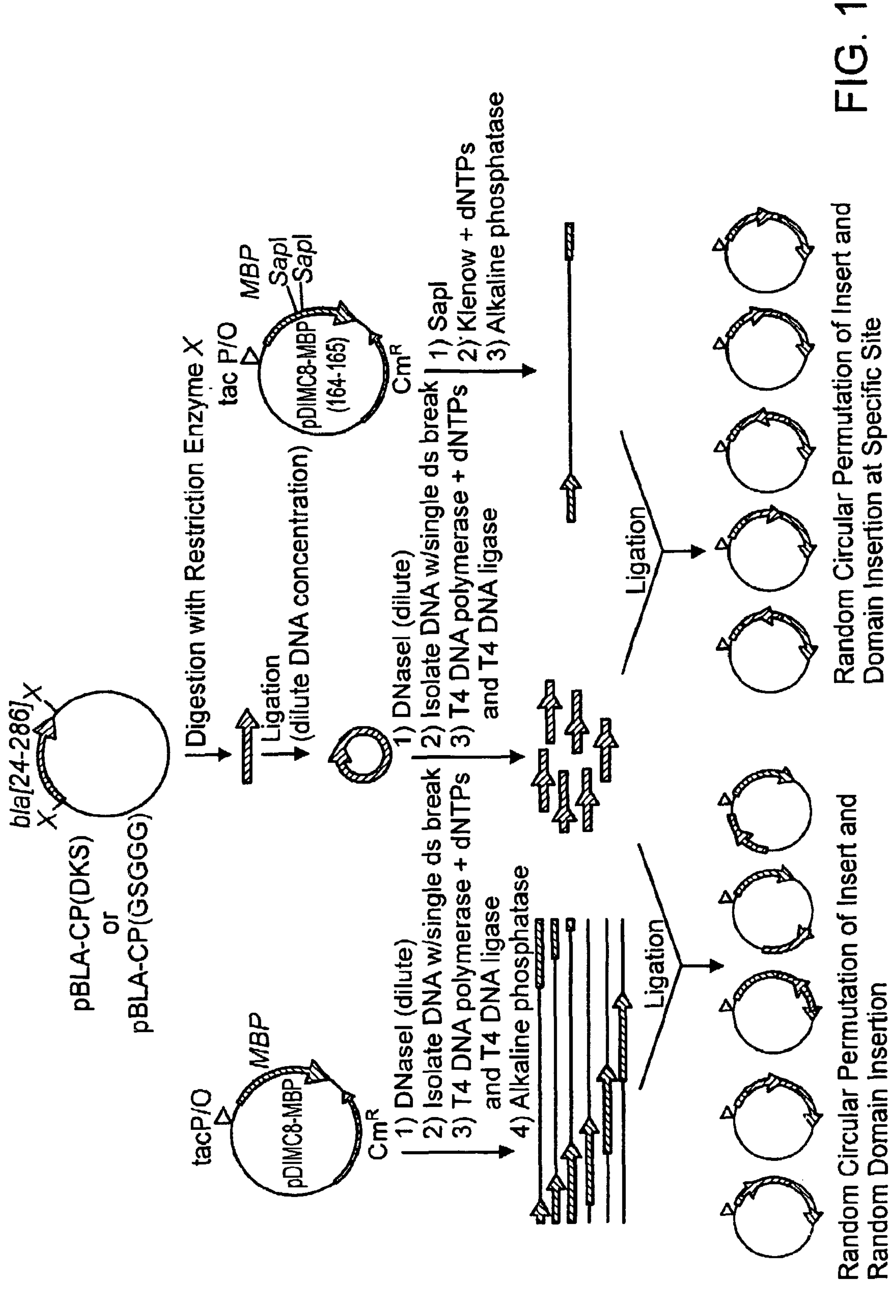
FIG. 1 is a schematic diagram illustrating two strategies using circular permutation and domain insertion for generating libraries of molecular switches according to the invention (GSGGG linker disclosed as SEQ ID NO: 1).

The invention provides improved molecular switches that couple external signals to functionality, methods of making these molecules involving circular permutation of nucleic acid and amino acid sequences, and methods of using the same. The switches according to the invention can be used, for example, to regulate gene transcription, target drug delivery to specific cells, transport drugs intracellularly, control drug release, provide conditionally active proteins, perform metabolic engineering, and modulate cell signaling pathways. Libraries comprising the switches generated by circular permutation, and expression vectors and host cells for expressing the switches are also provided.

DEFINITIONS

The following definitions are provided for specific terms which are used in the following written description.

As used herein, a "molecular switch" refers to a molecule which generates a measurable change in state in response to a signal. In one aspect, a molecular switch is capable of switching from at least one state to at least one other state in response to the signal. Preferably, when a portion of the molecule responds to the signal, the portion become activated (i.e., turns "ON") or inactivated (i.e., turns "OFF"). In response to this change in state, the state of another portion of the fusion molecule will change (e.g., turn ON or OFF). In one aspect, a switch molecule turns ON one portion of the molecule when another portion is turned OFF. In another aspect, the switch turns ON one portion of the molecule, when the other portion is turned ON. In still another aspect, the switch molecule turns OFF one portion of the molecule when the other portion is turned ON. In a further aspect, the switch molecule turns OFF when the other portion is turned OFF.

In some aspects of the invention, a molecular switch exists in more than two states, i.e., not simply ON or OFF. For example, a portion of the fusion molecule may display a series of states (e.g., responding to different levels of signal), while another portion of the fusion molecule responds at each state, with a change in one or more states. A molecular switch also can comprise a plurality of fusion molecules responsive to a signal and which mediate a function by changing the state of at least a portion of the molecule (preferably, in response to a change in state of another portion of the molecule). While the states of individual fusion molecules in the population may be ON or OFF, the aggregate population of molecules may not be able to mediate the function unless a threshold number of molecules switch states. Thus, the "state" of the population of molecules may be somewhere in between ON or OFF depending on the number of molecules which have switched states. In one aspect, a molecular switch comprises a heterogeneous population of fusion molecules comprising members which switch states upon exposure to different levels of signal. In other aspects of the invention, however, the state of a single molecule may be somewhere in between ON or OFF. For example, a molecule may comprise a given level of activity, ability to bind, etc., in one state which is switched to another given level of activity, ability to bind, etc., in another state (i.e., an activity, ability to bind, etc., measurably higher or lower than the activity, ability to bind, etc., observed in the previous state).

As used herein, a "state" refers to a condition of being. For example, a "state of a molecule" or a "state of a portion of a molecule" can be a conformation, binding affinity, or activity (e.g., including, but not limited to, ability to catalyze a substrate; ability to emit light, transfer electrons, transport or localize a molecule, modulate transcription, translation, replication, supercoiling, and the like).

As defined herein, a molecule, or portion thereof, whose state is "activated" refers to a molecule or portion thereof which performs an activity, such as catalyzing a substrate, emitting light, transferring electrons, transporting or localizing a molecule; changing conformation; binding to a molecule, etc.

As defined herein, a molecule, or portion thereof, whose state is "inactivated" refers to a molecule or portion thereof which is, at least temporarily, unable to perform an activity or exist in a particular state (e.g., bind to a molecule, change conformation, etc.).

As used herein, "coupled" refers to a state which is dependent on another state such that a measurable change in the other state is observed. As used herein, "measurable" refers to a state that is significantly different from a baseline or a previously existing state as determined in a suitable assay using routine statistical methods (e.g., setting $p<0.05$).

As used herein, "a signal" refers to a molecule or condition that causes a reaction. Signals include, but are not limited to, the presence, absence, or level, of molecules (nucleic acids, proteins, peptides, organic molecules, small molecules), ligands, metabolites, ions, organelles, cell membranes, cells, organisms (e.g., pathogens), and the like; as well as the presence, absence, or level of chemical, optical, magnetic, or electrical conditions, and can include conditions such as degrees of temperature and/or pressure. A chemical condition can include a level of ions, e.g., pH.

As used herein, "responsive to a signal" refers to a molecule whose state is coupled to the presence, absence, or level of the signal.

As used herein, "an insertion sequence" refers to a polymeric sequence which is contained within another polymeric sequence (e.g., an "acceptor sequence") and which conditionally alters the state of the other polymeric sequence. An insertion sequence or acceptor sequence can comprise a polypeptide sequence, nucleic acid sequence (DNA sequence, aptamer sequence, RNA sequence, ribozyme sequence, hybrid sequence, modified or analogous nucleic acid sequence, etc.), carbohydrate sequence, and the like. Nucleic acid and amino acid sequences for use as acceptor and insertion sequences in the invention can be naturally occurring sequences, engineered sequences (for example, modified natural sequences), or sequences designed de novo.

As used herein, an "effective fragment" of a nucleic acid or amino acid sequence can include any portion of a full length sequence useful in a molecular switch that has at least 80% of the functional activity of the corresponding full-length sequence, preferably at least about 90% and more preferably at least about 95% of that function. By an "effective fragment" of a molecular switch or related phrase is meant a portion of a molecular switch protein, or a nucleic acid encoding the same, that has at least 80% of the activity of the corresponding full-length protein or nucleic acid, determined by an appropriate assay for activity of the particular molecular switch.

As used herein, "multistable" refers to a fusion molecule which is capable of existing in at least two states.

As used herein, "bistable" refers to a fusion molecule capable of existing in two states.

As used herein, "range of states" refers to a series of states in which a fusion molecule can exist. For example, a range of states can comprise a range of binding activities, a range of light-emitting activities, a range of catalysis efficiencies, and the like.

As used herein, "a change in state" refers to a measurable difference in a state of being of a molecule, as determined by an assay appropriate for that state.

As used herein, "a graded response" refers to the ability of a fusion molecule to switch to a series of states in response to a particular threshold signal.

As used herein, "modulates" or "modulated" or "modulatable" refers to a measurable change in a state or activity or function. Preferably, where an activity is being described, "modulated" refers to an at least 2-fold, at least 5-fold, at least 10-fold, at least 20-fold or higher, increase or decrease in activity, or an at least 10%, at least 20%, at least 30%, at least 40% or at least 50% increase or decrease in activity. However, more generally, any difference which is measurable and statistically different from a baseline is encompassed within the term "modulated."

As used herein, a "less active state" is a state which is at least about 2-fold less active compared to a given reference state as measured using an assay suitable for measuring that state, or about at least 10%, at least about 20%, at least about 30%, at least about 40%, at least about 50%, at least about 60%, at least about 70%, at least about 80%, at least about 90% or at least about 100% less active. More generally, any decrease which is measurable and statistically different from baseline is encompassed within the term "less active state."

As used herein, a "less toxic state" refers to a measurable increase in the $LD_{50}$ (i.e., lethal dose which has a 50% probability of causing death) or $LC_{50}$ (i.e., lethal concentration which has a 50% probability of causing death). Preferably, a less toxic state is one which is associated with an at least about 10% increase, at least about 20%, at least about 30%, at least about 40%, at least about 50%, at least about 60%, at least about 70%, at least about 80%, at least about 90% or at least about 100% increase in $LD_{50}$ or $LC_{50}$.

As used herein, "a bio-effective molecule" refers to bioactive molecule which can have an effect on the physiology of a cell or which can be used to image a cell. In one aspect, a "bio-effective molecule" is a pharmaceutical agent or drug or other material that has a therapeutic effect on the cell.

As used herein, "a cellular marker of a pathological condition" refers to a molecule which is associated with a cell, e.g., intracellularly or extracellularly, and whose presence or level correlates with the presence of the disease, i.e., the marker is found in, or on, cells, or is secreted by cells, exhibiting the pathology at levels which are significantly different than observed for cells not exhibiting the pathology As used herein, "a molecular pathway molecule" refers to a molecule whose activity and/or expression affects the activity and/or expression of at least two other molecules. Preferably, a molecular pathway molecule is a molecule involved in a metabolic or signal transduction pathway. A pathway molecule can comprise a protein, polypeptide, peptide, small molecule, ion, cofactor, organic and inorganic molecule, and the like.

As used herein, "modulating a molecular pathway" refers to a change in the expression and/or activity of at least one pathway molecule.

As used herein, "at an insertion site" of a nucleic acid molecule refers to from about 1 to 21 nucleotides immediately flanking the insertion site.

As used herein, "randomly inserting" refers to insertion at non-selected sites in a polymeric sequence. In one aspect, "random insertion" refers to insertion that occurs in a substantially non-biased fashion, i.e., there is a substantially equal probability of inserting between members of any pairs of monomers (e.g., nucleotides or amino acids) in an acceptor molecule comprising a given number of monomeric sequences. However, in another aspect, random insertion has some degree of bias, e.g., there is a greater than equal probability of inserting at different sites. Minimally, the probability of insertion at a site in an acceptor sequence is greater than zero but less than one.

As used herein, "a new activity" refers to an activity which is not found in either donor or acceptor sequences. Generally, fusion molecules according to the invention comprise a new activity in that the activity of the acceptor sequence or insertion sequence is newly coupled to the state of the respective other portion of the sequence. An insertion or acceptor sequence also may comprise a catalytic site which responds to (e.g., catalyzes) a substrate provided in the form of the respective other portion of the fusion molecule, thereby producing a fusion molecule which comprises an activity present in neither the original catalytic site or the substrate (e.g., such as the ability to self-cleave in the presence of a signal).

As used herein, "a nuclear regulatory sequence" refers to a nucleic acid sequence which is capable of modulating the activity of another nucleic acid in cis or in trans. Types of activities regulated include, but are not limited to, modulating transcription, translation, replication, recombination, or supercoiling. A nucleic acid regulatory sequence can include promoter elements, operator elements, repressor elements, enhancer sequences, ribosome binding sites, IRES sequences, origins of replication, recombination hotspots, topoisomerase binding sequences, and the like.

As used herein, "altered by bisection" refers to a change in state upon fragmenting a polypeptide into two pieces. The term "bisection" does not imply that the polypeptide is divided into fragments of equal size; rather fragments can be generated by cleaving anywhere along the length of the primary sequence of the amino acid.

As used herein, "selecting for restoration of function or state" refers to selection for restoration of a function or state which is sufficiently similar to that of the original function under assay conditions suitable for evaluating the function or state. As used herein, "sufficiently similar" refers to a state that can achieve the original function in an effective manner. For example, when the function/state is binding, restoration of function/state can be evaluated by generating Scatchard plots and/or determining $K_d$. When the function/state is the ability of a molecule to generate light, restoration can be measured spectrophotometrically, for example.

As used herein, a "modification" of a polypeptide refers to an addition, substitution or deletion of one or more amino acids in a polypeptide which does not substantially alter the state of the polypeptide. For example, where a state is an activity of a polypeptide, a modification results in no more than a 10% decrease or increase in the activity of the polypeptide, and preferably no more than a 5% decrease or increase in the activity of the polypeptide.

As used herein, the terms "cyclization," and "cyclized" in respect to a nucleic acid or protein sequence or fragment thereof, refer to the process of taking a non-cyclized sequence of nucleic acid or amino acid and converting it to a cyclized form. For example, a "cyclized" nucleic acid is a form of nucleic acid in which every nucleotide in the nucleic acid sequence is covalently bonded to exactly two other nucleotides, typically through phosphate bridges between the 3' and 5' positions of the sugar residue of the nucleotide. This is distinguished from a "linear" form of a nucleic acid sequence in which the nucleotides on the 5' and 3' ends are attached to only one nucleotide. In a cyclized form of an amino acid sequence, the N- and C-termini are fused generally through a linker sequence. If the original N- and C-termini are proximal to one other, generally a shorter linker is used than if they are farther apart.

As used herein, the term "circularly permuted" refers to a nucleic acid or protein sequence in which the primary sequence differs from the original non-circularly permuted sequence in a specific way. For a nucleic acid, the circularly permuted sequence differs in that a continuous sequence that was on the 3' end in the non-circularly permuted sequence is attached to the 5' end in the circularly permuted sequence. The circularly permuted nucleic acid may or may not have a linker sequence between the original 5' and 3' ends. For a protein, the circularly permuted sequence differs in that a continuous sequence that was on the C-terminus in the non-circularly permuted sequence is attached to the N-terminus in the circularly permuted sequence. The circularly permuted protein may or may not have a linker sequence between the original N- and C-termini. A circularly permuted sequence can be conceptualized as joining the ends of an original, linear non-circularly permuted sequence to form a cyclized sequence, and converting the cyclized sequence back to a linear sequence by breaking the bonds at a new location. Although a circularly permuted sequence can be created in this manner, as used herein, the term "circularly permuted sequence" can also include the same sequence created by other means not involving a cyclized intermediate. "Randomly circularly permuted" as used herein refers to a sequence in which a circularly permuted sequence is created in which the site of circular permutation is determined by a random, semi-random or stochastic process.

Generating Fusion Molecules Using Random Circular Permutation

In one aspect, the invention includes a method for assembling a fusion molecule comprising randomly circularly permuting an insertion sequence and inserting the insertion sequence into an acceptor sequence. Exemplary insertion and acceptor sequences including known "domain" sequences that can be combined to form fusion molecules are discussed in further detail infra, and generally include any two sequences desired to be functionally combined in a fusion molecule to form a molecular switch.

By using a combinatorial approach, a plurality of potential switches is created from which to select switches with optimized characteristics. This method is advantageous over existing domain insertion methods in that vastly increased numbers of geometric configurations between the acceptor sequence and the insertion sequence can be generated and made available for testing. As discussed, the switching behavior achieved to date by existing methods is generally modest (i.e., less than about 2-fold effect). See, for example, PCT Publication WO 03/078575, herein incorporated by reference, and Guntas and Ostermeier (2004). As shown in Examples herein, the invention provides significantly improved molecular switches, for example with switching activity up to at least about 35-fold, and modified switches that respond to novel effector molecules.

A number of different strategies can be used to create the fusion molecules of the instant invention. FIG. 1 shows two preferred strategies for creating molecular switches using random circular permutation of DNA in combination with domain insertion. The strategies are generally applicable to creating any desired molecular switches, and are illustrated in FIG. 1 and several Examples herein, using exemplary fusions that combine sequences from two non-homologous proteins, in this case an enzyme (i.e., *E. coli* TEM β-lactamase, BLA) with sequences from an effector or signal protein (in this case, *E. coli* maltose binding protein, MBP) that responds to a signal (i.e., maltose). As shown below, the BLA-MBP fusion proteins produced by the methods of the invention can act as molecular switches, for example by functioning as BLA enzymes only in the presence of maltose.

Preparing Circularly Permuted Insert Genes

Referring to FIG. 1, circular permutation of at least one of the genes (in this case the insert gene) is central to the method. Although circular permutation of the insert gene is shown, circular permutation of the acceptor sequence, or both sequences, is within the invention. In the example shown in FIG. 1, BLA is the insert gene, and MBP is the acceptor gene.

As is known in the art, a circularly permuted protein has its original N- and C-termini fused and new N- and C-termini created by a break elsewhere in the sequence. The insert gene is circularly permutated using any suitable technique. Exemplary techniques for circular permutation by chemical or genetic methods include but are not limited to those described for example by Goldenberg and Creighton (1983), and Heinemann and Hahn (1995). A particularly preferred genetic method for random circular permutation is that of Graf and Schachmann (1996). See also Ostermeier and Benkovic (2001).

Referring to the central portion of FIG. 1, a preferred method of randomly circularly permuting a sequence can generally include the following steps:

(i) isolating a linear fragment of double-stranded DNA of the gene to be randomly circularly permuted with a linker sequence and flanking compatible ends;

(ii) cyclizing the DNA fragment by ligation under dilute conditions;

(iii) randomly linearizing the cyclized gene, for example using digestion by a nuclease such as DNaseI under conditions in which the enzyme, on average, makes one double-strand break;

(iv) repairing nicks and gaps, for example using enzymes such as DNA polymerase and DNA ligase, respectively; and (v) ligating the fragment into a desired vector comprising the acceptor sequence by blunt end ligation, to create a library of randomly circularly permuted sequences.

Preferred methods for preparing cyclized genes include a step of adding DNA that codes for a "linker" to link the original N- and C-termini. Any suitable linker sequences can be used for this purpose. Preferred methods of cyclizing a gene utilize linkers such a "DKS linker" (Osuna et al., 2002) or a flexible pentapeptide linker such as a "GSGGG linker" (SEQ ID NO: 1) having the amino acid sequence GSGGG (SEQ ID NO: 1). See also Example 1, infra, for further details.

Generally, the gene fragment of interest (for example a fragment encoding a selected amino acid sequence, such as amino acids 24-286 of the β-lactamase protein), is amplified by a suitable technique such as polymerase chain reaction (PCR) under conditions resulting in flanking of the selected sequence by restriction enzyme site sequences coding for the linkers, and is then cloned into a suitable vector such as pGem T-vector (Promega). Exemplary cloning vectors containing the sequences comprising linkers are indicated in FIG. 1 as pBLA-CP(DKS) or pBLA-CP(GSGGG) (linker disclosed as SEQ ID NO: 1).

Figure 2:
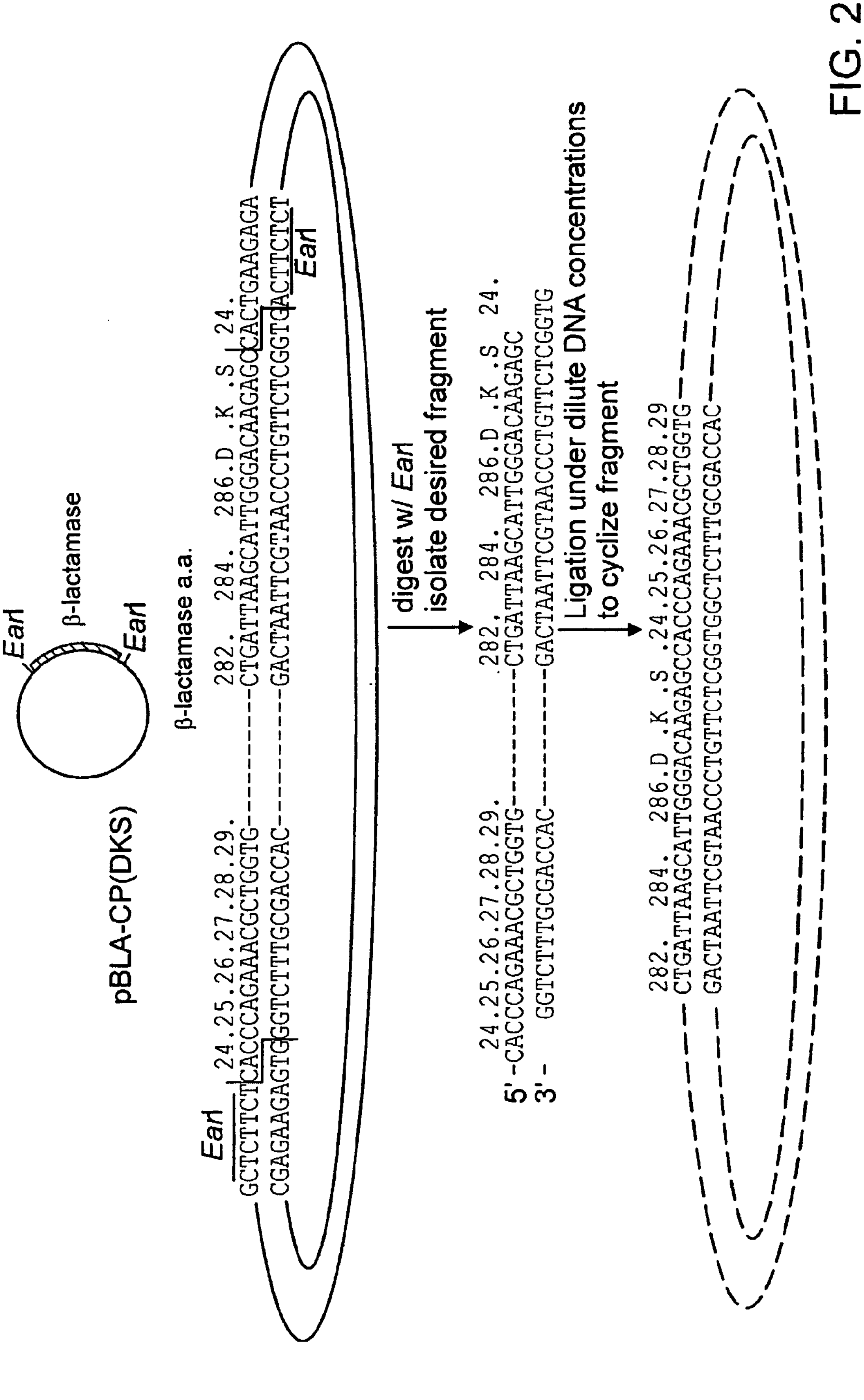
FIG. 2 illustrates steps in creating a cyclized gene using a DKS linker according to the invention (SEQ ID NOS 78-84, respectively in order of appearance).
Figure 3:
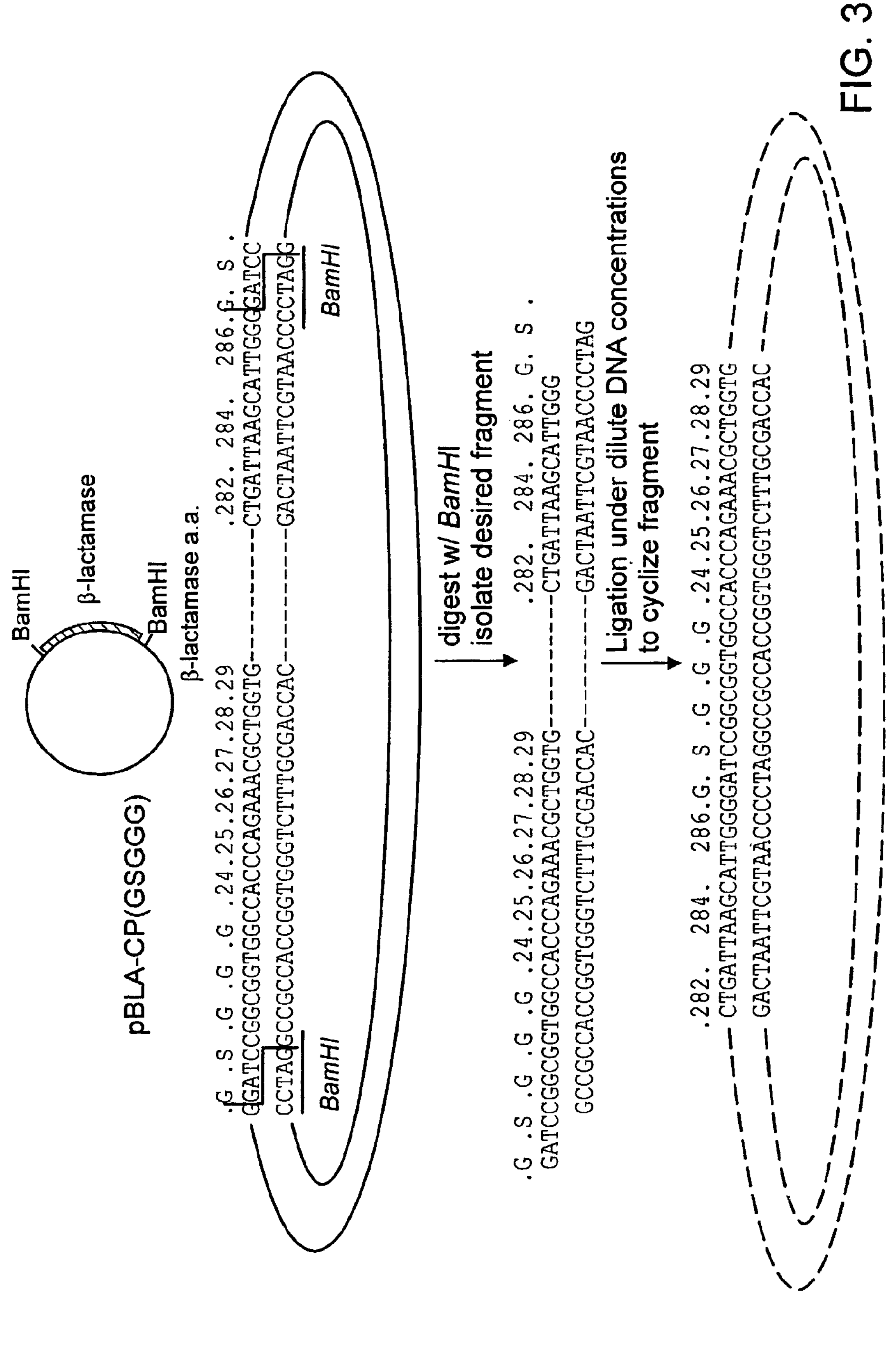
FIG. 3 illustrates steps in creating a cyclized gene using a GSGGG linker (SEQ ID NO: 1) according to the invention (SEQ ID NOS 85-91, respectively in order of appearance).

The fragments to be cyclized are then released from the cloning vector by digestion with a suitable restriction enzyme and purified, for example by agarose gel electrophoresis. Cyclizing is achieved, for example, by treating with a ligase such as T4 DNA ligase. The cyclized (circular) fragments are subsequently purified and subjected to circular permutation (step iii above). Exemplary circularized genes comprising DKS and GSGGG (SEQ ID NO: 1) linkers according to the invention are shown in FIGS. 2 and 3, respectively.

Referring again to FIG. 1, the circularized genes are randomly linearized, by subjecting them to cleavage with a digestion enzyme that makes on average one double-strand break in the circularized DNA. A preferred enzyme for use in this step is a nuclease. A particularly preferred enzyme is DNaseI. The conditions for nuclease digestion can be determined experimentally by varying the amount of enzyme added and analyzing the digested products by agarose gel electrophoresis. Generally, approximately 1 milliunit of DNaseI per microgram of DNA (at a concentration of 10 micrograms per ml) for an 8-minute digestion at 22° C. is suitable, but will vary somewhat for each library. See also Example 1 for further details of suitable conditions for the digestion step. In addition to digestion by nucleases (e.g., DNAse, S1, exonucleases, restriction endonucleases and the like), other methods for introducing breaks in sequences can be used. For example, mechanical shearing, chemical treatment, and/or radiation can be used. Generally, the method for introducing breaks is not intended to be limiting.

Libraries Comprising Circularly Permuted Insert Sequences

In one aspect, libraries comprising a plurality of library members are provided by the invention. Each library member comprises a first nucleic acid sequence encoding a first polypeptide having a first state, the first nucleic acid sequence having been randomly circularly permuted and inserted into a second nucleic acid encoding a second polypeptide having a second state. The libraries can be constructed in any suitable manner known in the art of molecular biology.

Figure 12:
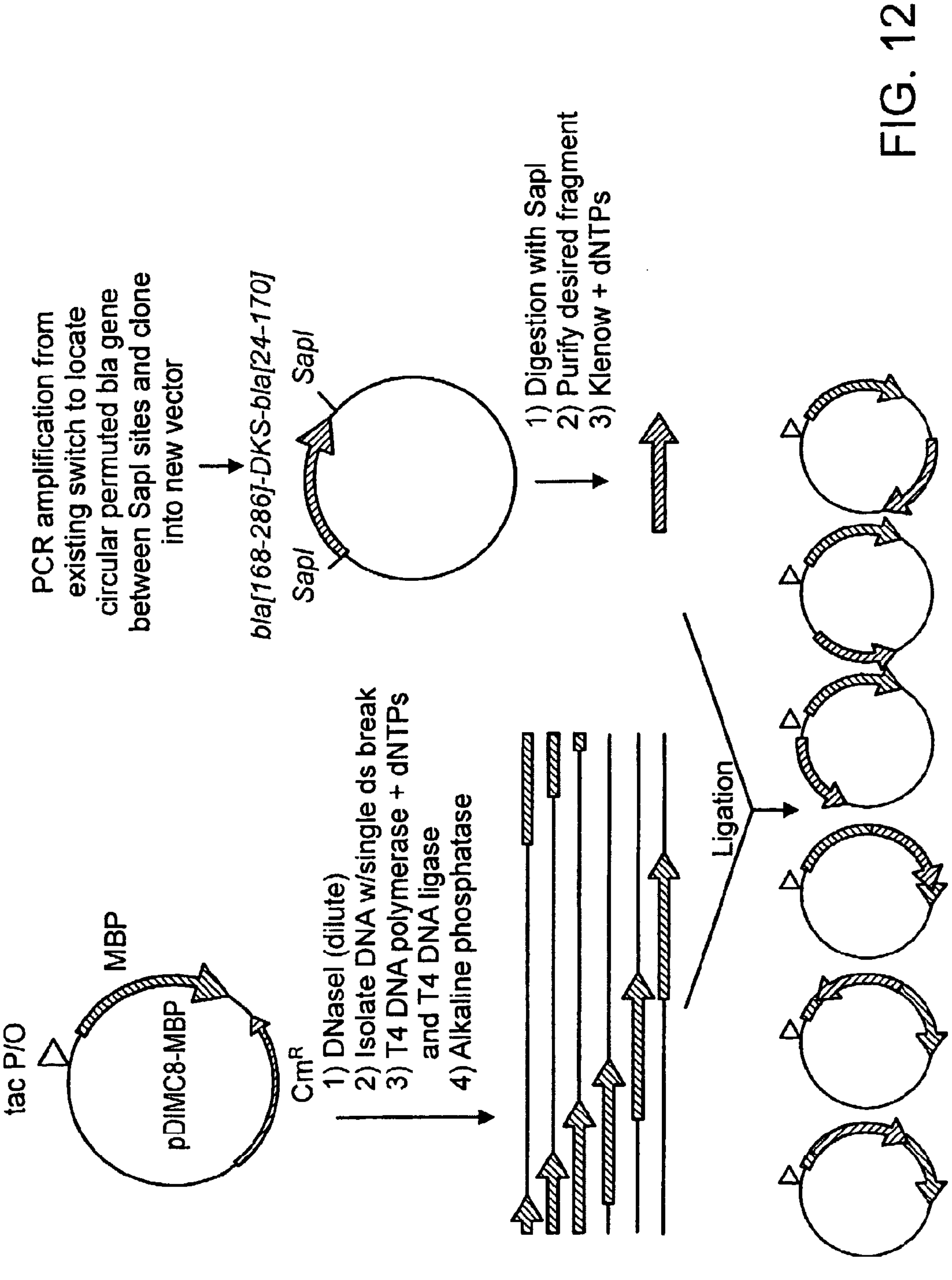
FIG. 12 is a schematic diagram illustrating a strategy for creating a library in which a specific circularly permuted version of the bla gene is randomly inserted into a plasmid containing the gene for MBP, according to an embodiment of the invention.
Figure 13A:
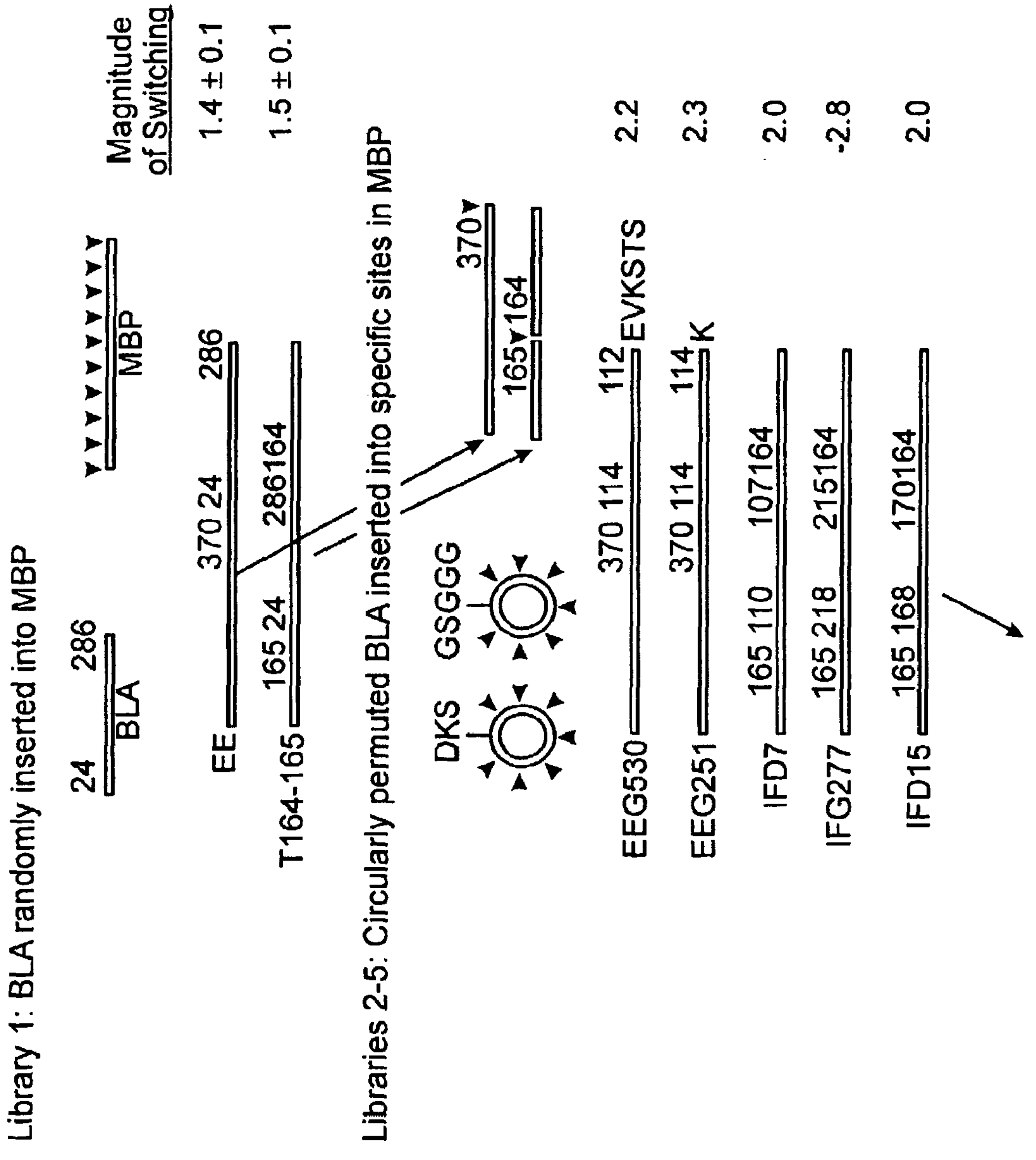
FIG. 13 is a schematic diagram illustrating construction schemes and structures of switches isolated from libraries constructed according to the invention (GSGGG linker disclosed as SEQ ID NO: 1).
Figure 13:
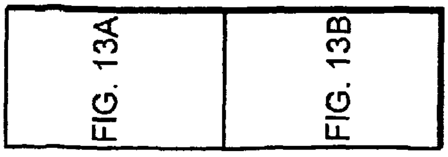
Figure 13B:
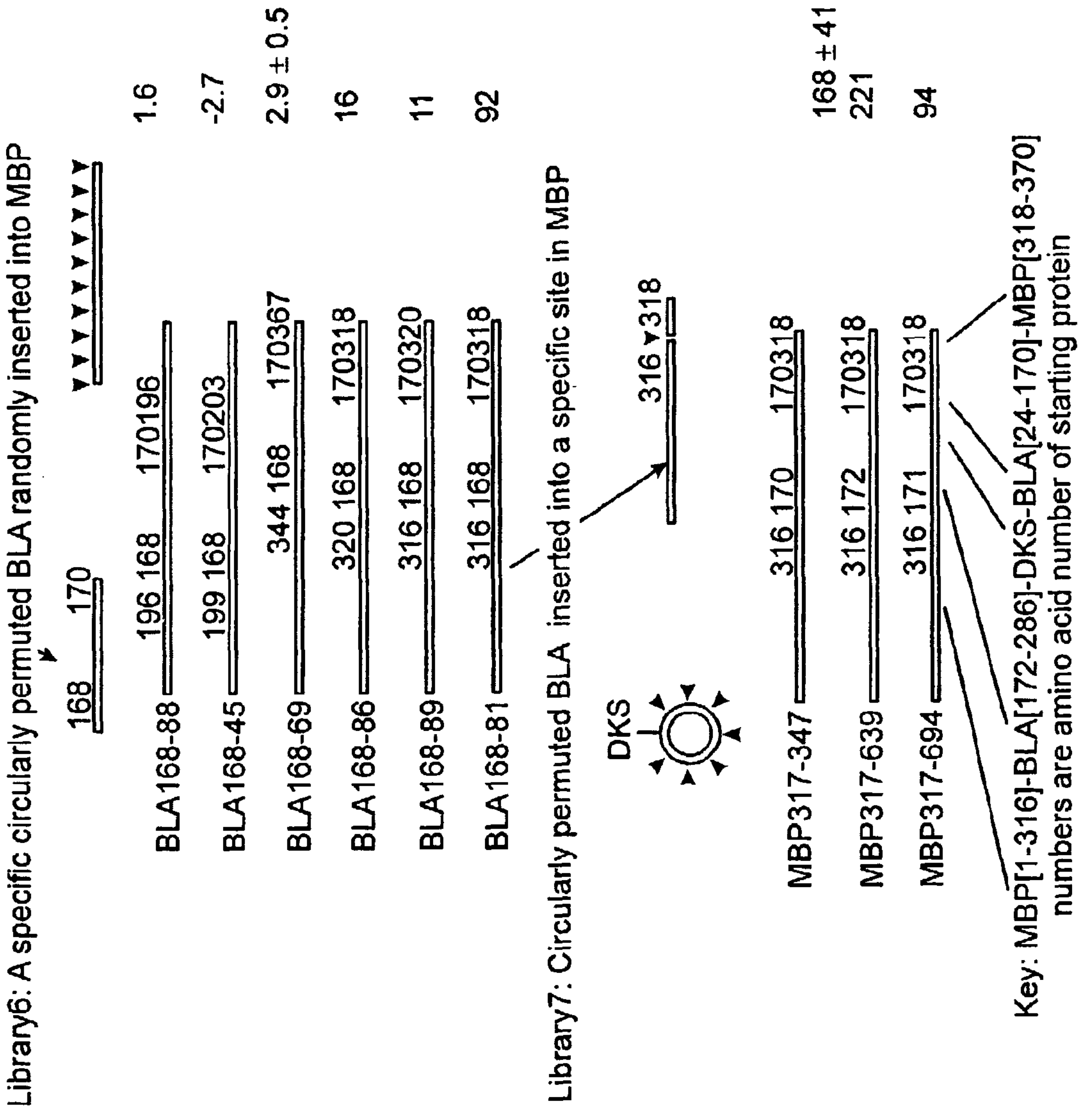

In one preferred type of library, the randomly circularly permuted sequences are randomly inserted into acceptor sequences, a strategy which maximizes the number of possible combinations of insertion and acceptor sequences. Several different strategies can be used to make such "random insertion" libraries. One preferred embodiment of the method, i.e., "Circular Permutation of Insert and Random Domain Insertion," is shown on the left side of FIG. 1. In this embodiment, the circularly permuted insertion sequence is inserted at a random site in a vector, such as a plasmid, comprising the acceptor sequence. In variations of this method, (both shown in FIG. 1), entire libraries of circularly permuted insert sequences can be randomly inserted into the acceptor sequences, or specific circularly permuted versions of a selected sequence can be randomly inserted into the vector. (See, for example, FIG. 12.) See also Example 5 and FIG. 13 showing various strategies including iterative approaches for constructing libraries using circularly permuted DNA, including selected preferred sequences previously generated by circular permutation according to the invention. See, for example, the descriptions of Libraries 6 and 7 in Example 5.

Preparing Target (Acceptor) DNA for Random Insertion Libraries

As discussed, in one aspect, libraries are constructed in which an insertion sequence has been randomly inserted into an acceptor sequence. Preferably, such libraries are generated by randomly inserting a nucleic acid fragment encoding an insertion sequence into a nucleic acid fragment encoding an acceptor sequence.

Existing methods for random insertion can be categorized into one of two strategies: insertion via transposons and insertion after a random double stranded break in DNA using one or a combination of nucleases. A variety of transposons have been used to deliver short, in-frame insertions of 4-93 amino acids (e.g., Hayes and Hallet, 2000, *Trends Microbiol.* 8: 571-7; and Manoil and Traxler, 2000, *Methods* 20: 55-61). However, although transposons are an efficient method for delivering an insertion, insertion methods are preferred which create libraries with direct insertions, deletions at the insertion site, or variability in the amount of deletions or tandem duplication or variability in the distribution of direct insertions, deletions and tandem duplications.

Random insertion using nuclease treatment, on the other hand, can create such libraries. These methods typically are used for the insertion of short sequences into a target gene for example during linker scanning mutagenesis. These methods generally differ in the strategy used to produce a random, double-strand break in supercoiled plasmid DNA containing the gene to be inserted.

Any suitable procedure for randomly inserting a first sequence into second sequence can be used. Exemplary methods are described, for example, in PCT Publication WO 03/078575, herein incorporated by reference. As discussed, the use of BLA and MBP as respective insertion and acceptor sequences, and the use of particular vectors are merely exemplary; potentially any two proteins can be functionally coupled in this manner following random circular permutation of one or both sequences.

To prepare a random insertion library, a target vector comprising the nucleic acid encoding the acceptor polypeptide is preferably randomly linearized (see FIG. 1, left side). For linearization, a variety of different nucleases and digestion schemes can be used. For example, the vector may be exposed to DNase/$Mn^{2+}$ digestion followed by polymerase/ligase repair; S1 nuclease digestion followed by polymerase/ligase repair; or S1 nuclease digestion which is not repaired. The three schemes differ in (a) the methods used to create the random double-stranded break in the target plasmid and (b) whether or not the nucleic acid (e.g., DNA) is repaired by polymerase/ligase treatment, or other methods. However, it should be apparent to those of skill in the art that any method of introducing breaks into a DNA molecule can be used (e.g., such as digestion by mung bean nucleases, endonucleases, restriction enzymes, exposure to chemical agents, irradiation, and/or mechanical shearing) and that the methods of introducing breaks described above are not intended to be limiting.

Preferably, digestion is controlled such that a significant fraction of DNA is undigested in order maximize the amount of linear DNA that has only one double strand break. Key features for optimizing DNase I digestion include the use of $Mg^{2+}$ free DNaseI (Roche Molecular Biochemicals), a digestion temperature of 22° C. and 1 mM $Mn^{2+}$ instead of $Mg^{2+}$ to increase the ratio of double strand breaks to nicks (see, e.g., as described in Campbell and Jackson, 1980, *J. Biol. Chem.* 255: 3726-35).

The DNA can be repaired using methods known in the art, for example, using T4 DNA ligase and T4 DNA polymerase (see, e.g., Graf and Schachman, 1996, *Proc. Natl. Acad. Sci. USA* 93: 11591-11596), and dephosphorylated. Ligation with nucleic acids encoding the insert is performed and nucleic acids (e.g., library members) are collected.

Preparing Target (Acceptor) DNA for Site-Specific Insertion Libraries

Referring again to FIG. 1, another aspect of the invention is shown on the right side of the Figure ("Random Circular Permutation of Insert and Domain Insertion at a Specific Site). In this approach, the circularly permuted insertion sequence is inserted into a selected site in the acceptor sequence. Any suitable site can be selected in the acceptor sequence, based upon desired functional outcome and knowledge of the structure of the acceptor sequence. For example, this site could be a site previously shown to be useful for creating molecular switches (as is demonstrated in Examples below) or a site that is predicted, by computational methods or other means, to be useful in creating a molecular switch.

Figure 4:
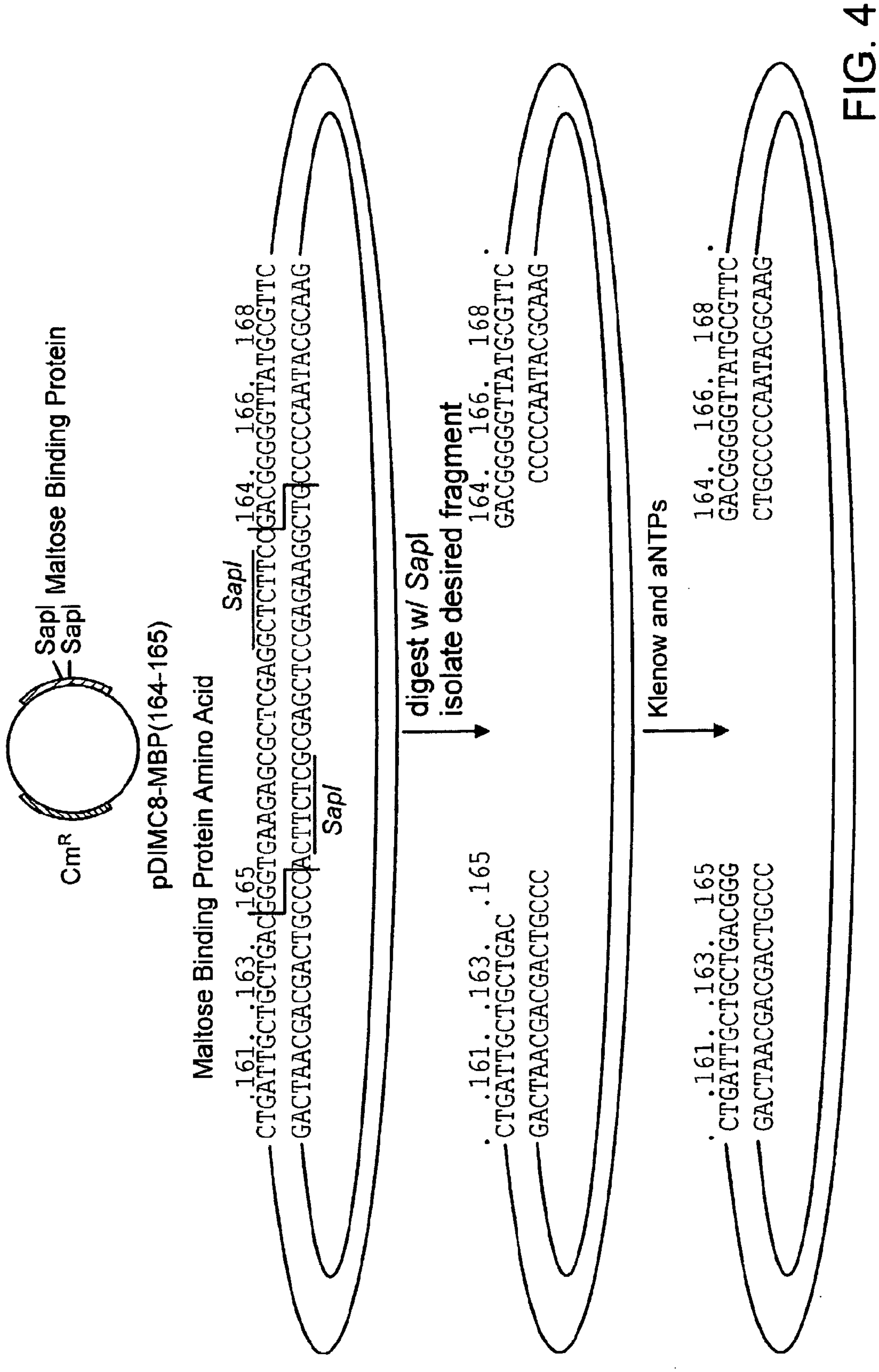
FIG. 4 is a diagram illustrating steps in preparing an acceptor DNA sequence for insertion of an insertion DNA sequence at a specific site in the acceptor DNA sequence according to the invention (SEQ ID NOS 92-97, and 94, respectively in order of appearance).
Figure 11:
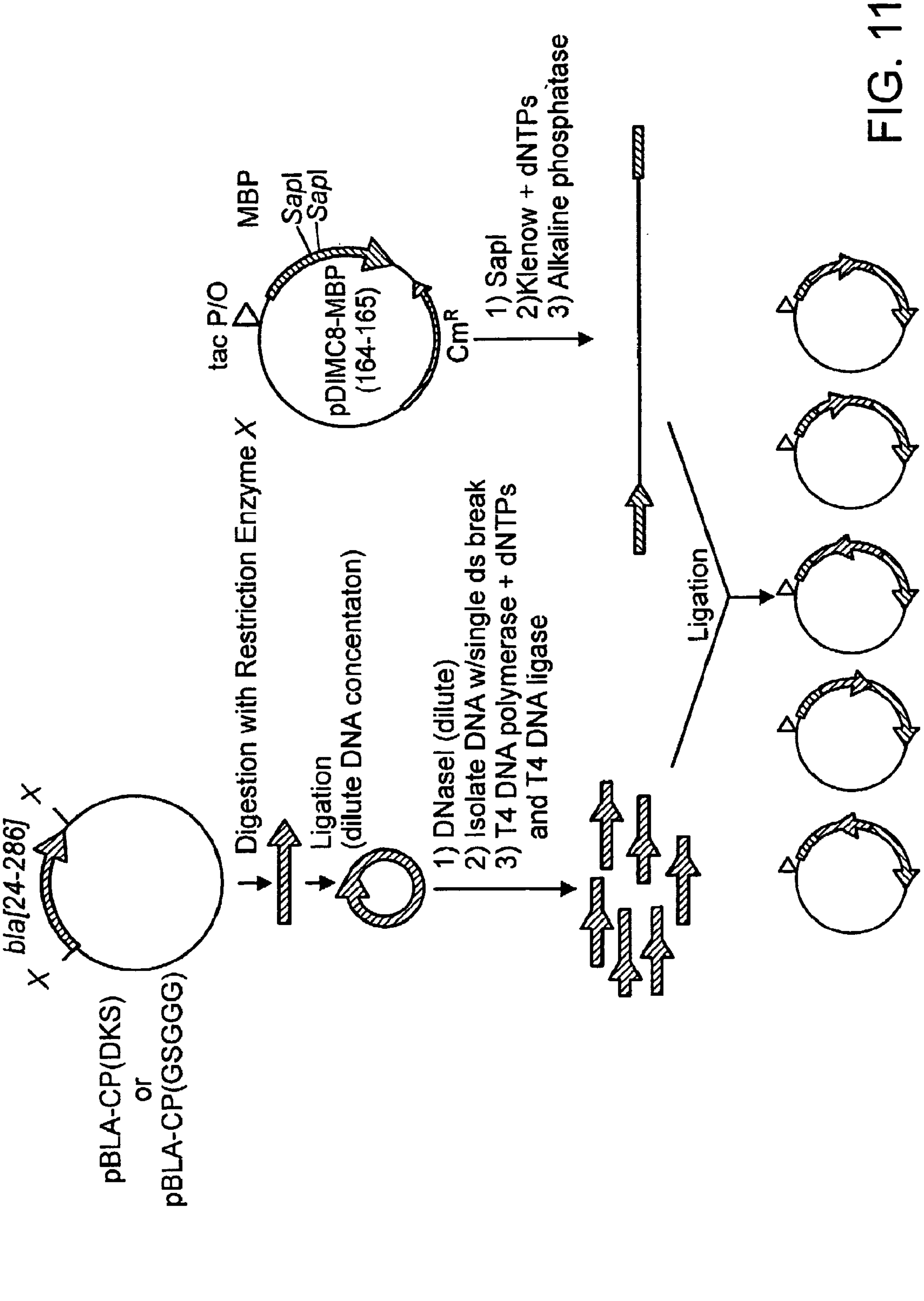
FIG. 11 is a schematic diagram illustrating a strategy for creating a library in which a circularly permuted bla gene is inserted into a specific location in the gene for MBP, according to an embodiment of the invention (GSGGG linker disclosed as SEQ ID NO: 1).

For insertion at a specific site, plasmids comprising insertion sequences can be modified as shown in FIG. 4, for example by insertion of inverted SapI sites between particular bases such that digestion with SapI and subsequent filling in of the resulting overhangs using Klenow polymerase in the presence of dNTPs results in a bisected perfectly blunt sequence on one side (e.g., MBP [1-165]) and a perfectly blunt sequence (e.g., MBP [164-370]) on the other side. SapI is a type IIS restriction enzyme that cuts outside its recognition sequence. Other type IIS restriction enzymes can also be used, as well as non-type IIS restriction enzymes. The randomly permuted insert sequence is subsequently inserted into the acceptor sequence at the selected site (FIGS. 1 and 11). See also Examples 1 and 4, supra.

Target Vectors Comprising Acceptor Sequences

In one aspect, construction of a library comprises the initial step of constructing and testing a target vector, i.e., a vector comprising a nucleic acid encoding an acceptor sequence. For example, a gene or gene fragment which encodes a polypeptide is cloned into a vector, such as a plasmid. Preferably, the polypeptide exists in a state at least under certain conditions, i.e., comprises an activity, can bind a molecule, exist in a conformation, emit light, transfer electrons, catalyze a substrate, etc. under those conditions.

Preferably, the plasmid comprises a reporter sequence for monitoring the efficacy of the cloning process. Suitable reporter genes include any genes that express a detectable gene product which may be RNA or protein. Examples of reporter genes, include, but are not limited to: CAT (chloramphenicol acetyl transferase); luciferase, and other enzyme detection systems, such as β-galactosidase, firefly luciferase, bacterial luciferase, phycobiliproteins (e.g., phycoerythrin); GFP; alkaline phosphatase; and genes encoding proteins conferring drug/antibiotic resistance, or which encode proteins required to complement an auxotrophic phenotype. Other useful reporter genes encode cell surface proteins for which antibodies or ligands are available. Expression of the reporter gene allows cells to be detected or affinity purified by the presence of the surface protein.

The reporter gene also may be a fusion gene that includes a desired transcriptional regulatory sequence, for example, to select for a fusion molecule whose switching functions include the ability to modulate transcription.

Vectors For Expressing Fusion Molecules

Identification of desired fusion molecules, whether created by random or site-specific insertions, can be facilitated by the use of expression vectors in creating the libraries described above. Such expression vectors additionally can be useful for generating large amounts of fusion molecules (e.g., for delivery to a cell, or organism, for use in vitro or in vivo).

Thus, in one aspect, library members comprise regulatory sequences (e.g., such as promoter sequences) which can be either constitutively active or inducible which are operatively linked to acceptor sequences comprising insertion sequences. Regulatory sequences can comprise promoters and/or enhancer regions from a single gene or can combine regulatory elements of more than one gene. In a preferred embodiment, the regulatory sequences comprise strong promoters which allow high expression in cells, particularly in mammalian cells. For example, the promoter can comprise a CMV promoter and/or a Tet regulatory element.

Library members also can comprise promoters to facilitate in vitro translation (e.g., T7, T4, or SP6 promoters). Such constructs can be used to produce amounts of fusion molecules in sufficient quantity to verify initial screening results (e.g., the ability of the molecules to function as molecular switches).

The expression vectors can be self-replicating extrachromosomal vectors and/or vectors which integrate into a host genome. In one aspect, the expression vectors are designed to have at least two replication systems, allowing them to be replicated and/or expressed and/or integrated in more than one host cell (e.g., a prokaryotic, yeast, insect, and/or mammalian cell). For example, the expression vectors can be replicated and maintained in a prokaryotic cell and then transferred (e.g., by transfection, transformation, electroporation, microinjection, cell fusion, and the like) to a mammalian cell.

The expression vectors can include sequences which facilitate integration into a host genome (e.g., such as a mammalian cell). For example, the expression vector can comprise two homologous sequences flanking the nucleic acid sequence encoding the fusion molecule, facilitating insertion of the nucleic acid expressing the fusion molecule into the host genome through recombination between the flanking sequences and sequences in the host genome. Sequences such as lox-cre sites also can be provided for tissue-specific inversion of the fusion molecule nucleic acid with respect to a regulatory sequence to which the fusion molecule nucleic acid is operably linked.

Integration into the host genome may be monitored by screening for the expression of a reporter sequence included in the expression vector, by the expression of the unique fusion molecule (e.g., by monitoring transcription via Northern blot analysis or translation by an immunoassay), and/or by the presence of the switching activity in the cell.

Evaluating Libraries for Identification of Fusion Molecules

In one aspect, transformants are selected which express a reporter gene included in the target vector, such as a drug resistance gene to initially screen for fusion molecules. Alternatively, or additionally, transformants can be selected in which the state of the insertion sequence is coupled to the state of the acceptor sequence. Thus, in one aspect, the existence of each state is assayed for, as is the dependence of each state on the existence of one or more other states. States may be assayed for simultaneously, or sequentially, in the same host cell or in clones of host cells. Fusion molecules also can be isolated from host cells (or clones thereof) and their states can be assayed for in vitro.

For example, in one aspect, the enzymatic activity of an insertion sequence or acceptor sequence is assayed for at the same time that the binding activity of the respective other portion of the fusion is evaluated to identify fusion molecules in which enzymatic activity is dependent on binding activity.

In another aspect, libraries are screened for fusion molecules which bind to a molecule, such as a bio-effective molecule (e.g., a drug, therapeutic agent, toxic agent, or agent for affecting cellular physiology). The bound fusion molecule is exposed to a cell, and the ability of the fusion molecule to be localized intracellularly is determined. Preferably, release of the bio-effective molecule in response to intracellular localization also is determined.

For example, a cell can be transiently permeabilized (e.g., by exposure to a chemical agent such as $Ca^{2+}$ or by electroporation) and exposed to a fusion molecule associated with the bio-effective molecule (e.g., bound to the bio-effective molecule), allowing the fusion molecule and bound molecule to gain entry into the cell. The ability of the fusion molecule to localize to an intracellular compartment (e.g., to the endoplasmic reticulum, to a lysosomal compartment, nucleus, etc.) along with the bio-effective molecule can be monitored through the presence of a label (e.g., such as a fluorescent label or radioactive label) on the fusion molecule, bio-effective molecule, or both. The label can be conjugated to the fusion molecule and/or the bio-effective molecule using routine chemical methods known in the art. A label also may be provided as part of an additional domain of the fusion molecule. For example, the fusion molecule can comprise a GFP polypeptide or modified form thereof. The localization of the label (and hence the fusion molecule and/or bio-effective molecule) can be determined for example using light microscopy. Release of the bio-effective molecule can be monitored by lysing the cell, immunoprecipitating the fusion molecule, and detecting the amount of labeled bio-effective molecule in the precipitated fraction.

In one aspect, the cell need not be permeabilized to allow entry of the fusion molecule because the fusion molecule comprises a signal sequence that enables the fusion molecule to traverse the cell membrane. Intracellular transport of the bio-effective molecule can be monitored by labeling the bio-effective molecule and examining its localization using light microscopy, FACs analysis, or other methods routine in the art.

In another aspect, insertion libraries are screened for fusion molecules which comprise an insertion sequence or acceptor sequence which associates with a bio-effective molecule and which releases the bio-effective molecule when the respective other portion of the fusion molecule binds to a cellular marker of a pathological condition. Thus, in one aspect, fusion molecules associated with a bio-effective molecule are contacted with cells expressing such a marker and the ability of the fusion molecules to specifically bind to the cell is assayed for, as well as the ability of the fusion molecule to release the bio-effective molecule in response to such binding. For example, as above, either, or both, the fusion molecule and the bio-effective molecule can be labeled and the localization of the molecules determined. The action of the bio-effective molecule also can be monitored (e.g., the effect of the bioeffective molecule on the cell can be monitored).

In still another aspect, insertion libraries are screened for fusion molecules which can switch from a non-toxic state to a toxic state upon binding of the insertion sequence or acceptor sequence to a cellular marker of a pathology. Fusion molecules can be selected which specifically bind to cells expressing the marker, and the effect of the fusion molecules on cell death can be assessed. Cell death can be monitored using methods routine in the art, including, but not limited to: staining cells with vital dyes, detecting spectral properties characteristic of dead or dying cells, evaluating the morphology of the cells, examining DNA fragmentation, detecting the presence of proteins associated with cell death, and the like. Cell death also can be evaluated by determining the $LD_{50}$ or $LC_{50}$ of the fusion molecule.

In a further aspect, the insertion library is screened for fusion molecules which comprise a molecular switch for controlling a cellular pathway. Preferably, the states of the insertion sequence and acceptor sequence in the fusion molecules are coupled and responsive to a signal such that in the presence of the signal, the state of either the insertion sequence or the acceptor sequence modulates the activity or expression of a molecular pathway molecule in a cell. A signal can be the presence, absence, or level, of an exogenous or endogenous binding molecule to which either the insertion sequence or acceptor sequence binds, or it can be a condition (e.g., chemical, optical, electrical, etc.) in an environment to which the fusion molecule is exposed. The ability of the fusion molecule to control a pathway can be monitored by examining the expression and/or activity of pathway molecules which act downstream of a pathway molecule whose expression and/or activity is being modulated.

In another aspect, fusion molecules are selected in which either the insertion sequence or acceptor sequence binds to a nucleic acid molecule. For example, the ability of the fusion molecules to bind to a nucleic acid immobilized on a solid phase can be monitored (e.g., membrane, chip, wafer, particle, slide, column, microbead, microsphere, capillary, and the like). Preferably, fusion molecules are selected in which nucleic acid binding activity is coupled to a change in state of the respective other sequence of the fusion molecule. For example, nucleic acid binding activity can be coupled to the binding activity of another portion of the fusion molecule, catalysis by the other portion, the light emitting function of the other portion, electron transferring ability of the other portion, ability of the other portion to change conformation, and the like. Preferably, nucleic acid binding activity is coupled to the response of the fusion molecule to a signal.

Nucleic acid binding activity also can be monitored by evaluating the activity of a target nucleic acid sequence to which the fusion molecule binds. For example, in one aspect, the fusion molecule binds to a nucleic acid regulatory sequence which modulates the activity (e.g., transcription, translation, replication, recombination, supercoiling) of another nucleic acid molecule to which the regulatory sequence is operably linked. The nucleic acid regulatory molecule and its regulated sequence can be provided as part of a nucleic acid molecule encoding the fusion molecule or can be provided as part of a separate molecule(s). The nucleic acid binding activity can be monitored in vitro or in vivo. The ability of fusion molecules to bind to a nucleic acid can also be determined in vivo using one-hybrid or two-hybrid systems (for example, see, Hu, et al., 2000, *Methods* 20: 80-94).

In certain aspects, fusion molecules are selected which bind to a known regulatory sequence or a sequence naturally found in a cell. In other aspects, a sequence which is not known to be a regulatory sequence in a cell is selected for. Preferably, such a sequence binds to the fusion molecule and modulates the activity of another nucleic acid (in cis or in trans), Thus, the fusion molecule can be used to select for novel nucleic acid regulatory sequences. Preferably, the fusion molecule modulates the regulatory activity of the nucleic acid molecule in response to a signal, as described above.

In still a further aspect, the insertion library is screened for fusion molecules which are sensor molecules. Preferably, fusion molecules are screened for in which either the insertion sequence or acceptor sequence binds to a target molecule and wherein the respective other portion of the fusion molecule generates a signal in response to binding. Signals can include: emission of light, transfer of electrons, catalysis of a substrate, binding to a detectable molecule, and the like. To assay for such fusions, members of the library can be screened in the presence of the target molecule (e.g., in solution, or immobilized on a solid support) for the production of the signal.

Fusion Molecules Comprising Coupled Insertion and Acceptor Sequences

In one aspect, a modulatable fusion molecule is provided which comprises an insertion sequence and an acceptor sequence which contains the insertion sequence (Several examples of such fusion molecules are shown, e.g., in FIG. 13). Preferably, the insertion sequence and acceptor sequence are polymeric molecules, e.g., such as polypeptides or nucleic acids. More preferably, both the insertion sequence and acceptor sequence are capable of existing in at least two states and the state of the insertion sequence is coupled to the state of the acceptor sequence upon fusion, such that a change in state in either the insertion sequence or acceptor sequence will result in a change in state of the respective other portion of the fusion. As discussed, a "estate" can be a conformation; binding affinity; ability or latent ability to catalyze a substrate; ability or latent ability to emit light; ability or latent ability to transfer electrons; ability or latent ability to withstand degradation (e.g., by a protease or nuclease); ability or latent ability to modulate transcription; ability or latent ability to modulate translation; ability or latent ability to modulate replication; ability or latent ability to initiate or mediate recombination or supercoiling; or otherwise perform a function; and the like.

Preferably, the change in state is triggered by a signal to which the fusion molecule is exposed, e.g., such as the presence, absence, or amount of a small molecule, ligand, metabolite, ion, organelle, cell membrane, cell, organism (e.g., such as a pathogen), temperature change, pressure change, and the like, to which the fusion molecule binds; a change in a condition, such as pH, or a change in the chemical, optical, electrical, or magnetic environment of the fusion molecule. In one aspect, a fusion molecule functions as an ON/OFF switch in response to a signal (e.g., changing from one state to another). For example, when an insertion sequence or acceptor sequence of the fusion molecule binds to a ligand, the respective other half of the fusion may change state (e.g., change conformation, bind to a molecule, release a molecule to which it is bound, catalyze a substrate or stop catalyzing a substrate, emit light or stop emitting light, transfer electrons or stop transferring electrons, activate or inhibit transcription, translation, replication, etc.).

Some fusion molecules according to the invention also can be used to generate graded responses. In this scenario, a fusion molecule can switch from a series of states (e.g., more than two different types of conformations, levels of activity, degrees of binding, levels of light transmission, electron transfer, transcription, translation, replication, etc.). Preferably, the difference in state is one which can be distinguished readily from other states (e.g., there is a significant measurable difference between one state and any other state, as determined using assays appropriate for measuring that state).

More generally, a molecular switch can generate a measurable change in state in response to a signal. For example, a molecular switch can comprise a plurality of fusion molecules each responsive to a signal and for mediating a function in response to a change in state of at least a portion of the molecule. As above, preferably, this change of state occurs in response to a change in the state of another portion of the molecule.

While the states of individual fusion molecules in the population may be ON or OFF, the aggregate population of molecules may not be able to mediate the function unless a threshold number of molecules switch states. Thus, the "state" of the population of molecules may be somewhere in between ON or OFF, depending on the number of molecules which have switched states. This provides an ability to more precisely tune a molecular response to a signal by selecting for molecules which respond to a range of signals and modifying the population of fusion molecules to provide selected numbers of fusion molecules, providing an aggregate switch which can respond to a narrow range or wider range of signal as desired. Thus, in one aspect, a heterogeneous population of fusion molecules is provided comprising members which respond to different levels or ranges of signals. Individual fusion molecules also may exist in states intermediate between ON or OFF; e.g., having a given level of activity, ability to bind to a molecule in one state and a measurably higher or lower level of activity, ability to bind, etc., in a different state.

Insertion Sequences

The size of the insertion in the fusion protein will vary depending on the size of insertion sequence required to confer a particular state on the insertion sequence without significantly disrupting the ability of the acceptor molecule into which it is inserted to change state. Preferably, the effect of the insertion is to couple the change in state of the acceptor molecule to a change in state of the insertion molecule, or vice versa.

Generally, for polypeptide insertions, the size of the insertion sequence can range from about two amino acids to at least about 1000, for example at least about 900, 800, 700, 600, 500, 400, 300, 200, 100, or fewer amino acids. In one aspect, the insertion comprises a domain sequence with a known characterized activity (e.g., a portion of a protein in which bioactivity resides); however, in other aspects, the insertion sequence comprises sequences up to an entire protein sequence.

Acceptor Sequences

Generally, there are no constraints on the size or type of acceptor sequence which can be used. However, in one aspect, an acceptor sequence is a polypeptide whose state resides in a discontinuous domain of a protein (e.g., the amino acids involved in conferring the state/activity of the acceptor sequence are not necessarily contiguous in the primary polypeptide sequence) (see, e.g., as described in Russell and Ponting, 1998, *Curr. Opin. Struct. Biol.* 8: 364-371, and Jones, et al., 1998, *Protein Sci.* 7: 233-42).

Suitable polypeptides for acceptor molecules can be identified using domain assignment algorithms such as are known in the art (e.g., such as the PUU, DETECTIVE, DOMAK, and DomainParser, programs). For example, a consensus approach may be used as described in Jones, et al., (1998). Information also can be obtained from a number of molecular modeling databases such as the web-based NIH Molecular Modeling Homepage, or the 3Dee Database described by Dengler, et al., 2001, *Proteins* 42(3): 332-44. However, the most important criterion for selecting a sequence is its function, e.g., the desired state parameters of the fusion molecule.

However, in a further aspect, no pre-screening is done and an acceptor sequence is selected simply on the basis of a desired activity. The power of the methods according to the invention is that they rely on combinatorial screening to identify any, and preferably, all, combinations of insertions that produce a desired coupling in states of acceptor and insertion molecules.

Domain Sequences in Fusion Proteins

In one aspect, the insertion sequence or acceptor sequence comprises a "domain" sequence having a known state. Domains can be minimal sequences, such as are known in the art, which are associated with a particular known state, or can be an entire protein comprising the domain or a functional fragment thereof.

Figure 6A:
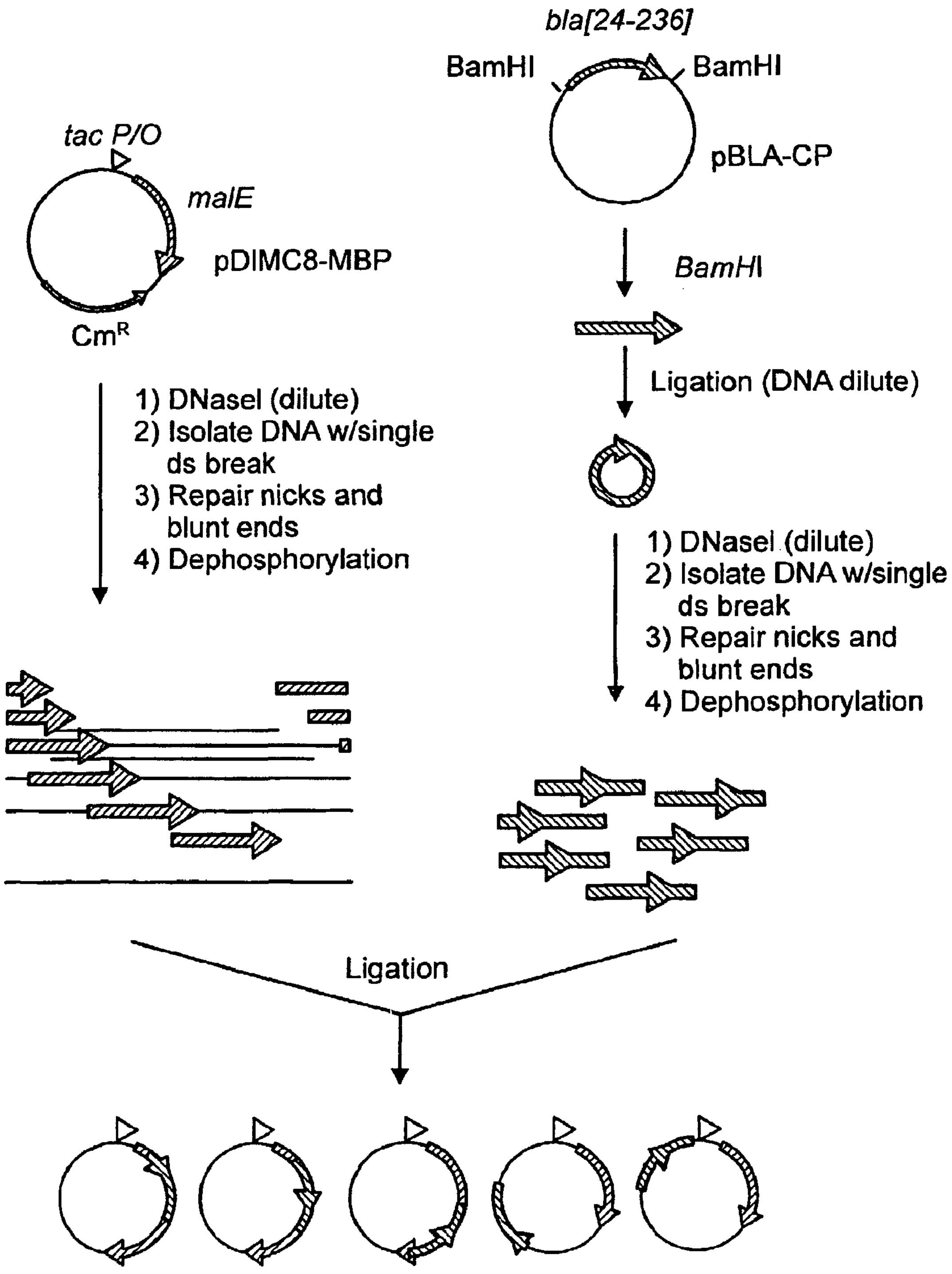
FIGS. 6A-C illustrate a novel fusion molecule comprising sequences from an effector protein (maltose binding protein, MBP) and an enzyme (13-lactamase, BLA) according to an aspect the invention.
Figure 6B:
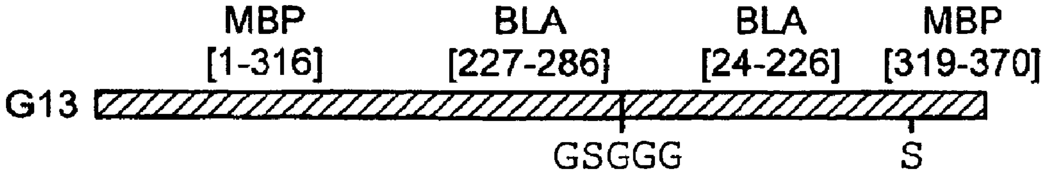

The insertion and acceptor sequences can be selected from any of the domain sequences described below and can be of like kind (e.g., both catalytic sites, both binding domains, both light emitting domains) or of different kind (e.g., a catalytic site and a binding site, as shown for example in FIG. 6B, a binding site and a light emitting domain; etc.). The domain sequences can be the minimal sequences required to confer a state or activity or can comprise additional sequences. Other insertion and acceptor sequences can be derived from known domain sequences or from newly identified sequences. Such sequences are also encompassed within the scope of the instant invention.

Minimal domain sequences can be defined by site-directed mutagenesis of a sequence having a desired state to determine the minimum amino acids necessary to confer the existence of the state under the appropriate conditions (e.g., such as a minimal binding site sequence or a minimum sequence necessary for catalysis, light emission, etc.). As discussed above, minimal domain sequences also can be defined virtually, using algorithms to identify consensus sequences or areas of likely protein folding. Once a domain sequence has been identified, it can be modified to include additional sequences, as well as insertions, deletions, and substitutions of amino acids so long as they do not substantially affect the state of the domain sequence. While domain sequences can be obtained using nucleic acids encoding appropriate fragments of polypeptides, they also can be synthesized, for example, based on a predicted consensus sequence for a class of molecules which is associated with a particular state. However, as discussed above, in some cases it may be desirable to provide the domain sequence in the form of a native protein comprising the domain.

Suitable domain sequences include extracellular domains which are portions of proteins normally found outside of the plasma membrane of a cell. Preferably, such domains bind to bio-effective molecules. For example, an extracellular domain can include the extracytoplasmic portion of a transmembrane protein, a secreted protein, a cell surface targeting protein, a cell adhesion molecule, and the like. In one aspect, an extracellular domain is a clustering domain, which, upon activation by a bio-effective molecule will dimerize or oligomerize with other molecules comprising extracellular domains.

Intracellular domains also can serve as insertion sequences or acceptor sequences. As used herein, "an intracellular domain" refers to a portion of a protein which generally resides inside of a cell with respect to the cellular membrane. In one aspect, an intracellular domain is one which transduces an extracellular signal into an intracellular response. For example, an intracellular domain can comprise a proliferation domain which signals a cell to enter mitosis (e.g., such as domains from Jak kinase polypeptides, I1-2 receptor β and/or gamma chains, and the like). Other transducer sequences include sequences from the zeta chain of the T cell receptor or any of its homologs (e.g., the eta chain, Fc epsilon R1-gamma and -62 chains, MB1 chain, B29 chain, and the like), CD3 polypeptides (gamma, beta and epsilon), syk family tyrosine kinases (Syk, ZAP 70, and the like), and src family tyrosine kinases (Lck, Fyn, Lyn, and the like).

A transmembrane domain also can be used as an insertion sequence or acceptor sequence. Preferably, a transmembrane domain is able to cross the plasma membrane and can, optionally, transduce an extracellular signal into an intracellular response. Preferred transmembrane sequences include, but are not limited to, sequences derived from CD8, ICAM-2, IL-8R, CD4, LFA-1, and the like.

Transmembrane sequences also can include GPI anchors, e.g., such as the DAF sequence (PNKGSGTTSGTTRLLS-GHTCFTLTGLLGTLVTMGLLT) (SEQ ID NO: 2) (see, e.g., Homans, et al., 1988, Nature 333(6170): 269-72; Moran, et al., 1991, J. Biol. Chem. 266: 1250); myristylation sequences (e.g., such as the src sequence MGSSKSKP-KDPSQR) (SEQ ID NO: 3) (see Cross, et al., 1984, Mol. Cell. Biol. 4(9): 1834; Spencer, et al., 1993, Science 262: 1019-1024); and palmitoylation sequences (e.g., such as the GRK6 sequence LLQRLFSRQDCCGNCSDSEEELPTR) (SEQ ID NO: 4).

Either the insertion sequence or the acceptor sequence can be a localization sequence for localizing a molecule comprising the sequence intracellularly. In one aspect, the localization sequence is a nuclear localization sequence. Generally, a nuclear localization sequence is a short, basic sequence that serves to direct a polypeptide in which it occurs to a cell's nucleus (Laskey, 1986, Ann. Rev. Cell Biol. 2:367-390; Bonnerot, et al., 1987, Proc. Natl. Acad. Sci. USA 84: 6795-6799; Galileo, et al., 1990, Proc. Natl. Acad. Sci. USA 87: 458-462, 1990). Suitable nuclear localization sequences include, but are not limited to, the SV40 (monkey virus) large T Antigen sequence (PKKKKKV) (SEQ ID NO: 5) (see, e.g., Kalderon, 1984, et al., Cell 39: 499-509); the human retinoic acid receptor nuclear localization signal (ARRRRP) (SEQ ID NO: 6); NF κβ p50 sequence (EEVQRKRQKL) (SEQ ID NO: 7) (Ghosh et al., 1990, Cell 62: 1019); the NF κB p65 sequence (EEKRKRTYE) (SEQ ID NO: 8) (Nolan et al., 1991, Cell 64: 961); and nucleoplasmin (Ala Val Lys Arg PAATLKK-AGQAKKKKLD) (SEQ ID NO: 9) (Dingwall, et al., 1982, Cell 30:449-458).

The localization sequence can comprise a signaling sequence for inserting at least a portion of the fusion molecule into the cell membrane. Suitable signal sequences include residues 1-26 of the IL-2 receptor beta-chain (see, Hatakeyama et al., 1989, Science 244: 551; von Heijne et al, 1988, Eur. J. Biochem. 174: 671); residues 1-27 of the insulin receptor β chain (see, Hatakeyama, et al., 1989, supra); residues 1-32 of CD8 (Nakauchi, et al., 1985, PNAS USA 82: 5126) and residues 1-21 of ICAM-2 (Staunton, et al., 1989, Nature (London) 339: 61).

The localization sequence also can comprise a lysozomal targeting sequence, including, for example, a lysosomal degradation sequence such as Lamp-2 (KFERQ) (SEQ ID NO: 10) (see, e.g., Dice, 1992, Ann. N.Y. Acad. Sci. 674: 58); a lysosomal membrane sequence from Lamp-1 (MLIPIAGF-FALAGLVLIVLIAYLIGRKRSHAGYQTI) (SEQ ID NO: 11) (see, e.g., Uthayakumar, et al., 1995, Cell. Mol. Biol. Res. 41: 405) or Lamp-2 (LVPIAVGAALAGVLILVLLAY-FIGLKHHHAGYEQF) (SEQ ID NO: 12) (see, e.g., Konecki et al., 1994, Biochem. Biophys. Res. Comm. 205: 1-5).

Alternatively, the localization sequence can comprise a mitrochondrial localization sequence, including, but not limited to: mitochondrial matrix sequences, such as the MLRTSSLFTRRVQPSLFSRNILRLQST (SEQ ID NO: 13) of yeast alcohol dehydrogenase III (Schatz, 1987, Eur. J. Biochem. 165:1-6); mitochondrial inner membrane sequences, such as the MLSLRQSIRFFKPATRTLCSS-RYLL (SEQ ID NO: 14) sequence of yeast cytochrome c oxidase subunit IV (Schatz, 1987, supra); mitochondrial intermembrane space sequences, such as the MFSML-SKRWAQRTLSKSFYSTATGAASKS-GKLTQKLVTAGVAAAGITASTLL YADSLTAEAMTA (SEQ ID NO: 15) sequence of yeast cytochrome c1 (Schatz, 1987, supra); or mitochondrial outer membrane sequences, such as the MKSFITRNKTAILATVAATG-TAIGAYYYYNQLQQQQQRGKK (SEQ ID NO: 16) sequence of yeast 70 kD outer membrane protein (see, e.g., Schatz, supra).

Other suitable localization sequences include endoplasmic reticulum localizing sequences, such as KDEL (SEQ ID NO: 17) from calreticulin (e.g., Pelham, 1992, Royal Society London Transactions B: 1-10) or the adenovirus E3/19K protein sequence LYLSRRSFIDEKKMP (SEQ ID NO: 18) (Jackson et al., 1990, EMBO J. 9: 3153); and peroxisome targeting sequences, such as the peroxisome matrix sequence (SKL) from Luciferase (Keller et al., 1987, Proc. Natl. Acad. Sci. USA 4: 3264).

In another aspect, the insertion sequence or acceptor sequence comprises a secretory signal sequence capable of effecting the secretion of the fusion molecule from a cell (see, e.g., Silhavy, et al., 1985, Microbiol. Rev. 49: 398-418). This may be useful for generating a switch molecule which can affect the activity of a cell other than a host cell in which it is expressed. Suitable secretory sequences, include, but are not limited to the MYRMQLLSCIALSLALVTNS (SEQ ID NO: 19) sequence of IL-2 (Villinger, et al., 1995, J. Immunol. 155: 3946); the MATGSRTSLLLAFGLLCLPWLQEGSAFPT (SEQ ID NO: 20) sequence of growth hormone (Roskam et al., 1979, Nucleic Acids Res. 7: 30); the MALWMRLLPLLA-LLALWGPDPAAAFVN (SEQ ID NO: 21) sequence of preproinsulin (Bell, et al., 1980, Nature 284: 26); the influenza HA protein sequence, MKAKLLVLLYAFVAGDQI (SEQ ID NO: 22) (Sekiwawa, et al., Proc. Natl. Acad. Sci. USA 80: 3563); or the signal leader sequence from the secreted cytokine IL4, MGLTSQLLPPLFFLLACAGNFVHG (SEQ ID NO: 23).

In a further aspect, the insertion sequence or acceptor sequence comprises a domain for binding a nucleic acid. The domain can comprise a DNA binding polypeptide or active fragment thereof from a prokaryote or eukaryote. For example, the domain can comprise a polypeptide sequence from a prokaryotic DNA binding protein such as gp 32; a domain from a viral protein, such as the papilloma virus E2 protein; or a domain from a eukaryotic protein, such as p53, Jun, Fos, GCN4, or GAL4. Novel DNA binding proteins also can be generated by mutagenic techniques (see, e.g., as described in U.S. Pat. No. 5,198,346).

The insertion sequence or acceptor sequence also can comprise the $Ca^{2+}$ binding domain of a $Ca^{2+}$ binding protein such as calmodulin, parvalbumin, troponin, annexin, and myosin or the ligand domain of a binding protein such as avidin, concanavalin A, ferritin, fibronectin, an immunoglobulin, a T cell receptor, an MHC Class I or Class II molecule, a lipid binding protein, a metal binding protein, a chaperone, a G-protein coupled receptor, and the like.

In addition, the insertion or acceptor sequence can comprise the transport domain of a transport protein such as hemerythrin, hemocyanin, hemoglobin, myoglobin, transferrin, lactoferrin, ovotransferrin, maltose binding protein and transthyretrin.

In another aspect, the insertion or acceptor sequence can comprise the active domain of a blood coagulation protein (e.g., a domain which mediates blood clotting). Exemplary blood clotting proteins include, but are not limited to: decorsin, factor IX, factor X, kallikrein, plasmin/plasminogen, protein C, thrombin/prothrombin, and tissue-type plasminogen activator.

In still another aspect, the insertion or acceptor sequence can comprise the active domain of an electron transport protein (e.g., a domain which confers electron transport activity on a protein). Electron transport proteins include, but are not limited to, amicyanin, azurin, a cytochrome protein, ferrodoxin, flavodoxin, glutaredoxin, methylamine dehydrogenase, plastocyanin, rubredoxin, and thioredoxin.

In a further aspect, the insertion sequence or acceptor sequence comprises the catalytic and/or substrate binding site of an enzyme. Suitable enzymes from which such sites are selected include: a β-lactamase; an acetylcholinesterase; an amylase; a barnase; a deaminase; a kinase (e.g., such as a tyrosine kinase or serine kinase); a phosphatase; an endonuclease; an exonuclease; an esterase; an enzyme involved in a metabolic pathway (e.g., fructose-1,6-bisphosphatase); a glycosidase; a heat shock protein; a lipase; a lysozyme; a neuramidase/sialidase; a phospholipase; a phosphorylase; a pyrophosphatase; a ribonuclease; a thiolase; a polymerase; an isomerase (such as a mutase; triosephosphate isomerase, xylose isomerase, topoisomerase, gyrase); a lyase (such as aconitase, carbonic anhydrase, pyruvate decarboxylase); an oxidoreductase (such as alcohol dehydrogenase, aldose reductase, a catalase, cytochrome C, a peroxidase, a cytochrome p450, a dehydrogenase, a dihydrofolate reductase, a glyceraldehydes-3-phosphate dehydrogenase, a hydroxybenzoate hydroxylase, a lactate dehydrogenase, a peroxidase, a superoxide dismutase, a protease (such as actinidin, α-lytic protease, aminopeptidase, carboxypeptidase, chymosin, chymotrypsin, elastase, endopeptidase, endothiapepsin, HIV protease, Hannuka factor, papain, pepsin, rennin, substilisin, thermolysin, thermitase, and trypsin), a transferase (such as acetyltransferase, aminotransferase, carbamoyltransferase, dihyrolipoamide acetyltransferase, dihydrolipoyl transacetylase, dihydrolipoamide succinyltransferase, a nucleotidyl transferase, a DNA methyltransferase, a formyltransferase, a glycosyltransferase, a phosphotransferase, a phosphoribosyltransferase), a dehalogenase, a racemase, and the like.

The catalytic domain also can be a rhodanese homology domain such as forms the active site in various phosphatases and transferases (e.g., such as found in the Cdc25 family of protein dual specificity phosphatases, the MKP1/PAC1 family of MAP-kinase phosphatases, the Pyp1/Pyp2 family of MAP-kinase phosphatases, and certain ubiquitin hydrolases) (see, e.g., Hofmann, et al., 1998, *J. Mol. Biol.* 282: 195-208).

Still other domains can include toxins such as cardiotoxin, conotoxin, erabutoxin, momorcharin, momordin, and ricin.

Other domains include, but are not limited to, signaling domains such as the FHA domain, found in protein kinases and transcription factors such as fork head, DUN1, RAD53, SPK1, cds1, MEK1, KAPP, NIPP1, Ki-67, fraH, and KIAA0170 (see, e.g., Hofmann and Bucher, 1995, *Trends Biochem. Sci.* 20: 347-349); the death domain, a heterodimerization domain present in proteins involved in apoptotic signal transduction and the NFkβ pathway (such as TNFR1, FAS/APO1, NGFR, MORT1/FADD, TRADD, RIP, ankyrin, MyD88, unc-5, unc-44, DAP-kinase, Rb-binding p84, pelle, NFkB, and tube polypeptides) (see, e.g., Hofmann and Tschopp, 1995, *FEBS Lett.* 371: 321-323); and the G-protein desensitization domain (found in ARK1, GRK, G-protein coupled receptor kinases, egl-10, GAIP, BL34 SST2, flbA, RGP3, RGP4Human G0/G1 switch regulatory protein 8, Human B-cell activation protein BL34, and G-protein coupled receptor kinases) (see, e.g., Hofmann and Bucher, "Conserved Sequence Domains in Cell Cycle Regulatory Proteins", abstract presented at the joint ISREC/AACR meeting "Cancer and the Cell cycle", January 1996 in Lausanne).

In one aspect, either the insertion or the acceptor sequence is a light-emitting polypeptide domain such as one obtained from a Green Fluorescent Protein, or modified, or mutant form thereof (collectively referred to as a "GFP"). The wild-type GFP is 238 amino acids in length (Prasher, et al., 1992, *Gene* 111(2): 229-233; Cody et al., *Biochem.* 32(5):1212-1218 (1993); Ormo, et al, 1996, *Science* 273: 1392-1395; and Yang, et al., 1996, *Nat. Biotech.* 14: 1246-1251). Modified forms are described in WO 98/06737 and U.S. Pat. No. 5,777,079. GFP deletion mutants also can be made. For example, at the N-terminus, it is known that only the first amino acid of the protein may be deleted without loss of fluorescence, while at the C-terminus, up to 7 residues can be deleted without loss of fluorescence (see, e.g., Phillips, et al., 1997, *Current Opin. Structural Biol.* 7: 821).

The insertion sequence or acceptor sequence additionally can comprise the light-reactive portion of a photoreceptor such as bacteriochlorophyll-A, bacteriorhodopsin, photoactive yellow protein, phycocyanin, and rhodopsin.

Additional domain sequences include ligand-binding domains of ligand-binding proteins. Such proteins include, but not limited to: biotin-binding proteins, lipid-binding proteins, periplasmic binding proteins (e.g., maltose binding protein), lectins, serum albumins, immunoglobulins, T cell receptors, inactivated enzymes, pheromone-binding proteins, odorant-binding proteins, immunosuppressant-binding proteins (e.g., immunophilins such as cyclophilins and FK506-binding proteins), phosphate-binding proteins, sulfate-binding proteins, and the like. Additional binding proteins are described in De Wolf and Brett, 2000, *Pharmacological Reviews* 52(2): 207-236.]

The domain sequences of the proteins described above are known in the art and can be obtained from a database such as available at the NIH Molecular Modeling Homepage.

Additional Sequences in Fusion Proteins

Fusion molecules can further comprise domain sequences, as described above, in addition to insertion and acceptor sequences. Such domains can comprise states which may or may not be coupled with the states of the other portions of the fusion molecule.

Additional sequences also can be included as part of the fusion molecule which do not alter substantially the states of the insertion sequence or acceptor sequence portion of the fusion molecule. For example, affinity tag sequences can be provided to facilitate the purification or isolation of the fusion molecule. Thus, His6 tags (SEQ ID NO: 99) can be employed (for use with nickel-based affinity columns), as well as epitope tags (e.g., for detection, immunoprecipitation, or FACS analysis), such as myc, BSP biotinylation target sequences of the bacterial enzyme BirA, flu tags, lacZ, GST, and Strep tags I and II. Nucleic acids encoding such tag molecules are commercially available.

Stability sequences can be added to the fusion molecule to protect the molecule from degradation (e.g., by a protease). Suitable stability sequences include, but are not limited to, glycine molecules incorporated after the initiation methionine (e.g., MG or MGG) to protect the fusion molecule from ubiquitination; two prolines incorporated at the C-terminus (conferring protection against carboxypeptidase action), and the like.

In some aspects, the fusion molecule can include a linking or tethering sequence between insertion and acceptor sequences or between insertion or acceptor sequences and other domain sequences. For example, useful linkers include glycine polymers, glycine-serine polymers, glycine-alanine polymers, alanine-serine polymers, alanine polymers, and other flexible linkers as are known in the art (see, e.g., Huston, et al., 1988, *Proc. Natl. Acad. Sci. USA* 85: 4879; U.S. Pat. No. 5,091,513).

These additional sequences can be included to optimize the properties of the fusion molecules described herein.

Exemplary Fusion Molecules

Exemplary fusion molecules according to the invention are described herein and illustrated schematically in FIGS. 5A-G. Methods of using these fusion molecules as molecular switches in cells are further described infra. It should be apparent to those of skill in the art that these are merely examples of combinations of insertion and acceptor sequences that can be used to form a molecular switch, and are not intended to be limiting.

Figure 5A:
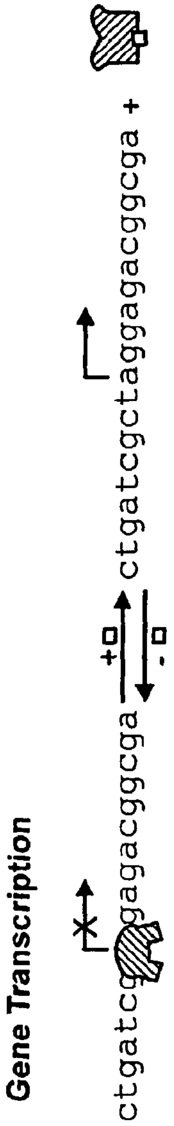
FIGS. 5A-G are schematic diagrams depicting several applications of the molecular switches of the invention (oliqonucleotide disclosed as SEQ ID NO: 98).

In one aspect, the invention provides a fusion protein comprising an insertion sequence and an acceptor sequence, wherein either the inserted sequence or the acceptor sequence binds to a DNA molecule, and wherein DNA binding activity is coupled to the response of the respective other sequence of the fusion molecule to a signal. (FIG. 5A.)

Figure 5B:
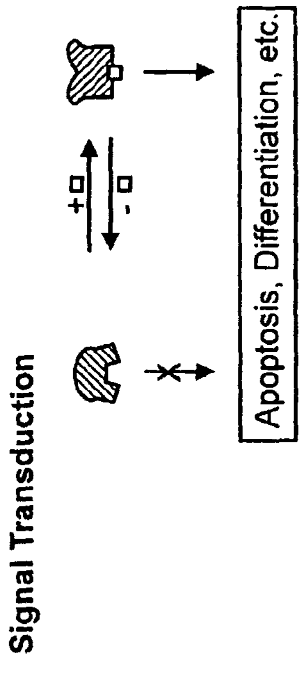

In a further aspect, the fusion molecule comprises a molecular switch for controlling a cellular pathway. The fusion molecule comprises an insertion sequence and an acceptor sequence and the states of the insertion sequence and acceptor sequence are coupled, such that the state of either the insertion sequence or the acceptor sequence modulates the activity or expression of a molecular pathway molecule in a cell. Preferably, modulation of activity or expression occurs when the respective other portion of the fusion molecule responds to a signal, e.g., binds to an exogenous or endogenous binding molecule (e.g., ligands, small molecules, ions, metabolites, and the like), responds to electrical or chemical properties of a cell, or responds to the optical environment in which a cell is found (e.g., responding to the presence or absence of a particular wavelength(s) of light) (FIG. 5B).

Figure 5C:
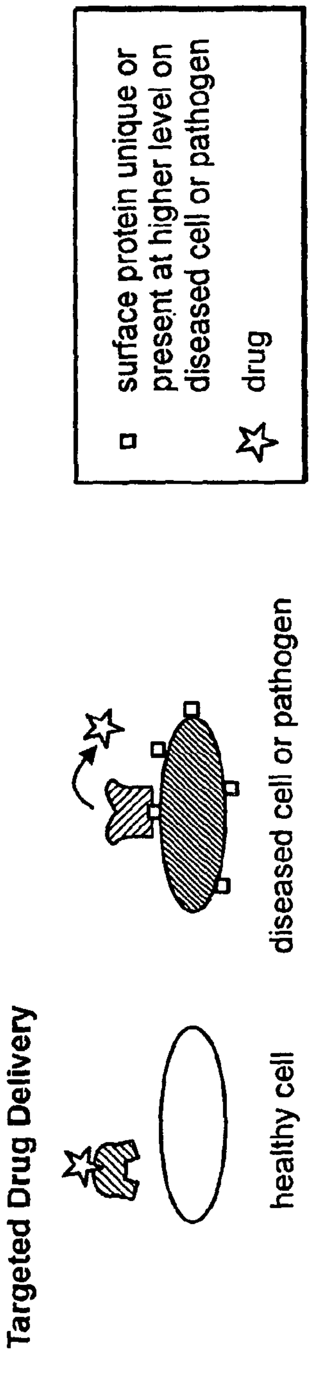

The fusion molecule also can comprise an insertion sequence and acceptor sequence, wherein either the inserted sequence or the acceptor sequence associates with a bio-effective molecule, and disassociates from the bio-effective molecule, when the respective other sequence of the fusion binds to a cellular marker of a pathological condition (FIG. 5C). Such markers can comprise polypeptides, nucleic acids, glycoproteins, lipids, carbohydrates, small molecules, metabolites, pH, ions and the like. Examples of cellular markers of pathological conditions include, but are not limited to cancer-specific or tumor-specific antigens, pathogen-encoded polypeptides (e.g., viral-, bacterial-, protist-, and parasite-encoded polypeptides) as are known in the art.

In another aspect, the insertion sequence or the acceptor sequence localizes the fusion molecule intracellularly. Preferably, intracellular localization is coupled to the binding of the fusion molecule to a bio-effective molecule (FIG. 5D).

In still another aspect, the fusion molecule is capable of switching from a non-toxic state to a toxic state. Either the insertion sequence or acceptor sequence may bind to a cellular marker of a pathology (e.g., such as a tumor antigen). Binding of the marker to the fusion protein switches the fusion protein from a non-toxic state or a less toxic state to a toxic state. Similarly, a marker of a healthy cell could be used as a trigger to switch a fusion molecule from a toxic state to a non-toxic state, or to a less toxic state (FIG. 5E).

In yet a further aspect, the fusion molecule can affect a metabolic state in a cell. Either the insertion sequence or the acceptor sequence may bind to an effector molecule. Binding of the effector molecule to the fusion protein triggers enzymatic activity by the enzyme. (See FIG. 5F and Examples, infra.)

Figures 5D, 5E, 5F, 5G:
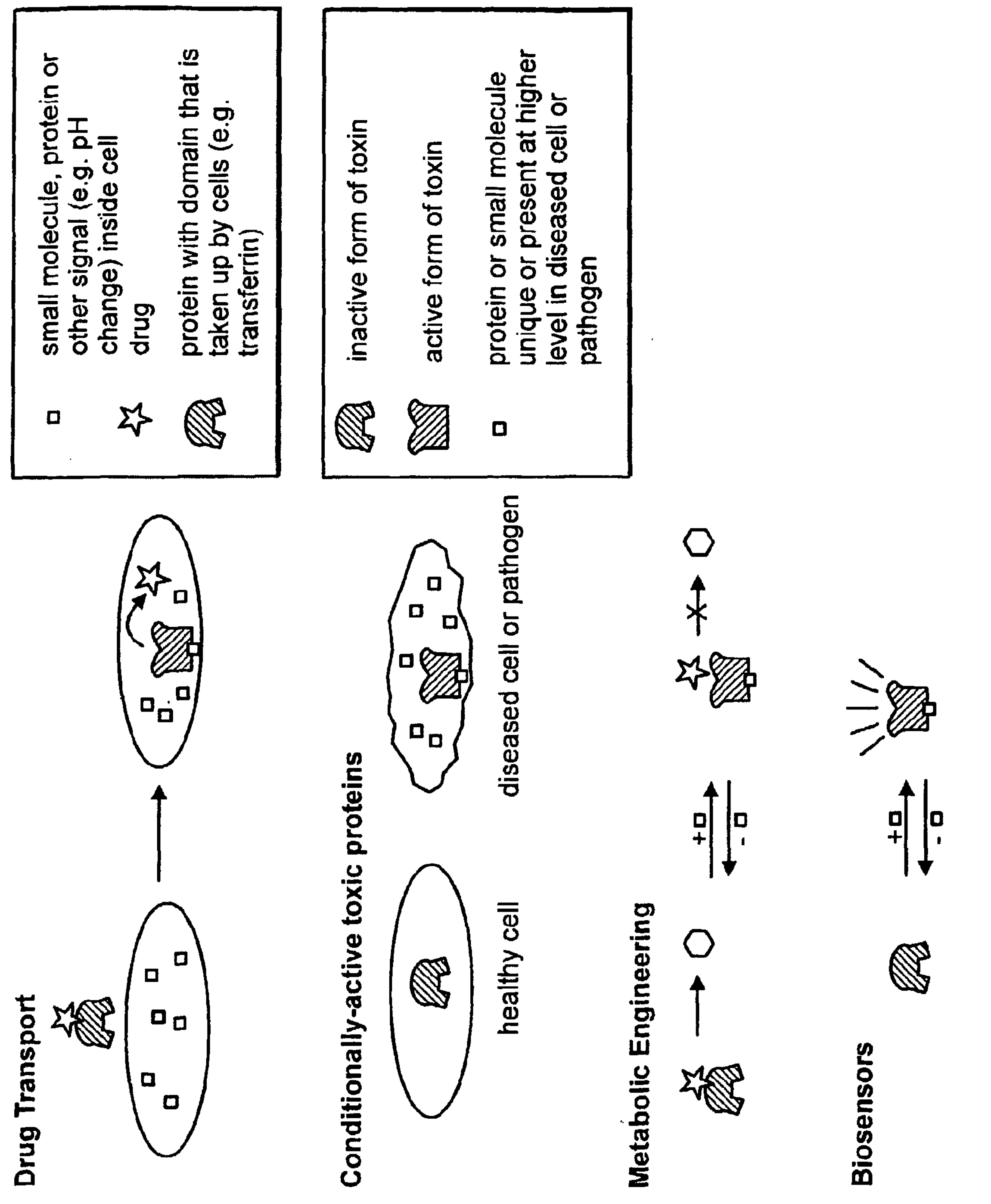

The invention also provides a sensor molecule comprising an insertion sequence and an acceptor sequence, wherein either the insertion sequence or the acceptor sequence binds to a target molecule and wherein the respective other sequence generates a signal in response to binding (FIG. 5G).

Methods of Using Molecular Switches

In one aspect, the invention provides a method for using a molecular switch to modulate a cellular activity. The cellular activity can include an enzyme activity, the activity of one or more cellular pathway molecules, the transduction of a signal, and the like. Modulation may direct, e.g., the switch itself may alter the activity, or indirect, e.g., the switch may function by delivering a bio-effective molecule to the cell which itself modulates the activity. Modulation can occur in vitro (e.g., in cell culture or in a cell extract) or in vivo (e.g., such as in a transgenic organism). Molecular switches comprising fusion polypeptides also can be administered to a cell by delivering such molecules systemically (e.g., through intravenous, intramuscular, or intraperitoneal injections, or through oral administration of either the polypeptides themselves or nucleic acids encoding the polypeptides) or locally (e.g., via injection into a tumor or into an open surgical field, or through a catheter or other medical access device, or via topical administration).

In one aspect, molecular switches are used to conditionally modulate an enzymatic activity in a cell. For example, a switch molecule can be introduced into a cell that comprises an insertion sequence or acceptor sequence which provides the enzymatic activity. Catalysis by the insertion or acceptor sequence is coupled to the response of the respective other portion of the fusion molecule to a signal, such as binding of the other portion to a molecule (e.g., such as an agent administered to the cell or a naturally occurring small molecule), exposure of the cell to particular chemical conditions (e.g., such as pH), electrical conditions (e.g., potential differences), optical conditions (e.g., exposure of the cell to light of specific wavelengths), magnetic conditions and the like.

In another aspect, a molecular switch is provided which modulates the activity or expression of a molecular pathway molecule in a cell. FIG. 5B shows an example of a switch molecule comprising a pathway molecule which is conditionally active in the presence of a signal (schematically illustrated as "□" in the Figure). The switch molecule is used to alter a cell signaling pathway, e.g., altering the expression and/or activity of downstream pathway molecules (turning such molecules ON or OFF, or altering the level of expression and/or activity of such molecules). In doing so, the switch molecule can be used to regulate the fate of one or more cells.

Similarly, the molecular switches according to the invention can be used to control metabolic pathways, e.g., providing a fusion molecule which provides an enzymatic activity coupled to the binding of a small molecule, or response to some other signal (as shown in FIG. 5F). Preferably, modulation of the enzyme activity in response to the signal, in turn, modulates the expression and/or activity of molecules downstream in the metabolic pathway.

More preferably, the states of the fusion molecules are coupled to a signal, such as the presence of an exogenous or endogenous binding molecules to which either the insertion sequence or acceptor sequence binds. The ability of the fusion molecule to control a pathway can be monitored by examining the expression and/or activity of pathway molecules which act downstream of a pathway molecule whose expression and/or activity is being modulated/controlled by the fusion molecule. Preferably, control of the pathway is coupled to the presence of the signal, e.g., binding of the fusion molecule to the exogenous or endogenous binding molecule, the presence of particular electrical or chemical properties of a cell, the presence or absence of particular wavelength(s) of light, and the like.

Pathways of interest include the phosphatidylinositol-specific phospholipase pathway, which is normally involved with hydrolysis of phosphatidylinositol-4,5-bisphosphate and which results in production of the secondary messengers inositol-1,4,5-trisphosphate and diacylglycerol. Other pathways include, but are not limited to: a kinase pathway, a pathway involving a G protein coupled receptor, a glucerebrosidase-mediated pathway, a cylin pathway, an anaerobic or aerobic metabolic pathway, a blood clotting pathway, and the like.

In still another aspect, a fusion molecule is provided which delivers a bio-effective molecule (e.g., a drug, therapeutic agent, diagnostic or imaging agent, and the like) to a cell. In one scenario, shown in FIG. 5C, the fusion molecule comprises an insertion or acceptor sequence which binds to the bio-effective molecule, while the respective other portion of the fusion binds to a cellular marker that is a signature of a pathology, e.g., a small molecule, polypeptide, nucleic acid, metabolite, whose expression (presence or level) is associated with the pathology. Preferably, the fusion molecule releases the bio-effective molecule only in the presence of the marker of the pathology.

FIG. 5D shows an alternative method of transporting a bio-effective molecule. In this aspect, the insertion sequence or acceptor sequence comprises a transport sequence for transporting a bio-effective molecule bound to the fusion molecule intracellularly. Preferably, the insertion sequence and acceptor sequence are functionally coupled such that a conformational change in the transport sequence is coupled to intracellular release of the bio-effective agent. Successful delivery can be monitored by measuring the effect of the bio-effective agent (e.g., its ability to mediate a drug action or therapeutic effect, or to image a cell). More preferably, the conformation change occurs upon response of the respective other portion of the fusion to a signal (indicated schematically in the Figure as "□"), enabling conditional intracellular transport of the bio-effective molecule. When the bio-effective agent is delivered to one or more cells in an organism, the effect of the agent on the physiological responses of the organism can be monitored, e.g., by observing clinical or therapeutic endpoints as is routine in the art. Where the bio-effective molecule is an imaging molecule, the localization of the bio-effective molecule in the organism can be monitored by MRI, X-ray, angiography, and the like.

In still another aspect, the invention provides a method for killing undesired cells, such as abnormally proliferating cells, e.g., cancer cells (FIG. 5E). For example, a fusion protein comprising a conditionally toxic molecule which targets to a cell having a pathology can be administered to a cell (or an organism comprising the cell). Preferably, the toxic state of the fusion protein is coupled to the response of the fusion protein to a signal, such as exposure to a marker of a pathology, causing the fusion protein to switch from a non-toxic state to a toxic state when it encounters the cell comprising the pathology. In one aspect, the change in state from a toxic to a non-toxic or less toxic molecule is coupled to binding of the fusion protein to the marker of the pathology.

In a further aspect, a fusion molecule is provided for regulating an activity of a nucleic acid regulatory sequence in vitro or in vivo. Activities which can be regulated include transcription, translation, replication, recombination, supercoiling, and the like (FIG. 5A). Preferably, fusion molecules are selected in which binding of the insertion sequence or acceptor sequence of the fusion molecule to the nucleic acid regulatory sequence is coupled to the response of the respective other sequence of the fusion molecule to a signal. Such fusion molecules can be used to create cells with conditional knockouts or knock-ins of a gene product whose expression is mediated by the activity of the nucleic acid regulatory sequence to which the fusion molecule binds, e.g., by providing or withdrawing the signal as appropriate. In one aspect, the signal is a drug or therapeutic agent. In another aspect, the signal is a change in pH, a change in cellular potential, or a change in exposure of a cell (and/or organism) to light. For example, a probe for delivering particular wavelengths of light can be used to provide a highly localized signal to a cell expressing a fusion molecule in vivo.

In still a further aspect, the fusion molecules according to the invention comprise sensor molecules that can be used to detect target analytes in vitro or in vivo (FIG. 5G). Target analytes include, but are not limited to: small molecules, metabolites, lipids, glycoproteins, carbohydrates, amino acids, peptides, polypeptides, proteins, antigens, nucleotides, nucleic acids, cells, cell organelles, and small organisms (e.g., microorganisms such as bacteria, yeast, protests, and the like).

The fusion molecule can be exposed to a target molecule in solution or stably associated with a solid support that can be exposed to a sample suspected of containing the target molecule. Alternatively, the fusion molecule can be expressed in a cell, i.e., for detecting intracellular or extracellular targets (for example, where the fusion molecule comprises an extracellular binding domain). Analyte present in the sample will bind to the fusion molecule, triggering production of a signal by the signaling portion of the molecule. Suitable signaling molecules from which this portion can be obtained include molecules capable of emitting light, e.g., such as GFP, or modified, or mutant forms thereof (e.g., EGFP, YFP, CFP, EYFP, ECFP, BFP, and the like). Other signaling molecules include electron transferring domains (e.g., such that the electrical characteristics of the fusion molecule can be monitored to provide a measure of target analyte), binding domains (e.g., domains capable of binding to a labeled molecule), and catalytic domains (e.g., β-lactamase, luciferase, alkaline phosphatase, and the like).

Signaling molecules which comprise catalytic domains can be detected by monitoring changes in the level of a fluorescent substrate. For example, when the catalytic domain is obtained from β-lactamase, fluorescent substrates such as CCF2/FA and CCF2/AM can be used (see, e.g., Zlokarnik, et al., *Science* 279: 84-88 (1998)).

In a further aspect, the invention provides a method for modulating a cellular response by conditionally providing a pair of fusion polypeptides to a cell to mediate the response. For example, the pair of fusion polypeptides can comprise a binding activity, an enzymatic activity, a signaling activity, a metabolic activity, and the like. In one aspect, the pair of fusion polypeptides modulate transcription, translation, or replication of the cell and/or alters a cellular phenotype in response to a signal

Host Cells For Expressing Fusion Molecules

Fusion molecules according to the invention can be expressed in a variety of host cells, including, but not limited to: prokaryotic cells (e.g., *E. coli, Staphylococcus* sp., *Bacillus* sp.); yeast cells (e.g., *Saccharomyces* sp.); insect cells; nematode cells; plant cells; amphibian cells (e.g., *Xenopus*); fish cells (e.g., zebrafish cells); avian cells; and mammalian cells (e.g., human cells, mouse cells, mammalian cell lines, primary cultured mammalian cells, such as from dissected tissues).

The molecules can be expressed in host cells isolated from an organism, host cells which are part of an organism, or host cells which are introduced into an organism. In one aspect, fusion molecules are expressed in host cells in vitro, e.g., in culture. In another aspect, fusion molecules are expressed in a transgenic organism (e.g., a transgenic mouse, rat, rabbit, pig, primate, etc.) that comprises somatic and/or germline cells comprising nucleic acids encoding the fusion molecules.

Fusion molecule also can be introduced into cells in vitro, and the cells (e.g., such as stem cells, hematopoietic cells, lymphocytes, and the like) can be introduced into the host organism. The cells may be heterologous or autologous with respect to the host organism. For example, cells can be obtained from the host organism, fusion molecules introduced into the cells in vitro, and then reintroduced into the host organism.

EXAMPLES

The invention will now be further illustrated with reference to the following examples. It will be appreciated that what follows is by way of example only and that modifications to detail may be made while still falling within the scope of the invention.

Example 1

Generating Fusion Molecules by Circular Permutation and Domain Insertion

This example describes a model system combining *E. coli* maltose binding protein ("MBP") as the acceptor polypeptide sequence and the penicillin-hydrolyzing enzyme TEM1 β-lactamase ("BLA") as the insertion polypeptide sequence. The BLA-MBP fusion molecule was chosen to demonstrate the circular permutation domain insertion strategy for producing molecular switches capable of coupling the functions of the two proteins. The desired property of the model switch is the ability to modulate β-lactamase activity through changes in maltose concentration. FIG. 1 is a schematic summary diagram of the cloning steps used in this Example.

Linkers for Circular Permutation

In order to circularly permute a gene it is generally necessary to include DNA that codes for a linker to link the original N- and C-termini. We chose to test two different linkers. For the first (the "DKS linker"), □-lactamase was randomly circularly permuted by fusing the 5'- and 3'-ends with a DNA sequence coding for the tripeptide linker DKS, previously found in a combinatorial library of linkers to be most conducive for circularly permuting □-lactamase when the new N- and C-termini were located at a specific location (Osuna, Pérez-Blancas et al. 2002). For the second selected linker, (the "GSGGG linker" SEQ ID NO: 1), the □-lactamase was randomly circularly permuted by fusing the 5'- and 3'-ends with a DNA sequence coding for the flexible pentapeptide linker GSGGG (SEQ ID NO:1)

Preparation of BLA Insert DNA

The □-lactamase gene fragment bla [24-286] (encoding amino acids 24-286) was selected for this study. DNA coding for amino acids 1-23 was not desired because it codes for the signal sequence that targets β-lactamase to the periplasm and is not part of the mature, active β-lactamase. The fragment was amplified by PCR from pBR322 such that it was flanked by EarI or BamHI restriction enzyme site sequences coding for the linkers described above and cloned into pGem T-vector (Promega) to create pBLA-CP(DKS) (FIG. 2) and pBLA-CP(GSGGG), (FIG. 3) (linker disclosed as SEQ ID NO: 1).

One hundred and thirty micrograms of pBLA-CP (GSGGG) (linker disclosed as SEQ ID NO: 1) was digested with 2000 units of BamHI and 140 micrograms of pBLA-CP (DKS) was digested with 600 units of EarI in the buffers and conditions recommended by the manufacturer of the restriction enzyme. The fragment containing the BLA gene was purified by agarose gel electrophoresis using the QIAquick™ gel purification kit. This DNA was treated with T4 DNA ligase under dilute concentrations to cyclize the DNA (18 hours at 16° C. with 600 Weiss units of T4 DNA ligase in the presence of 50 mM Tris-HCl (pH 7.5), 10 mM $MgCl_2$, 10 mM dithiothreitol, 1 mM ATP, 25 ug/ml BSA in a total volume of 5.1 ml). The ligation reaction was stopped by incubation at 65° C. for 20 minutes. The DNA was concentrated by vacufuge and desalted using the QIAquick™ PCR purification kit. Circular fragments were purified by agarose gel electrophoresis using the QIAquick™ gel purification kit.

The conditions for DNaseI digestion were determined experimentally by adding different amounts of DNaseI and analyzing the digested products by agarose gel electrophoresis. The digestion conditions were chosen such that a significant fraction of DNA was undigested in order maximize the amount of linear DNA that only had one double strand break. In general, approximately 1 milliunit of DNaseI per microgram of DNA (at a concentration 10 micrograms/ml) for an 8 minute digestion at 22° C. was found to be optimal. Sometimes more or less DNaseI was required and thus preferably for each library constructed the correct amount of DNaseI is determined experimentally by test digestions. The following conditions are a representative example. Six micrograms of circular DNA was digested with 6 milliunits of DNase I (Roche) for 8 minutes at 22° C. in the presence of 50 mM Tris HCl (pH 7.4), 1 mM $MnCl_2$ and 50 micrograms/ml BSA in 0.6 ml reaction volume. The reaction was stopped by adding EDTA to a concentration of 5 mM. The DNA was desalted using the QIAquick™ PCR purification kit and repaired by 6 units of T4 DNA polymerase and 6 Weiss Units of T4 DNA ligase at 12° C. for 15 minutes in the presence of 100 micromolar dNTP, 50 mM Tris-HCl (pH 7.5), 10 mM $MgCl_2$, mM dithiothreitol, 1 mM ATP and 25 ug/ml BSA. The repaired, linear DNA was purified by agarose gel electrophoresis using the QIAquick gel purification kit. This circularly permuted DNA was in a form ready for insertion into another plasmid.

Preparation of Target DNA for Random Domain Insertion Libraries

Forty µg of pDIM-C8-Mal was digested with DNaseI (0.01 units) for 8 minutes at 22° C. in the presence of 50 mM Tris-HCl, pH 7.4, 10 mM $MnCl_2$ and 50 µg/ml BSA in a total volume of 1 ml. The reaction was quenched by the addition of EDTA to a concentration of 5 mM and the solution was desalted using four Qiaquick™ PCR purification columns into 200 µl elution buffer which was subsequently concentrated by vacufuge. Nicks and gaps were repaired by incubating at 12° C. for 1 hour in a total volume of 120 µl in the presence of T4 DNA polymerase (15 units) and T4 DNA ligase (12 Weiss units) in the presence of 50 mM Tris-HCl, pH 7.5, 10 mM $MgCl_2$, 10 mM DTT, 1 mM ATP, 25 µg/ml BSA and 125 µM dNTPs. The reaction was stopped by incubating at 80° C. for 10 minutes. Sodium chloride was added to 100 mM and the DNA was dephosphorylated by adding alkaline phosphatase (60 units) and incubating at 37° C. for 1 hour. The DNA was desalted as before and the linear DNA (corresponding to the randomly linearized pDIM-C8-Mal) was isolated from circular forms of the plasmid by agarose gel electrophoresis using the Qiaquick gel purification kit.

Preparation of Target DNA for Site-Specific Insertion Libraries

Referring to FIG. 4, plasmid pDIM-C8-Mal was modified using overlap extension (Horton, Hunt et al. 1989) to be suitable for insertion of the circularly permuted BLA at two specific sites: (a) between MBP [1-165] and MBP [164-370] and (b) at the C-terminus of MBP. The plasmids were modified in analogous ways. The modifications for insertion between MBP [1-165] and MBP [164-370] to create plasmid pDIMC8-MBP(164-165) are described below and shown in FIG. 4. Two inverted SapI sites were inserted between DNA coding for MBP [1-165] and MBP [164-370] in such a manner that digestion with SapI and subsequent filling in of the resulting overhangs using Klenow polymerase in the presence of dNTPs results in a perfectly blunt MBP [1-165] on one side and a perfectly blunt MBP [164-370] on the other side. This is achieved by virtue of the fact that SapI is a type IIS restriction enzyme that cuts outside of its recognition sequence. Other type IIS restriction enzymes could have been used. Non-type IIS restriction enzymes could also be used if it is acceptable to have their recognition site as part of the gene fragment that is being inserted into.

Three micrograms of pDIMC8-MBP(164-165) was digested with 6 units of SapI at 37° C. in the presence of 50 mM potassium acetate, 20 mM Tris-acetate, 10 mM magnesium acetate, 1 mM dithiothreitol (pH 7.9), 100 ug/ml BSA for 2.5 hours. The DNA was desalted using the QIAquick™ PCR purification kit and repaired with 5 units of Klenow at 25° C. for 20 minutes in the presence of 33 micromolar dNTPs, 100 mM NaCl, 50 mM Tris-HCl, 10 mM $MgCl_2$ and 1 mM dithiothreitol (pH 7.9). The enzyme was heat inactivated by incubation at 75° C. for 20 minutes. Sodium chloride was added to 100 mM and ten units of Calf Intestinal Phosphatase was added and the solution was incubated for 1 hour at 37° C. Dephosphorylation was performed to prevent recircularization of the vector without receiving an insert in the subsequent ligation step. The vector DNA was purified by agarose gel electrophoresis using the QIAquick™ gel purification kit.

Ligation of Inserts Into Target DNA

Insert DNA (85 ng) comprising the circularly permuted BLA was ligated to the prepared target DNA (100 ng) at 22° C. overnight in the presence of T4 DNA ligase (30 Weiss units) and the ligase buffer provided by the manufacturer in a total volume of 13 µl. After ethanol precipitation, 10% of the ligase-treated DNA was electroporated into 50 µl Electromax™ DH5α-E electrocompetent cells (Invitrogen, Carlsbad, Calif.). Transformed cells were plated on large (248 mm×248 mm) LB agar plate supplemented with 50 µg/ml chloramphenicol (Cm). The naïve domain insertion library was recovered from the large plate (Ostermeier, Nixon et al. 1999) and stored in frozen aliquots.

Screening for Allosteric Enzymes

The libraries were diluted from frozen aliquots and plated on LB plates containing different concentrations of ampicillin (Tables 1 and 2). A number of colonies were picked (Tables 3) and grown in LB overnight in 96 well plates (0.5 ml/well) in the presence of 1 mM IPTG and 50 µg/ml Cm.

TABLE 1

Library Statistics.

| Insertion site in MBP | Linker in BLA | Library size (Number of transformants with BLA insert). | Number of library members that can grow on 50 µg/ml AMP (see Table 2) | Number of colonies screened for switching (see Table 3) | Number of unique switches found with ≧2-fold effect* | Increase in velocity (of nitrocefin hydrolysis in presence of maltose) of best switch |
|---|---|---|---|---|---|---|
| 164-165 | DKS | $0.44 \times 10^6$ | 515 | 848 | 2 | +97% |
| | GSGGG | $1.05 \times 10^6$ | 361 | 1248 | 1 | −250% |
| C-terminus | DKS | $1.03 \times 10^6$ | 2414 | 576 | 0 | |
| | GSGGG | $0.30 \times 10^6$ | 1615 | 1920 | 1-4 | +234% |
| Random | DKS | $0.41 \times 10^6$ | 191 | 384 | 0 | |
| | GSGGG | $1.20 \times 10^6$ | 1156 | 3312 | 5 | +1650% |

i. *≧2-fold change in velocity of nitrocefin hydrolysis in the presence of 5 mM maltose.

(GSGGG linker discolsed as SEQ ID NO: 1

TABLE 2

| Number of Library Members Capable of Grow on Plates with Ampicillin (With or Without Maltose). | | | | | | | |
|---|---|---|---|---|---|---|---|
| Ampicillin (μg/ml) | Maltose? (5 mM) | T164-165 DKS | T164-165 GSGGG | EE DKS | EE GSGGG | Random DKS | Random GSGGG |
| 5 | no | 734 | 878 | 7052 | 3510 | nd | 2458 |
| 50 | no | 394 | 294 | 1747 | 1159 | nd | 783 |
| 200 | no | 220 | nd | 1080 | 298 | nd | nd |
| 1000 | no | nd | 74 | nd | nd | nd | 60 |
| 5 | yes | 1098 | 761 | 8354 | 4056 | nd | 1969 |
| 50 | yes | 515 | 361 | 2414 | 1615 | 191 | 1156 |
| 200 | yes | 182 | 240 | 1525 | 630 | nd | 272 |
| 1000 | yes | nd | 88 | nd | nd | nd | 34 |

(GSGGG linker disclosed as SEQ ID NO: 1)

TABLE 3

| Number of Library Members Screened (Picked from Plates with Indicated Ampicillin and Maltose Levels). | | | | | | | |
|---|---|---|---|---|---|---|---|
| Ampicillin (μg/ml) | Maltose? (5 mM) | T164-165 DKS | T164-165 GSGGG | EE DKS | EE GSGGG | Random DKS | Random GSGGG |
| 5 | no | — | 96 | — | 288 | — | 96 |
| 50 | no | — | — | — | — | — | — |
| 200 | no | — | — | — | — | — | 480 |
| 1000 | no | — | — | — | — | — | — |
| 5 | yes | 96 | 192 | — | 864 | — | 768 |
| 50 | yes | 672 | 576 | 576 | 768 | 384 | 960 |
| 200 | yes | 80 | 384 | — | — | — | 1008 |
| 1000 | yes | — | — | — | — | — | — |

EE = end-to-end (insertion at C-terminus)
(GSGGG linker disclosed as SEQ ID NO: 1)

Next, 50 μl of PopCulture (Novagen) and 2.5 unit of benzonase nuclease was added to each well and incubated for 15 minutes at room temperature to lyse the cells. The cells debris and any unlysed cells were pelleted by centrifugation and supernatant was recovered. In 96-well format, 60 μl of lysate was assayed for hydrolysis of nitrocefin (50 μM) by monitoring the increase in absorbance at 490 nm in 100 mM sodium phosphate buffer, pH 7.0, both with and without 5 mM maltose. Any lysate in which there was a difference in rate of more than 2-fold (between with and without maltose) was selected for retesting and further investigation.

Confirmation and Identification of Positives

Library members identified as having more than 200% switching activity in the 96-well plate screen were grown 24-48 hours in 100 ml LB media in 500 ml shaker flasks at 22° C. without IPTG. The cells were pelleted and resuspended in 8 ml assay buffer (100 mM sodium phosphate buffer, pH 7.0) and lysed by French press. The soluble fraction of this lysate was assayed for hydrolysis of nitrocefin (50 μM) at 22° C. as previously described (Guntas and Ostermeier 2004) both with and without 5 mM maltose. Initial rates were determined from absorbance at 486 nm monitored as a function of time. The enzyme was incubated at the assay temperature in the absence or presence of 5 mM maltose for four minutes prior to performing the assay. All assays contained 100 mM sodium phosphate buffer, pH 7.0. Library members for which there was a difference in the initial rate of more than about 2-fold were sequenced (Table 4). Switches RG-5-169 and RG-200-13 were also assayed in the presence of 5 mM sucrose or 5 mM glucose. Neither sugar affected the velocity of nitrocefin hydrolysis, indicating that the switching effect was specific for maltose, a ligand to which MBP binds.

TABLE 4

| Switching Effect of Selected BLA-MBP Molecular Switches. | | |
|---|---|---|
| Switch | Sequence | Switching effect* |
| IFG-5-277 | MBP[1-165]-BLA[218-286]-GSGGG-BLA[24-215]-MBP[164-370] | −250% |
| IFD-5-7 | MBP[1-165]-BLA[110-286]-DKS-BLA[24-107]-MBP[164-370] | +96% |
| IFD-5-15 | MBP[1-165]-BLA[168-286]-DKS-BLA[24-170]-MBP[164-370] | +97% |
| EEG-50-530 | MBP[1-370]-BLA[114-286]-GSGGG-BLA[24-112]-GSQQH | +228% |
| EEG-50-251 | MBP[1-370]-BLA[114-286]-GSGGG-BLA[24-114]-K | +234% |

TABLE 4-continued

| Switching Effect of Selected BLA-MBP Molecular Switches. | | |
|---|---|---|
| Switch | Sequence | Switching effect* |
| RG-5-169 | MBP[1-338]-BLA[34-286]-GSGGG-BLA[24-29]-MBP[337-370] | +855% |
| RG-200-13 | MBP[1-316]-BLA[227-286]-GSGGG-BLA[24-226]-S-MBP[319-370] | +1650% |

*Percent change in velocity of nitrocefin hydrolysis (50 μM nitrocefin) in the presence of 5 mM maltose in 100 mM sodium phosphate buffer, pH 7.0.
(GSGGG linker disclosed as SEQ ID NO: 1)

Analysis of Purified Switch RG-200-13

A 6×His tag (SEQ ID NO: 99) was added to the C-terminus of RG-200-13 (also termed "RG13" in Examples below) and the fusion was purified as previously described (Guntas and Ostermeier 2004). The protein was purified to approximately 60% purity. The kinetic constants and binding constants were determined from Eadie-Hofstee plots and Eadie plot equivalents, respectively, using a spectrophotometric assay for nitrocefin hydrolysis. Initial rates for nitrocefin hydrolysis were determined from absorbance at 486 nm monitored as a function of time. The enzyme was incubated at the assay temperature in the absence or presence of saccharide for four minutes prior to performing the assay. All assays contained 100 mM sodium phosphate buffer, pH 7.0. The dissociation constant for maltose was determined using change in velocity of nitrocefin hydrolysis as a signal.

Only sugars known to bind to MBP had an effect on nitrocefin hydrolysis (Table 5). Those sugars that produce a large conformational change upon binding MBP (Quiocho, Spurlino et al. 1997) (maltose and maltotriose) produced the largest change in the velocity of nitrocefin hydrolysis. Beta-cyclodextrin, which produces a small conformational change upon binding MBP (Evenas, Tugarinov et al. 2001), has a small effect. The effect of maltotetraitol is intermediate, consistent with the fact that maltotetraitol-binding to MBP results in a mixture of open and closed structures (Duan, Hall et al. 2001).

TABLE 5

| Sugar Dependence of Switching Effect of RG-200-13*. | | |
|---|---|---|
| Sugar | Binds to MBP? | Change in velocity of nitrocefin hydrolysis in presence of sugar |
| Sucrose | No | −5% |
| Lactose | No | −4% |
| Galactose | No | −3% |
| Maltose | Yes | +1800% |
| Maltotriose | Yes | +1700% |
| Maltotetraitol | Yes | +400% |
| β-cyclodextrin | Yes | +150% |

*50 μM nitrocefin, 100 mM sodium phosphate buffer, pH 7.0, 22° C., 5 mM sugar except for β-cyclodextrin (3 mM).

The kinetic parameters of RG-200-13 are reported in Table 6. The kinetic parameters of RG-200-13 at 22° C. in the presence of maltose ($k_{cat}$=~520 $s^{-1}$; $K_m$=~85 □M) are very similar to previously reported values for TEM-1 β-lactamase at 30° C. ($k_{cat}$=930 $s^{-1}$; $K_m$=52 μM) (Raquet, Lamotte-Brasseur et al. 1994) indicating that RG-200-13 is essentially a fully functional TEM-1 β-lactamase in the presence of maltose. The $k_{cat}/K_m$ in the presence of 5 mM maltose is approximately 25-fold higher than in the absence of maltose. The $K_d$ for maltose binding to RG-200-13 at 22° C. was ~5 μM, similar to the $K_d$ previously reported for maltose binding to MBP (1-1.5 μM) (Schwartz, Kellermann et al. 1976).

TABLE 6

| Kinetic Parameters of Nitrocefin Hydrolysis of RG-200-13 Molecular Switch. | | | | | | | |
|---|---|---|---|---|---|---|---|
| | $k_{cat}$ ($s^{-1}$) | | | $K_m$ (μM) | | | |
| Substrate | No maltose | 5 mM maltose | Ratio[a] | No maltose | 5 mM maltose | Ratio[a] | $k_{cat}/K_m$ Ratio[a] |
| nitrocefin | ~80 | ~520 | ~6.5 | ~325 | ~85 | ~0.26 | ~25 |

[a](with maltose)/(without maltose). Conditions: 100 mM sodium phosphate buffer, pH 7.0, 22° C.

The effect of 5 mM maltose on other substrates of BLA is shown in Table 7. Maltose binding had the largest effect on cephalothin (of the substrates tested), with the velocity of cephalothin hydrolysis being 32-fold higher in the presence of maltose than in its absence. Based on the effects on other substrates, the actual switching effect on $k_{cat}/K_m$ for cephalothin is likely to be much higher than 32-fold.

TABLE 7

| Effect of Maltose on Other Substrates of Switch RG-200-13. | | | |
|---|---|---|---|
| Substrate | Substrate concentration | $K_m$ for TEM-1 β-lactamase[a] | Approximate fold increase in velocity of nitrocefin hydrolysis in the presence of 5 mM maltose |
| cephalothin | 250 μM | 246 μM | 32 |
| ampicillin | 100 μM | 32 μM | 26 |
| | 500 μM | | 10 |
| benzylpenicillin | 100 μM | 19 μM | 17 |
| | 500 μM | | 7 |
| carbenicillin | 1 mM | ? | 4 |
| oxacillin | 1 mM | 3 μM | 5 |

Conditions: 100 mM sodium phosphate buffer, pH 7.0, 22° C.
[a](Raquet, Lamotte-Brasseur et al. 1994)

The fact that the magnitude of the switching effect of RG-200-13 is dependent on substrate identity and concentration strongly argues that maltose is converting the protein from a less active to a more active conformation. If an alternative explanation, i.e., that maltose affects the equilibrium between unfolded (inactive) and folded (active) forms of the protein were true, the observed switching effect would be independent of the substrate being tested and independent of substrate concentration, which was not the case.

Example 2

Construction and Characterization of a Molecular Switches Created by In Vitro Recombination of Non-Homologous Genes This example describes further studies of exemplary molecular switches comprising BLA-MBP fusions made by the methods of the invention.

Materials and Methods

All restriction enzymes, T4 DNA ligase, T4 DNA polymerase, and calf intestinal phosphatase were purchased from New England Biolabs (Beverly, Mass.). pGEM T-vector cloning kit and Taq polymerase were purchased from Promega (Madison, Wis.). DNAseI was purchased from Roche Biochemicals (Indianapolis, Ind.). Qiaquick™ PCR purification kit and Qiaquick gel extraction kit were purchased from Qiagen (Valencia, Calif.). Popculture reagent, rLysozyme, benzonase nuclease, and His-tag protein purification kit were purchased from Novagen (Madison, Wis.). Oligonucleotides and Electromax™ DH5α-E electrocompetent cells were purchased from Invitrogen (Carlsbad, Calif.). Nitrocefin was purchased from Oxoid (Hampshire, UK). Maltotriose and β-cyclodextrin were purchased from Sigma (St. Louis, Mo.). Antibiotics, maltose, lactose, galactose and sucrose were purchased from Fisher Scientific (Pittsburgh, Pa.).

Random Circular Permutation

The portion of the bla gene encoding the mature BLA was fused to a sequence coding for a GSGGG linker (SEQ ID NO: 1) and containing a BamHI site by PCR amplification using the forward primer:

(SEQ ID NO: 24)
5'-TGCCGGATCCGGCGGTGGCCACCCAGAAACGCTGGTG-3'
and the reverse primer
(SEQ ID NO: 25)
5'-GTCTGAGGATCCCCAATGCTTAATCAGTGA-3'.

Portions of the primers encoding the GSGGG linker (SEQ ID NO: 1) are underlined and the BamHI site is highlighted in bold. The PCR product was desalted using Qiaquick PCR purification kit and ligated to the pGEM T-vector to create plasmid pGEMT-BLA. One hundred and fifty □g of pGEMT-BLA was digested with 1000 units of BamHI and the DNA fragment that encodes BLA was gel purified using Qiaquick gel purification kit. Eighteen □g of this DNA was cyclized by ligation at 16° C. for 18 hours in a reaction volume of 5.1 ml in the presence of ligase buffer (50 mM Tris-HCl, 10 mM $MgCl_2$, 10 mM DTT, 1 mM ATP, 25 □g/ml BSA pH 7.5) and 600 Weiss units of T4 DNA ligase. After heat inactivation of the ligase, the concentrated reaction mixture was desalted and the circular DNA was purified by agarose gel electrophoresis using Qiaquick Gel Extraction kit.

To introduce the random double stranded break, 8 μg of circular DNA was digested with 8 milliunits of DNAse I in the presence of 50 mM Tris-HCl, pH 7.4, 10 mM $MnCl_2$ and 50 μg/ml BSA in a total volume of 0.8 ml for 8 minutes. The reaction was quenched by the addition of EDTA to a concentration of 5 mM and the solution was desalted using a Qiaquick PCR purification column. Nicks and gaps were repaired by incubating at 12° C. for 30 minutes in a total volume of 90 μl in the presence of T4 DNA polymerase (6 units) and T4 DNA ligase (12 Weiss units) in the presence of 50 mM Tris-HCl, pH 7.5, 10 mM $MgCl_2$, 10 mM DTT, 1 mM ATP, 25 μg/ml BSA and 125 μM dNTPs. The DNA was desalted as before and the linear DNA (corresponding to the randomly circularly permuted bla) was isolated from circular forms by agarose gel electrophoresis using the Qiaquick gel purification kit.

Random Domain Insertion

Plasmid pDIM-C8MalE has the malE gene encoding MBP under the IPTG inducible tac promoter. Introduction of a random double stranded breaks (one per molecule of pDIM-C8MalE) was performed as described (Spencer et al. 1993). One hundred ng of randomly linearized plasmid pDIMC8-MalE was ligated to 85 ng of randomly circularly permuted BLA fragment (5:1 insert/vector molar ratio) in a reaction volume of 15 μl. The ligation was carried out at 22° C. overnight in the presence of ligase buffer and 45 Weiss units T4 DNA ligase. After ethanol precipitation, the ligated DNA was transformed into Electromax DH5α-E electrocompetent cells by performing ten electroporations of 40 μl cells each. Cells were plated on two 245×245 mm LB agar plates supplemented with 50 μg/ml chloramphenicol and incubated at 37° C. overnight. The naïve library was recovered from the large plates and stored in frozen aliquots as described (Picard 2000).

Library Selection and Screening

The naïve library was plated on LB agar plates supplemented with 200 μg/ml ampicillin and 50 mM maltose and incubated at 37° C. overnight. From these plates, 1056 colonies were picked to inoculate 1 ml LB media (supplemented with 50 μg/ml chloramphenicol and 1 mM IPTG) in 96-well format. After incubation overnight at 37° C., each culture was lysed using 0.1 ml Popculture reagent, 40 units of rLysozyme, and 2.5 units of benzonase nuclease. Lysates were centrifuged to pellet the insoluble material and the soluble fractions were assayed in 96-well format for nitrocefin hydrolysis in the presence or absence of 5 mM maltose using a colorimetric assay for nitrocefin hydrolysis (Posey et al. 2002). The assays were carried out at room temperature using the Spectramax-384 Plus microplate reader (Molecular Devices) in the presence of 100 mM sodium phosphate buffer and 50 μM nitrocefin in a 200 μl reaction volume. Clones whose lysates exhibited a greater than 2-fold increase in the rate of nitrocefin hydrolysis were recultured and their lysates assayed again to verify the effect.

Protein Modifications and Mutagenesis

A $GGSGH_9$ sequence (SEQ ID NO: 77) was appended to the sequence of RG13 by PCR amplification with the appropriate primers. The PCR product was cloned between NdeI and XhoI sites of pET24b (Novagen) to create pET24b-RG13. Mutations 1329W and A96W were introduced into pET24b-RG13 by a combination of overlap extension PCR and Quickchange mutagenesis.

Protein Purification

One liter LB media containing 50 μg/ml kanamycin was inoculated with 2% overnight culture and shaken at 37° C. The culture was induced with 1 mM IPTG when the $OD_{600}$ reached 0.5 and incubated at 22° C. for 16 hours. Pelleted cells were resuspended in 20 ml binding buffer supplied by the His-tag protein purification kit (Novagen, Madison, Wis.) and lysed by French press. The soluble fraction was recovered and the protein was purified using the protein purification kit. Eluted protein was dialyzed at 4° C. against three liters of 100 mM sodium chloride, 50 mM sodium phosphate buffer overnight followed by dialysis against one liter of the same buffer with 20% glycerol for four hours. Protein was stored in aliquots at −80° C. Fusion proteins RG13 and RG13(1329W) were purified as described above. To improve the yield of RG13(A96W/1329W), 10 mM maltose was added to the culture at induction. RG13(A96W/1329W) was dialyzed more extensively after purification and complete removal of maltose was verified by enzymatic assay on successive rounds of dialysis in the presence and absence of maltose. The purities of the proteins were estimated by Coomassie blue staining of SDS-PAGE gels. The purities of RG13, RG13 (1329W), and RG13(A96W/1329W) were greater than 98%, 95% and 97%, respectively. The extinction coefficients of RG13, RG13(1329W), and RG13(A96W/1329W) at 280 nm were calculated (Saghatelian et al. 2003) to be 126,000; 120, 500 and 116,100 Abs $M^{-1}$ $cm^{-1}$, respectively.

Steady State Kinetics

All kinetic assays were performed at 25° C. in the presence of 100 mM sodium phosphate buffer, pH 7.0. Ten µl of enzyme stock was added to 1.59 ml buffer (containing the saccharide, if desired). After incubation for 30 seconds, 0.4 ml of 5× substrate was added and the absorbance at the appropriate wavelength was recorded using the Cary50 UV-VIS spectrophotometer. The wavelength monitored was 486 nm, 240 nm, and 232 nm for nitrocefin, carbenicillin, and ampicillin respectively. From the initial rate of reaction the kinetic constants were determined using Eadie-Hofstee plots. In the absence of maltose, the time course of the reaction for RG13, RG13(1329W), and RG13(A96W/1329W) displayed a slight lag in the reaction rate that became more pronounced at higher substrate concentrations. The rate data was consistent with a small hysteretic effect (Brennan et al. 1994) and not substrate inhibition as preincubation of the enzyme with the substrate for one minute prevented the lag from occurring upon addition of more substrate. Therefore, the steady state parameters for nitrocefin hydrolysis in the absence of maltose were determined by measuring the rate at 1-2 minutes (well after the lag) and correcting the substrate concentration by subtracting the amount of substrate hydrolyzed. In all cases the extent of reaction at the point the rate was measured was less than 25%. In the presence of maltose, no lag was observed.

Maltose Affinity

Maltose affinity for RG13 (in presence and absence of 10 mM carbenicillin) and RG13(1329W) (in the absence of substrate) was determined using intrinsic protein fluorescence measured on a Photon Technology QuantaMaster QM-4 spectrofluorometer. Fluorescence spectra were obtained at 25° C. at different concentrations of maltose in 50 mM sodium phosphate buffer, pH 7.0, containing 100 mM sodium chloride. The protein concentration was 50-100 nM. Excitation was at 280 nm. The quenching in fluorescence intensity at 341 nm caused by maltose was used in Eadie-Hofstee equivalent plots to determine $K_d$ using the following equation:

$$\Delta F = \Delta F_{max} - K_d \frac{\Delta F}{[L]}$$

where ΔF is the change in fluorescence intensity, $\Delta F_{max}$ is the difference in fluorescence between no maltose and saturating amounts of maltose and [L] is the maltose concentration. The fluorescence quenching of RG13(I329W/A96W) upon addition of maltose was insufficient to accurately determine a $K_d$ by this method. The dissociation constant for maltose and RG13(I329W) in the presence of saturating carbenicillin (2 mM) was determined by measuring the initial rate of carbenicillin hydrolysis as a function of maltose concentration. The apparent dissociation constant in the presence of subsaturating concentrations of nitrocefin (25 µM) for all three proteins was determined by measuring the initial rate of nitrocefin hydrolysis as a function of maltose concentration.

In Vivo Characterization of Switches

Overnight inoculums of DH5α-E cells expressing RG13, BLA or BLA(W208G) were diluted into LB media and plated on LB plates, either in the absence or presence of 50 µM maltose, in the presence of increasing amounts of ampicillin. Ampicillin was present in the plates at the following concentrations: 0, 2, 4, 8, 16, 32, 64, 128, 256, 512, and 2000 µg/ml. Cells were plated at approximately 1000 CFU (no antibiotic) per plate. The plates were incubated at 37° C. for 20 hours. The minimum inhibitory concentration (MIC) was defined as the lowest ampicillin concentration at which no colonies were present, or that at which the number of colonies present was <1% of the number of colonies at the next lowest level of ampicillin.

Characterization of BLA-MBP Molecular Switches

As discussed, the approach to construction of a model molecular switch involved recombination of the genes encoding TEM-1 β-lactamase (BLA) and the *E. coli* maltose binding protein (MBP). BLA and MBP lack any sequence, structural or functional relationship except for the fact that they are periplasmic proteins of bacterial origin. BLA is a monomeric enzyme that hydrolyzes the amide bond of the β-lactam ring of β-lactam antibiotics. The presence of maltose has no effect on wild type BLA enzymatic activity, with or without the presence of an equimolar amount of MBP (Guntas et al. 2004). MBP is a member of the periplasmic binding protein superfamily and is involved in chemotactic response and the transport of maltodextrins. MBP consists of a single polypeptide chain that folds into two domains connected by a hinge region. The single binding site for maltose is at the interface of these two domains. In the absence of maltose, MBP exists in an open form. Maltose-binding is concomitant with a 35° bending motion about the hinge resulting in the closed form of the protein (Sharff et al. 1992).

We sought to create a molecular switch by combining BLA and MBP in such a manner that the rate of β-lactam hydrolysis was coupled to maltose binding and maltose concentration. We reasoned that in such a switch the conformational change in the MBP domain upon maltose binding would propagate to the active site of the BLA domain and alter its catalytic properties, a mechanism analogous to natural allosteric effects.

The fragment of the BLA gene coding for the mature protein was circularly permuted in a random fashion (Graf et al. 1996; Ostermeier et al. 2001) and subsequently randomly inserted into a plasmid containing the *E. coli* malE gene that codes for MBP. FIG. 6A is a schematic diagram showing the strategy used to make the molecular switch. More particularly, FIG. 6A shows that the fragment of the BLA gene coding for the mature protein (codons 24-286) is flanked by sequences coding for a GSGGG linker (SEQ ID NO: 1) (each of which contains a BamHI site). The fragment is excised by digestion with BamHI and cyclized by ligation under dilute DNA concentrations. A single, randomly-located double strand break is introduced by DNaseI digestion to create the circularly permuted library. This library is randomly inserted into plasmid pDIMC8-MBP containing the MBP gene (malE) under control of the tac promoter (tacP/O). The site for insertion in pDIMC8-MBP is created by introduction of a randomly located double-stranded break by digestion with dilute concentrations of DNaseI.

For the random circular permutation of bla [24-286], we fused the 5' and 3' ends by an oligonucleotide sequence that would result in a GSGGG flexible peptide linker (SEQ ID NO: 1) between the original N- and C-termini of the protein. This linker was designed to be of sufficient length to connect the termini without perturbing BLA structure.

Statistical analysis on the resulting library indicated that a minimum of 27,000 members contained a circularly permuted bla[24-286] inserted into malE in the correct orientation with both fusion points in-frame with malE. Approximately 0.33% of these members were able to form colonies on rich media plates containing 200 μg/ml ampicillin and 50 mM maltose. These library members were screened in 96-well format for a maltose dependence on β-lactamase activity using a colorimetric assay for nitrocefin hydrolysis.

We identified one protein (RG13; FIG. 6B) in which the initial velocity of nitrocefin hydrolysis (at 50 μM nitrocefin) increased by 17-fold in the presence of maltose. FIG. 6B is a schematic illustration of the sequence of the RG13 switch. The numbers in parentheses indicate the amino acid number of the starting proteins. The numbering system for MBP does not include the signal sequence. The numbering system for BLA does include the signal sequence and does not follow the consensus numbering system for β-lactamases.

Figure 6C:
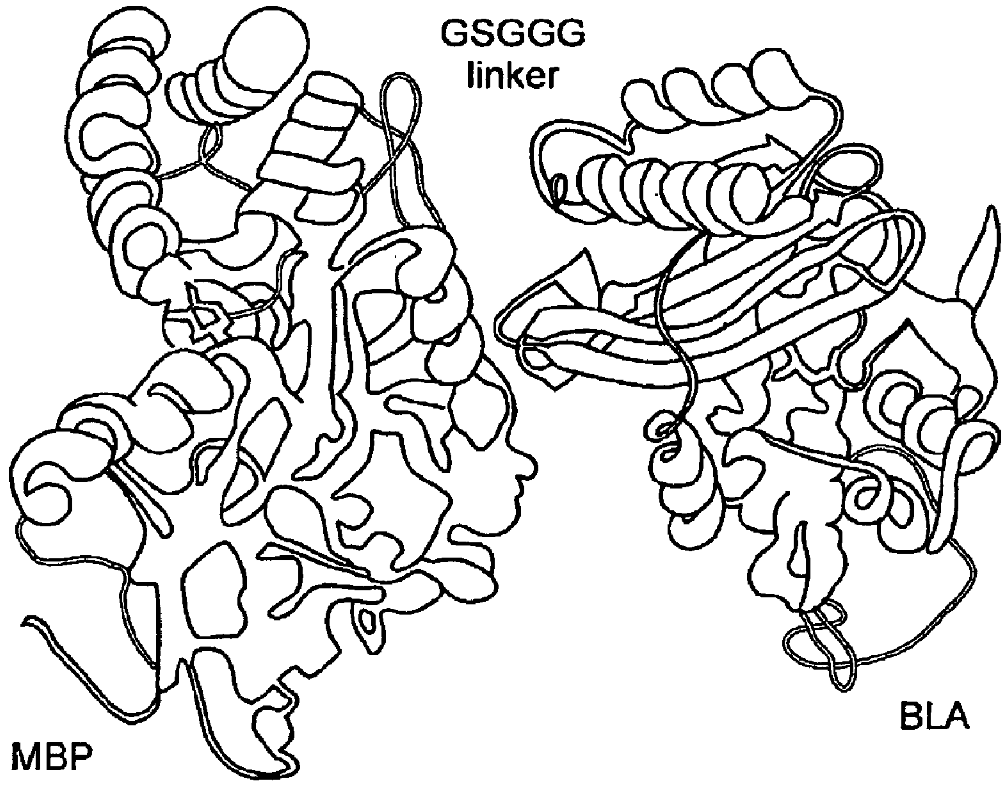

Referring to FIG. 6C, it was determined that in RG13, the BLA was circularly permuted in a loop that precedes a β-sheet that lines the active site of the enzyme. The circular permuted BLA was inserted at the beginning of an α-helix of MBP such that two MBP residues were deleted. More particularly, FIG. 6C shows structures of maltose-bound MBP (Quicho et al. 1997) and BLA bound to an active-site inhibitor (Maveyraud et al. 1996) oriented such that the fusion sites in RG13 are proximal.

Figure 7A:
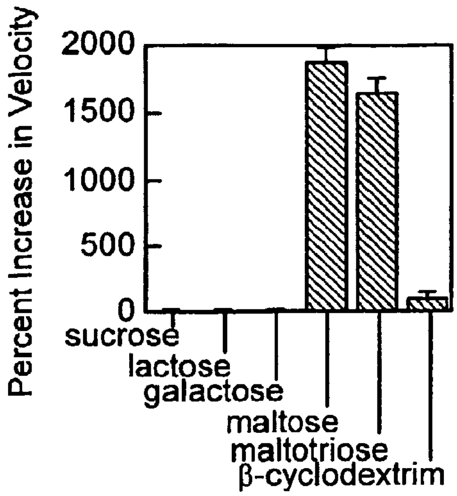
FIGS. 7A-C are three graphs demonstrating characteristics of switch activity of RG13, a model molecular switch of the invention.

Using purified RG13, we confirmed that the increase in catalytic activity occurred only in the presence of sugars that are known to bind and induce a conformational change in MBP (FIG. 7). FIG. 7A shows the percent increase in the initial velocity of nitrocefin hydrolysis at 20 μM nitrocefin upon addition 5 mM of the indicated ligands (maltose, maltotriose and β-cyclodextrin) and non-ligands (sucrose, lactose and galactose). It is seen that sugars known to induce a large conformational change (Quicho et al. 1997) (i.e., maltose and maltotriose; 35° closure angle) produced a 15- to 20-fold increase in the rate of nitrocefin hydrolysis. β-cyclodextrin, which only induces a 10° hinge bending motion in MBP (Evenas et al. 2001), increased the rate 2-fold. Non-ligands such as sucrose, lactose and galactose had no effect.

Figure 7B:
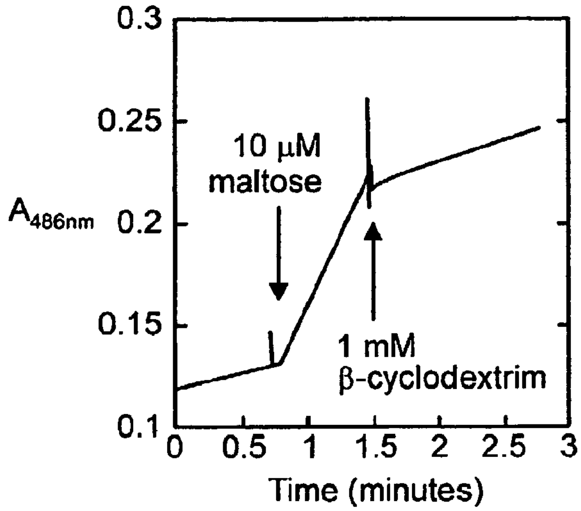

We next determined that the switching was reversible (i.e., upon removing maltose, the activity returned to its pre-maltose level). This was first demonstrated by competing bound maltose off RG13 using β-cyclodextrin (FIG. 7B). FIG. 7B shows reversible switching using the competing ligand. During the enzymatic hydrolysis of nitrocefin, formation of product was monitored by absorbance at 486 nm. At time zero the reaction was started in 2 ml phosphate buffer (0.1 M) with 20 μM nitrocefin and 2.5 nM RG13. At the time indicated by the first arrow, 20 μl of 1 M maltose was added resulting in a 10-fold increase in the reaction rate. This maltose concentration is above the $K_d$ for maltose but is subsaturating. At the time indicated by the second arrow, 230 μl of 10 mM β-cyclodextrin was added (final concentrations are 1.0 mM β-cyclodextrin and 8.9 μM maltose). Because RG13 has similar affinities for maltose and β-cyclodextrin but β-cyclodextrin is present at a >100-fold higher concentration, the β-cyclodextrin preferentially replaces the maltose bound to RG13 and the rate of reaction decreases to a level consistent with β-cyclodextrin's modest effect on nitrocefin hydrolysis.

Figure 7C:
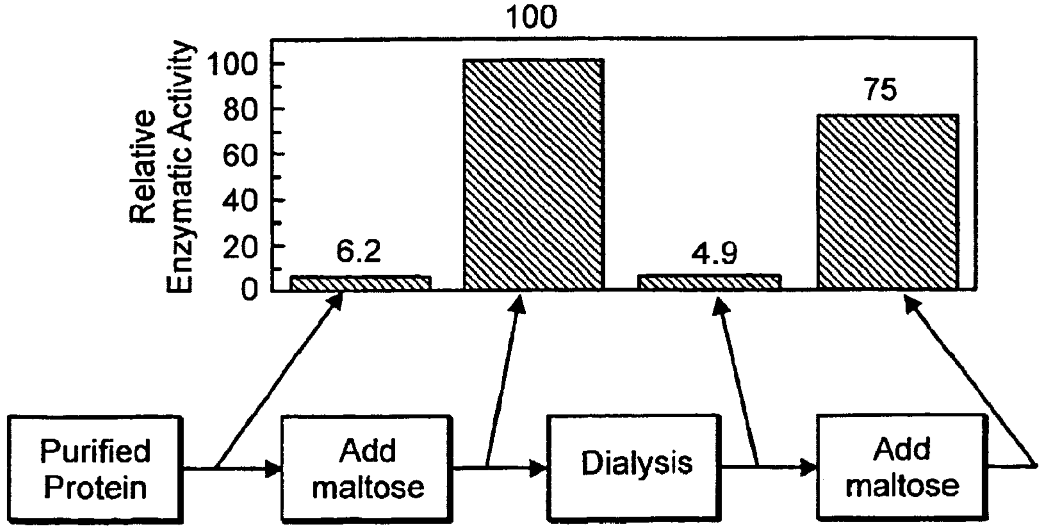

Reversibility of the switch was also demonstrated by subjecting RG13 to repeated rounds of dialysis and addition of maltose to cycle between low and high levels of enzymatic activity. FIG. 7C shows reversible switching after dialysis. The initial rate of nitrocefin hydrolysis at 25 μM nitrocefin was measured at the indicated steps. Maltose was added to a final concentration of 5 mM.

This demonstrated reversibility is one of the features that differentiates our approach from methods such as conditional protein splicing (Mootz et al. 2002; Buskirk et al. 2004) that produce non-reversible switches that control the production of active protein rather than activity of the protein per se.

From steady state kinetics experiments, we determined the Michaelis-Menten parameters of RG13 for nitrocefin hydrolysis at 25° C. in the absence and presence of maltose. In the absence of maltose, the catalytic constants were $k_{cat}$=200±40 $s^{-1}$ and $K_m$=550±120 μM. With the addition of saturating amounts of maltose, $k_{cat}$ increased 3-fold and $K_m$ decreased 8-fold, resulting in a 25-fold increase in $k_{cat}/K_m$. The kinetic constants of RG13 in the presence of saturating concentrations of maltose ($k_{cat}$=620±60 $s^{-1}$ and $K_m$=68±4 μM) were comparable to that previously reported for BLA at 24° C. ($k_{cat}$=900 $s^{-1}$ and $K_m$=110 μM (Sigal et al. 1984)). This finding shows that RG13 is a very active TEM1 β-lactamase in the presence of maltose. RG13 has exhibited switching behavior with all seven BLA substrate tested to date including ampicillin (16-fold rate increase at 50 μM ampicillin) and carbenicillin (12-fold rate increase at 50 μM carbenicillin).

The increase in $k_{cat}$ indicates that maltose binding affects the catalytic steps. However, since $K_m$ is a combination of the rate constants for substrate binding as well as catalysis (Christensen et al. 1990), $K_m$ could not be directly used to ascertain the effect of maltose on substrate binding. Instead, the effect of maltose on substrate binding was determined indirectly by measuring the effect of substrate on maltose binding using intrinsic protein fluorescence. These studies suggested that RG13 undergoes a conformational change much like MBP does upon maltodextrin binding, since maltose-induced quenching of total fluorescence (~10%) and shifting of the maximum fluorescence wavelength (i.e., a 1.5 nm red-shift for maltose and a 4 nm blue-shift for β-cyclodextrin) were similar to that previously reported for MBP (Hall et al. 1997). The presence of saturating amounts of the substrate carbenicillin decreased the dissociation constant of maltose and RG13 from 5.5±0.5 μM to 1.3±0.5 μM. Thus, maltose binding must decrease the dissociation constant of carbenicillin and RG13 by the same factor (FIG. 7).

Figure 8:
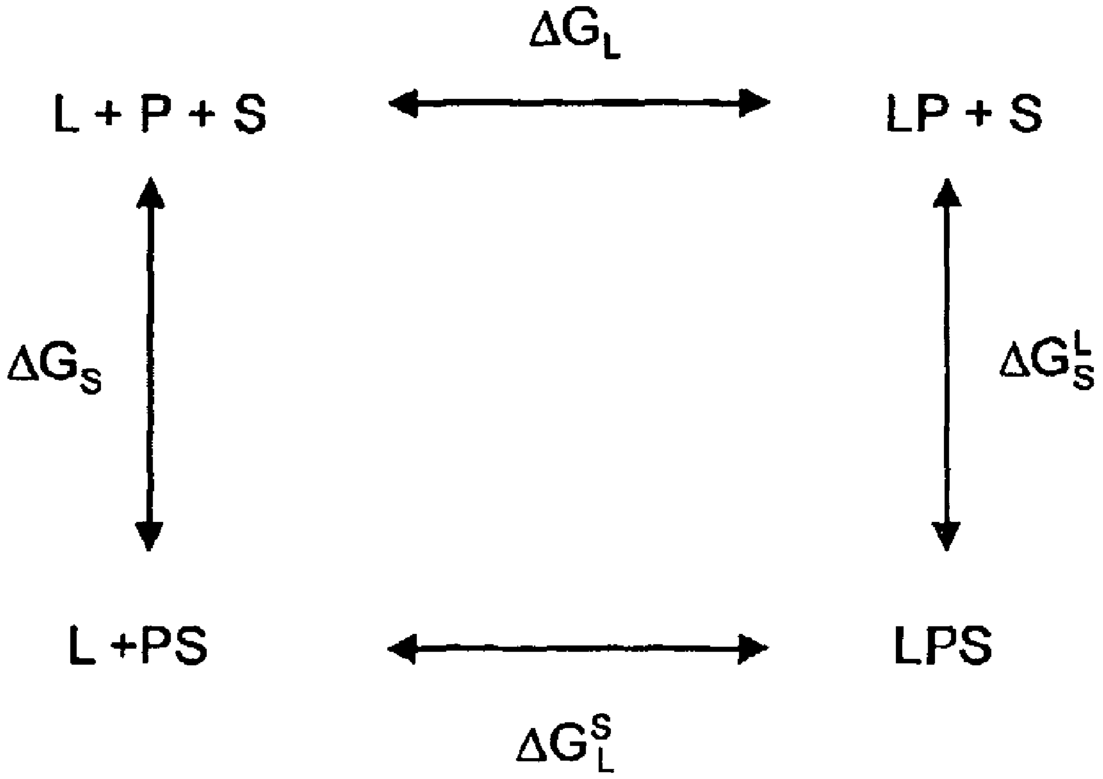
FIG. 8 is a schematic diagram illustrating coupling of ligand and substrate binding.

FIG. 8 is a schematic diagram depicting coupling of ligand and substrate binding. More particularly, FIG. 8 shows that the change in free energy upon protein (P) binding ligand (L) and substrate (S) is the same whether the ligand or substrate binds first. Adding the free energy changes of the two different paths from L+P+S to LPS, it is seen that: $\Delta G_L + \Delta G_S^L = \Delta G_S + \Delta G_L^S$ since the total free energy change is path independent. By rearranging this equation to: $\Delta G_L - \Delta G_L^S = \Delta G_S - \Delta G_S^L$ it is seen that the left hand side represents the effect that the presence of bound substrate has on ligand binding and the right hand side represents the effect that the presence of bound ligand has on substrate binding. The effects must be equal. This corresponds to a coupling energy of approximately 1 kcal/mol. Without intending to be bound by theory, this observation offers an additional explanation for the increase in β-lactam hydrolysis in the presence of maltose: a positive heterotropic allosteric effect on substrate binding.

Presumably, the BLA domain of the apo, open form of RG13 exists in a compromised, less active conformation. In the ligand-bound state, the BLA domain exists in a more normal, active conformation. We sought to determine the state of the BLA domain in the process of closing. We investigated at what closure angle the catalytic properties of RG13 improved To address these questions, we took advantage of mutations in the hinge region of MBP that manipulate the conformational equilibria between the open and closed state (Marvin et al. 2001). Residual dipolar couplings have been used to establish that the apo forms of these mutants are partially closed relative to the apo wildtype MBP with the ensemble average closure angles being 9.5° and 28.40 for 1329W and 1329W/A96W, respectively (Millet et al. 2003). The ligand-bound closed forms of MBP, i.e., MBP(I329W) and MBP(I329W/A96W) have closure angles of 35°. Partial closing shifts the equilibrium towards the ligand-bound state and thus the mutations increase the affinity for maltose (Marvin et al. 2001).

Introduction of these mutations into RG13 resulted in the creation of more sensitive switches—i.e., switches that respond to lower concentrations of maltose (FIG. 9). FIG. 9A shows dissociation constants for maltose determined in the absence (white bars) and presence (black bars) of saturating concentrations of carbenicillin. The apparent dissociation constants in the presence of subsaturating concentrations (25 μM) of nitrocefin (grey bars) were also determined. The dissociation constants for maltose of MBP, MBP(I329W), MBP (I329W/A96W) (dashed line) reported by Marvin and Hellinga (2001) are shown for comparison (FIG. 9A).

Without intending to be bound by theory, the fact that we observed qualitatively similar changes in maltose affinity when the mutations are introduced into RG13 strongly suggests that the relative order and magnitude of the angles of closure of RG13, RG13(I329W) and RG13(I329W/A96W) are similar to that of MBP, MBP(I329W) and MBP(I329W/A96W). Thus, the apo forms of the two RG13 mutants offer conformations intermediate between the open to the closed form of RG13—conformations that may reflect that of RG13 in the process of closing. Assuming that the process of closing in RG13 passes through the conformations of the apo forms of the two RG13 mutants, kinetic characterization of RG13 (I329W) and RG13(I329W/A96W) suggested that the initial stages of closing do not result in changes in the BLA domain that substantially affect catalysis.

Figure 9A:
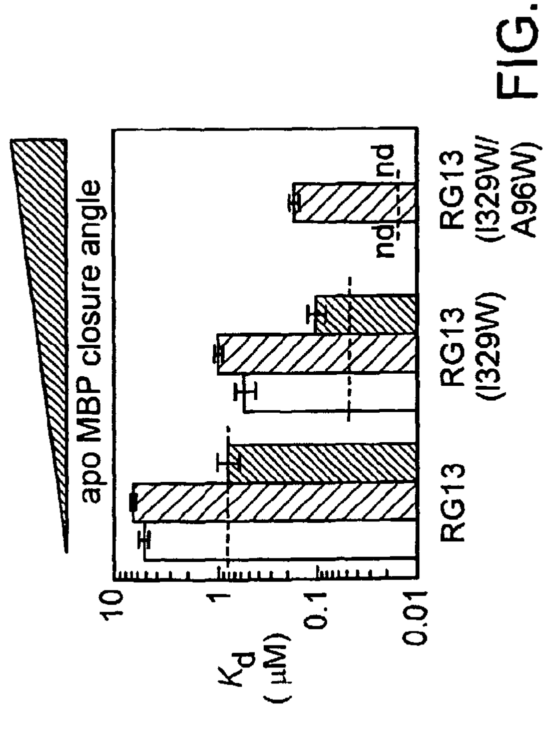
FIGS. 9A-D show comparisons of characteristics of molecular switches according to the invention.
Figure 9B:
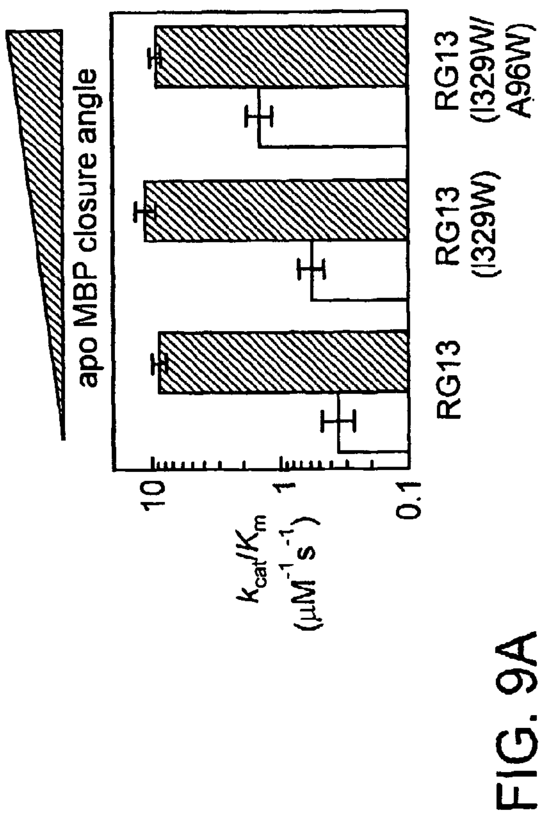
Figure 9C:
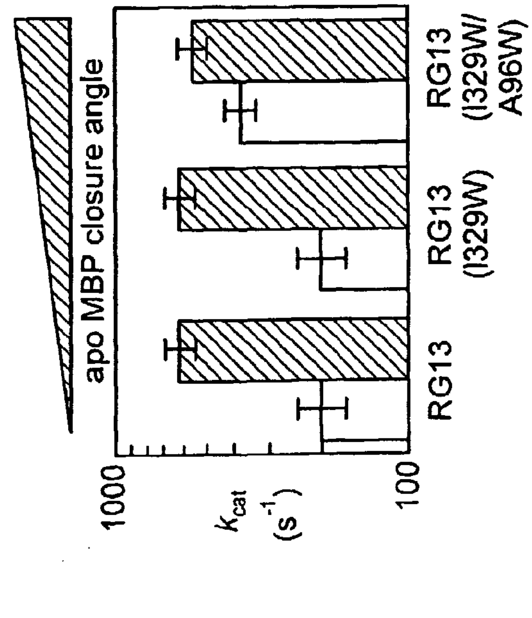
Figure 9D:
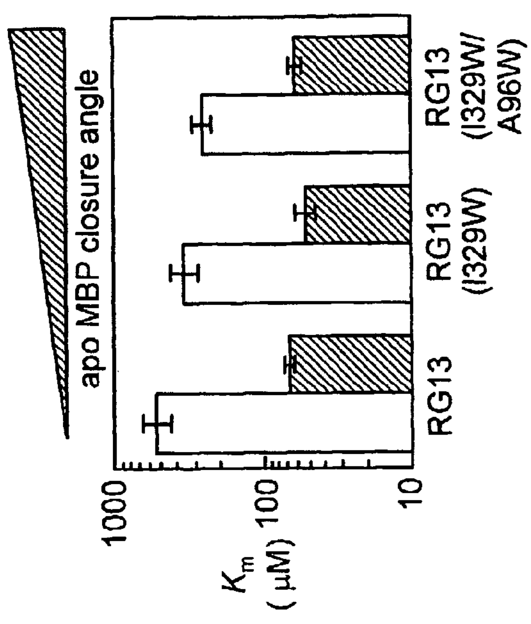

FIGS. 9B-D show steady state kinetic parameters of nitrocefin hydrolysis for RG13, RG13(I329W) and RG13(I329W/A96W) in the presence (black bars) or absence (white bars) of saturating concentrations of maltose. Experimental conditions were as follows: 100 mM sodium phosphate buffer, pH 7.0, 25° C. Both $k_{cat}$ and $K_m$ improved during the intermediate stages of closing, but the majority of the effect on $K_m$ occurred during the final stages of closing.

As the magnitude of the allosteric effect was on the same order as that of many natural allosteric enzymes, we next examined the biological effects of RG13. We found that the switching activity was sufficient to result in an observable phenotype: maltose-dependent resistance to ampicillin (Table 8). *E. coli* cells expressing RG13 had a minimum inhibitory concentration (MIC) for ampicillin that was increased four-fold in the presence of 50 μM maltose. In contrast, the addition of the same concentration of sucrose or glucose to a plate did not affect the MIC (Table 8). Thus, RG13 serves to couple the previously unrelated functions of ampicillin resistance and maltose concentration. *E. coli* cells expressing RG13 function as a growth/no growth sensor for maltose.

TABLE 8

Ampicillin Resistance of *E. coli* Cells in the Presence and Absence of Maltose.

| Expressed | Minimum Inhibitory Concentration of Ampicillin (μg/ml)* | |
|---|---|---|
| Protein | No maltose | 50 μM maltose |
| none | 4 | 4 |
| RG13 | 128 | 512 |
| BLA(W208G)† | 32 | 32 |
| BLA | ≧2000 | ≧2000 |

*Conditions: DH5α-E cells on LB plates (with or without maltose) incubated at 37° C. for 20 hours.
†A mutant of BLA with reduced activity.

We have shown herein that two unrelated proteins can be systematically recombined in order to link their respective functions and create molecular switches. A combination of random circular permutation and random domain insertion enabled the creation of a MBP-BLA fusion geometry in which conformational changes induced upon maltose binding could propagate to the active site of BLA and increase BLA enzymatic activity up to 25-fold. The functional coupling of two proteins with no evolutionary or functional relationship is a powerful strategy for engineering novel molecular function. For example, coupling a ligand-binding protein and a protein with good signal transduction properties would result in the creation of a molecular sensor for the ligand. Furthermore, switches that establish connections between cellular components with no previous relationship can result in novel cellular circuitry and phenotypes. As discussed above, we expect such switches to establish connections between molecular signatures of disease (e.g., abnormal concentrations of proteins, metabolites, signaling or other molecules) and functions that serve to treat the disease (e.g., delivery of drugs, modulation of signaling pathways or modulation of gene expression) and therefore possess selective therapeutic properties.

Example 3

Design Considerations and Properties of Molecular Switches

This Example describes design considerations, kinetic properties and characteristics of families of molecular switches that can be constructed according to the methods of the invention.

Molecular switch RG13, described above, has a dissociation constant for maltose of about 5-6 μM in the absence of a BLA substrate. In the presence of saturating amounts of the substrate carbenicillin, the dissociation constant for maltose decreases to about 1 μM. This shows that the binding of maltose and substrate (carbenicillin) are coupled. The coupling energy is on the order of 1 kcal/mol. This is consistent with a decrease in $K_m$ for nitrocefin in the presence of maltose (See Tables 9 and 10, supra)

Switches Responding to a Range of Signal Concentrations

It is believed that a switch is most useful if the range of the concentration of the signal (maltose, in the case of RG13)

overlaps with the range of signal concentration that the dependent function responds to. When a ligand-binding protein is used as the signal detector and the ligand is the signal, the latter range corresponds approximately to the range 0.1 $K_d$-10 $K_d$, where $K_d$ is the dissociation constant of the switch and the signal. This can be seen from the following example.

In the case of RG13, the velocity of nitrocefin hydrolysis is the dependent function. The velocity (v) of nitrocefin hydrolysis depends on the steady state kinetic parameters by the Michaelis-Menten (Equation 1).

$$v = \frac{[E]_0[S]k_{cat}}{K_m + [S]} \quad (1)$$

where $[E]_0$ is the concentration of the switch, [S] is the concentration of nitrocefin and $k_{cat}$ and $K_m$ are the Michaelis-Menten kinetic parameters. In the absence of maltose, the velocity is found by Equation 2

$$v^- = \frac{[E]_0[S]k_{cat}^-}{K_m^- + [S]} \quad (2)$$

where the superscript "−" designates that the parameters are those when maltose is not bound to the switch. In the presence of saturating concentrations of maltose (i.e. maltose is bound to all switches; this occurs at very high concentrations of maltose relative to the dissociation constant $K_d$ for maltose), the velocity is found by Equation 3:

$$v^+ = \frac{[E]_0[S]k_{cat}^+}{K_m^+ + [S]} \quad (3)$$

where the superscript "+" designates that the parameters are those when maltose is bound to the switch. At intermediate concentrations of maltose, the velocity depends on the fraction of switches that have maltose bound. If we make the approximation that the small cooperative effect of maltose- and substrate-binding can be ignored, the fraction F of switches that are bound to maltose can be found by Equation 4:

$$F = \frac{[M]}{[K_d] + [M]} \quad (4)$$

where [M] is the concentration of maltose. The velocity of nitrocefin hydrolysis is thus found by Equation 5:

$$v = F\frac{[E]_0[S]k_{cat}^+}{K_m^+ + [S]} + (1 - F)\frac{[E]_0[S]k_{cat}^-}{K_m^- + [S]} \quad (5)$$

Equation 5 is true for all concentrations of maltose as it reduces to Equations 2 and 3 in the limiting cases of no maltose bound and saturating maltose, respectively. The fold-increase in the rate of nitrocefin velocity Z is found by dividing the right hand side of Equation 5 by the velocity in the absence of maltose to get Equation 6:

$$Z = F\frac{k_{cat}^+(K_m^- + [S])}{k_{cat}^-(K_m^+ + [S])} + (1 - F) \quad (6)$$

Figure 10:
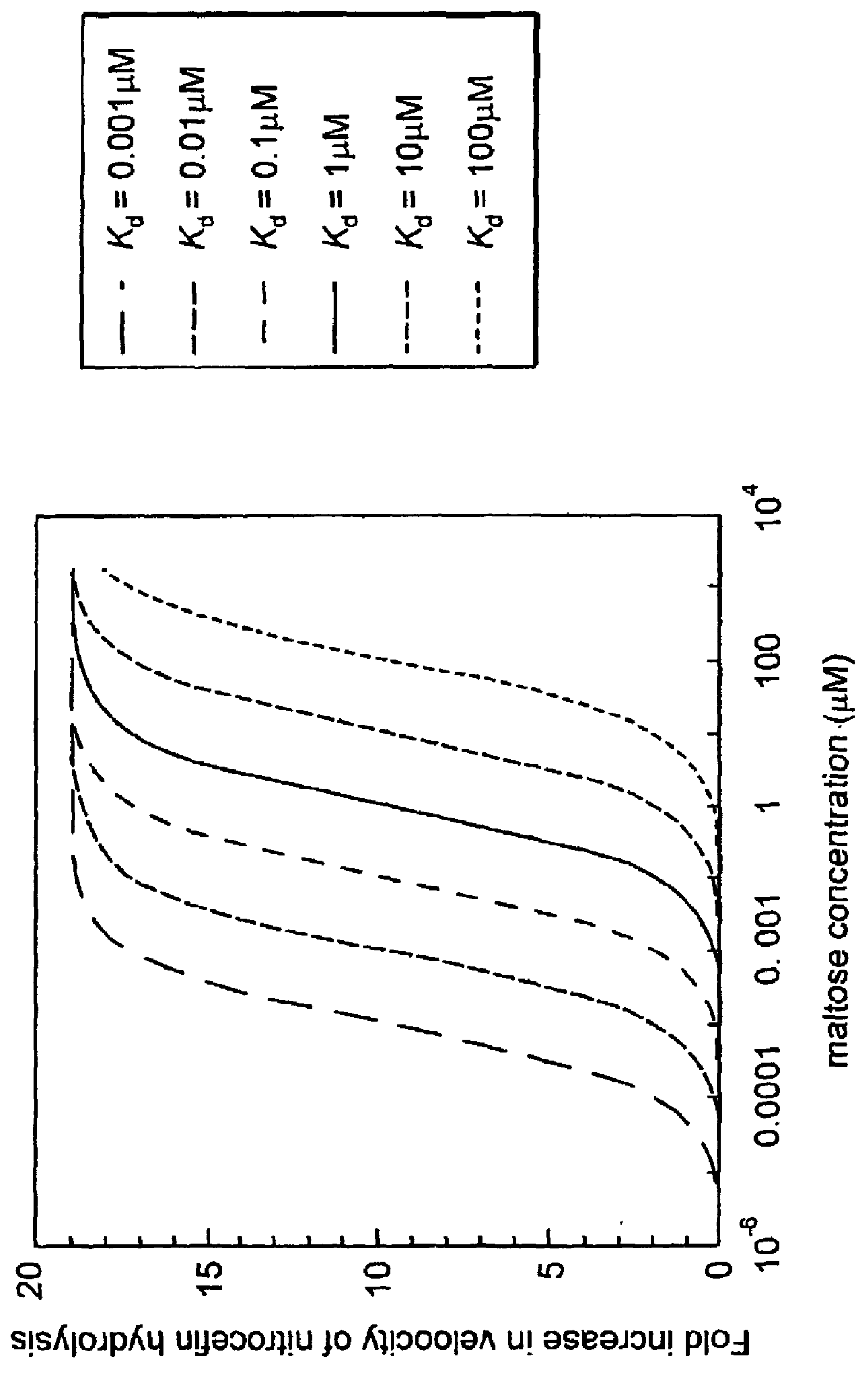
FIG. 10 is a graph showing velocity of nitrocefin hydrolysis by a molecular switch according to the invention as a function of effector (maltose) concentration.

Referring to FIG. 10, Equation 6 is plotted for the case of RG13 hydrolysis of 25 μM nitrocefin using a range of different dissociation constants for maltose. More particularly, FIG. 10 shows the fold increase in velocity of switch RG13 with different dissociation concentrations ($K_d$) for maltose. The concentration of nitrocefin was 25 μM. The kinetic parameters of RG13 with and without maltose are those shown in Table 9. Equation 6 was used to generate the curves. It is apparent that the velocity is changing most in the range of one order of magnitude higher or lower than the dissociation constant for maltose. The switch is expected to have the largest change in the dependent function if the concentration of the signal (maltose in the case of RG13) changes within this range or changes through this range. Thus, it is desirable for the application of molecular switches to create switches with different affinities for the signal so as to be useful for different concentration ranges of the signal.

Altering Affinity for Signals

Exemplary switches were created by the method having different affinities for maltose. For example switch RG-5-169 (sequence MBP[1-338]-BLA[34-286]-GSGGG-BLA[24-29]-MBP[337-370] (GSGGG linker disclosed as SEQ ID NO: 1) was created having a $K_d$ for maltose (>1 mM) that is much greater than that of RG13 for maltose (1-5 □M).

The affinity of switches for effectors (signals) can also be altered by a variety of methods, including rational design and directed evolution methods. As long as the resulting altered-affinity switch maintains a conformational change upon binding the effector that results in changes the dependent function, switching will be maintained. For example, mutations known to alter the affinity of the ligand recognition domain (for RG13 this is MBP) can be introduced into the switch to create switches with altered affinity for the ligand. These mutations consist of those that make direct contact with the ligand, those that make contact with residues that make direct contact with the ligand and those that are more distal from the binding site pocket.

For instance, as discussed in Example 2, mutations have been made in the hinge region of MBP that manipulate the conformational equilibria between the open and closed state (Marvin and Hellinga 2001). Residual dipolar couplings have been used to establish that the apo forms of these mutants are partially closed relative to the apo wildtype MBP with the closure angles being 9.5° and 28.40 for I329W and A96W/I329W, respectively (the ligand-bound closed form of MBP has a closure angle of 35°) (Millet, Hudson et al. 2003). Because partial closing shifts the equilibrium towards the ligand-bound state, the I329W mutation results in about a 20-fold increase in affinity for maltose and the A96W/I329W double mutant results in a 60-fold increase in the affinity for maltose compared to wildtype MBP at 25° C. (Marvin and Hellinga 2001). The affinities of MBP, MBP(I329W) and MBP(I329W/A96W) are 800 nM, 35 nM and 13 nM, respectively.

Introduction of the above MBP mutations into RG13 resulted in mutants with increased affinity for maltose (Table 9) while still maintaining switching behavior (Table 10). In addition, the level of activity in the presence of saturating amounts of maltose (the "on" state) was not affected by the mutations (Table 10).

TABLE 9

Maltose Affinity of RG13-Based Molecular Switches.

| | | $K_d$ maltose (μM)[a] | | | |
|---|---|---|---|---|---|
| | | | | Saturating Carbenicillin | |
| Protein | Ligand | No Substrate[b] | 25 μM nitrocefin[c] | IPF[b] | Enzymatic assay[d] |
| RG13 | maltose | 5.5 ± 0.5 | 6.7 ± 0.03 | 1.3 ± 0.5 | 0.9 ± 0.1 |
| RG13 I329W | maltose | 0.55 ± 0.13 | 1.0 ± 0.04 | nd | 0.11 ± 0.01 |
| RG13 I329W/A96W | maltose | nd | 0.17 ± 0.02 | nd | nd |

[a]Conditions: 100 mM NaCl, 50 mM $NaPO_4$, pH 7.0, 25° C.

[b]Determined by measuring intrinsic protein fluorescence (IPF) as a function of maltose concentration. When using IPF at saturating carbenicillin, a concentration of 10 mM carbenicillin was used.

[c]Determined by measuring the initial rate of nitrocefin hydrolysis as a function of maltose concentration. 25 μM nitrocefin is well below the $K_m$ of nitrocefin. Thus, most molecules of RG13 will not have nitrocefin bound and the effective $K_d$ that is measured is close to what it would be in the absence of substrate.

[d]Determined by measuring the initial rate of carbenicillin hydrolysis as a function of maltose concentration. A concentration of 1.5 mM carbenicillin was used, which is well above the $K_m$ of carbenicillin. Thus, most molecules of RG13 will have carbenicillin bound and the $K_d$ that is measured is in the presence of bound substrate (carbenicillin).

TABLE 10

Kinetic Parameters of Nitrocefin Hydrolysis[a] of RG13-Based Molecular Switches.

| Protein | Effector | $k_{cat}$ ($s^{-1}$)[a] | $k_{cat}$ Ratio[b] | $K_m$ (μM)[a] | $K_m$ Ratio[b] | $k_{cat}/K_m$[a] ($s^{-1}$ $\mu M^{-1}$) | $k_{cat}/K_m$ Ratio[b] |
|---|---|---|---|---|---|---|---|
| RG13 | — | 200 ± 40 | — | 550 ± 120 | | 0.37 ± 0.10 | |
| RG13 I329W | — | 190 ± 30 | — | 350 ± 60 | | 0.54 ± 0.11 | |
| RG13 I329W/A96W | — | 360 ± 40 | — | 260 ± 40 | | 1.4 ± 0.3 | |
| RG13 | maltose | 620 ± 30 | 3.1 ± 0.6 | 68 ± 4 | 0.12 ± 0.03 | 9.2 ± 0.7 | 25 ± 7 |
| RG13 I329W | maltose | 590 ± 50 | 3.1 ± 0.5 | 53 ± 7 | 0.15 ± 0.03 | 11.0 ± 1.8 | 20 ± 5 |
| RG13 I329W/A96W | maltose | 530 ± 20 | 1.5 ± 0.2 | 60 ± 4 | 0.23 ± 0.04 | 8.9 ± 0.8 | 6.4 ± 1.3 |
| RG13 | β-cyclo[c] | 590 ± 60 | 2.9 ± 0.6 | 870 ± 90 | 1.6 ± 0.4 | 0.67 ± 0.10 | 1.8 ± 0.6 |

[a]Conditions: 100 mM sodium phosphate buffer, pH 7.0, 25° C.; concentration of effector is 5 mM

[b](with effector)/(without effector).

[c]β-cyclodextrin

From a practical standpoint, the increase in maltose affinity of these hinge mutants indicates that ligand-affinity of RG13 can be systematically changed to create molecular switches that respond to different concentration ranges of effector while still maintaining switching ability and high activity in the presence of the effector. By increasing the affinity for maltose one increases the sensitivity of the switch (i.e., it will switch to a higher level of activity at lower concentrations of maltose). Combinations of these affinity-altered switches are expected to behave as a composite switch with a high dynamic range.

Example 4

Modified Molecular Switches with Altered Signal Recognition

The invention further encompasses methods to alter the specificity of the signal recognition domain so that it recognizes other signals. This allows for the construction of "modified" molecular switches in which the dependent function responds to new signals without the need to construct entirely new molecular switches. For the example of RG13, in which the signal binding domain is the maltose binding protein, these methods can change the ligand to which the switch binds. This would allow the construction of molecular switches in which BLA activity could be modulated by different ligands. In one aspect of the method, the identity of the signal to which the switch responds is altered by introducing mutations into existing switches. For example, mutations in the signal recognition domain already known to alter the ligand-binding specificity can be introduced into the switch to create switches that respond to new ligands. For instance, Hellinga and colleagues have computationally designed periplasmic binding proteins with radically altered binding specificities (Looger, Dwyer et al. 2003) including designing MBP to bind $Zn^{2+}$ (Marvin and Hellinga 2001) instead of maltose. MBP binds maltose with high affinity ($K_d$=0.8 μM) but does not bind $Zn^{2+}$. MBP with the A* set of mutations (A63H/R66H/Y155E/W340E) has high affinity for $Zn^{2+}$ ($K_d$=5.1 M) and does not bind maltose (Marvin and Hellinga 2001). Accordingly, introduction of the A* set of mutations into a fusion such as RG13 may result in a switch that responds to $Zn^{2+}$ but not maltose.

The signal recognition domain can be altered by rational design or directed evolution to bind to new effectors. With respect to testing mutations predicted by rational design or screening or selecting libraries created for a directed evolution approach, existing switches are used to efficiently test or select for binding to new ligands in vivo. For example, *E. coli* cells expressing the MBP-BLA switch RG13 from the lac promoter on pDIMC8 have a higher MIC for ampicillin (Amp) in the presence of maltose than in their absence (Table 11) because the BLA enzymatic activity of RG13 (hydrolysis of ampicillin) is higher in the presence of maltose. Thus, for example, mutations created in RG13 (either by rational design or by a stochastic or semi-stochastic method) such that mutant forms of RG13 bind another ligand X (and behave as a switch) can be screened or selected for in vivo. *E. coli* producing such a new switch will grow at 200 μg/ml Amp in the presence of X but not in the absence of X.

TABLE 11

Minimum Inhibitory Concentration of Ampicillin for *E. coli* Cells Expressing RG13[a].

| Supplement to plate | MIC ampicillin (μg/ml) |
|---|---|
| none | 100 |
| 50 μM maltose | 400 |
| 5 mM maltose | 400 |

[a]conditions: LB plates, 37° C., supplemented with maltose as indicated. Approximately 100 colony forming units (without ampicillin) per plate. Concentrations of ampicillin tested 0, 25, 50, 100, 200, 400 and 800 μg/ml.

Ligands that bind to the signal recognition domain in a different manner have different switching ability. This is demonstrated by the fact that β-cyclodextrin, which is known to bind to MBP but with a different conformational change (Skrynnikov, Goto et al. 2000; Hwang, Skrynnikov et al. 2001), changes the activity of the RG13 switch in a different manner than maltose (see Table 10).

Example 5

Creation of Libraries Containing Families of Molecular Switches

This example describes several strategies, including use of iterative approaches, for producing various types of libraries that contain families of related molecular switches.

Materials and Methods

MBP-BLA Library Constructions

Random domain insertion and random circular permutation of the bla gene were performed generally as described in Examples above. Libraries designated 2-5 and 7 (having inserts at a particular site in the MBP gene) were constructed as shown schematically in FIG. 11. (See also FIGS. 2 and 3 supra for details on construction of the circular bla gene, and FIG. 4 for details on preparation of the MBP-containing plasmid.) FIG. 12 is a schematic diagram showing the construction of Library 6, in which a specific circular permuted version of bla was randomly inserted into the plasmid containing the MBP gene. (See also FIG. 1, left side).

MBP-BLA Library Selection and Screening

Libraries were plated on LB plates containing 5 mM maltose at the indicated concentrations of ampicillin and incubated at 37° C. overnight. From these plates, colonies were picked to inoculate 1 ml LB media (supplemented with 50 μg/ml chloramphenicol and 1 mM IPTG) in 96-well format. Lysates from these cultures were assayed for nitrocefin hydrolysis activity in the presence and absence of maltose as described above.

Protein Characterization

His-tagged proteins were purified as described in Examples above. All enzymatic assays were performed in the presence of 100 mM sodium phosphate buffer, pH 7.0. Enzyme stock was added to 1.9 ml buffer (containing the saccharide, if desired). After incubation at the desired temperature for 5 minutes, 0.1 ml of 20× substrate was added and the absorbance at the appropriate wavelength was recorded using the Cary50 UV-VIS spectrophotometer. The wavelengths monitored were as follows: nitrocefin (486 nm), carbenicillin (240 nm), ampicillin (235 nm), cefazolin (260 nm), cefotaxime (260 nm), and cephalothin (260 nm). Ligand affinity was determined as described above. The oligomeric state of MBP317-347 was determined by analysis of size exclusion chromatography data using a pre-packed column of superose 6 (Pharmacia, Pscataway, N.J.) with a separation range of 5-5000 kDa on a Pharmacia FPLC system. The mobile phase was phosphate buffer at pH 7.0 (0.1 M sodium phosphate, 0.15 M NaCl) with or without 5 mM maltose and flow rate was set at 0.5 ml/min. Elution peaks were detected by UV absorbance at 254 nm. The column was calibrated using ribonuclease A (13.7 kD), albumin (67 kD), aldolase (158 kD), catalase (232 kD) as molecular weight standards.

Characteristics of Libraries

Libraries 2-7 were plated on different levels of ampicillin in the presence of 50 mM maltose. Colonies that grew were used to inoculate 96-well plates. The resulting cultures were lysed and assayed at room temperature for nitrocefin hydrolysis in the presence and absence of maltose in 96-well format. Library members in which the addition of maltose resulted in a 2-fold or greater difference in the rate of nitrocefin hydrolysis were chosen for further study. Statistics on all libraries and screening can are shown in Tables 12-14.

TABLE 12

Library Statistics for Libraries 2-7.

| Library | Library size (number of transformants with bla insert). |
|---|---|
| Library 2 (T164-165/DKS) | $0.44 \times 10^6$ |
| Library 3 (T164-165/GSGGG) | $1.05 \times 10^6$ |
| Library 4 (EE/DKS) | $1.03 \times 10^6$ |
| Library 5 (EE/GSGGG) | $0.30 \times 10^6$ |
| Library 6 | $0.75 \times 10^6$ |
| Library 7 | $1.16 \times 10^6$ |

(GSGGG linker disclosed as SEQ ID NO: 1)

Table 13 shows the number of library members that could grow on plates containing different amounts of maltose and ampicillin. Based in part on this information, colonies from different plates were screened.

TABLE 13

Number of Original Transformants Capable of Growth In Presence of Ampicillin

| | Number of original transformants that could grow on . . . | | | | | | | |
|---|---|---|---|---|---|---|---|---|
| | No Maltose | | | | 50 mM maltose | | | |
| Library | Amp5 | Amp50 | Amp200 | Amp1000 | Amp5 | Amp50 | Amp200 | Amp1000 |
| 2 | 734 | 394 | 220 | — | 1098 | 515 | 182 | — |
| 3 | 878 | 294 | — | 74 | 761 | 361 | 240 | 88 |
| 4 | 7052 | 1747 | 1080 | — | 8354 | 2414 | 1525 | — |
| 5 | 3510 | 1159 | 298 | — | 4056 | 1615 | 630 | — |
| 6 | — | 3138 | 383 | 64 | — | 4439 | 765 | 65 |
| 7 | — | 2008 | 990 | 138 | — | 1806 | 1337 | 275 |

The number of colonies screened from plates containing different amounts of maltose and ampicillin is shown in Table 14. Colonies were screened as described in the Methods section. For Libraries 2-5, all switches originated from plates with 50 mM maltose and 5 μg/ml ampicillin. For Libraries 6 and 7, all switches originated from plates with 50 mM maltose and 200 μg/ml ampicillin.

TABLE 14

Number of Colonies Screened.

| | Number of colonies screened from plates containing . . . | | | | | | | |
|---|---|---|---|---|---|---|---|---|
| | No Maltose | | | | 50 mM maltose | | | |
| Library | Amp5 | Amp50 | Amp200 | Amp1000 | Amp5 | Amp50 | Amp200 | Amp1000 |
| 2 | — | — | — | — | 96 | 672 | 80 | — |
| 3 | 96 | — | — | — | 192 | 576 | 384 | — |
| 4 | — | — | — | — | — | 576 | — | — |
| 5 | 288 | — | — | — | 864 | 768 | — | — |
| 6 | — | — | — | — | — | — | 576 | 192 |
| 7 | — | — | — | — | — | — | 1056 | — |

Molecular Switches Isolated from BLA-MBP Libraries 2-7

FIG. 13 is a schematic depiction of the library construction schemes for Libraries 2-7, and of particular switches identified from these libraries. The arrowheads indicate the sites of insertion. Multiple arrowheads on one gene indicate random insertion sites. Dashed arrows indicate a particular switch on which successive libraries were based. The magnitude of switching was determined on the soluble fraction of cell lysates at room temperature using 50 μM nitrocefin. For switches with a rate increase in the presence of maltose, the ratio is of "with maltose" to "without maltose" (indicated by no sign in front of the value). For switches with a rate decrease with maltose, the rate is of "without maltose" to "with maltose" (indicated by a negative sign in front of the value).

Referring to FIG. 13, five new switches were identified with improved switching activity, including one (designated IFG277) in which maltose was a negative effector. Another switch (designated IFD15) was permuted such that residues 168-170 of BLA were tandemly duplicated. Residues 168-170 are part of the Q-loop associated with the active site of the enzyme that includes a key catalytic residue, Glu166. IFD15 was not a better switch than the other four identified from these libraries. However, the fact that BLA could be permuted so near the active site without elimination of activity, combined with the notion that a connection between BLA and MBP near the active site of BLA would be more likely to produce switches with superior properties, led us to choose this particular circular permutation of the b/a gene for Library 6.

Library 6 contained this particular circularly permuted variation of b/a randomly inserted into the gene for MBP (FIGS. 12, 13). From this library several new switches were identified, including BLA168-89 in which 22 residues near the C-terminus of MBP were deleted. However, the best switches found had BLA inserted in the region between residues 316 to 320. BLA168-81, whose catalytic activity increased almost two orders of magnitude in the presence of maltose, had the circular permuted BLA inserted in place of residue 317 of MBP. Interestingly, RG13 also consists of an insertion in place of residue 317, but with a different circular permutation of BLA.

To exhaustively explore insertions of circular permuted variants of BLA that replace residue 317 of MBP, Library 7 was constructed. For selecting library members from Library 7 for further examination, a criterion of 30-fold or better difference in catalytic activity with maltose was selected. Three switches with sequences very similar to BLA168-81 were identified from Library 7 (FIG. 13).

Characterization of Switches

Figure 14A:
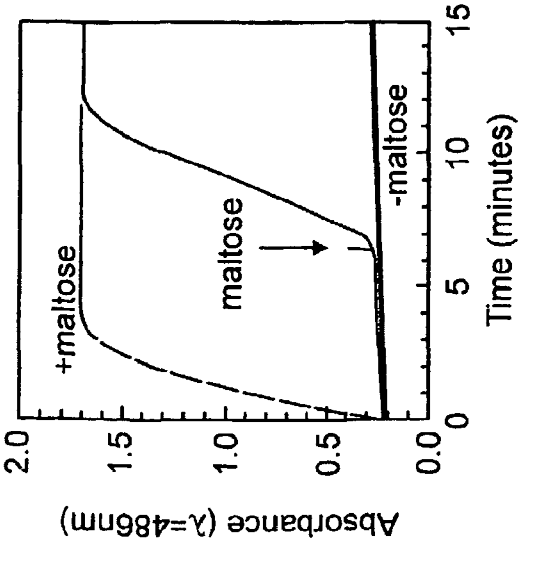
FIGS. 14A-D are four graphs showing enzymatic characteristics of particular embodiments of molecular switches according to the invention.

A 10x-His tag was added to the C-terminus of switches MBP317-347, MBP317-639 and BLA168-81 and the proteins were purified to >95% purity via nickel-affinity chromatography. The enzymatic activity of the switches was characterized using the colorimetric substrate nitrocefin (FIG. 14). FIG. 14A shows hydrolysis of 80 μM nitrocefin by 27 nM MBP317-347 in the presence and absence of maltose at 25° C. More particularly, the reaction was started by the addition of nitrocefin at time zero to samples lacking (solid lines) or containing (dashed line) 5 mM maltose. For the reaction traced by the solid grey line, 5 mM maltose was added to the reaction at about 6 minutes. As can be seen in FIG. 14A, the rate of nitrocefin hydrolysis was profoundly affected by maltose. Only sugars known to bind MBP were effectors; sucrose, galactose and lactose had no effect on the rate of hydrolysis.

Figure 14B:
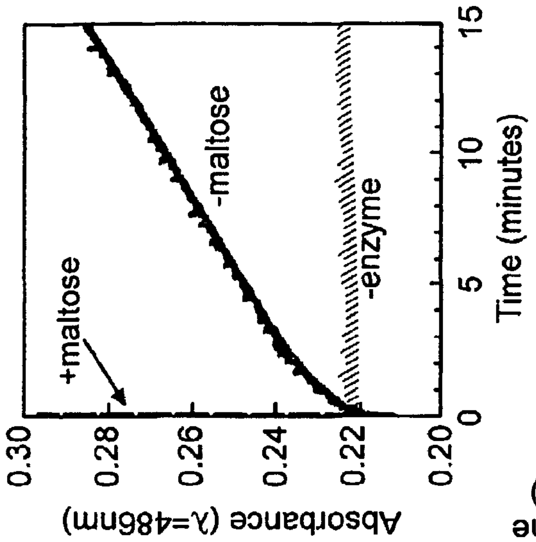

In none of the three switches did enzymatic activity obeyed Michaelis-Menten kinetics. In the absence of maltose, catalysis was characterized by a small burst lasting on the order of several minutes followed by a slower steady state rate (FIG. 14B). FIG. 14B shows the same data as FIG. 14A with a narrower range of absorbance shown. The grey line is the background rate of nitrocefin hydrolysis in the absence of enzyme. The size of the burst was much greater than 1 mol product/mol of enzyme and was consistent with a branched pathway mechanism involving substrate induced progressive inactivation (Waley, S. G., 1991). Such kinetics have been observed previously in class A β-lactamases on substrates with bulky side chain substituents (Citri et al., 1976) that orient towards the Ω-loop (Chen et al., 1993; Strynadka et al., 1992) as well as in mutants of *Staphylococcus aureus* PC1 β-lactamase in which the Ω-loop has been perturbed (Chen et al., 1999). Similar burst kinetics were seen in the presence of maltose; thus substrate-induced inactivation cannot be an explanation for the compromised activity in the absence of maltose.

Figure 14C:
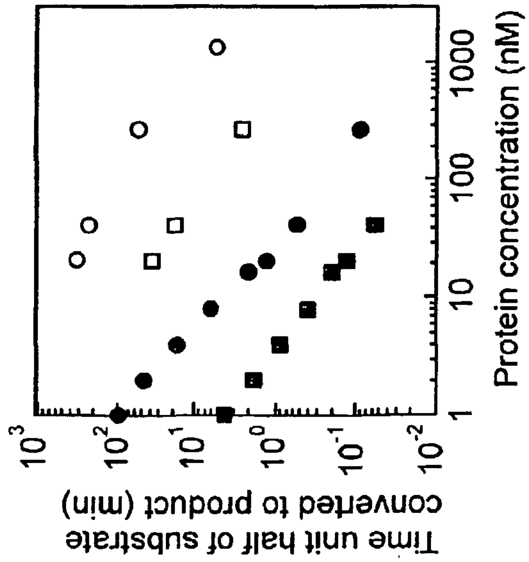

Preliminary characterization indicated that switch MBP317-347 had the largest switching activity, and this switch was characterized in more detail. In order to get an effective measure of the difference in catalytic activity between with and without maltose, the amount of time necessary to convert half of the substrate to product was characterized as a function of switch concentration and nitrocefin concentration (FIG. 14C). Because the catalytic activities with and without maltose differed so greatly, there was only a limited protein concentration range in which both activities could be measured. In this range, the amount of time necessary to convert half the substrate to product was 240-590 times greater in the absence of maltose than in its presence. More particularly, FIG. 13C shows the time necessary for MBP317-347 to convert half of the nitrocefin to product at 25° C. as a function of nitrocefin concentration, maltose and MBP317-347 concentration. Squares indicate 5 μM nitrocefin; circles indicate 100 μM nitrocefin; filled symbols indicate with maltose; open symbols indicate without maltose.

Figure 14D:
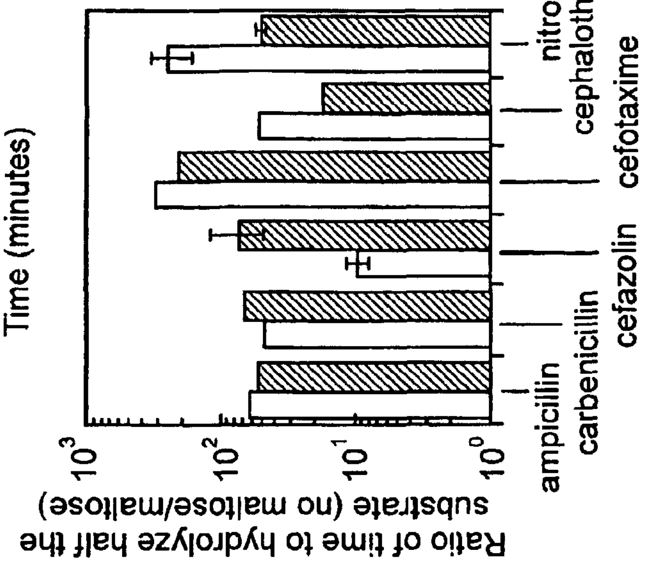

Referring to FIG. 14D, it was seen that the effect of temperature and substrate on switching activity was complex, with no clear trend. FIG. 14D shows the ratio of time necessary for MBP317-347 to convert half of substrate to product in the absence of maltose to that in the presence of maltose as a function of substrate and temperature. White bars indicate 25° C.; black bars indicate 37° C. Concentrations of MBP317-347/concentration of substrate are: ampicillin (113 nM/200 μM), carbenicillin, (453 nM/200 μM), cefazolin (113 nM/200 μM), cefotaxime (453 nM/100 μM), cephalothin (226 nM/150 μM), and nitrocefin (22.6 nM/100 μM) Interestingly, the effect of switching the temperature from 25 to 37° C. was a uniform ~2-fold decrease in activity in the presence of maltose, whereas the effect in the absence of maltose ranged from a 3.5-fold increase to a 23-fold decrease in activity.

The oligomeric state of switch MBP317-347 at 25° C. was investigated using size exclusion chromatography. This analysis was consistent with a monomer-dimer equilibrium with a dissociation constant of about 5 μM in the absence of maltose and about 20 μM in the presence of maltose. The importance of the dimerization and its minor maltose-dependence to the switching activity is likely minimal—the difference in activity between with and without maltose does not have a significant dependence on protein concentration (FIG. 14C) and all the protein concentrations assayed are well-below the dissociation constant of the dimer.

Example 6

Creation of Molecular Switches Binding Novel Ligands

Creation of Ligand-binding Site Library in MBP317-347 (Library SB3)

A library of variants of MBP317-347 was constructed in which each of the codons coding for the five positions (D14, K15, W62, E111, and W230) was completely random. Five sets of primers (in which the above codons were varied as 5'-NNK-3') were used to amplify fragments of the MBP317-347 gene. Sequences of primers for creating Library SB3 are as shown.

```
Primer set #1
DIMC8Malfor
                                  (SEQ ID NO: 76)
5'-GGACCAGGATCCATGAAAATAAAAACAGGT-3'

MBP1415rev
                                  (SEQ ID NO: 26)
5'-GCCGTTAATCCAGATTAC-3'
```

-continued

```
Primer set #2
MBP1415for
                                  (SEQ ID NO: 27)
5'-GTAATCTGGATTAAGGCNNKNNKGGCTATAACGGTCTCGCT-3'

MBP62rev
                                  (SEQ ID NO: 28)
5'-GAAGATAATGTCAGGGCC-3'

Primer set #3
MBP62for
                                  (SEQ ID NO: 29)
5'-GGCCCTGACATTATCTTCNNKGCACACGACCGCTTTGGT-3'

MBP111rev
                                  (SEQ ID NO: 30)
5'-AACAGCGATCGGGTAAGC-3'

Primer set #4
MBP111for
                                  (SEQ ID NO: 31)
5'-GCTTACCCGATCGCTGTTNNKGCGTTATCGCTGATTTAT-3'

MBP230rev
                                  (SEQ ID NO: 32)
5'-CGGGCCGTTGATGGTCAT-3'

Primer set #5
MBP230for
                                  (SEQ ID NO: 33)
5'-ATGACCATCAACGGCCCGNNKGCATGGTCCAACATCGAC-3'

DIMC8Malback
                                  (SEQ ID NO: 34)
5'-ATCCGGACTAGTAGGCCTTTACTTGGTGATACGAGT-3'
```

These fragments were assembled into a full gene by overlap extension PCR in a single PCR reaction. The assembled gene library was inserted between the BamHI and SpeI sites of pDIM-C8 to create a library of 1.58×10^7 transformants.

Selection and Screening of Library SB3

The library was plated on LB plates containing 256 μg/ml ampicillin and various amounts of sucrose as shown in Table 15. The number of transformants in the original library that could grow under these conditions was determined by the product of frequency of colonies that grew and the number of transformants in the library (1.575×10^7). Individual colonies were screened as described in the Methods section for the MBP-BLA libraries except that sucrose was used instead of maltose. The number of colonies screened from the different plate types is shown in Table 15.

TABLE 15

Analysis of Library BS3.

| | Sucrose on plate | | | |
|---|---|---|---|---|
| Quantity | none | 0.5 mM | 5 mM | 50 mM |
| Transformants that can grow on 256 μg/ml Amp | 220 | 255 | 372 | >886 |
| Colonies screened | — | 369 | 46 | 170 |

Switch MBP317-347, described above, conferred upon *E. coli* cells a maltose-dependent ampicillin resistance phenotype. The MIC at 37° C. for cells plated on media containing 5 mM maltose was 512 Hg/ml, which was four-fold higher than the MIC on plates lacking maltose. Other sugars, including sucrose, had no effect on the MIC. The only four-fold difference in MIC was somewhat surprising considering the much large effect of maltose on β-lactam hydrolysis in vitro.

Figure 15:
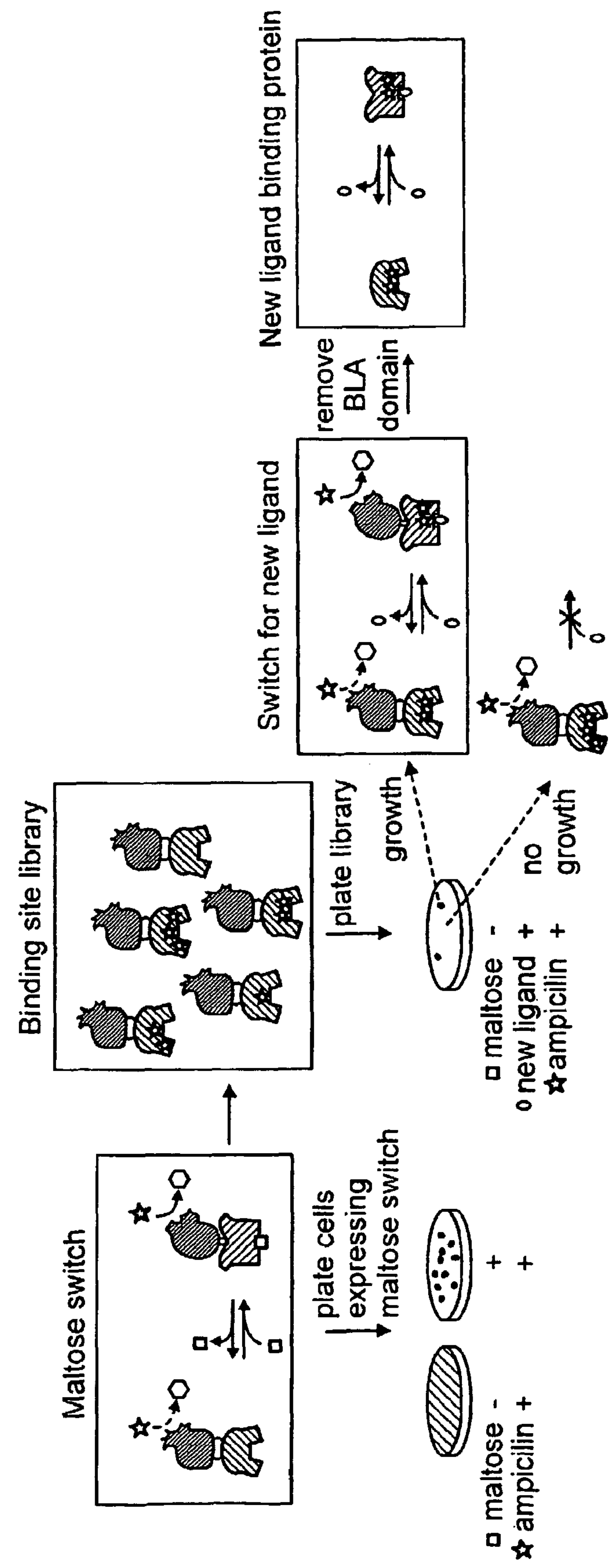
FIG. 15 is a schematic diagram depicting strategies for creating a novel switch from an existing switch that responds to a particular signal molecule (in this case maltose).

Switch MBP317-347 connects the presence of a ligand (i.e., maltose) to a growth/no growth phenotype when cells producing MBP317-347 are plated on β-lactam antibiotics. We sought to exploit this phenotype to create switches that respond to new effectors (FIG. 15). We reasoned that if the maltose-binding site of the switch was altered such that it bound a new ligand, and if binding of this new ligand induced a similar conformational change in the switch, then the β-lactamase activity of the switch would increase to a higher level of activity. Thus, from a library in which the maltose-binding site of the switch was randomized, one could select for those members that bound a new ligand by plating in the presence of the new ligand on plates containing a level of β-lactam antibiotic that was not permissive for growth in the absence of the old ligand. We also predicted that once mutations necessary to convert the maltose switch into one for the new ligand were identified, introduction of these mutations into MBP would result in a binding protein for the new ligand (FIG. 15).

This was tested by attempting to convert MBP317-347 into a switch that responds to sucrose. Maltose is a disaccharide of glucose whereas sucrose is a disaccharide of glucose and fructose. Neither MBP nor MBP317-347 show any detectable binding of sucrose ($K_d$>>50 mM). By inspection of the crystal structure of MBP bound to maltose, we identified five residues proximal to the glucose that is replaced with fructose in sucrose: D14, K15, W62, E111, and W230. A library of variants of MBP317-347, in which each of the five positions was randomized using 5'-NNK-3' for each codon, was created by overlap extension that consisted of $1.58 \times 10^7$ transformants (with a theoretical degeneracy on the protein level of $4.08 \times 10^6$). This library was plated at 37° C. in the presence of 256 µg/ml ampicillin and increasing concentrations of sucrose.

In the absence of sucrose, the frequency of library members that grew was $\sim 1.6 \times 10^{-5}$. We speculate that these false positives result from mutations that increase the production of the switch or alleviate the deficiency in ampicillin hydrolysis in the absence of bound ligand. The frequency of colonies on plates with 500 µM sucrose was not statistically different than that on plates with no maltose. However the frequencies of colonies growing at 5 mM and 50 mM sucrose were $\sim 2.6 \times 10^{-5}$ and $>6 \times 10^{-5}$, respectively.

Colonies (arising from the first library) from plates containing 256 µg/ml ampicillin containing 500 µM sucrose or 50 mM sucrose were used to inoculate 96-well plates. Lysates of these cultures were screened (using the 96-well nitrocefin assay) for those members for which the rate of nitrocefin hydrolysis increased in the presence of 5 mM sucrose. Two library members (designated 5-7 and 6-47) were found to respond to sucrose from the 500 µM sucrose plate (Table 15). Many library members that grew on the 50 mM sucrose plate were found to respond to sucrose. These were further screened for those that responded to lower levels of sucrose resulting in the identification of two more sucrose switches (designated 1-59 and 1-68).

TABLE 16

Sequences, Ligand Affinity and Switching Activity of Engineered Proteins.

| | | | | | | $K_d$ for ligand (µM) at 25° C. in presence of | | | | |
|---|---|---|---|---|---|---|---|---|---|---|
| | Amino acid number | | | | | No substrate[a] | | 5 µM nitrocefin[b] | | |
| Protein | 14 | 15 | 62 | 111 | 230 | Sucrose | Maltose | Sucrose | Maltose | Switching[c] |
| MBP317-347 | D | K | W | E | W | nb[d] | 0.5 ± 0.1 | nb[d] | 1.9 ± 0.2 | 240 |
| 5-7 | L | F | Y | Y | W | 0.7 ± 0.1 | 23 ± 13 | 6.7 ± 0.2 | 35 ± 5 | 82 |
| 6-47 | L | Q | Y | Q | W | — | — | 220 ± 10 | 3.2 ± 0.3 | 91 |
| 1-59[e] | K | E | Y | R | W | — | — | 340 ± 20 | 44 ± 2 | 28 |
| 1-68[e] | L | E | Y | R | W | — | — | — | — | 32 |
| SBP(5-7) | L | F | Y | Y | W | 6.6 ± 0.6 | 24 ± 4 | n/a | n/a | n/a |
| MBP | D | K | W | E | W | nb[d] | 1 | n/a | n/a | n/a |

Abbreviations; nb, no binding; n/a, not applicable
[a]Dissociation constants determined by change in intrinsic protein fluorescence as a function of ligand concentration (Hall et al., 1997).
[b]Apparent dissociation constants in the presence of nitrocefin were calculated using change in initial rates of nitrocefin hydrolysis as a function of ligand concentration².
[c]Ratio (without ligand to with ligand) of time necessary to hydrolyze one-half of the substrate (100 µM nitrocefin; 25° C.; 20 nM protein; saturating ligand concentration). The ligand used was sucrose except maltose was used for MBP317-347. For 1-59 and 1-68, ligand affinity and switching was determined in the soluble fraction of cell lysates, so the exact protein concentration is unknown.
[d]No binding can be detected. Kd >> 50 mM.
[e]characterized in the soluble fraction of cell lysates Characterization of Sucrose Switches A 10×-His tag was added to the C-terminus of switches 5-7 and 6-47, described above, and the proteins were purified to >95% purity via nickel-affinity chromatography. The binding to sucrose and to maltose was characterized by two different methods. Intrinsic protein fluorescence (Hall et al., 1997) was used to directly determine a $K_d$ for the ligand. Switch 6-47 showed too little change in fluorescence upon incubation with sucrose or maltose, presumably in part due to the W62Y mutation. An apparent $K_d$ was estimated using the effect of the ligand on the initial rate of nitrocefin hydrolysis (Guntas et al., 2004). This was performed at both low and high substrate to illustrate how the presence of bound nitrocefin has a negative effect on ligand binding; thus, the presence of bound ligand has a negative effect on substrate binding. Since sucrose-binding results in an increase in catalytic activity, large increases in the rates of the catalytic steps in the presence of sucrose must compensate for the decreased substrate affinity.

All of the switches still retained significant maltose affinity, with 5-7 being the switch with both the highest affinity for sucrose ($K_d$=0.7 μM) and the highest specificity for sucrose over maltose (33-fold higher affinity for sucrose). No binding or switching in response to lactose or galactose was observed. Sucrose and maltose increased β-lactamase activity of by equal amounts. However, the switching magnitude (ratio of activity with and without maltose) was less than that observed in the parental maltose switch MBP317-347. The reasons for this were examined in 5-7. In the absence of either sucrose or maltose, 5-7's activity was about 3-fold higher than MBP317-347's. The measured activity of 5-7 and MBP317-347 in the presence of bound ligand did not differ significantly. This suggests that the apo form of 5-7 is less compromised than MBP317-347 in nitrocefin hydrolysis activity and that the conformation of 5-7 bound to maltose or sucrose is the same—at least as far as its effect on 5-7's β-lactamase activity.

Creation of a Sucrose Binding Protein (SBP)

The D14L, K15F, W62Y and E111Y mutations of sucrose switch 5-7 were introduced into a His-tag version of MBP to create SBP. SBP was purified to >95% purity via nickel-affinity chromatography. The affinity of SBP for maltose was the same as that of sucrose switch 5-7 but the affinity for sucrose was decreased by about 10-fold. Still, SBP maintained a 4-fold preference for sucrose. The conversion of MBP to SBP represents a >>$10^6$ conversion in binding specificity.

Example 7

Exemplary Molecular Switches

This example provides nucleic acid and amino acid sequences of several exemplary molecular switches according to the invention.

```
Switch BLA168-81:
Nucleic Acid Sequence:
                                           (SEQ ID NO: 35)
atgaaaataaaaacaggtgcacgcatcctcgcattatccgcattaacgac

gatgatgttttccgcctcggctctcgccaaaatcgaagaaggtaaactgg

taatctggattaacggcgataaaggctataacggtctcgctgaagtcggt

aagaaattcgagaaagataccggaattaaagtcaccgttgagcatccgga

taaactggaagagaaattcccacaggttgcggcaactggcgatggccctg

acattatcttctgggcacacgaccgctttggtggctacgctcaatctggc

ctgttggctgaaatcaccccggacaaagcgttccaggacaagctgtatcc

gtttacctgggatgccgtacgttacaacggcaagctgattgcttacccga

tcgctgttgaagcgttatcgctgatttataacaaagatctgctgccgaac

ccgccaaaaacctgggaagagatcccggcgctggataaagaactgaaagc

gaaaggtaagagcgcgctgatgttcaacctgcaagaaccgtacttcacct

ggccgctgattgctgctgacggggttatgcgttcaagtatgaaaacggc

aagtacgacattaaagacgtgggcgtggataacgctggcgcgaaagcggg
```

-continued

```
tctgaccttcctggttgacctgattaaaaacaaacacatgaatgcagaca

ccgattactccatcgcagaagctgcctttaataaaggcgaaacagcgatg

accatcaacggcccgtgggcatggtccaacatcgacaccagcaaagtgaa

ttatggtgtaacggtactgccgaccttcaagggtcaaccatccaaaccgt

tcgttggcgtgctgagcgcaggtattaacgccgccagtccgaacaaagag

ctggcgaaagagttcctcgaaaactatctgctgactgatgaaggtctgga

agcggttaataaagacaaaccgctgggtgccgtagcgctgaagtcttacg

aggaagagttggcgaaagatccacgtAATGAAGCCATACCAAACGACGAG

CGTGACACCACGATGCCTGCAGCAATGGCAACAACGTTGCGCAAACTATT

AACTGGCGAACTACTTACTCTAGCTTCCCGGCAACAATTAATAGACTGGA

TGGAGGCGGATAAAGTTGCAGGACCACTTCTGCGCTCGGCCCTTCCGGCT

GGCTGGTTTATTGCTGATAAATCTGGAGCCGGTGAGCGTGGGTCTCGCGG

TATCATTGCAGCACTGGGGCCAGATGGTAAGCCCTCCCGTATCGTAGTTA

TCTACACGACGGGGAGTCAGGCAACTATGGATGAACGAAATAGACAGATC

GCTGAGATAGGTGCCTCACTGATTAAGCATTGGGACAAGAGCCACCCAGA

AACGCTGGTGAAAGTAAAAGATGCTGAAGATCAGTTGGGTGCACGAGTGG

GTTACATCGAACTGGATCTCAACAGCGGTAAGATCCTTGAGAGTTTTCGC

CCCGAAGAACGTTTTCCAATGATGAGCACTTTTAAAGTTCTGCTATGTGG

CGCGGTATTATCCCGTGTTGACGCCGGGCAAGAGCAACTCGGTCGCCGCA

TACACTATTCTCAGAATGACTTGGTTGAGTACTCACCAGTCACAGAAAAG

CATCTTACGGATGGCATGACAGTAAGAGAATTATGCAGTGCTGCCATAAC

CATGAGTGATAACACTGCGGCCAACTTACTTCTGACAACGATCGGAGGAC

CGAAGGAGCTAACCGCTTTTTTGCACAACATGGGGGATCATGTAACTCGC

CTTGATCGTTGGGAACCGGAACTGAATGAAGCCgccgccaccatggaaaa

cgcccagaaaggtgaaatcatgccgaacatcccgcagatgtccgctttct

ggtatgccgtgcgtactgcggtgatcaacgccgccagcggtcgtcagact

gtcgatgaagccctgaaagacgcgcagactcgtatcaccaagtaa

Amino Acid Sequence:
                                           (SEQ ID NO: 36)
MKIKTGARILALSALTTMMFSASALAKIEEGKLVIWINGDKGYNGLAEVG

KKFEKDTGIKVTVEHPDKLEEKFPQVAATGDGPDIIFWAHDRFGGYAQSG

LLAEITPDKAFQDKLYPFTWDAVRYNGKLIAYPIAVEALSLIYNKDLLPN

PPKTWEEIPALDKELKAKGKSALMFNLQEPYFTWPLIAADGGYAFKYENG

KYDIKDVGVDNAGAKAGLTFLVDLIKNKHMNADTDYSIAEAAFNKGETAM

TINGPWAWSNIDTSKVNYGVTVLPTFKGQPSKPFVGVLSAGINAASPNKE

LAKEFLENYLLTDEGLEAVNKDKPLGAVALKSYEEELAKDPRNEAIPNDE

RDTTMPAAMATTLRKLLTGELLTLASRQQLIDWMEADKVAGPLLRSALPA

GWFIADKSGAGERGSRGIIAALGPDGKPSRIVVIYTTGSQATMDERNRQI

AEIGASLIKHWDKSHPETLVKVKDAEDQLGARVGYIELDLNSGKILESFR

PEERFPMMSTFKVLLCGAVLSRVDAGQEQLGRRIHYSQNDLVEYSPVTEK

HLTDGMTVRELCSAAITMSDNTAANLLLTTIGGPKELTAFLHNMGDHVTR
```

-continued

LDRWEPELNEAAATMENAQKGEIMPNIPQMSAFWYAVRTAVINAASGRQT

VDEALKDAQTRITK

Switch MBP 317-347:
Nucleic Acid Sequence:

(SEQ ID NO: 37)

atgaaaataaaaacaggtgcacgcatcctcgcattatccgcattaacgac gatgatgttttccgcctcggctctcgccaaaatcgaagaaggtaaactgg taatctggattaacggcgataaaggctataacggtctcgctgaagtcggt aagaaattcgagaaagataccggaattaaagtcaccgttgagcatccgga taaactggaagagaaattcccacaggttgcggcaactggcgatggccctg acattatcttctgggcacacgaccgctttggtggctacgctcaatctggc ctgttggctgaaatcaccccggacaaagcgttccaggacaagctgtatcc gtttacctgggatgccgtacgttacaacggcaagctgattgcttacccga tcgctgttgaagcgttatcgctgatttataacaaagatctgctgccgaac ccgccaaaaacctgggaagagatcccggcgctggataaagaactgaaagc gaaaggtaagagcgcgctgatgttcaacctgcaagaaccgtacttcacct ggccgctgattgctgctgacggggggttatgcgttcaagtatgaaaacggc aagtacgacattaaagacgtgggcgtggataacgctggcgcgaaagcggg tctgaccttcctggttgacctgattaaaaacaaacacatgaatgcagaca ccgattactccatcgcagaagctgcctttaataaaggcgaaacagcgatg accatcaacggcccgtgggcatggtccaacatcgacaccagcaaagtgaa ttatggtgtaacggtactgccgaccttcaagggtcaaccatccaaaccgt tcgttggcgtgctgagcgcaggtattaacgccgccagtccgaacaaagag ctggcgaaagagttcctcgaaaactatctgctgactgatgaaggtctgga agcggttaataaagacaaaccgctgggtgccgtagcgctgaagtcttacg aggaagagttggcgaaagatccacgtGCCATACCAAACGACGAGCGTGAC

ACCACGATGCCTGCAGCAATGGCAACAACGTTGCGCAAACTATTAACTGG

CGAACTACTTACTCTAGCTTCCCGGCAACAATTAATAGACTGGATGGAGG

CGGATAAAGTTGCAGGACCACTTCTGCGCTCGGCCCTTCCGGCTGGCTGG

TTTATTGCTGATAAATCTGGAGCCGGTGAGCGTGGGTCTCGCGGTATCAT

TGCAGCACTGGGGCCAGATGGTAAGCCCTCCCGTATCGTAGTTATCTACA

CGACGGGGAGTCAGGCAACTATGGATGAACGAAATAGACAGATCGCTGAG

ATAGGTGCCTCACTGATTAAGCATTGGGACAAGAGCCACCCAGAAACGCT

GGTGAAAGTAAAAGATGCTGAAGATCAGTTGGGTGCACGAGTGGGTTACA

TCGAACTGGATCTCAACAGCGGTAAGATCCTTGAGAGTTTTCGCCCCGAA

GAACGTTTTCCAATGATGAGCACTTTTAAAGTTCTGCTATGTGGCGCGGT

ATTATCCCGTGTTGACGCCGGGCAAGAGCAACTCGGTCGCCGCATACACT

ATTCTCAGAATGACTTGGTTGAGTACTCACCAGTCACAGAAAAGCATCTT

ACGGATGGCATGACAGTAAGAGAATTATGCAGTGCTGCCATAACCATGAG

TGATAACACTGCGGCCAACTTACTTCTGACAACGATCGGAGGACCGAAGG

AGCTAACCGCTTTTTTGCACAACATGGGGGATCATGTAACTCGCCTTGAT

CGTTGGGAACCGGAACTGAATGAAGCCgccgccaccatggaaaacgccca

-continued gaaaggtgaaatcatgccgaacatcccgcagatgtccgctttctggtatg ccgtgcgtactgcggtgatcaacgccgccagcggtcgtcagactgtcgat gaagccctgaaagacgcgcagactcgtatcaccaagtaa Amino Acid Sequence:

(SEQ ID NO: 38)

MKIKTGARILALSALTTMMFSASALAKIEEGKLVIWINGDKGYNGLAEVG

KKFEKDTGIKVTVEHPDKLEEKFPQVAATGDGPDIIFWAHDRFGGYAQSG

LLAEITPDKAFQDKLYPFTWDAVRYNGKLIAYPIAVEALSLIYNKDLLPN

PPKTWEEIPALDKELKAKGKSALMFNLQEPYFTWPLIAADGGYAFKYENG

KYDIKDVGVDNAGAKAGLTFLVDLIKNKHMNADTDYSIAEAAFNKGETAM

TINGPWAWSNIDTSKVNYGVTVLPTFKGQPSKPFVGVLSAGINAASPNKE

LAKEFLENYLLTDEGLEAVNKDKPLGAVALKSYEEELAKDPRAIPNDERD

TTMPAAMATTLRKLLTGELLTLASRQQLIDWMEADKVAGPLLRSALPAGW

FIADKSGAGERGSRGIIAALGPDGKPSRIVVIYTTGSQATMDERNRQIAE

IGASLIKHWDKSHPETLVKVKDAEDQLGARVGYIELDLNSGKILESFRPE

ERFPMMSTFKVLLCGAVLSRVDAGQEQLGRRIHYSQNDLVEYSPVTEKHL

TDGMTVRELCSAAITMSDNTAANLLLTTIGGPKELTAFLHNMGDHVTRLD

RWEPELNEAAATMENAQKGEIMPNIPQMSAFWYAVRTAVINAASGRQTVD

EALKDAQTRITK

Switch MBP 317-639:
Nucleic Acid Sequence:

(SEQ ID NO:39)

atgaaaataaaaacaggtgcacgcatcctcgcattatccgcattaacgac gatgatgttttccgcctcggctctcgccaaaatcgaagaaggtaaactgg taatctggattaacggcgataaaggctataacggtctcgctgaagtcggt aagaaattcgagaaagataccggaattaaagtcaccgttgagcatccgga taaactggaagagaaattcccacaggttgcggcaactggcgatggccctg acattatcttctgggcacacgaccgctttggtggctacgctcaatctggc ctgttggctgaaatcaccccggacaaagcgttccaggacaagctgtatcc gtttacctgggatgccgtacgttacaacggcaagctgattgcttacccga tcgctgttgaagcgttatcgctgatttataacaaagatctgctgccgaac ccgccaaaaacctgggaagagatcccggcgctggataaagaactgaaagc gaaaggtaagagcgcgctgatgttcaacctgcaagaaccgtacttcacct ggccgctgattgctgctgacggggggttatgcgttcaagtatgaaaacggc aagtacgacattaaagacgtgggcgtggataacgctggcgcgaaagcggg tctgaccttcctggttgacctgattaaaaacaaacacatgaatgcagaca ccgattactccatcgcagaagctgcctttaataaaggcgaaacagcgatg accatcaacggcccgtgggcatggtccaacatcgacaccagcaaagtgaa ttatggtgtaacggtactgccgaccttcaagggtcaaccatccaaaccgt tcgttggcgtgctgagcgcaggtattaacgccgccagtccgaacaaagag ctggcgaaagagttcctcgaaaactatctgctgactgatgaaggtctgga agcggttaataaagacaaaccgctgggtgccgtagcgctgaagtcttacg aggaagagttggcgaaagatccacgtCCAAACGACGAGCGTGACACCACG -continued

ATGCCTGCAGCAATGGCAACAACGTTGCGCAAACTATTAACTGGCGAACT

ACTTACTCTAGCTTCCCGGCAACAATTAATAGACTGGATGGAGGCGGATA

AAGTTGCAGGACCACTTCTGCGCTCGGCCCTTCCGGCTGGCTGGTTTATT

GCTGATAAATCTGGAGCCGGTGAGCGTGGGTCTCGCGGTATCATTGCAGC

ACTGGGGCCAGATGGTAAGCCCTCCCGTATCGTAGTTATCTACACGACGG

GGAGTCAGGCAACTATGGATGAACGAAATAGACAGATCGCTGAGATAGGT

GCCTCACTGATTAAGCATTGGGACAAGAGCCACCCAGAAACGCTGGTGAA

AGTAAAAGATGCTGAAGATCAGTTGGGTGCACGAGTGGGTTACATCGAAC

TGGATCTCAACAGCGGTAAGATCCTTGAGAGTTTTCGCCCCGAAGAACGT

TTTCCAATGATGAGCACTTTTAAAGTTCTGCTATGTGGCGCGGTATTATC

CCGTGTTGACGCCGGGCAAGAGCAACTCGGTCGCCGCATACACTATTCTC

AGAATGACTTGGTTGAGTACTCACCAGTCACAGAAAAGCATCTTACGGAT

GGCATGACAGTAAGAGAATTATGCAGTGCTGCCATAACCATGAGTGATAA

CACTGCGGCCAACTTACTTCTGACAACGATCGGAGGACCGAAGGAGCTAA

CCGCTTTTTTGCACAACATGGGGGATCATGTAACTCGCCTTGATCGTTGG

GAACCGGAACTGAATGAAGCCgccgccaccatggaaaacgcccagaaagg tgaaatcatgccgaacatcccgcagatgtccgctttctggtatgccgtgc gtactgcggtgatcaacgccgccagcggtcgtcagactgtcgatgaagcc ctgaaagacgcgcagactcgtatcaccaagtaa Amino Acid Sequence:

(SEQ ID NO: 40)

MKIKTGARILALSALTTMMFSASALAKIEEGKLVIWINGDKGYNGLAEVG

KKFEKDTGIKVTVEHPDKLEEKFPQVAATGDGPDIIFWAHDRFGGYAQSG

LLAEITPDKAFQDKLYPFTWDAVRYNGKLIAYPIAVEALSLIYNKDLLPN

PPKTWEEIPALDKELKAKGKSALMFNLQEPYFTWPLIAADGGYAFKYENG

KYDIKDVGVDNAGAKAGLTFLVDLIKNKHMNADTDYSIAEAAFNKGETAM

TINGPWAWSNIDTSKVNYGVTVLPTFKGQPSKPFVGVLSAGINAASPNKE

LAKEFLENYLLTDEGLEAVNKDKPLGAVALKSYEEELAKDPRPNDERDTT

MPAAMATTLRKLLTGELLTLASRQQLIDWMEADKVAGPLLRSALPAGWFI

ADKSGAGERGSRGIIAALGPDGKPSRIVVIYTTGSQATMDERNRQIAEIG

ASLIKHWDKSHPETLVKVKDAEDQLGARVGYIELDLNSGKILESFRPEER

FPMMSTFKVLLCGAVLSRVDAGQEQLGRRIHYSQNDLVEYSPVTEKHLTD

GMTVRELCSAAITMSDNTAANLLLTTIGGPKELTAFLHNMGDHVTRLDRW

EPELNEAAATMENAQKGEIMPNIPQMSAFWYAVRTAVINAASGRQTVDEA

LKDAQTRITK

Switch MBP 317-694:

Nucleic Acid Sequence:

(SEQ ID NO: 41)

atgaaaataaaaacaggtgcacgcatcctcgcattatccgcattaacgac gatgatgttttccgcctcggctctcgccaaaatcgaagaaggtaaactgg taatctggattaacggcgataaaggctataacggtctcgctgaagtcggt aagaaattcgagaaagataccggaattaaagtcaccgttgagcatccgga taaactggaagagaaattcccacaggttgcggcaactggcgatggccctg acattatcttctgggcacacgaccgctttggtggctacgctcaatctggc ctgttggctgaaatcaccccggacaaagcgttccaggacaagctgtatcc gtttacctgggatgccgtacgttacaacggcaagctgattgcttacccga tcgctgttgaagcgttatcgctgatttataacaaagatctgctgccgaac ccgccaaaaacctgggaagagatcccggcgctggataaagaactgaaagc gaaaggtaagagcgcgctgatgttcaacctgcaagaaccgtacttcacct ggccgctgattgctgctgacgggggttatgcgttcaagtatgaaaacggc aagtacgacattaaagacgtgggcgtggataacgctggcgcgaaagcggg tctgaccttcctggttgacctgattaaaaacaaacacatgaatgcagaca ccgattactccatcgcagaagctgcctttaataaaggcgaaacagcgatg accatcaacggcccgtgggcatggtccaacatcgacaccagcaaagtgaa ttatggtgtaacggtactgccgaccttcaagggtcaaccatccaaaccgt tcgttggcgtgctgagcgcaggtattaacgccgccagtccgaacaaagag ctggcgaaagagttcctcgaaaactatctgctgactgatgaaggtctgga agcggttaataaagacaaaccgctgggtgccgtagcgctgaagtcttacg aggaagagttggcgaaagatccacgtATACCAAACGACGAGCGTGACACC

ACGATGCCTGCAGCAATGGCAACAACGTTGCGCAAACTATTAACTGGCGA

ACTACTTACTCTAGCTTCCCGGCAACAATTAATAGACTGGATGGAGGCGG

ATAAAGTTGCAGGACCACTTCTGCGCTCGGCCCTTCCGGCTGGCTGGTTT

ATTGCTGATAAATCTGGAGCCGGTGAGCGTGGGTCTCGCGGTATCATTGC

AGCACTGGGGCCAGATGGTAAGCCCTCCCGTATCGTAGTTATCTACACGA

CGGGGAGTCAGGCAACTATGGATGAACGAAATAGACAGATCGCTGAGATA

GGTGCCTCACTGATTAAGCATTGGGACAAGAGCCACCCAGAAACGCTGGT

GAAAGTAAAAGATGCTGAAGATCAGTTGGGTGCACGAGTGGGTTACATCG

AACTGGATCTCAACAGCGGTAAGATCCTTGAGAGTTTTCGCCCCGAAGAA

CGTTTTCCAATGATGAGCACTTTTAAAGTTCTGCTATGTGGCGCGGTATT

ATCCCGTGTTGACGCCGGGCAAGAGCAACTCGGTCGCCGCATACACTATT

CTCAGAATGACTTGGTTGAGTACTCACCAGTCACAGAAAAGCATCTTACG

GATGGCATGACAGTAAGAGAATTATGCAGTGCTGCCATAACCATGAGTGA

TAACACTGCGGCCAACTTACTTCTGACAACGATCGGAGGACCGAAGGAGC

TAACCGCTTTTTTGCACAACATGGGGGATCATGTAACTCGCCTTGATCGT

TGGGAACCGGAACTGAATGAAGCCgccgccaccatggaaaacgcccagaa aggtgaaatcatgccgaacatcccgcagatgtccgctttctggtatgccg tgcgtactgcggtgatcaacgccgccagcggtcgtcagactgtcgatgaa gccctgaaagacgcgcagactcgtatcaccaagtaa Amino Acid Sequence:

(SEQ ID NO: 42)

MKIKTGARILALSALTTMMFSASALAKIEEGKLVIWINGDKGYNGLAEVG

KKFEKDTGIKVTVEHPDKLEEKFPQVAATGDGPDIIFWAHDRFGGYAQSG

LLAEITPDKAFQDKLYPFTWDAVRYNGKLIAYPIAVEALSLIYNKDLLPN

PPKTWEEIPALDKELKAKGKSALMFNLQEPYFTWPLIAADGGYAFKYENG

KYDIKDVGVDNAGAKAGLTFLVDLIKNKHMNADTDYSIAEAAFNKGETAM

-continued

TINGPWAWSNIDTSKVNYGVTVLPTFKGQPSKPFVGVLSAGINAASPNKE

LAKEFLENYLLTDEGLEAVNKDKPLGAVALKSYEEELAKDPRIPNDERDT

TMPAAMATTLRKLLTGELLTLASRQQLIDWMEADKVAGPLLRSALPAGWF

IADKSGAGERGSRGIIAALGPDGKPSRIVVIYTTGSQATMDERNRQIAEI

GASLIKHWDKSHPETLVKVKDAEDQLGARVGYIELDLNSGKILESFRPEE

RFPMMSTFKVLLCGAVLSRVDAGQEQLGRRIHYSQNDLVEYSPVTEKHLT

DGMTVRELCSAAITMSDNTAANLLLTTIGGPKELTAFLHNMGDHVTRLDR

WEPELNEAAATMENAQKGEIMPNIPQMSAFWYAVRTAVINAASGRQTVDE

ALKDAQTRITK

Switch BLA168-88:
Nucleic Acid Sequence:

(SEQ ID NO: 43)

atgaaaataaaaacaggtgcacgcatcctcgcattatccgcattaacgac gatgatgttttccgcctcggctctcgccaaaatcgaagaaggtaaactgg taatctggattaacggcgataaaggctataacggtctcgctgaagtcggt aagaaattcgagaaagataccggaattaaagtcaccgttgagcatccgga taaactggaagagaaattcccacaggttgcggcaactggcgatggccctg acattatcttctgggcacacgaccgctttggtggctacgctcaatctggc ctgttggctgaaatcaccccggacaaagcgttccaggacaagctgtatcc gtttacctgggatgccgtacgttacaacggcaagctgattgcttacccga tcgctgttgaagcgttatcgctgatttataacaaagatctgctgccgaac ccgccaaaaacctgggaagagatcccggcgctggataaagaactgaaagc gaaaggtaagagcgcgctgatgttcaacctgcaagaaccgtacttcacct ggccgctgattgctgctgacgggggttatgcgttcaagtatgaaaacggc aagtacgacattaaagacgtgggcgtggataacgctggcgcgaaagcggg tctgaccttcctggttAATGAAGCCATACCAAACGACGAGCGTGACACCA

CGATGCCTGCAGCAATGGCAACAACGTTGCGCAAACTATTAACTGGCGAA

CTACTTACTCTAGCTTCCCGGCAACAATTAATAGACTGGATGGAGGCGGA

TAAAGTTGCAGGACCACTTCTGCGCTCGGCCCTTCCGGCTGGCTGGTTTA

TTGCTGATAAATCTGGAGCCGGTGAGCGTGGGTCTCGCGGTATCATTGCA

GCACTGGGGCCAGATGGTAAGCCCTCCCGTATCGTAGTTATCTACACGAC

GGGGAGTCAGGCAACTATGGATGAACGAAATAGACAGATCGCTGAGATAG

GTGCCTCACTGATTAAGCATTGGGACAAGAGCCACCCAGAAACGCTGGTG

AAAGTAAAAGATGCTGAAGATCAGTTGGGTGCACGAGTGGGTTACATCGA

ACTGGATCTCAACAGCGGTAAGATCCTTGAGAGTTTTCGCCCCGAAGAAC

GTTTTCCAATGATGAGCACTTTTAAAGTTCTGCTATGTGGCGCGGTATTA

TCCCGTGTTGACGCCGGGCAAGAGCAACTCGGTCGCCGCATACACTATTC

TCAGAATGACTTGGTTGAGTACTCACCAGTCACAGAAAAGCATCTTACGG

ATGGCATGACAGTAAGAGAATTATGCAGTGCTGCCATAACCATGAGTGAT

AACACTGCGGCCAACTTACTTCTGACAACGATCGGAGGACCGAAGGAGCT

AACCGCTTTTTTGCACAACATGGGGGATCATGTAACTCGCCTTGATCGTT

GGGAACCGGAACTGAATGAAGCCgttgacctgattaaaaacaaacacatg aatgcagacaccgattactccatcgcagaagctgcctttaataaaggcga aacagcgatgaccatcaacggcccgtgggcatggtccaacatcgacacca gcaaagtgaattatggtgtaacggtactgccgaccttcaagggtcaacca tccaaaccgttcgttggcgtgctgagcgcaggtattaacgccgccagtcc gaacaaagagctggcgaaagagttcctcgaaaactatctgctgactgatg aaggtctggaagcggttaataaagacaaaccgctgggtgccgtagcgctg aagtcttacgaggaagagttggcgaaagatccacgtattgccgccaccat ggaaaacgcccagaaaggtgaaatcatgccgaacatcccgcagatgtccg ctttctggtatgccgtgcgtactgcggtgatcaacgccgccagcggtcgt cagactgtcgatgaagccctgaaagacgcgcagactcgtatcaccaagta a Amino Acid Sequence:

(SEQ ID NO: 44)

MKIKTGARILALSALTTMMFSASALAKIEEGKLVIWINGDKGYNGLAEVG

KKFEKDTGIKVTVEHPDKLEEKFPQVAATGDGPDIIFWAHDRFGGYAQSG

LLAEITPDKAFQDKLYPFTWDAVRYNGKLIAYPIAVEALSLIYNKDLLPN

PPKTWEEIPALDKELKAKGKSALMFNLQEPYFTWPLIAADGGYAFKYENG

KYDIKDVGVDNAGAKAGLTFLVNEAIPNDERDTTMPAAMATTLRKLLTGE

LLTLASRQQLIDWMEADKVAGPLLRSALPAGWFIADKSGAGERGSRGIIA

ALGPDGKPSRIVVIYTTGSQATMDERNRQIAEIGASLIKHWDKSHPETLV

KVKDAEDQLGARVGYIELDLNSGKILESFRPEERFPMMSTFKVLLCGAVL

SRVDAGQEQLGRRIHYSQNDLVEYSPVTEKHLTDGMTVRELCSAAITMSD

NTAANLLLTTIGGPKELTAFLHNMGDHVTRLDRWEPELNEAVDLIKNKHM

NADTDYSIAEAAFNKGETAMTINGPWAWSNIDTSKVNYGVTVLPTFKGQP

SKPFVGVLSAGINAASPNKELAKEFLENYLLTDEGLEAVNKDKPLGAVAL

KSYEEELAKDPRIAATMENAQKGEIMPNIPQMSAFWYAVRTAVINAASGR

QTVDEALKDAQTRITK

Switch BLA168-45:
Nucleic Acid Sequence:

(SEQ ID NO: 45)

atgaaaataaaaacaggtgcacgcatcctcgcattatccgcattaacgac gatgatgttttccgcctcggctctcgccaaaatcgaagaaggtaaactgg taatctggattaacggcgataaaggctataacggtctcgctgaagtcggt aagaaattcgagaaagataccggaattaaagtcaccgttgagcatccgga taaactggaagagaaattcccacaggttgcggcaactggcgatggccctg acattatcttctgggcacacgaccgctttggtggctacgctcaatctggc ctgttggctgaaatcaccccggacaaagcgttccaggacaagctgtatcc gtttacctgggatgccgtacgttacaacggcaagctgattgcttacccga tcgctgttgaagcgttatcgctgatttataacaaagatctgctgccgaac ccgccaaaaacctgggaagagatcccggcgctggataaagaactgaaagc gaaaggtaagagcgcgctgatgttcaacctgcaagaaccgtacttcacct ggccgctgattgctgctgacgggggttatgcgttcaagtatgaaaacggc aagtacgacattaaagacgtgggcgtggataacgctggcgcgaaagcggg -continued tctgaccttcctggttgacctgattAATGAAGCCATACCAAACGACGAGC

GTGACACCACGATGCCTGCAGCAATGGCAACAACGTTGCGCAAACTATTA

ACTGGCGAACTACTTACTCTAGCTTCCCGGCAACAATTAATAGACTGGAT

GGAGGCGGATAAAGTTGCAGGACCACTTCTGCGCTCGGCCCTTCCGGCTG

GCTGGTTTATTGCTGATAAATCTGGAGCCGGTGAGCGTGGGTCTCGCGGT

ATCATTGCAGCACTGGGGCCAGATGGTAAGCCCTCCCGTATCGTAGTTAT

CTACACGACGGGGAGTCAGGCAACTATGGATGAACGAAATAGACAGATCG

CTGAGATAGGTGCCTCACTGATTAAGCATTGGGACAAGAGCCACCCAGAA

ACGCTGGTGAAAGTAAAAGATGCTGAAGATCAGTTGGGTGCACGAGTGGG

TTACATCGAACTGGATCTCAACAGCGGTAAGATCCTTGAGAGTTTTCGCC

CCGAAGAACGTTTTCCAATGATGAGCACTTTTAAAGTTCTGCTATGTGGC

GCGGTATTATCCCGTGTTGACGCCGGGCAAGAGCAACTCGGTCGCCGCAT

ACACTATTCTCAGAATGACTTGGTTGAGTACTCACCAGTCACAGAAAAGC

ATCTTACGGATGGCATGACAGTAAGAGAATTATGCAGTGCTGCCATAACC

ATGAGTGATAACACTGCGGCCAACTTACTTCTGACAACGATCGGAGGACC

GAAGGAGCTAACCGCTTTTTTGCACAACATGGGGGATCATGTAACTCGCC

TTGATCGTTGGGAACCGGAACTGAATGAAGCCcacatgaatgcagacacc gattactccatcgcagaagctgcctttaataaaggcgaaacagcgatgac catcaacggcccgtgggcatggtccaacatcgacaccagcaaagtgaatt atggtgtaacggtactgccgaccttcaagggtcaaccatccaaaccgttc gttggcgtgctgagcgcaggtattaacgccgccagtccgaacaaagagct ggcgaaagagttcctcgaaaactatctgctgactgatgaaggtctggaag cggttaataaagacaaaccgctgggtgccgtagcgctgaagtcttacgag gaagagttggcgaaagatccacgtattgccgccaccatggaaaacgccca gaaaggtgaaatcatgccgaacatcccgcagatgtccgctttctggtatg ccgtgcgtactgcggtgatcaacgccgccagcggtcgtcagactgtcgat gaagccctgaaagacgcgcagactcgtatcaccaagtaa Amino Acid Sequence:

(SEQ ID NO: 46)

MKIKTGARILALSALTTMMFSASALAKIEEGKLVIWINGDKGYNGLAEVG

KKFEKDTGIKVTVEHPDKLEEKFPQVAATGDGPDIIFWAHDRFGGYAQSG

LLAEITPDKAFQDKLYPFTWDAVRYNGKLIAYPIAVEALSLIYNKDLLPN

PPKTWEEIPALDKELKAKGKSALMFNLQEPYFTWPLIAADGGYAFKYENG

KYDIKDVGVDNAGAKAGLTFLVDLINEAIPNDERDTTMPAAMATTLRKLL

TGELLTLASRQQLIDWMEADKVAGPLLRSALPAGWFIADKSGAGERGSRG

IIAALGPDGKPSRIVVIYTTGSQATMDERNRQIAEIGASLIKHWDKSHPE

TLVKVKDAEDQLGARVGYIELDLNSGKILESFRPEERFPMMSTFKVLLCG

AVLSRVDAGQEQLGRRIHYSQNDLVEYSPVTEKHLTDGMTVRELCSAAIT

MSDNTAANLLLTTIGGPKELTAFLHNMGDHVTRLDRWEPELNEAHMNADT

DYSIAEAAFNKGETAMTINGPWAWSNIDTSKVNYGVTVLPTFKGQPSKPF

VGVLSAGINAASPNKELAKEFLENYLLTDEGLEAVNKDKPLGAVALKSYE

-continued

EELAKDPRIAATMENAQKGEIMPNIPQMSAFWYAVRTAVINAASGRQTVD

EALKDAQTRITK

Switch BLA168-69:
Nucleic Acid Sequence:

(SEQ ID NO: 47)

atgaaaataaaaacaggtgcacgcatcctcgcattatccgcattaacgac gatgatgttttccgcctcggctctcgccaaaatcgaagaaggtaaactgg taatctggattaacggcgataaaggctataacggtctcgctgaagtcggt aagaaattcgagaaagataccggaattaaagtcaccgttgagcatccgga taaactggaagagaaattcccacaggttgcggcaactggcgatggccctg acattatcttctgggcacacgaccgctttggtggctacgctcaatctggc ctgttggctgaaatcaccccggacaaagcgttccaggacaagctgtatcc gtttacctgggatgccgtacgttacaacggcaagctgattgcttacccga tcgctgttgaagcgttatcgctgatttataacaaagatctgctgccgaac ccgccaaaaacctgggaagagatcccggcgctggataaagaactgaaagc gaaaggtaagagcgcgctgatgttcaacctgcaagaaccgtacttcacct ggccgctgattgctgctgacggggttatgcgttcaagtatgaaaacggc aagtacgacattaaagacgtgggcgtggataacgctggcgcgaaagcggg tctgaccttcctggttgacctgattaaaaacaaacacatgaatgcagaca ccgattactccatcgcagaagctgcctttaataaaggcgaaacagcgatg accatcaacggcccgtgggcatggtccaacatcgacaccagcaaagtgaa ttatggtgtaacggtactgccgaccttcaagggtcaaccatccaaaccgt tcgttggcgtgctgagcgcaggtattaacgccgccagtccgaacaaagag ctggcgaaagagttcctcgaaaactatctgctgactgatgaaggtctgga agcggttaataaagacaaaccgctgggtgccgtagcgctgaagtcttacg aggaagagttggcgaaagatccacgtAATGAAGCCATACCAAACGACGAG

CGTGACACCACGATGCCTGCAGCAATGGCAACAACGTTGCGCAAACTATT

AACTGGCGAACTACTTACTCTAGCTTCCCGGCAACAATTAATAGACTGGA

TGGAGGCGGATAAAGTTGCAGGACCACTTCTGCGCTCGGCCCTTCCGGCT

GGCTGGTTTATTGCTGATAAATCTGGAGCCGGTGAGCGTGGGTCTCGCGG

TATCATTGCAGCACTGGGGCCAGATGGTAAGCCCTCCCGTATCGTAGTTA

TCTACACGACGGGGAGTCAGGCAACTATGGATGAACGAAATAGACAGATC

GCTGAGATAGGTGCCTCACTGATTAAGCATTGGGACAAGAGCCACCCAGA

AACGCTGGTGAAAGTAAAAGATGCTGAAGATCAGTTGGGTGCACGAGTGG

GTTACATCGAACTGGATCTCAACAGCGGTAAGATCCTTGAGAGTTTTCGC

CCCGAAGAACGTTTTCCAATGATGAGCACTTTTAAAGTTCTGCTATGTGG

CGCGGTATTATCCCGTGTTGACGCCGGGCAAGAGCAACTCGGTCGCCGCA

TACACTATTCTCAGAATGACTTGGTTGAGTACTCACCAGTCACAGAAAAG

CATCTTACGGATGGCATGACAGTAAGAGAATTATGCAGTGCTGCCATAAC

CATGAGTGATAACACTGCGGCCAACTTACTTCTGACAACGATCGGAGGAC

CGAAGGAGCTAACCGCTTTTTTGCACAACATGGGGGATCATGTAACTCGC

CTTGATCGTTGGGAACCGGAACTGAATGAAGCCaccatggaaaacgccca

-continued gaaaggtgaaatcatgccgaacatcccgcagatgtccgctttctggtatg ccgtgcgtactgcggtgatcaacgcCgccagcggtcgtcagactgtcgat gaagccctgaaagacgcgcagactcgtatcaccaagtaa Amino Acid Sequence:

(SEQ ID NO: 48)

MKIKTGARILALSALTTMMFSASALAKIEEGKLVIWINGDKGYNGLAEVG

KKFEKDTGIKVTVEHPDKLEEKFPQVAATGDGPDIIFWAHDRFGGYAQSG

LLAEITPDKAFQDKLYPFTWDAVRYNGKLIAYPIAVEALSLIYNKDLLPN

PPKTWEEIPALDKELKAKGKSALMFNLQEPYFTWPLIAADGGYAFKYENG

KYDIKDVGVDNAGAKAGLTFLVDLIKNKHMNADTDYSIAEAAFNKGETAM

TINGPWAWSNIDTSKVNYGVTVLPTFKGQPSKPFVGVLSAGINAASPNKE

LAKEFLENYLLTDEGLEAVNKDKPLGAVALKSYEEELAKDPRNEAIPNDE

RDTTMPAAMATTLRKLLTGELLTLASRQQLIDWMEADKVAGPLLRSALPA

GWFIADKSGAGERGSRGIIAALGPDGKPSRIVVIYTTGSQATMDERNRQI

AEIGASLIKHWDKSHPETLVKVKDAEDQLGARVGYIELDLNSGKILESFR

PEERFPMMSTFKVLLCGAVLSRVDAGQEQLGRRIHYSQNDLVEYSPVTEK

HLTDGMTVRELCSAAITMSDNTAANLLLTTIGGPKELTAFLHNMGDHVTR

LDRWEPELNEATMENAQKGEIMPNIPQMSAFWYAVRTAVINAASGRQTVD

EALKDAQTRITK

Switch BLA168-86:

Nucleic Acid Sequence:

(SEQ ID NO: 49)

atgaaaataaaaacaggtgcacgcatcctcgcattatccgcattaacgac gatgatgttttccgcctcggctctcgccaaaatcgaagaaggtaaactgg taatctggattaacggcgataaaggctataacggtctcgctgaagtcggt aagaaattcgagaaagataccggaattaaagtcaccgttgagcatccgga taaactggaagagaaattcccacaggttgcggcaactggcgatggccctg acattatcttctgggcacacgaccgctttggtggctacgctcaatctggc ctgttggctgaaatcaccccggacaaagcgttccaggacaagctgtatcc gtttacctgggatgccgtacgttacaacggcaagctgattgcttacccga tcgctgttgaagcgttatcgctgatttataacaaagatctgctgccgaac ccgccaaaaacctgggaagagatcccggcgctggataaagaactgaaagc gaaaggtaagagcgcgctgatgttcaacctgcaagaaccgtacttcacct ggccgctgattgctgctgacggggttatgcgttcaagtatgaaaacggc aagtacgacattaaagacgtgggcgtggataacgctggcgcgaaagcggg tctgaccttcctggttgacctgattaaaaacaaacacatgaatgcagaca ccgattactccatcgcagaagctgcctttaataaaggcgaaacagcgatg accatcaacggcccgtgggcatggtccaacatcgacaccagcaaagtgaa ttatggtgtaacggtactgccgaccttcaagggtcaaccatccaaaccgt tcgttggcgtgctgagcgcaggtattaacgccgccagtccgaacaaagag ctggcgaaagagttcctcgaaaactatctgctgactgatgaaggtctgga agcggttaataaagacaaaccgctgggtgccgtagcgctgaagtcttacg aggaagagttggcgaaagatccacgtattgccgccaccAATGAAGCCATA

CCAAACGACGAGCGTGACACCACGATGCCTGCAGCAATGGCAACAACGTT

GCGCAAACTATTAACTGGCGAACTACTTACTCTAGCTTCCCGGCAACAAT

TAATAGACTGGATGGAGGCGGATAAAGTTGCAGGACCACTTCTGCGCTCG

GCCCTTCCGGCTGGCTGGTTTATTGCTGATAAATCTGGAGCCGGTGAGCG

TGGGTCTCGCGGTATCATTGCAGCACTGGGGCCAGATGGTAAGCCCTCCC

GTATCGTAGTTATCTACACGACGGGGAGTCAGGCAACTATGGATGAACGA

AATAGACAGATCGCTGAGATAGGTGCCTCACTGATTAAGCATTGGGACAA

GAGCCACCCAGAAACGCTGGTGAAAGTAAAAGATGCTGAAGATCAGTTGG

GTGCACGAGTGGGTTACATCGAACTGGATCTCAACAGCGGTAAGATCCTT

GAGAGTTTTCGCCCCGAAGAACGTTTTCCAATGATGAGCACTTTTAAAGT

TCTGCTATGTGGCGCGGTATTATCCCGTGTTGACGCCGGGCAAGAGCAAC

TCGGTCGCCGCATACACTATTCTCAGAATGACTTGGTTGAGTACTCACCA

GTCACAGAAAAGCATCTTACGGATGGCATGACAGTAAGAGAATTATGCAG

TGCTGCCATAACCATGAGTGATAACACTGCGGCCAACTTACTTCTGACAA

CGATCGGAGGACCGAAGGAGCTAACCGCTTTTTTGCACAACATGGGGGAT

CATGTAACTCGCCTTGATCGTTGGGAACCGGAACTGAATGAAGCCgccgc caccatggaaaacgcccagaaaggtgaaatcatgccgaacatcccgcaga tgtccgctttctggtatgccgtgcgtactgcggtgatcaacgccgccagc ggtcgtcagactgtcgatgaagccctgaaagacgcgcagactcgtatcac caagtaa Amino Acid Sequence:

(SEQ ID NO: 50)

MKIKTGARILALSALTTMMFSASALAKIEEGKLVIWINGDKGYNGLAEVG

KKFEKDTGIKVTVEHPDKLEEKFPQVAATGDGPDIIFWAHDRFGGYAQSG

LLAEITPDKAFQDKLYPFTWDAVRYNGKLIAYPIAVEALSLIYNKDLLPN

PPKTWEEIPALDKELKAKGKSALMFNLQEPYFTWPLIAADGGYAFKYENG

KYDIKDVGVDNAGAKAGLTFLVDLIKNKHMNADTDYSIAEAAFNKGETAM

TINGPWAWSNIDTSKVNYGVTVLPTFKGQPSKPFVGVLSAGINAASPNKE

LAKEFLENYLLTDEGLEAVNKDKPLGAVALKSYEEELAKDPRIAATNEAI

PNDERDTTMPAAMATTLRKLLTGELLTLASRQQLIDWMEADKVAGPLLRS

ALPAGWFIADKSGAGERGSRGIIAALGPDGKPSRIVVIYTTGSQATMDER

NRQIAEIGASLIKHWDKSHPETLVKVKDAEDQLGARVGYIELDLNSGKIL

ESFRPEERFPMMSTFKVLLCGAVLSRVDAGQEQLGRRIHYSQNDLVEYSP

VTEKHLTDGMTVRELCSAAITMSDNTAANLLLTTIGGPKELTAFLHNMGD

HVTRLDRWEPELNEAAATMENAQKGEIMPNIPQMSAFWYAVRTAVINAAS

GRQTVDEALKDAQTRITK

Switch BLA168-89:

Nucleic Acid Sequence:

(SEQ ID NO: 51)

atgaaaataaaaacaggtgcacgcatcctcgcattatccgcattaacgac gatgatgttttccgcctcggctctcgccaaaatcgaagaaggtaaactgg taatctggattaacggcgataaaggctataacggtctcgctgaagtcggt aagaaattcgagaaagataccggaattaaagtcaccgttgagcatccgga -continued taaactggaagagaaattcccacaggttgcggcaactggcgatggccctg
acattatcttctgggcacacgaccgctttggtggctacgctcaatctggc
ctgttggctgaaatcaccccggacaaagcgttccaggacaagctgtatcc
gtttacctgggatgccgtacgttacaacggcaagctgattgcttacccga
tcgctgttgaagcgttatcgctgatttataacaaagatctgctgccgaac
ccgccaaaaacctgggaagagatcccggcgctggataaagaactgaaagc
gaaaggtaagagcgcgctgatgttcaacctgcaagaaccgtacttcacct
ggccgctgattgctgctgacgggggttatgcgttcaagtatgaaaacggc
aagtacgacattaaagacgtgggcgtggataacgctggcgcgaaagcggg
tctgaccttcctggttgacctgattaaaaacaaacacatgaatgcagaca
ccgattactccatcgcagaagctgcctttaataaaggcgaaacagcgatg
accatcaacggcccgtgggcatggtccaacatcgacaccagcaaagtgaa
ttatggtgtaacggtactgccgaccttcaagggtcaaccatccaaaccgt
tcgttggcgtgctgagcgcaggtattaacgccgccagtccgaacaaagag
ctggcgaaagagttcctcgaaaactatctgctgactgatgaaggtctgga
agcggttaataaagacaaaccgctgggtgccgtagcgctgaagtcttacg
aggaagagttggcgaaagatccacgtAATGAAGCCATACCAAACGACGAG
CGTGACACCACGATGCCTGCAGCAATGGCAACAACGTTGCGCAAACTATT
AACTGGCGAACTACTTACTCTAGCTTCCCGGCAACAATTAATAGACTGGA
TGGAGGCGGATAAAGTTGCAGGACCACTTCTGCGCTCGGCCCTTCCGGCT
GGCTGGTTTATTGCTGATAAATCTGGAGCCGGTGAGCGTGGGTCTCGCGG
TATCATTGCAGCACTGGGGCCAGATGGTAAGCCCTCCCGTATCGTAGTTA
TCTACACGACGGGGAGTCAGGCAACTATGGATGAACGAAATAGACAGATC
GCTGAGATAGGTGCCTCACTGATTAAGCATTGGGACAAGAGCCACCCAGA
AACGCTGGTGAAAGTAAAAGATGCTGAAGATCAGTTGGGTGCACGAGTGG
GTTACATCGAACTGGATCTCAACAGCGGTAAGATCCTTGAGAGTTTTCGC
CCCGAAGAACGTTTTCCAATGATGAGCACTTTTAAAGTTCTGCTATGTGG
CGCGGTATTATCCCGTGTTGACGCCGGGCAAGAGCAACTCGGTCGCCGCA
TACACTATTCTCAGAATGACTTGGTTGAGTACTCACCAGTCACAGAAAAG
CATCTTACGGATGGCATGACAGTAAGAGAATTATGCAGTGCTGCCATAAC
CATGAGTGATAACACTGCGGCCAACTTACTTCTGACAACGATCGGAGGAC
CGAAGGAGCTAACCGCTTTTTTGCACAACATGGGGGATCATGTAACTCGC
CTTGATCGTTGGGAACCGGAACTGAATGAAGCCaccatggaaaacgccca
gaaaggtgaaatcatgccgaacatcccgcagatgtccgctttctggtatg
ccgtgcgtactgcggtgatcaacgccgccagcggtcgtcagactgtcgat
gaagccctgaaagacgcgcagactcgtatcaccaagtaa Amino Acid Sequence:

(SEQ ID NO: 52)

MKIKTGARILALSALTTMMFSASALAKIEEGKLVIWINGDKGYNGLAEVG
KKFEKDTGIKVTVEHPDKLEEKFPQVAATGDGPDIIFWAHDRFGGYAQSG
LLAEITPDKAFQDKLYPFTWDAVRYNGKLIAYPIAVEALSLIYNKDLLPN
PPKTWEEIPALDKELKAKGKSALMFNLQEPYFTWPLIAADGGYAFKYENG

-continued

KYDIKDVGVDNAGAKAGLTFLVDLIKNKHMNADTDYSIAEAAFNKGETAM
TINGPWAWSNIDTSKVNYGVTVLPTFKGQPSKPFVGVLSAGINAASPNKE
LAKEFLENYLLTDEGLEAVNKDKPLGAVALKSYEEELAKDPRNEAIPNDE
RDTTMPAAMATTLRKLLTGELLTLASRQQLIDWMEADKVAGPLLRSALPA
GWFIADKSGAGERGSRGIIAALGPDGKPSRIVVIYTTGSQATMDERNRQI
AEIGASLIKHWDKSHPETLVKVKDAEDQLGARVGYIELDLNSGKILESFR
PEERFPMMSTFKVLLCGAVLSRVDAGQEQLGRRIHYSQNDLVEYSPVTEK
HLTDGMTVRELCSAAITMSDNTAANLLLTTIGGPKELTAFLHNMGDHVTR
LDRWEPELNEATMENAQKGEIMPNIPQMSAFWYAVRTAVINAASGRQTVD
EALKDAQTRITK

Sucrose Switch 5-7:

Nucleic Acid Sequence:

(SEQ ID NO: 53)

atgaaaataaaaacaggtgcacgcatcctcgcattatccgcattaacgac
gatgatgttttccgcctcggctctcgccaaaatcgaagaaggtaaactgg
taatctggattaacggcttgtttggctataacggtctcgctgaagtcggt
aagaaattcgagaaagataccggaattaaagtcaccgttgagcatccgga
taaactggaagagaaattcccacaggttgcggcaactggcgatggccctg
acattatcttctatgcacacgaccgctttggtggctacgctcaatctggc
ctgttggctgaaatcaccccggacaaagcgttccaggacaagctgtatcc
gtttacctgggatgccgtacgttacaacggcaagctgattgcttacccga
tcgctgtttatgcgttatcgctgatttataacaaagatctgctgccgaac
ccgccaaaaacctgggaagagatcccggcgctggataaagaactgaaagc
gaaaggtaagagcgcgctgatgttcaacctgcaagaaccgtacttcacct
ggccgctgattgctgctgacgggggttatgcgttcaagtatgaaaacggc
aagtacgacattaaagacgtgggcgtggataacgctggcgcgaaagcggg
tctgaccttcctggttgacctgattaaaaacaaacacatgaatgcagaca
ccgattactccatcgcagaagctgcctttaataaaggcgaaacagcgatg
accatcaacggcccgtgggcatggtccaacatcgacaccagcaaagtgaa
ttatggtgtaacggtactgccgaccttcaagggtcaaccatccaaaccgt
tcgttggcgtgctgagcgcaggtattaacgccgccagtccgaacaaagag
ctggcgaaagagttcctcgaaaactatctgctgactgatgaaggtctgga
agcggttaataaagacaaaccgctgggtgccgtagcgctgaagtcttacg
aggaagagttggcgaaagatccacgtGCCATACCAAACGACGAGCGTGAC
ACCACGATGCCTGCAGCAATGGCAACAACGTTGCGCAAACTATTAACTGG
CGAACTACTTACTCTAGCTTCCCGGCAACAATTAATAGACTGGATGGAGG
CGGATAAAGTTGCAGGACCACTTCTGCGCTCGGCCCTTCCGGCTGGCTGG
TTTATTGCTGATAAATCTGGAGCCGGTGAGCGTGGGTCTCGCGGTATCAT
TGCAGCACTGGGGCCAGATGGTAAGCCCTCCCGTATCGTAGTTATCTACA
CGACGGGGAGTCAGGCAACTATGGATGAACGAAATAGACAGATCGCTGAG
ATAGGTGCCTCACTGATTAAGCATTGGGACAAGAGCCACCCAGAAACGCT
GGTGAAAGTAAAAGATGCTGAAGATCAGTTGGGTGCACGAGTGGGTTACA -continued

TCGAACTGGATCTCAACAGCGGTAAGATCCTTGAGAGTTTTCGCCCCGAA

GAACGTTTTCCAATGATGAGCACTTTTAAAGTTCTGCTATGTGGCGCGGT

ATTATCCCGTGTTGACGCCGGGCAAGAGCAACTCGGTCGCCGCATACACT

ATTCTCAGAATGACTTGGTTGAGTACTCACCAGTCACAGAAAAGCATCTT

ACGGATGGCATGACAGTAAGAGAATTATGCAGTGCTGCCATAACCATGAG

TGATAACACTGCGGCCAACTTACTTCTGACAACGATCGGAGGACCGAAGG

AGCTAACCGCTTTTTTGCACAACATGGGGGATCATGTAACTCGCCTTGAT

CGTTGGGAACCGGAACTGAATGAAGCCgccgccaccatggaaaacgccca gaaaggtgaaatcatgccgaacatcccgcagatgtccgctttctggtatg ccgtgcgtactgcggtgatcaacgccgccagcggtcgtcagactgtcgat gaagccctgaaagacgcgcagactcgtatcaccaagtaa Amino Acid Sequence:

(SEQ ID NO: 54)

MKIKTGARILALSALTTMMFSASALAKIEEGKLVIWINGLFGYNGLAEVG

KKFEKDTGIKVTVEHPDKLEEKFPQVAATGDGPDIIFYAHDRFGGYAQSG

LLAEITPDKAFQDKLYPFTWDAVRYNGKLIAYPIAVYALSLIYNKDLLPN

PPKTWEEIPALDKELKAKGKSALMFNLQEPYFTWPLIAADGGYAFKYENG

KYDIKDVGVDNAGAKAGLTFLVDLIKNKHMNADTDYSIAEAAFNKGETAM

TINGPWAWSNIDTSKVNYGVTVLPTFKGQPSKPFVGVLSAGINAASPNKE

LAKEFLENYLLTDEGLEAVNKDKPLGAVALKSYEEELAKDPRAIPNDERD

TTMPAAMATTLRKLLTGELLTLASRQQLIDWMEADKVAGPLLRSALPAGW

FIADKSGAGERGSRGIIAALGPDGKPSRIVVIYTTGSQATMDERNRQIAE

IGASLIKHWDKSHPETLVKVKDAEDQLGARVGYIELDLNSGKILESFRPE

ERFPMMSTFKVLLCGAVLSRVDAGQEQLGRRIHYSQNDLVEYSPVTEKHL

TDGMTVRELCSAAITMSDNTAANLLLTTIGGPKELTAFLHNMGDHVTRLD

RWEPELNEAAATMENAQKGEIMPNIPQMSAFWYAVRTAVINAASGRQTVD

EALKDAQTRITK

Sucrose Switch 6-47:
Amino Acid Sequence:

(SEQ ID NO: 55)

MKIKTGARILALSALTTMMFSASALAKIEEGKLVIWINGLQGYNGLAEVG

KKFEKDTGIKVTVEHPDKLEEKFPQVAATGDGPDIIFYAHDRFGGYAQSG

LLAEITPDKAFQDKLYPFTWDAVRYNGKLIAYPIAVQALSLIYNKDLLPN

PPKTWEEIPALDKELKAKGKSALMFNLQEPYFTWPLIAADGGYAFKYENG

KYDIKDVGVDNAGAKAGLTFLVDLIKNKHMNADTDYSIAEAAFNKGETAM

TINGPWAWSNIDTSKVNYGVTVLPTFKGQPSKPFVGVLSAGINAASPNKE

LAKEFLENYLLTDEGLEAVNKDKPLGAVALKSYEEELAKDPRAIPNDERD

TTMPAAMATTLRKLLTGELLTLASRQQLIDWMEADKVAGPLLRSALPAGW

FIADKSGAGERGSRGIIAALGPDGKPSRIVVIYTTGSQATMDERNRQIAE

IGASLIKHWDKSHPETLVKVKDAEDQLGARVGYIELDLNSGKILESFRPE

ERFPMMSTFKVLLCGAVLSRVDAGQEQLGRRIHYSQNDLVEYSPVTEKHL

TDGMTVRELCSAAITMSDNTAANLLLTTIGGPKELTAFLHNMGDHVTRLD

-continued

RWEPELNEAAATMENAQKGEIMPNIPQMSAFWYAVRTAVINAASGRQTVD

EALKDAQTRITK

Sucrose Switch 1-59:
Nucleic Acid Sequence:

(SEQ ID NO: 56)

atgaaaataaaaacaggtgcacgcatcctcgcattatccgcattaacgac gatgatgttttccgcctcggctctcgccaaaatcgaagaaggtaaactgg taatctggattaacggcaaggagggctataacggtctcgctgaagtcggt aagaaattcgagaaagataccggaattaaagtcaccgttgagcatccgga taaactggaagagaaattcccacaggttgcggcaactggcgatggccctg acattatcttctatgcacacgaccgctttggtggctacgctcaatctggc ctgttggctgaaatcaccccggacaaagcgttccaggacaagctgtatcc gtttacctgggatgccgtacgttacaacggcaagctgattgcttacccga tcgctgttcgggcgttatcgctgatttataacaaagatctgctgccgaac ccgccaaaaacctgggaagagatcccggcgctggataaagaactgaaagc gaaaggtaagagcgcgctgatgttcaacctgcaagaaccgtacttcacct ggccgctgattgctgctgacggggttatgcgttcaagtatgaaaacggc aagtacgacattaaagacgtgggcgtggataacgctggcgcgaaagcggg tctgaccttcctggttgacctgattaaaaacaaacacatgaatgcagaca ccgattactccatcgcagaagctgcctttaataaaggcgaaacagcgatg accatcaacggcccgtgggcatggtccaacatcgacaccagcaaagtgaa ttatggtgtaacggtactgccgaccttcaagggtcaaccatccaaaccgt tcgttggcgtgctgagcgcaggtattaacgccgccagtccgaacaaagag ctggcgaaagagttcctcgaaaactatctgctgactgatgaaggtctgga agcggttaataaagacaaaccgctgggtgccgtagcgctgaagtcttacg aggaagagttggcgaaagatccacgtGCCATACCAAACGACGAGCGTGAC

ACCACGATGCCTGCAGCAATGGCAACAACGTTGCGCAAACTATTAACTGG

CGAACTACTTACTCTAGCTTCCCGGCAACAATTAATAGACTGGATGGAGG

CGGATAAAGTTGCAGGACCACTTCTGCGCTCGGCCCTTCCGGCTGGCTGG

TTTATTGCTGATAAATCTGGAGCCGGTGAGCGTGGGTCTCGCGGTATCAT

TGCAGCACTGGGGCCAGATGGTAAGCCCTCCCGTATCGTAGTTATCTACA

CGACGGGGAGTCAGGCAACTATGGATGAACGAAATAGACAGATCGCTGAG

ATAGGTGCCTCACTGATTAAGCATTGGGACAAGAGCCACCCAGAAACGCT

GGTGAAAGTAAAAGATGCTGAAGATCAGTTGGGTGCACGAGTGGGTTACA

TCGAACTGGATCTCAACAGCGGTAAGATCCTTGAGAGTTTTCGCCCCGAA

GAACGTTTTCCAATGATGAGCACTTTTAAAGTTCTGCTATGTGGCGCGGT

ATTATCCCGTGTTGACGCCGGGCAAGAGCAACTCGGTCGCCGCATACACT

ATTCTCAGAATGACTTGGTTGAGTACTCACCAGTCACAGAAAAGCATCTT

ACGGATGGCATGACAGTAAGAGAATTATGCAGTGCTGCCATAACCATGAG

TGATAACACTGCGGCCAACTTACTTCTGACAACGATCGGAGGACCGAAGG

AGCTAACCGCTTTTTTGCACAACATGGGGGATCATGTAACTCGCCTTGAT

CGTTGGGAACCGGAACTGAATGAAGCCgccgccaccatggaaaacgccca gaaaggtgaaatcatgccgaacatcccgcagatgtccgctttctggtatg ccgtgcgtactgcggtgatcaacgccgccagcggtcgtcagactgtcgat gaagccctgaaagacgcgcagactcgtatcaccaagtaa Amino Acid Sequence:

(SEQ ID NO: 57)

MKIKTGARILALSALTTMMFSASALAKIEEGKLVIWINGKEGYNGLAEVG

KKFEKDTGIKVTVEHPDKLEEKFPQVAATGDGPDIIFYAHDRFGGYAQSG

LLAEITPDKAFQDKLYPFTWDAVRYNGKLIAYPIAVRALSLIYNKDLLPN

PPKTWEEIPALDKELKAKGKSALMFNLQEPYFTWPLIAADGGYAFKYENG

KYDIKDVGVDNAGAKAGLTFLVDLIKNKHMNADTDYSIAEAAFNKGETAM

TINGPWAWSNIDTSKVNYGVTVLPTFKGQPSKPFVGVLSAGINAASPNKE

LAKEFLENYLLTDEGLEAVNKDKPLGAVALKSYEEELAKDPRAIPNDERD

TTMPAAMATTLRKLLTGELLTLASRQQLIDWMEADKVAGPLLRSALPAGW

FIADKSGAGERGSRGIIAALGPDGKPSRIVVIYTTGSQATMDERNRQIAE

IGASLIKHWDKSHPETLVKVKDAEDQLGARVGYIELDLNSGKILESFRPE

ERFPMMSTFKVLLCGAVLSRVDAGQEQLGRRIHYSQNDLVEYSPVTEKHL

TDGMTVRELCSAAITMSDNTAANLLLTTIGGPKELTAFLHNMGDHVTRLD

RWEPELNEAAATMENAQKGEIMPNIPQMSAFWYAVRTAVINAASGRQTVD

EALKDAQTRITK

Sucrose Switch 1-68:
Nucleic Acid Sequence:

(SEQ ID NO: 58)

atgaaaataaaaacaggtgcacgcatcctcgcattatccgcattaacgac gatgatgttttccgcctcggctctcgccaaaatcgaagaaggtaaactgg taatctggattaacggcttggagggctataacggtctcgctgaagtcggt aagaaattcgagaaagataccggaattaaagtcaccgttgagcatccgga taaactggaagagaaattcccacaggttgcggcaactggcgatggccctg acattatcttctatgcacacgaccgctttggtggctacgctcaatctggc ctgttggctgaaatcaccccggacaaagcgttccaggacaagctgtatcc gtttacctgggatgccgtacgttacaacggcaagctgattgcttacccga tcgctgttcgtgcgttatcgctgatttataacaaagatctgctgccgaac ccgccaaaaacctgggaagagatcccggcgctggataaagaactgaaagc gaaaggtaagagcgcgctgatgttcaacctgcaagaaccgtacttcacct ggccgctgattgctgctgacggggggttatgcgttcaagtatgaaaacggc aagtacgacattaaagacgtgggcgtggataacgctggcgcgaaagcggg tctgaccttcctggttgacctgattaaaaacaaacacatgaatgcagaca ccgattactccatcgcagaagctgcctttaataaaggcgaaacagcgatg accatcaacggcccgtgggcatggtccaacatcgacaccagcaaagtgaa ttatggtgtaacggtactgccgaccttcaagggtcaaccatccaaaccgt tcgttggcgtgctgagcgcaggtattaacgccgccagtccgaacaaagag ctggcgaaagagttcctcgaaaactatctgctgactgatgaaggtctgga agcggttaataaagacaaaccgctgggtgccgtagcgctgaagtcttacg aggaagagttggcgaaagatccacgtGCCATACCAAACGACGAGCGTGAC

ACCACGATGCCTGCAGCAATGGCAACAACGTTGCGCAAACTATTAACTGG

CGAACTACTTACTCTAGCTTCCCGGCAACAATTAATAGACTGGATGGAGG

CGGATAAAGTTGCAGGACCACTTCTGCGCTCGGCCCTTCCGGCTGGCTGG

TTTATTGCTGATAAATCTGGAGCCGGTGAGCGTGGGTCTCGCGGTATCAT

TGCAGCACTGGGGCCAGATGGTAAGCCCTCCCGTATCGTAGTTATCTACA

CGACGGGGAGTCAGGCAACTATGGATGAACGAAATAGACAGATCGCTGAG

ATAGGTGCCTCACTGATTAAGCATTGGGACAAGAGCCACCCAGAAACGCT

GGTGAAAGTAAAAGATGCTGAAGATCAGTTGGGTGCACGAGTGGGTTACA

TCGAACTGGATCTCAACAGCGGTAAGATCCTTGAGAGTTTTCGCCCCGAA

GAACGTTTTCCAATGATGAGCACTTTTAAAGTTCTGCTATGTGGCGCGGT

ATTATCCCGTGTTGACGCCGGGCAAGAGCAACTCGGTCGCCGCATACACT

ATTCTCAGAATGACTTGGTTGAGTACTCACCAGTCACAGAAAAGCATCTT

ACGGATGGCATGACAGTAAGAGAATTATGCAGTGCTGCCATAACCATGAG

TGATAACACTGCGGCCAACTTACTTCTGACAACGATCGGAGGACCGAAGG

AGCTAACCGCTTTTTTGCACAACATGGGGGATCATGTAACTCGCCTTGAT

CGTTGGGAACCGGAACTGAATGAAGCCgccgccaccatggaaaacgccca gaaaggtgaaatcatgccgaacatcccgcagatgtccgctttctggtatg ccgtgcgtactgcggtgatcaacgccgccagcggtcgtcagactgtcgat gaagccctgaaagacgcgcagactcgtatcaccaagtaa Amino Acid Sequence:

(SEQ ID NO: 59)

MKIKTGARILALSALTTMMFSASALAKIEEGKLVIWINGLEGYNGLAEVG

KKFEKDTGIKVTVEHPDKLEEKFPQVAATGDGPDIIFYAHDRFGGYAQSG

LLAEITPDKAFQDKLYPFTWDAVRYNGKLIAYPIAVRALSLIYNKDLLPN

PPKTWEEIPALDKELKAKGKSALMFNLQEPYFTWPLIAADGGYAFKYENG

KYDIKDVGVDNAGAKAGLTFLVDLIKNKHMNADTDYSIAEAAFNKGETAM

TINGPWAWSNIDTSKVNYGVTVLPTFKGQPSKPFVGVLSAGINAASPNKE

LAKEFLENYLLTDEGLEAVNKDKPLGAVALKSYEEELAKDPRAIPNDERD

TTMPAAMATTLRKLLTGELLTLASRQQLIDWMEADKVAGPLLRSALPAGW

FIADKSGAGERGSRGIIAALGPDGKPSRIVVIYTTGSQATMDERNRQIAE

IGASLIKHWDKSHPETLVKVKDAEDQLGARVGYIELDLNSGKILESFRPE

ERFPMMSTFKVLLCGAVLSRVDAGQEQLGRRIHYSQNDLVEYSPVTEKHL

TDGMTVRELCSAAITMSDNTAANLLLTTIGGPKELTAFLHNMGDHVTRLD

RWEPELNEAAATMENAQKGEIMPNIPQMSAFWYAVRTAVINAASGRQTVD

EALKDAQTRITK

Switch RG 13:
Nucleic Acid Sequence:

(SEQ ID NO: 60)

atgaaaataaaaacaggtgcacgcatcctcgcattatccgcattaacgac gatgatgttttccgcctcggctctcgccaaaatcgaagaaggtaaactgg taatctggattaacggcgataaaggctataacggtctcgctgaagtcggt aagaaattcgagaaagataccggaattaaagtcaccgttgagcatccgga taaactggaagagaaattcccacaggttgcggcaactggcgatggccctg -continued acattatcttctgggcacacgaccgctttggtggctacgctcaatctggc ctgttggctgaaatcaccccggacaaagcgttccaggacaagctgtatcc gtttacctgggatgccgtacgttacaacggcaagctgattgcttacccga tcgctgttgaagcgttatcgctgatttataacaaagatctgctgccgaac ccgccaaaaacctgggaagagatcccggcgctggataaagaactgaaagc gaaaggtaagagcgcgctgatgttcaacctgcaagaaccgtacttcacct ggccgctgattgctgctgacggggggttatgcgttcaagtatgaaaacggc aagtacgacattaaagacgtgggcgtggataacgctggcgcgaaagcggg tctgaccttcctggttgacctgattaaaaacaaacacatgaatgcagaca ccgattactccatcgcagaagctgcctttaataaaggcgaaacagcgatg accatcaacggcccgtgggcatggtccaacatcgacaccagcaaagtgaa ttatggtgtaacggtactgccgaccttcaagggtcaaccatccaaaccgt tcgttggcgtgctgagcgcaggtattaacgccgccagtccgaacaaagag ctggcgaaagagttcctcgaaaactatctgctgactgatgaaggtctgga agcggttaataaagacaaaccgctgggtgccgtagcgctgaagtcttacg aggaagagttggcgaaagatccacGCTGGTTTATTGCTGATAAATCTGGA

GCCGGTGAGCGTGGGTCTCGCGGTATCATTGCAGCACTGGGGCCAGATGG

TAAGCCCTCCCGTATCGTAGTTATCTACACGACGGGGAGTCAGGCAACTA

TGGATGAACGAAATAGACAGATCGCTGAGATAGGTGCCTCACTGATTAAG

CATTGGGGATCCGGCGGTGGCCACCCAGAAACGCTGGTGAAAGTAAAAGA

TGCTGAAGATCAGTTGGGTGCACGAGTGGGTTACATCGAACTGGATCTCA

ACAGCGGTAAGATCCTTGAGAGTTTTCGCCCCGAAGAACGTTTTCCAATG

ATGAGCACTTTTAAAGTTCTGCTATGTGGCGCGGTATTATCCCGTGTTGA

CGCCGGGCAAGAGCAACTCGGTCGCCGCATACACTATTCTCAGAATGACT

TGGTTGAGTACTCACCAGTCACAGAAAAGCATCTTACGGATGGCATGACA

GTAAGAGAATTATGCAGTGCTGCCATAACCATGAGTGATAACACTGCGGC

CAACTTACTTCTGACAACGATCGGAGGACCGAAGGAGCTAACCGCTTTTT

TGCACAACATGGGGGATCATGTAACTCGCCTTGATCGTTGGGAACCGGAG

CTGAATGAAGCCATACCAAACGACGAGCGTGACACCACGATGCCTGCAGC

AATGGCAACAACGTTGCGCAAACTATTAACTGGCGAACTACTTACTCTAG

CTTCCCGGCAACAATTAATAGACTGGATGGAGGCGGATAAAGTTGCAGGA

CCACTTCTGCGCTCGGCCCTTCCGGCTGGCTccgccaccatggaaaacgc ccagaaaggtgaaatcatgccgaacatcccgcagatgtccgctttctggt atgccgtgcgtactgcggtgatcaacgccgccagcggtcgtcagactgtc gatgaagccctgaaagacgcgcagactcgtatcaccaagtaa Amino Acid Sequence:

(SEQ ID NO: 61)

MKIKTGARILALSALTTMMFSASALAKIEEGKLVIWINGDKGYNGLAEVG

KKFEKDTGIKVTVEHPDKLEEKFPQVAATGDGPDIIFWAHDRFGGYAQSG

LLAEITPDKAFQDKLYPFTWDAVRYNGKLIAYPIAVEALSLIYNKDLLPN

PPKTWEEIPALDKELKAKGKSALMFNLQEPYFTWPLIAADGGYAFKYENG

KYDIKDVGVDNAGAKAGLTFLVDLIKNKHMNADTDYSIAEAAFNKGETAM

-continued

TINGPWAWSNIDTSKVNYGVTVLPTFKGQPSKPFVGVLSAGINAASPNKE

LAKEFLENYLLTDEGLEAVNKDKPLGAVALKSYEEELAKDPRWFIADKSG

AGERGSRGIIAALGPDGKPSRIVVIYTTGSQATMDERNRQIAEIGASLIK

HWGSGGGHPETLVKVKDAEDQLGARVGYIELDLNSGKILESFRPEERFPM

MSTFKVLLCGAVLSRVDAGQEQLGRRIHYSQNDLVEYSPVTEKHLTDGMT

VRELCSAAITMSDNTAANLLLTTIGGPKELTAFLHNMGDHVTRLDRWEPE

LNEAIPNDERDTTMPAAMATTLRKLLTGELLTLASRQQLIDWMEADKVAG

PLLRSALPAGSATMENAQKGEIMPNIPQMSAFWYAVRTAVINAASGRQTV

DEALKDAQTRITK

Switch RG13 I329W:

Nucleic Acid Sequence:

(SEQ ID NO: 62)

atgaaaataaaaacaggtgcacgcatcctcgcattatccgcattaacgac gatgatgttttccgcctcggctctcgccaaaatcgaagaaggtaaactgg taatctggattaacggcgataaaggctataacggtctcgctgaagtcggt aagaaattcgagaaagataccggaattaaagtcaccgttgagcatccgga taaactggaagagaaattcccacaggttgcggcaactggcgatggccctg acattatcttctgggcacacgaccgctttggtggctacgctcaatctggc ctgttggctgaaatcaccccggacaaagcgttccaggacaagctgtatcc gtttacctgggatgccgtacgttacaacggcaagctgattgcttacccga tcgctgttgaagcgttatcgctgatttataacaaagatctgctgccgaac ccgccaaaaacctgggaagagatcccggcgctggataaagaactgaaagc gaaaggtaagagcgcgctgatgttcaacctgcaagaaccgtacttcacct ggccgctgattgctgctgacggggggttatgcgttcaagtatgaaaacggc aagtacgacattaaagacgtgggcgtggataacgctggcgcgaaagcggg tctgaccttcctggttgacctgattaaaaacaaacacatgaatgcagaca ccgattactccatcgcagaagctgcctttaataaaggcgaaacagcgatg accatcaacggcccgtgggcatggtccaacatcgacaccagcaaagtgaa ttatggtgtaacggtactgccgaccttcaagggtcaaccatccaaaccgt tcgttggcgtgctgagcgcaggtattaacgccgccagtccgaacaaagag ctggcgaaagagttcctcgaaaactatctgctgactgatgaaggtctgga agcggttaataaagacaaaccgctgggtgccgtagcgctgaagtcttacg aggaagagttggcgaaagatccacGCTGGTTTATTGCTGATAAATCTGGA

GCCGGTGAGCGTGGGTCTCGCGGTATCATTGCAGCACTGGGGCCAGATGG

TAAGCCCTCCCGTATCGTAGTTATCTACACGACGGGGAGTCAGGCAACTA

TGGATGAACGAAATAGACAGATCGCTGAGATAGGTGCCTCACTGATTAAG

CATTGGGGATCCGGCGGTGGCCACCCAGAAACGCTGGTGAAAGTAAAAGA

TGCTGAAGATCAGTTGGGTGCACGAGTGGGTTACATCGAACTGGATCTCA

ACAGCGGTAAGATCCTTGAGAGTTTTCGCCCCGAAGAACGTTTTCCAATG

ATGAGCACTTTTAAAGTTCTGCTATGTGGCGCGGTATTATCCCGTGTTGA

CGCCGGGCAAGAGCAACTCGGTCGCCGCATACACTATTCTCAGAATGACT

TGGTTGAGTACTCACCAGTCACAGAAAAGCATCTTACGGATGGCATGACA

-continued

GTAAGAGAATTATGCAGTGCTGCCATAACCATGAGTGATAACACTGCGGC

CAACTTACTTCTGACAACGATCGGAGGACCGAAGGAGCTAACCGCTTTTT

TGCACAACATGGGGGATCATGTAACTCGCCTTGATCGTTGGGAACCGGAG

CTGAATGAAGCCATACCAAACGACGAGCGTGACACCACGATGCCTGCAGC

AATGGCAACAACGTTGCGCAAACTATTAACTGGCGAACTACTTACTCTAG

CTTCCCGGCAACAATTAATAGACTGGATGGAGGCGGATAAAGTTGCAGGA

CCACTTCTGCGCTCGGCCCTTCCGGCTGGCTccgccaccatggaaaacgc ccagaaaggtgaaTGGatgccgaacatcccgcagatgtccgctttctggt atgccgtgcgtactgcggtgatcaacgccgccagcggtcgtcagactgtc gatgaagccctgaaagacgcgcagactcgtatcaccaagtaa Amino Acid Sequence:

(SEQ ID NO: 63)

MKIKTGARILALSALTTMMFSASALAKIEEGKLVIWINGDKGYNGLAEVG

KKFEKDTGIKVTVEHPDKLEEKFPQVAATGDGPDIIFWAHDRFGGYAQSG

LLAEITPDKAFQDKLYPFTWDAVRYNGKLIAYPIAVEALSLIYNKDLLPN

PPKTWEEIPALDKELKAKGKSALMFNLQEPYFTWPLIAADGGYAFKYENG

KYDIKDVGVDNAGAKAGLTFLVDLIKNKHMNADTDYSIAEAAFNKGETAM

TINGPWAWSNIDTSKVNYGVTVLPTFKGQPSKPFVGVLSAGINAASPNKE

LAKEFLENYLLTDEGLEAVNKDKPLGAVALKSYEEELAKDPRWFIADKSG

AGERGSRGIIAALGPDGKPSRIVVIYTTGSQATMDERNRQIAEIGASLIK

HWGSGGGHPETLVKVKDAEDQLGARVGYIELDLNSGKILESFRPEERFPM

MSTFKVLLCGAVLSRVDAGQEQLGRRIHYSQNDLVEYSPVTEKHLTDGMT

VRELCSAAITMSDNTAANLLLTTIGGPKELTAFLHNMGDHVTRLDRWEPE

LNEAIPNDERDTTMPAAMATTLRKLLTGELLTLASRQQLIDWMEADKVAG

PLLRSALPAGSATMENAQKGEWMPNIPQMSAFWYAVRTAVINAASGRQTV

DEALKDAQTRITK

Switch RG13 I329W/A96W:
Nucleic Acid Sequence:

(SEQ ID NO: 64)

atgaaaataaaaacaggtgcacgcatcctcgcattatccgcattaacgac gatgatgttttccgcctcggctctcgccaaaatcgaagaaggtaaactgg taatctggattaacggcgataaaggctataacggtctcgctgaagtcggt aagaaattcgagaaagataccggaattaaagtcaccgttgagcatccgga taaactggaagagaaattcccacaggttgcggcaactggcgatggccctg acattatcttctgggcacacgaccgctttggtggctacgctcaatctggc ctgttggctgaaatcaccccggacaaagcgttccaggacaagctgtatcc gtttacctgggatTGGgtacgttacaacggcaagctgattgcttacccga tcgctgttgaagcgttatcgctgatttataacaaagatctgctgccgaac ccgccaaaaacctgggaagagatcccggcgctggataaagaactgaaagc gaaaggtaagagcgcgctgatgttcaacctgcaagaaccgtacttcacct ggccgctgattgctgctgacgggggttatgcgttcaagtatgaaaacggc aagtacgacattaaagacgtgggcgtggataacgctggcgcgaaagcggg tctgaccttcctggttgacctgattaaaaacaaacacatgaatgcagaca ccgattactccatcgcagaagctgcctttaataaaggcgaaacagcgatg accatcaacggcccgtgggcatggtccaacatcgacaccagcaaagtgaa ttatggtgtaacggtactgccgaccttcaagggtcaaccatccaaaccgt tcgttggcgtgctgagcgcaggtattaacgccgccagtccgaacaaagag ctggcgaaagagttcctcgaaaactatctgctgactgatgaaggtctgga agcggttaataaagacaaaccgctgggtgccgtagcgctgaagtcttacg aggaagagttggcgaaagatccacGCTGGTTTATTGCTGATAAATCTGGA

GCCGGTGAGCGTGGGTCTCGCGGTATCATTGCAGCACTGGGGCCAGATGG

TAAGCCCTCCCGTATCGTAGTTATCTACACGACGGGGAGTCAGGCAACTA

TGGATGAACGAAATAGACAGATCGCTGAGATAGGTGCCTCACTGATTAAG

CATTGGGGATCCGGCGGTGGCCACCCAGAAACGCTGGTGAAAGTAAAAGA

TGCTGAAGATCAGTTGGGTGCACGAGTGGGTTACATCGAACTGGATCTCA

ACAGCGGTAAGATCCTTGAGAGTTTTCGCCCCGAAGAACGTTTTCCAATG

ATGAGCACTTTTAAAGTTCTGCTATGTGGCGCGGTATTATCCCGTGTTGA

CGCCGGGCAAGAGCAACTCGGTCGCCGCATACACTATTCTCAGAATGACT

TGGTTGAGTACTCACCAGTCACAGAAAAGCATCTTACGGATGGCATGACA

GTAAGAGAATTATGCAGTGCTGCCATAACCATGAGTGATAACACTGCGGC

CAACTTACTTCTGACAACGATCGGAGGACCGAAGGAGCTAACCGCTTTTT

TGCACAACATGGGGGATCATGTAACTCGCCTTGATCGTTGGGAACCGGAG

CTGAATGAAGCCATACCAAACGACGAGCGTGACACCACGATGCCTGCAGC

AATGGCAACAACGTTGCGCAAACTATTAACTGGCGAACTACTTACTCTAG

CTTCCCGGCAACAATTAATAGACTGGATGGAGGCGGATAAAGTTGCAGGA

CCACTTCTGCGCTCGGCCCTTCCGGCTGGCTccgccaccatggaaaacgc ccagaaaggtgaaTGGatgccgaacatcccgcagatgtccgctttctggt atgccgtgcgtactgcggtgatcaacgccgccagcggtcgtcagactgtc gatgaagccctgaaagacgcgcagactcgtatcaccaagtaa Amino Acid Sequence:

(SEQ ID NO: 65)

MKIKTGARILALSALTTMMFSASALAKIEEGKLVIWINGDKGYNGLAEVG

KKFEKDTGIKVTVEHPDKLEEKFPQVAATGDGPDIIFWAHDRFGGYAQSG

LLAEITPDKAFQDKLYPFTWDWVRYNGKLIAYPIAVEALSLIYNKDLLPN

PPKTWEEIPALDKELKAKGKSALMFNLQEPYFTWPLIAADGGYAFKYENG

KYDIKDVGVDNAGAKAGLTFLVDLIKNKHMNADTDYSIAEAAFNKGETAM

TINGPWAWSNIDTSKVNYGVTVLPTFKGQPSKPFVGVLSAGINAASPNKE

LAKEFLENYLLTDEGLEAVNKDKPLGAVALKSYEEELAKDPRWFIADKSG

AGERGSRGIIAALGPDGKPSRIVVIYTTGSQATMDERNRQIAEIGASLIK

HWGSGGGHPETLVKVKDAEDQLGARVGYIELDLNSGKILESFRPEERFPM

MSTFKVLLCGAVLSRVDAGQEQLGRRIHYSQNDLVEYSPVTEKHLTDGMT

VRELCSAAITMSDNTAANLLLTTIGGPKELTAFLHNMGDHVTRLDRWEPE

LNEAIPNDERDTTMPAAMATTLRKLLTGELLTLASRQQLIDWMEADKVAG

PLLRSALPAGSATMENAQKGEWMPNIPQMSAFWYAVRTAVINAASGRQTV

DEALKDAQTRITK

-continued

Switch IFD7:
Nucleic Acid Sequence:

(SEQ ID NO: 66)

atgaaaataaaaacaggtgcacgcatcctcgcattatccgcattaacgac gatgatgttttccgcctcggctctcgccaaaatcgaagaaggtaaactgg taatctggattaacggcgataaaggctataacggtctcgctgaagtcggt aagaaattcgagaaagataccggaattaaagtcaccgttgagcatccgga taaactggaagagaaattcccacaggttgcggcaactggcgatggccctg acattatcttctgggcacacgaccgctttggtggctacgctcaatctggc ctgttggctgaaatcaccccggacaaagcgttccaggacaagctgtatcc gtttacctgggatgccgtacgttacaacggcaagctgattgcttacccga tcgctgttgaagcgttatcgctgatttataacaaagatctgctgccgaac ccgccaaaaacctgggaagagatcccggcgctggataaagaactgaaagc gaaaggtaagagcgcgctgatgttcaacctgcaagaaccgtacttcacct ggccgctgattgctgctgacgggcatcttacggatggcatgacagtaaga gaattatgcagtgctgccataaccatgagtgataacactgcggccaactt acttctgacaacgatcggaggaccgaaggagctaaccgcttttttgcaca acatgggggatcatgtaactcgccttgatcgttgggaaccggaactgaat gaagccataccaaacgacgagcgtgacaccacgatgcctgcagcaatggc aacaacgttgcgcaaactattaactggcgaactacttactctagcttccc ggcaacaattaatagactggatggaggcggataaagttgcaggaccactt ctgcgctcggcccttccggctggctggtttattgctgataaatctggagc cggtgagcgtgggtctcgcggtatcattgcagcactggggccagatggta agccctcccgtatcgtagttatctacacgacggggagtcaggcaactatg gatgaacgaaatagacagatcgctgagataggtgcctcactgattaagca ttgggacaagagccacccagaaacgctggtgaaagtaaaagatgctgaag atcagttgggtgcacgagtgggttacatcgaactggatctcaacagcggt aagatccttgagagttttcgccccgaagaacgttttccaatgatgagcac ttttaaagttctgctatgtggcgcggtattatcccgtgttgacgccgggc aagagcaactcggtcgccgcatacactattctcagaatgacttggttgag tactcaccagtcacagacggggttatgcgttcaagtatgaaaacggcaa gtacgacattaaagacgtgggcgtggataacgctggcgcgaaagcgggtc tgaccttcctggttgacctgattaaaaacaaacacatgaatgcagacacc gattactccatcgcagaagctgcctttaataaaggcgaaacagcgatgac catcaacggcccgtgggcatggtccaacatcgacaccagcaaagtgaatt atggtgtaacggtactgccgaccttcaagggtcaaccatccaaaccgttc gttggcgtgctgagcgcaggtattaacgccgccagtccgaacaaagagct ggcgaaagagttcctcgaaaactatctgctgactgatgaaggtctggaag cggttaataaagacaaaccgctgggtgccgtagcgctgaagtcttacgag gaagagttggcgaaagatccacgtattgccgccaccatggaaaacgccca gaaaggtgaaatcatgccgaacatcccgcagatgtccgctttctggtatg -continued ccgtgcgtactgcggtgatcaacgccgccagcggtcgtcagactgtcgat gaagccctgaaagacgcgcagactcgtatcaccaagtaa Amino acid Sequence:

(SEQ ID NO: 67)

MKIKTGARILALSALTTMMFSASALAKIEEGKLVIWINGDKGYNGLAEVG

KKFEKDTGIKVTVEHPDKLEEKEPQVAATGDGPDIIFWAHDRFGGYAQSG

LLAEITPDKAFQDKLYPFTWDAVRYNGKLIAYPIAVEALSLIYNKDLLPN

PPKTWEEIPALDKELKAKGKSALMFNLQEPYFTWPLIAADGHLTDGMTVR

ELCSAAITMSDNTAANLLLTTIGGPKELTAFLHNMGDHVTRLDRWEPELN

EAIPNDERDTTMPAAMATTLRKLLTGELLTLASRQQLIDWMEADKVAGPL

LRSALPAGWFIADKSGAGERGSRGIIAALGPDGKPSRIVVIYTTGSQATM

DERNRQIAEIGASLIKHWDKSHPETLVKVKDAEDQLGARVGYIELDLNSG

KILESFRPEERFPMMSTFKVLLCGAVLSRVDAGQEQLGRRIHYSQNDLVE

YSPVTDGGYAFKYENGKYDIKDVGVDNAGAKAGLTFLVDLIKNKHMNADT

DYSIAEAAFNKGETAMTINGPWAWSNIDTSKVNYGVTVLPTFKGQPSKPF

VGVLSAGINAASPNKELAKEFLENYLLTDEGLEAVNKDKPLGAVALKSYE

EELAKDPRIAATMENAQKGEIMPNIPQMSAFWYAVRTAVINAASGRQTVD

EALKDAQTRITK

Switch IFG277:
Nucleic Acid Sequence:

(SEQ ID NO: 68)

atgaaaataaaaacaggtgcacgcatcctcgcattatccgcattaacgac gatgatgttttccgcctcggctctcgccaaaatcgaagaaggtaaactgg taatctggattaacggcgataaaggctataacggtctcgctgaagtcggt aagaaattcgagaaagataccggaattaaagtcaccgttgagcatccgga taaactggaagagaaattcccacaggttgcggcaactggcgatggccctg acattatcttctgggcacacgaccgctttggtggctacgctcaatctggc ctgttggctgaaatcaccccggacaaagcgttccaggacaagctgtatcc gtttacctgggatgccgtacgttacaacggcaagctgattgcttacccga tcgctgttgaagcgttatcgctgatttataacaaagatctgctgccgaac ccgccaaaaacctgggaagagatcccggcgctggataaagaactgaaagc gaaaggtaagagcgcgctgatgttcaacctgcaagaaccgtacttcacct ggccgctgattgctgctgacgggcttctgcgctcggcccttccggctggc tggtttattgctgataaatctggagccggtgagcgtgggtctcgcggtat cattgcagcactggggccagatggtaagccctcccgtatcgtagttatct acacgacggggagtcaggcaactatggatgaacgaaatagacagatcgct gagataggtgcctcactgattaagcattggggatccggcggtggccaccc agaaacgctggtgaaagtaaaagatgctgaagatcagttgggtgcacgag tgggttacatcgaactggatctcaacagcggtaagatccttgagagtttt cgccccgaagaacgttttccaatgatgagcacttttaaagttctgctatg tggcgcggtattatcccgtgttgacgccgggcaagagcaactcggtcgcc gcatacactattctcagaatgacttggttgagtactcaccagtcacagaa aagcatcttacggatggcatgacagtaagagaattatgcagtgctgccat -continued aaccatgagtgataacactgcggccaacttacttctgacaacgatcggag gaccgaaggagctaaccgcttttttgcacaacatgggggatcatgtaact cgccttgatcgttgggaaccggagctgaatgaagccataccaaacgacga gcgtgacaccacgatgcctgcagcaatggcaacaacgttgcgcaaactat taactggcgaactacttactctagcttcccggcaacaattaatagactgg atggaggcggataaagttgcagacgggggttatgcgttcaagtatgaaaa cggcaagtacgacattaaagacgtgggcgtggataacgctggcgcgaaag cgggtctgaccttcctggttgacctgattaaaaacaaacacatgaatgca gacaccgattactccatcgcagaagctgcctttaataaaggcgaaacagc gatgaccatcaacggcccgtgggcatggtccaacatcgacaccagcaaag tgaattatggtgtaacggtactgccgaccttcaagggtcaaccatccaaa ccgttcgttggcgtgctgagcgcaggtattaacgccgccagtccgaacaa agagctggcgaaagagttcctcgaaaactatctgctgactgatgaaggtc tggaagcggttaataaagacaaaccgctgggtgccgtagcgctgaagtct tacgaggaagagttggcgaaagatccacgtattgccgccaccatggaaaa cgcccagaaaggtgaaatcatgccgaacatcccgcagatgtccgctttct ggtatgccgtgcgtactgcggtgatcaacgccgccagcggtcgtcagact gtcgatgaagccctgaaagacgcgcagactcgtatcaccaagtaa Amino Acid Sequence:

(SEQ ID NO: 69)

MKIKTGARILALSALTTMMFSASALAKIEEGKLVIWINGDKGYNGLAEVG

KKFEKDTGIKVTVEHPDKLEEKFPQVAATGDGPDIIFWAHDRFGGYAQSG

LLAEITPDKAFQDKLYPFTWDAVRYNGKLIAYPIAVEALSLIYNKDLLPN

PPKTWEEIPALDKELKAKGKSALMFNLQEPYFTWPLIAADGLLRSALPAG

WFIADKSGAGERGSRGIIAALGPDGKPSRIVVIYTTGSQATMDERNRQIA

EIGASLIKHWGSGGGHPETLVKVKDAEDQLGARVGYIELDLNSGKILESF

RPEERFPMMSTFKVLLCGAVLSRVDAGQEQLGRRIHYSQNDLVEYSPVTE

KHLTDGMTVRELCSAAITMSDNTAANLLLTTIGGPKELTAFLHNMGDHVT

RLDRWEPELNEAIPNDERDTTMPAAMATTLRKLLTGELLTLASRQQLIDW

MEADKVADGGYAFKYENGKYDIKDVGVDNAGAKAGLTFLVDLIKNKHMNA

DTDYSIAEAAFNKGETAMTINGPWAWSNIDTSKVNYGVTVLPTFKGQPSK

PFVGVLSAGINAASPNKELAKEFLENYLLTDEGLEAVNKDKPLGAVALKS

YEEELAKDPRIAATMENAQKGEIMPNIPQMSAFWYAVRTAVINAASGRQT

VDEALKDAQTRITK

Switch IFD15:

Nucleic Acid Sequence:

(SEQ ID NO: 70)

atgaaaataaaaacaggtgcacgcatcctcgcattatccgcattaacgac gatgatgttttccgcctcggctctcgccaaaatcgaagaaggtaaactgg taatctggattaacggcgataaaggctataacggtctcgctgaagtcggt aagaaattcgagaaagataccggaattaaagtcaccgttgagcatccgga taaactggaagagaaattcccacaggttgcggcaactggcgatggccctg acattatcttctgggcacacgaccgctttggtggctacgctcaatctggc ctgttggctgaaatcaccccggacaaagcgttccaggacaagctgtatcc gtttacctgggatgccgtacgttacaacggcaagctgattgcttacccga tcgctgttgaagcgttatcgctgatttataacaaagatctgctgccgaac ccgccaaaaacctgggaagagatcccggcgctggataaagaactgaaagc gaaaggtaagagcgcgctgatgttcaacctgcaagaaccgtacttcacct ggccgctgattgctgctgacgggaatgaagccataccaaacgacgagcgt gacaccacgatgcctgcagcaatggcaacaacgttgcgcaaactattaac tggcgaactacttactctagcttcccggcaacaattaatagactggatgg aggcggataaagttgcaggaccacttctgcgctcggcccttccggctggc tggtttattgctgataaatctggagccggtgagcgtgggtctcgcggtat cattgcagcactggggccagatggtaagccctcccgtatcgtagttatct acacgacggggagtcaggcaactatggatgaacgaaatagacagatcgct gagataggtgcctcactgattaagcattgggacaagagccacccagaaac gctggtgaaagtaaaagatgctgaagatcagttgggtgcacgagtgggtt acatcgaactggatctcaacagcggtaagatccttgagagttttcgcccc gaagaacgttttccaatgatgagcacttttaaagttctgctatgtggcgc ggtattatcccgtgttgacgccgggcaagagcaactcggtcgccgcatac actattctcagaatgacttggttgagtactcaccagtcacagaaaagcat cttacggatggcatgacagtaagagaattatgcagtgctgccataaccat gagtgataacactgcggccaacttacttctgacaacgatcggaggaccga aggagctaaccgcttttttgcacaacatgggggatcatgtaactcgcctt gatcgttgggaaccggaactgaatgaagccgacgggggttatgcgttcaa gtatgaaaacggcaagtacgacattaaagacgtgggcgtggataacgctg gcgcgaaagcgggtctgaccttcctggttgacctgattaaaaacaaacac atgaatgcagacaccgattactccatcgcagaagctgcctttaataaagg cgaaacagcgatgaccatcaacggcccgtgggcatggtccaacatcgaca ccagcaaagtgaattatggtgtaacggtactgccgaccttcaagggtcaa ccatccaaaccgttcgttggcgtgctgagcgcaggtattaacgccgccag tccgaacaaagagctggcgaaagagttcctcgaaaactatctgctgactg atgaaggtctggaagcggttaataaagacaaaccgctgggtgccgtagcg ctgaagtcttacgaggaagagttggcgaaagatccacgtattgccgccac catggaaaacgcccagaaaggtgaaatcatgccgaacatcccgcagatgt ccgctttctggtatgccgtgcgtactgcggtgatcaacgccgccagcggt cgtcagactgtcgatgaagccctgaaagacgcgcagactcgtatcaccaa gtaa Amino Acid Sequence:

(SEQ ID NO: 71)

MKIKTGARILALSALTTMMFSASALAKIEEGKLVIWINGDKGYNGLAEVG

KKFEKDTGIKVTVEHPDKLEEKFPQVAATGDGPDIIFWAHDRFGGYAQSG

LLAEITPDKAFQDKLYPFTWDAVRYNGKLIAYPIAVEALSLIYNKDLLPN

PPKTWEEIPALDKELKAKGKSALMFNLQEPYFTWPLIAADGNEAIPNDER

DTTMPAAMATTLRKLLTGELLTLASRQQLIDWMEADKVAGPLLRSALPAG

-continued

WFIADKSGAGERGSRGIIAALGPDGKPSRIVVIYTTGSQATMDERNRQIA

EIGASLIKHWDKSHPETLVKVKDAEDQLGARVGYIELDLNSGKILESFRP

EERFPMMSTFKVLLCGAVLSRVDAGQEQLGRRIHYSQNDLVEYSPVTEKH

LTDGMTVRELCSAAITMSDNTAANLLLTTIGGPKELTAFLHNMGDHVTRL

DRWEPELNEADGGYAFKYENGKYDIKDVGVDNAGAKAGLTFLVDLIKNKH

MNADTDYSIAEAAFNKGETAMTINGPWAWSNIDTSKVNYGVTVLPTFKGQ

PSKPFVGVLSAGINAASPNKELAKEFLENYLLTDEGLEAVNKDKPLGAVA

LKSYEEELAKDPRIAATMENAQKGEIMPNIPQMSAFWYAVRTAVINAASG

RQTVDEALKDAQTRITK

Switch EEG251:
Nucleic Acid Sequence:

(SEQ ID NO: 72)

atgaaaataaaaacaggtgcacgcatcctcgcattatccgcattaacgac gatgatgttttccgcctcggctctcgccaaaatcgaagaaggtaaactgg taatctggattaacggcgataaaggctataacggtctcgctgaagtcggt aagaaattcgagaaagataccggaattaaagtcaccgttgagcatccgga taaactggaagagaaattcccacaggttgcggcaactggcgatggccctg acattatcttctgggcacacgaccgctttggtggctacgctcaatctggc ctgttggctgaaatcaccccggacaaagcgttccaggacaagctgtatcc gtttacctgggatgccgtacgttacaacggcaagctgattgcttacccga tcgctgttgaagcgttatcgctgatttataacaaagatctgctgccgaac ccgccaaaaacctgggaagagatcccggcgctggataaagaactgaaagc gaaaggtaagagcgcgctgatgttcaacctgcaagaaccgtacttcacct ggccgctgattgctgctgacggggggttatgcgttcaagtatgaaaacggc aagtacgacattaaagacgtgggcgtggataacgctggcgcgaaagcggg tctgaccttcctggttgacctgattaaaaacaaacacatgaatgcagaca ccgattactccatcgcagaagctgcctttaataaaggcgaaacagcgatg accatcaacggcccgtgggcatggtccaacatcgacaccagcaaagtgaa ttatggtgtaacggtactgccgaccttcaagggtcaaccatccaaaccgt tcgttggcgtgctgagcgcaggtattaacgccgccagtccgaacaaagag ctggcgaaagagttcctcgaaaactatctgctgactgatgaaggtctgga agcggttaataaagacaaaccgctgggtgccgtagcgctgaagtcttacg aggaagagttggcgaaagatccacgtattgccgccaccatggaaaacgcc cagaaaggtgaaatcatgccgaacatcccgcagatgtccgctttctggta tgccgtgcgtactgcggtgatcaacgccgccagcggtcgtcagactgtcg atgaagccctgaaagacgcgcagactcgtatcaccaagggcatgacagta agagaattatgcagtgctgccataaccatgagtgataacactgcggccaa cttacttctgacaacgatcggaggaccgaaggagctaaccgcttttttgc acaacatgggggatcatgtaactcgccttgatcgttgggaaccggagctg aatgaagccataccaaacgacgagcgtgacaccacgatgcctgcagcaat ggcaacaacgttgcgcaaactattaactggcgaactacttactctagctt cccggcaacaattaatagactggatggaggcggataaagttgcaggacca cttctgcgctcggcccttccggctggctggtttattgctgataaatctgg agccggtgagcgtgggtctcgcggtatcattgcagcactggggccagatg gtaagccctcccgtatcgtagttatctacacgacggggagtcaggcaact atggatgaacgaaatagacagatcgctgagataggtgcctcactgattaa gcattggggatccggcggtggccacccagaaacgctggtgaaagtaaaag atgctgaagatcagttgggtgcacgagtgggttacatcgaactggatctc aacagcggtaagatccttgagagttttcgccccgaagaacgttttccaat gatgagcacttttaaagttctgctatgtggcgcggtattatcccgtgttg acgccgggcaagagcaactcggtcgccgcatacactattctcagaatgac ttggttgagtactcaccagtcacagaaaagcatcttacggatggcaagtg a Amino Acid Sequence:

(SEQ ID NO: 73)

MKIKTGARILALSALTTMMFSASALAKIEEGKLVIWINGDKGYNGLAEVG

KKFEKDTGIKVTVEHPDKLEEKEPQVAATGDGPDIIFWAHDRFGGYAQSG

LLAEITPDKAFQDKLYPFTWDAVRYNGKLIAYPIAVEALSLIYNKDLLPN

PPKTWEEIPALDKELKAKGKSALMFNLQEPYFTWPLIAADGGYAFKYENG

KYDIKDVGVDNAGAKAGLTFLVDLIKNKHMNADTDYSIAEAAFNKGETAM

TINGPWAWSNIDTSKVNYGVTVLPTFKGQPSKPFVGVLSAGINAASPNKE

LAKEFLENYLLTDEGLEAVNKDKPLGAVALKSYEEELAKDPRIAATMENA

QKGEIMPNIPQMSAFWYAVRTAVINAASGRQTVDEALKDAQTRITKGMTV

RELCSAAITMSDNTAANLLLTTIGGPKELTAFLHNMGDHVTRLDRWEPEL

NEAIPNDERDTTMPAAMATTLRKLLTGELLTLASRQQLIDWMEADKVAGP

LLRSALPAGWFIADKSGAGERGSRGIIAALGPDGKPSRIVVIYTTGSQAT

MDERNRQIAEIGASLIKHWGSGGGHPETLVKVKDAEDQLGARVGYIELDL

NSGKILESFRPEERFPMMSTFKVLLCGAVLSRVDAGQEQLGRRIHYSQND

LVEYSPVTEKHLTDGK

Switch EEG530:
Nucleic Acid Sequence:

(SEQ ID NO: 74)

atgaaaataaaaacaggtgcacgcatcctcgcattatccgcattaacgac gatgatgttttccgcctcggctctcgccaaaatcgaagaaggtaaactgg taatctggattaacggcgataaaggctataacggtctcgctgaagtcggt aagaaattcgagaaagataccggaattaaagtcaccgttgagcatccgga taaactggaagagaaattcccacaggttgcggcaactggcgatggccctg acattatcttctgggcacacgaccgctttggtggctacgctcaatctggc ctgttggctgaaatcaccccggacaaagcgttccaggacaagctgtatcc gtttacctgggatgccgtacgttacaacggcaagctgattgcttacccga tcgctgttgaagcgttatcgctgatttataacaaagatctgctgccgaac ccgccaaaaacctgggaagagatcccggcgctggataaagaactgaaagc gaaaggtaagagcgcgctgatgttcaacctgcaagaaccgtacttcacct ggccgctgattgctgctgacggggggttatgcgttcaagtatgaaaacggc aagtacgacattaaagacgtgggcgtggataacgctggcgcgaaagcggg -continued tctgaccttcctggttgacctgattaaaaacaaacacatgaatgcagaca ccgattactccatcgcagaagctgcctttaataaaggcgaaacagcgatg accatcaacggcccgtgggcatggtccaacatcgacaccagcaaagtgaa ttatggtgtaacggtactgccgaccttcaagggtcaaccatccaaaccgt tcgttggcgtgctgagcgcaggtattaacgccgccagtccgaacaaagag ctggcgaaagagttcctcgaaaactatctgctgactgatgaaggtctgga agcggttaataaagacaaaccgctgggtgccgtagcgctgaagtcttacg aggaagagttggcgaaagatccacgtattgccgccaccatggaaaacgcc cagaaaggtgaaatcatgccgaacatcccgcagatgtccgctttctggta tgccgtgcgtactgcggtgatcaacgccgccagcggtcgtcagactgtcg atgaagccctgaaagacgcgcagactcgtatcaccaagggcatgacagta agagaattatgcagtgctgccataaccatgagtgataacactgcggccaa cttacttctgacaacgatcggaggaccgaaggagctaaccgctttttgc acaacatgggggatcatgtaactcgccttgatcgttgggaaccggagctg aatgaagccataccaaacgacgagcgtgacaccacgatgcctgcagcaat ggcaacaacgttgcgcaaactattaactggcgaactacttactctagctt cccggcaacaattaatagactggatggaggcggataaagttgcaggacca cttctgcgctcggcccttccggctggctggtttattgctgataaatctgg agccggtgagcgtgggtctcgcggtatcattgcagcactggggccagatg gtaagccctcccgtatcgtagttatctacacgacggggagtcaggcaact atggatgaacgaaatagacagatcgctgagataggtgcctcactgattaa gcattggggatccggcggtggccacccagaaacgctggtgaaagtaaaag atgctgaagatcagttgggtgcacgagtgggttacatcgaactggatctc aacagcggtaagatccttgagagttttcgccccgaagaacgttttccaat gatgagcacttttaaagttctgctatgtggcgcggtattatcccgtgttg acgccgggcaagagcaactcggtcgccgcatacactattctcagaatgac ttggttgagtactcaccagtcacagaaaagcatcttacggaagtgaagag cactagttag Amino Acid Sequence:

(SEQ ID NO: 75)

MKIKTGARILALSALTTMMFSASALAKIEEGKLVIWINGDKGYNGLAEVG

KKFEKDTGIKVTVEHPDKLEEKFPQVAATGDGPDIIFWAHDRFGGYAQSG

LLAEITPDKAFQDKLYPFTWDAVRYNGKLIAYPIAVEALSLIYNKDLLPN

PPKTWEEIPALDKELKAKGKSALMFNLQEPYFTWPLIAADGGYAFKYENG

KYDIKDVGVDNAGAKAGLTFLVDLIKNKHMNADTDYSIAEAAFNKGETAM

TINGPWAWSNIDTSKVNYGVTVLPTFKGQPSKPFVGVLSAGINAASPNKE

LAKEFLENYLLTDEGLEAVNKDKPLGAVALKSYEEELAKDPRIAATMENA

QKGEIMPNIPQMSAFWYAVRTAVINAASGRQTVDEALKDAQTRITKGMTV

RELCSAAITMSDNTAANLLLTTIGGPKELTAFLHNMGDHVTRLDRWEPEL

NEATPNDERDTTMPAAMATTLRKLLTGELLTLASRQQLIDWMEADKVAGP

LLRSALPAGWFIADKSGAGERGSRGIIAALGPDGKPSRIVVIYTTGSQAT

MDERNRQIAEIGASLIKHWGSGGGHPETLVKVKDAEDQLGARVGYIELDL

-continued

NSGKILESFRPEERFPMMSTFKVLLCGAVLSRVDAGQEQLGRRTHYSQND

LVEYSPVTEKHLTEVKSTS

LITERATURE CITED

Reference to the following citations may assist in understanding of the invention.

Arnold, F. H. (2001). Combinatorial and computational challenges for biocatalyst design. *Nature* 409(6817): 253-7.

Ataka, K. and V. A. Pieribone (2002). A genetically targetable fluorescent probe of channel gating with rapid kinetics. *Biophys J* 82(1 Pt 1): 509-16.

Aÿ, J., F. Götz, et al. (1998). Structure and function of the *Bacillus* hybrid enzyme GluXyn-1: native-like jellyroll fold preserved after insertion of autonomous globular domain. *Proc. Natl. Acad. Sci. USA* 95: 6613-6618.

Baird, G. S., D. A. Zacharias, et al. (1999). Circular permutation and receptor insertion within green fluorescent proteins. *Proc. Natl. Acad. Sci. U.S.A* 96(20): 11241-11246.

Barany, F. (1985). Single-stranded hexameric linkers: a system for in-phase insertion mutagenesis and protein engineering. *Gene* 37(1-3): 111-23.

Barany, F. (1985). Two-codon insertion mutagenesis of plasmid genes by using single-stranded hexameric oligonucleotides. *Proc Natl Acad Sci USA* 82(12): 4202-6.

Barany, F. (1987). A genetic system for isolation and characterization of TaqI restriction endonuclease mutants. *Gene* 56(1): 13-27.

Betton, J.-M., J. P. Jacob, et al. (1997). Creating a bifunctional protein by insertion of β-lactamase into the maltodextrin-binding protein. *Nat. Biotechnology* 15: 1276-1279.

Bibi, E. and O. Beja (1994). Membrane topology of multidrug resistance protein expressed in *Escherichia coli*. N-terminal domain. *J Biol Chem* 269(31): 19910-5.

Biondi, R. M., P. J. Baehler, et al. (1998). Random insertion of GFP into the cAMP-dependent protein kinase regulatory subunit from *Dictyostelium discoideum. Nucleic Acids Res.* 26(21): 4946-4952.

Bishop, A., O. Buzko, et al. (2000). Unnatural ligands for engineered proteins: new tools for chemical genetics. *Annu Rev Biophys Biomol Struct* 29: 577-606.

Boeke, J. D. (1981). One and two codon insertion mutants of bacteriophage f1. *Mol Gen Genet.* 181(3): 288-91.

Burcin, M. M., O. M. B W, et al. (1998). A regulatory system for target gene expression. Front Biosci 3: c1-7.

Burcin, M. M., G. Schiedner, et al. (1999). Adenovirus-mediated regulable target gene expression in vivo. *Proc Natl Acad Sci USA* 96(2): 355-60.

Carter, P. and J. A. Wells (1987). Engineering enzyme specificity by "substrate-assisted catalysis. *Science* 237(4813): 394-9.

Chen, C. C. & Herzberg, O. Relocation of the catalytic carboxylate group in class A beta-lactamase: the structure and function of the mutant enzyme Glu166-->Gln:Asn170-->Asp. *Protein Eng* 12, 573-579 (1999).

Chen, C. C., Rahil, J., Pratt, R. F. & Herzberg, O, Structure of a phosphonate-inhibited beta-lactamase. An analog of the tetrahedral transition state/intermediate of beta-lactam hydrolysis. *J Mol Biol* 234, 165-178 (1993).

Citri, N., Samuni, A. & Zyk, N. Acquisition of substrate-specific parameters during the catalytic reaction of penicillinase. *Proc Natl Acad Sci USA* 73, 1048-1052 (1976).

Collinet, B., M. Herve, et al. (2000). Functionally accepted insertions of proteins within protein domains. *J Biol Chem* 275(23): 17428-33.

Cosgriff, A. J. and A. J. Pittard (1997). A topological model for the general aromatic amino acid permease, AroP, of *Escherichia coli*. *J Bacteriol* 179(10): 3317-23.

de Lorimier, R. M., J. J. Smith, et al. (2002). Construction of a fluorescent biosensor family. *Protein Sci* 11(11): 2655-75.

Ding, Z., R. B. Fong, et al. (2001). Size-dependent control of the binding of biotinylated proteins to streptavidin using a polymer shield. *Nature* 411(6833): 59-62.

Doi, N., M. Itaya, et al. (1997). Insertion of foreign random sequences of 120 amino acid residues into an active enzyme. *FEBS Lett.* 402(2-3): 177-180.

Doi, N. and H. Yanagawa (1999). Design of generic biosensors based on green fluorescent proteins with allosteric sites by directed evolution. *FEBS Lett.* 453: 305-307.

Duan, X., J. A. Hall, et al. (2001). Crystal structures of the maltodextrin/maltose-binding protein complexed with reduced oligosaccharides: flexibility of tertiary structure and ligand binding. *J Mol Biol* 306(5): 1115-26.

Ehrmann, M., D. Boyd, et al. (1990). Genetic analysis of membrane protein topology by a sandwich gene fusion approach. *Proc Natl Acad Sci USA* 87(19): 7574-8.

Eilers, M., D. Picard, et al. (1989). Chimaeras of myc oncoprotein and steroid receptors cause hormone-dependent transformation of cells. *Nature* 340(6228): 66-8.

Evenas, J., V. Tugarinov, et al. (2001). Ligand-induced structural changes to maltodextrin-binding protein as studied by solution NMR spectroscopy. *J Mol Biol* 309(4): 961-74.

Farrar, M. A., S. H. Olson, et al. (2000). Coumermycin-induced dimerization of GyrB-containing fusion proteins. *Methods Enzymol* 327: 421-9.

Fehr, M., W. B. Frommer, et al. (2002). Visualization of maltose uptake in living yeast cells by fluorescent nanosensors. *Proc Natl Acad Sci USA* 99(15): 9846-51.

Freimuth, P. I. and H. S. Ginsberg (1986). Codon insertion mutants of the adenovirus terminal protein. *Proc Natl Acad Sci USA* 83(20): 7816-20.

Gao, W., B. Xing, et al. (2003). Novel fluorogenic substrates for imaging B-Lactamase Gene Expression. *J. Am. Chem. Soc.* 125: 11146-11147.

Gill, S. C., and von Hippel, P. H. (1989). Calculation of protein extinction coefficients from amino acid sequence data. Anal Biochem 182, 319-326.

Goldenberg, D. P. and T. E. Creighton (1983). Circular and circularly permuted forms of bovine pancreatic trypsin inhibitor. *J. Mol. Biol.* 165(2): 407-413.

Graf, R. and H. K. Schachman (1996). Random circular permutation of genes and expressed polypeptide chains: Application of the method to the catalytic chains of aspartate transcarbamoylase. *Proc. Natl. Acad. Sci. USA* 93: 11591-11596.

Guerrero, G. and E. Y. Isacoff (2001). Genetically encoded optical sensors of neuronal activity and cellular function. *Curr Opin Neurobiol* 11(5): 601-7.

Guntas, G., Mitchell, S. F. & Ostermeier, M. A molecular switch created by in vitro recombination of nonhomologous genes. *Chem Biol* 11, 1483-1487 (2004).

Guntas, G. and M. Ostermeier (2004). Creation of an allosteric enzyme by domain insertion. *J Mol Biol* 336:2633-273, 2004.

Guo, Z., D. Zhou, et al. (2000). Designing small-molecule switches for protein-protein interactions. *Science* 288(5473): 2042-5.

Hall, J. A., Gehring, K. & Nikaido, H. Two modes of ligand binding in maltose-binding protein of *Eschericia coli*: correlation with the structure of ligands and the structure of binding protein. *J Biol Chem* 272, 17605-17609 (1997)

Hallet, B., D. J. Sherratt, et al. (1997). Pentapeptide scanning mutagenesis: random insertion of a variable five amino acid cassette in a target protein. *Nucleic Acids Res.* 25(9): 1866-1867.

Hamad-Schifferli, K., J. J. Schwartz, et al. (2002). Remote electronic control of DNA hybridization through inductive coupling to an attached metal nanocrystal antenna. *Nature* 415(6868): 152-5.

Heinemann, U. and M. Hahn (1995). Circular permutation of polypeptide chains: implications for protein folding and stability. *Prog. Biophys. Mol. Biol.* 64(2-3): 121-143.

Hennecke, J., P. Sebbel, et al. (1999). Random circular permutation of DsbA reveals segments that are essential for protein folding and stability. *J. Mol. Biol.* 286(4): 1197-1215.

Horton, R. M., H. D. Hunt, et al. (1989). Engineered hybrid genes without the use of restriction enzymes: gene splicing by overlap extension. *Gene* 77: 61-68.

Hwang, P. M., N. R. Skrynnikov, et al. (2001). Domain orientation in beta-cyclodextrin-loaded maltose binding protein: diffusion anisotropy measurements confirm the results of a dipolar coupling study. *J Biomol NMR* 20(1): 83-8.

Iwakura, M., T. Nakamura, et al. (2000). Systematic circular permutation of an entire protein reveals essential folding elements. *Nat Struct Biol* 7(7): 580-5.

Jones, S., M. Stewart, et al. (1998). Domain assignment for protein structures using a consensus approach: characterization and analysis. *Protein Sci* 7(2): 233-42.

Kratz, P. A., B. Bottcher, et al. (1999). Native display of complete foreign protein domains on the surface of hepatitis B virus capsids. *Proc Natl Acad Sci USA* 96(5): 1915-20.

Kyriakides, T. R., C. Y. Cheung, et al. (2002). pH-sensitive polymers that enhance intracellular drug delivery in vivo. *J Control Release* 78(1-3): 295-303.

Lacatena, R. M., A. Cellini, et al. (1994). Topological analysis of the human beta 2-adrenergic receptor expressed in *Escherichia coli*. *Proc Natl Acad Sci USA* 91(22): 10521-5.

Ladant, D., P. Glaser, et al. (1992). Insertional mutagenesis of *Bordetella pertussis* adenylate cyclase. *J. Biol. Chem.* 267 (4): 2244-2250.

Looger, L. L., M. A. Dwyer, et al. (2003). Computational design of receptor and sensor proteins with novel functions. *Nature* 423(6936): 185-90.

Lu, Z., K. S. Murray, et al. (1995). Expression of thioredoxin random peptide libraries on the *Escherichia coli* cell surface as functional fusions to flagellin: a system designed for exploring protein-protein interactions. *Biotechnology* (NY) 13(4): 366-72.

Luque, I. and E. Freire (2000). Structural stability of binding sites: consequences for binding affinity and allosteric effects. *Proteins* Suppl(4): 63-71.

Marvin, J. S, and H. W. Hellinga (2001). Conversion of a maltose receptor into a zinc biosensor by computational design. *Proc Natl Acad Sci USA* 98(9): 4955-60.

Marvin, J. S, and H. W. Hellinga (2001). Manipulation of ligand binding affinity by exploitation of conformational coupling. *Nat Struct Biol* 8(9): 795-8.

Millet, O., R. P. Hudson, et al. (2003). The energetic cost of domain reorientation in maltose-binding protein as studied by NMR and fluorescence spectroscopy. *Proc Natl Acad Sci USA* 100(22): 12700-5.

Nagai, T., A. Sawano, et al. (2001). Circularly permuted green fluorescent proteins engineered to sense Ca2+. *Proc Natl Acad Sci USA* 98(6): 3197-202.

Neet, K. E., and Ainslie, G. R., Jr. (1980). Hysteretic enzymes. Methods Enzymol 64, 192-226.
O'Callaghan, C. H., Morris, A., Kirby, S. M., and Shingler, A. H. (1972). Novel method for detection of beta-lactamases by using a chromogenic cephalosporin substrate. Antimicrob Agents Chemother 1, 283-288.
Ostermeier, M. and S. J. Benkovic (2001). Construction of hybrid gene libraries involving the circular permutation of DNA. *Biotechnol. Lett.* 23: 303-310.
Ostermeier, M., A. E. Nixon, et al. (1999). Combinatorial protein engineering by incremental truncation. *Proc. Natl. Acad. Sci. USA* 96: 3562-3567.
Osuna, J., A. Pérez-Blancas, et al. (2002). Improving a circularly permuted TEM-1 β-lactmase by directed evolution. *Protein Eng* 15(6): 463-470.
Pi, J. and A. J. Pittard (1996). Topology of the phenylalanine-specific permease of *Escherichia coli. J Bacteriol* 178(9): 2650-5.
Picard, D. (2000). Posttranslational regulation of proteins by fusions to steroid-binding domains. *Methods Enzymol* 327: 385-401.
Picard, D., S. J. Salser, et al. (1988). A movable and regulable inactivation function within the steroid binding domain of the glucocorticoid receptor. *Cell* 54(7): 1073-80.
Pigeon, R. P. and R. P. Silver (1994). Topological and mutational analysis of KpsM, the hydrophobic component of the ABC-transporter involved in the export of polysialic acid in *Escherichia coli* K1. *Mol Microbiol* 14(5): 871-81.
Quiocho, F. A., J. C. Spurlino, et al. (1997). Extensive features of tight oligosaccharide binding revealed in high-resolution structures of the maltodextrin transport/chemosensory receptor. *Structure* 5(8): 997-1015.
Raquet, X., J. Lamotte-Brasseur, et al. (1994). TEM beta-lactamase mutants hydrolysing third-generation cephalosporins. A kinetic and molecular modelling analysis. *J Mol Biol* 244(5): 625-39.
Rivera, V. M. (1998). Controlling gene expression using synthetic ligands. *Methods* 14(4): 421-9.
Rivera, V. M., X. Wang, et al. (2000). Regulation of protein secretion through controlled aggregation in the endoplasmic reticulum. *Science* 287(5454): 826-30.
Russell, R. B. and C. P. Ponting (1998). Protein fold irregularities that hinder sequence analysis. *Curr. Opin. Struct. Biol* 8(3): 364-371.
Sarsero, J. P. and A. J. Pittard (1995). Membrane topology analysis of *Escherichia coli* K-12 Mtr permease by alkaline phosphatase and beta-galactosidase fusions. *J Bacteriol* 177(2): 297-306.
Schwartz, M., O. Kellermann, et al. (1976). Further studies on the binding of maltose to the maltose-binding protein of *Escherichia coli. Eur J Biochem* 71(1): 167-70.
Siegel, M. S, and E. Y. Isacoff (1997). A genetically encoded optical probe of membrane voltage. *Neuron* 19(4): 735-41.
Siegel, M. S, and E. Y. Isacoff (2000). Green fluorescent protein-based sensors for detecting signal transduction and monitoring ion channel function. *Methods Enzymol* 327: 249-59.
Skrynnikov, N. R., N. K. Goto, et al. (2000). Orienting domains in proteins using dipolar couplings measured by liquid-state NMR: differences in solution and crystal forms of maltodextrin binding protein loaded with beta-cyclodextrin. *J Mol Biol* 295(5): 1265-73
Spencer, D. M. (1996). Creating conditional mutations in mammals. *Trends Genet.* 12(5): 181-7.
Spencer, D. M., T. J. Wandless, et al. (1993). Controlling signal transduction with synthetic ligands. *Science* 262 (5136): 1019-24.
Starzyk, R. M., J. J. Burbaum, et al. (1989). Insertion of new sequences into the catalytic domain of an enzyme. *Biochemistry* 28(21): 8479-8484.
Stayton, P. S., T. Shimoboji, et al. (1995). Control of protein-ligand recognition using a stimuli-responsive polymer. *Nature* 378(6556): 472-4.
Stone, J. C., T. Atkinson, et al. (1984). Identification of functional regions in the transforming protein of Fujinami sarcoma virus by in-phase insertion mutagenesis. *Cell* 37(2): 549-58.
Strynadka, N. C. et al. Molecular structure of the acyl-enzyme intermediate in beta-lactam hydrolysis at 1.7 A resolution. *Nature* 359, 700-705 (1992).
Tucker, C. L. and S. Fields (2001). A yeast sensor of ligand binding. *Nat Biotechnol* 19(11): 1042-6.
Waley, S. G. The kinetics of substrate-induced inactivation. *Biochem J*279 (Pt 1), 87-94 (1991).
Williams, D. M., D. Wang, et al. (2000). Chemical rescue of a mutant protein-tyrosine kinase. *J Biol Chem* 275(49): 38127-30.
Zebala, J. and F. Barany (1991). Mapping catalytically important regions of an enzyme using two-codon insertion mutagenesis: a case study correlating β-lactamase mutants with the three-dimensional structure. *Gene* 100: 51-57.
Zlokarnik, G., P. A. Negulescu, et al. (1998). Quantitation of transcription and clonal selection of single living cells with beta-lactamase as reporter. *Science* 279(5347): 84-8.
Posey, K. L., and Gimble, F. S. (2002). Insertion of a reversible redox switch into a rare-cutting DNA endonuclease. Biochemistry 41, 2184-2190.
Saghatelian, A., Guckian, K. M., Thayer, D. A., and Ghadiri, M. R. (2003). DNA detection and signal amplification via an engineered allosteric enzyme. J Am Chem Soc 125, 344-345.
Brennan, C., Cristianson, K., Surowy, T., and Mandecki, W. (1994). Modulation of enzyme activity by antibody binding to an alkaline phosphatase-epitope hybrid protein. Protein Eng. 7, 509-514.
Pelletier, J. N., Campbell-Valois, F. X., and Michnick, S. W. (1998). Oligomerization domain-directed reassembly of active dihydrofolate reductase from rationally designed fragments. Proc. Natl. Acad. Sci. USA 95, 12141-12146.
Dueber, J. E., Yeh, B. J., Chak, K., and Lim, W. A. (2003). Reprogramming control of an allosteric signaling switch through modular recombination. Science 301, 1904-1908.
Mootz, H. D., and Muir, T. W. (2002). Protein splicing triggered by a small molecule. J Am Chem Soc 124, 9044-9045.
Gryczynski, U., and Schleif, R. (2004). A portable allosteric mechanism. Proteins 57, 9-11.
Tucker, C. L., and Fields, S. (2001). A yeast sensor of ligand binding. Nat Biotechnol 19, 1042-1046.
Doi, N., and Yanagawa, H. (1999). Insertional gene fusion technology. FEBS Lett 457, 1-4.
Radley, T. L., Markowska, A. I., Bettinger, B. T., Ha, J. H., and Loh, S. N. (2003). Allosteric switching by mutually exclusive folding of protein domains. J Mol Biol 332, 529-536.
Buskirk, A. R., Ong, Y. C., Gartner, Z. J., and Liu, D. R. (2004). Directed evolution of ligand dependence: Small-molecule-activated protein splicing. Proc Natl Acad Sci USA 101, 10505-10510.
Ostermeier, M., and Benkovic, S. J. (2000). Evolution of protein function by domain swapping. Adv. Protein Chem. 55, 29-77.
Apic, G., Gough, J., and Teichmann, S. A. (2001). Domain combinations in archaeal, eubacterial and eukaryotic proteomes. J Mol Biol 310, 311-325.

Sharff, A. J., Rodseth, L. E., Spurlino, J. C., and Quiocho, F. A. (1992). Crystallographic evidence of a large ligand-induced hinge-twist motion between the two domains of the maltodextrin binding protein involved in active transport and chemotzxis. Biochemistry 31, 10657-10663.

Maveyraud, L., Massova, I., Birck, C., Miyashita, K., Samama, J.-P., and Mobashery, S. (1996). Crystal structure of 6alpha-(hydroxymethyl)penicillanate complexed to the TEM-1 β-lactamase from *Escherichia coli*: evidence on the mechanism of action of a novel inhibitor designed by a computer-aided process. J. Am. Chem. Soc. 118, 7435-7440.

Evenas, J., Tugarinov, V., Skrynnikov, N. R., Goto, N. K., Muhandiram, R., and Kay, L. E. (2001). Ligand-induced structural changes to maltodextrin-binding protein as studied by solution NMR spectroscopy. J Mol Biol 309, 961-974.

Sigal, I. S., DeGrado, W. F., Thomas, B. J., and Petteway, S. R., Jr. (1984). Purification and properties of thiol beta-lactamase. A mutant of pBR322 beta-lactamase in which the active site serine has been replaced with cysteine. J Biol Chem 259, 5327-5332. Christensen, H., Martin, M. T., and Waley, S. G. (1990). Beta-lactamases as fully efficient enzymes. Determination of all the rate constants in the acyl-enzyme mechanism. Biochem J 266, 853-861.

Hall, J. A., Gehring, K., and Nikaido, H. (1997). Two modes of ligand binding in maltose-binding protein of *Eschericia coli*: correlation with the structure of ligands and the structure of binding protein. J Biol Chem 272, 17605-17609.

Marvin, J. S., and Hellinga, H. W. (2001). Manipulation of ligand binding affinity by exploitation of conformational coupling. Nat Struct Biol 8, 795-798.

Millet, O., Hudson, R. P., and Kay, L. E. (2003). The energetic cost of domain reorientation in maltose-binding protein as studied by NMR and fluorescence spectroscopy. Proc Natl Acad Sci USA 100, 12700-12705.

Other Embodiments

Variations, modifications, and other implementations of what is described herein will occur to those of ordinary skill in the art without departing from the spirit and scope of the invention and the following claims.

All patents, patent applications, and publications referenced herein are incorporated in their entirety herein.

---

What is claimed is:

1. A method for assembling a modulatable fusion molecule polypeptide, comprising:

generating a circular permutation of an insertion nucleic acid sequence, wherein the insertion nucleic acid sequence encodes a polypeptide that recognizes an input signal; and inserting the insertion sequence into an acceptor nucleic acid sequence, wherein the acceptor sequence encodes a polypeptide that produces an output signal provided the output signal is not fluorescence, wherein the fused insertion and acceptor sequences encode a modulatable fusion polypeptide having the output signal functionally coupled to the input signal.

2. The method according to claim 1, wherein the insertion sequence is inserted at a selected site in the acceptor sequence.

3. The method according to claim 1, wherein the insertion sequence is inserted at a random site in the acceptor sequence.

4. A method for assembling a modulatable fusion molecule polypeptide, comprising:

generating a circular permutation of an insertion nucleic acid sequence, wherein the insertion nucleic acid sequence encodes a polypeptide that produces an output signal provided the output signal is not fluorescence; and inserting the insertion sequence into an acceptor nucleic acid sequence, wherein the acceptor sequence encodes a polypeptide that recognizes an input signal, wherein the fused insertion and acceptor sequences encode a modulatable fusion polypeptide having the output signal functionally coupled to the input signal.

5. The method according to claim 4, wherein the insertion sequence is inserted at a selected site in the acceptor sequence.

6. The method according to claim 4, wherein the insertion sequence is inserted at a random site in the acceptor sequence.

7. A method for assembling a modulatable fusion molecule polypeptide, comprising:

generating a circular permutation of an acceptor nucleic acid sequence, wherein the acceptor nucleic acid sequence encodes a polypeptide that recognizes an input signal; and inserting the insertion sequence into an acceptor nucleic acid sequence, wherein the insertion sequence encodes a polypeptide that produces an output signal provided the output signal is not fluorescence, wherein the fused insertion and acceptor sequences encode a modulatable fusion polypeptide having the output signal functionally coupled to the input signal.

8. The method according to claim 7, wherein the insertion sequence is inserted at a selected site in the acceptor sequence.

9. The method according to claim 7, wherein the insertion sequence is inserted at a random site in the acceptor sequence.

10. A method of assembling a modulatable fusion molecule polypeptide, comprising:

generating a circular permutation of an acceptor nucleic acid sequence, wherein the acceptor nucleic acid sequence encodes a polypeptide that produces an output signal provided the output signal is not fluorescence; and inserting the insertion sequence into an acceptor nucleic acid sequence, wherein the insertion sequence encodes a polypeptide that recognizes an input signal, wherein the fused insertion and acceptor sequences encode a modulatable fusion polypeptide having the output signal functionally coupled to the input signal.

11. The method according to claim 10, wherein the insertion sequence is inserted at a selected site in the acceptor sequence.

12. The method according to claim 10, wherein the insertion sequence is inserted at a random site in the acceptor sequence.

* * * * *

SEQUENCE LISTING

```
<160> NUMBER OF SEQ ID NOS: 99

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide linker

<400> SEQUENCE: 1

Gly Ser Gly Gly Gly
1               5


<210> SEQ ID NO 2
<211> LENGTH: 37
<212> TYPE: PRT
<213> ORGANISM: Homo sapiens

<400> SEQUENCE: 2

Pro Asn Lys Gly Ser Gly Thr Thr Ser Gly Thr Thr Arg Leu Leu Ser
1               5                   10                  15

Gly His Thr Cys Phe Thr Leu Thr Gly Leu Leu Gly Thr Leu Val Thr
            20                  25                  30

Met Gly Leu Leu Thr
        35


<210> SEQ ID NO 3
<211> LENGTH: 14
<212> TYPE: PRT
<213> ORGANISM: Rous sarcoma virus

<400> SEQUENCE: 3

Met Gly Ser Ser Lys Ser Lys Pro Lys Asp Pro Ser Gln Arg
1               5                   10


<210> SEQ ID NO 4
<211> LENGTH: 25
<212> TYPE: PRT
<213> ORGANISM: Unknown
```

<220> FEATURE:
<223> OTHER INFORMATION: Description of Unknown: GRK6 peptide
sequence

<400> SEQUENCE: 4

```
Leu Leu Gln Arg Leu Phe Ser Arg Gln Asp Cys Cys Gly Asn Cys Ser
  1               5                  10                  15

Asp Ser Glu Glu Glu Leu Pro Thr Arg
             20                  25
```

<210> SEQ ID NO 5
<211> LENGTH: 7
<212> TYPE: PRT
<213> ORGANISM: Monkey virus SV40

<400> SEQUENCE: 5

```
Pro Lys Lys Lys Lys Lys Val
  1               5
```

<210> SEQ ID NO 6
<211> LENGTH: 6
<212> TYPE: PRT
<213> ORGANISM: Homo sapiens

<400> SEQUENCE: 6

```
Ala Arg Arg Arg Arg Pro
  1               5
```

<210> SEQ ID NO 7
<211> LENGTH: 10
<212> TYPE: PRT
<213> ORGANISM: Unknown
<220> FEATURE:
<223> OTHER INFORMATION: Description of Unknown: NF kappa-B p50
sequence

<400> SEQUENCE: 7

```
Glu Glu Val Gln Arg Lys Arg Gln Lys Leu
  1               5                  10
```

<210> SEQ ID NO 8
<211> LENGTH: 9
<212> TYPE: PRT
<213> ORGANISM: Unknown
<220> FEATURE:
<223> OTHER INFORMATION: Description of Unknown: NF kappa-B p65
sequence

<400> SEQUENCE: 8

```
Glu Glu Lys Arg Lys Arg Thr Tyr Glu
  1               5
```

<210> SEQ ID NO 9
<211> LENGTH: 21
<212> TYPE: PRT
<213> ORGANISM: Unknown
<220> FEATURE:
<223> OTHER INFORMATION: Description of Unknown: Nucleoplasmin
sequence

<400> SEQUENCE: 9

```
Ala Val Lys Arg Pro Ala Ala Thr Leu Lys Lys Ala Gly Gln Ala Lys
  1               5                  10                  15

Lys Lys Lys Leu Asp
             20
```

-continued

```
<210> SEQ ID NO 10
<211> LENGTH: 5
<212> TYPE: PRT
<213> ORGANISM: Homo sapiens

<400> SEQUENCE: 10

Lys Phe Glu Arg Gln
  1               5


<210> SEQ ID NO 11
<211> LENGTH: 36
<212> TYPE: PRT
<213> ORGANISM: Homo sapiens

<400> SEQUENCE: 11

Met Leu Ile Pro Ile Ala Gly Phe Phe Ala Leu Ala Gly Leu Val Leu
  1               5                  10                  15

Ile Val Leu Ile Ala Tyr Leu Ile Gly Arg Lys Arg Ser His Ala Gly
             20                  25                  30

Tyr Gln Thr Ile
         35


<210> SEQ ID NO 12
<211> LENGTH: 35
<212> TYPE: PRT
<213> ORGANISM: Homo sapiens

<400> SEQUENCE: 12

Leu Val Pro Ile Ala Val Gly Ala Ala Leu Ala Gly Val Leu Ile Leu
  1               5                  10                  15

Val Leu Leu Ala Tyr Phe Ile Gly Leu Lys His His His Ala Gly Tyr
             20                  25                  30

Glu Gln Phe
         35


<210> SEQ ID NO 13
<211> LENGTH: 27
<212> TYPE: PRT
<213> ORGANISM: Saccharomyces cerevisiae

<400> SEQUENCE: 13

Met Leu Arg Thr Ser Ser Leu Phe Thr Arg Arg Val Gln Pro Ser Leu
  1               5                  10                  15

Phe Ser Arg Asn Ile Leu Arg Leu Gln Ser Thr
             20                  25


<210> SEQ ID NO 14
<211> LENGTH: 25
<212> TYPE: PRT
<213> ORGANISM: Saccharomyces cerevisiae

<400> SEQUENCE: 14

Met Leu Ser Leu Arg Gln Ser Ile Arg Phe Phe Lys Pro Ala Thr Arg
  1               5                  10                  15

Thr Leu Cys Ser Ser Arg Tyr Leu Leu
             20                  25


<210> SEQ ID NO 15
<211> LENGTH: 64
<212> TYPE: PRT
<213> ORGANISM: Saccharomyces cerevisiae
```

<400> SEQUENCE: 15

Met Phe Ser Met Leu Ser Lys Arg Trp Ala Gln Arg Thr Leu Ser Lys
1 5 10 15

Ser Phe Tyr Ser Thr Ala Thr Gly Ala Ala Ser Lys Ser Gly Lys Leu
20 25 30

Thr Gln Lys Leu Val Thr Ala Gly Val Ala Ala Ala Gly Ile Thr Ala
35 40 45

Ser Thr Leu Leu Tyr Ala Asp Ser Leu Thr Ala Glu Ala Met Thr Ala
50 55 60

<210> SEQ ID NO 16
<211> LENGTH: 41
<212> TYPE: PRT
<213> ORGANISM: Saccharomyces cerevisiae

<400> SEQUENCE: 16

Met Lys Ser Phe Ile Thr Arg Asn Lys Thr Ala Ile Leu Ala Thr Val
1 5 10 15

Ala Ala Thr Gly Thr Ala Ile Gly Ala Tyr Tyr Tyr Tyr Asn Gln Leu
20 25 30

Gln Gln Gln Gln Gln Arg Gly Lys Lys
35 40

<210> SEQ ID NO 17
<211> LENGTH: 4
<212> TYPE: PRT
<213> ORGANISM: Unknown
<220> FEATURE:
<223> OTHER INFORMATION: Description of Unknown: Endoplasmic reticulum localizing sequence

<400> SEQUENCE: 17

Lys Asp Glu Leu
1

<210> SEQ ID NO 18
<211> LENGTH: 15
<212> TYPE: PRT
<213> ORGANISM: Human adenovirus type 19

<400> SEQUENCE: 18

Leu Tyr Leu Ser Arg Arg Ser Phe Ile Asp Glu Lys Lys Met Pro
1 5 10 15

<210> SEQ ID NO 19
<211> LENGTH: 20
<212> TYPE: PRT
<213> ORGANISM: Unknown
<220> FEATURE:
<223> OTHER INFORMATION: Description of Unknown: Interleukin-2 sequence

<400> SEQUENCE: 19

Met Tyr Arg Met Gln Leu Leu Ser Cys Ile Ala Leu Ser Leu Ala Leu
1 5 10 15

Val Thr Asn Ser
20

<210> SEQ ID NO 20
<211> LENGTH: 29
<212> TYPE: PRT
<213> ORGANISM: Homo sapiens

<400> SEQUENCE: 20

Met Ala Thr Gly Ser Arg Thr Ser Leu Leu Leu Ala Phe Gly Leu Leu
1 5 10 15

Cys Leu Pro Trp Leu Gln Glu Gly Ser Ala Phe Pro Thr
20 25

<210> SEQ ID NO 21
<211> LENGTH: 27
<212> TYPE: PRT
<213> ORGANISM: Homo sapiens

<400> SEQUENCE: 21

Met Ala Leu Trp Met Arg Leu Leu Pro Leu Leu Ala Leu Leu Ala Leu
1 5 10 15

Trp Gly Pro Asp Pro Ala Ala Ala Phe Val Asn
20 25

<210> SEQ ID NO 22
<211> LENGTH: 18
<212> TYPE: PRT
<213> ORGANISM: Influenza A virus

<400> SEQUENCE: 22

Met Lys Ala Lys Leu Leu Val Leu Leu Tyr Ala Phe Val Ala Gly Asp
1 5 10 15

Gln Ile

<210> SEQ ID NO 23
<211> LENGTH: 24
<212> TYPE: PRT
<213> ORGANISM: Unknown
<220> FEATURE:
<223> OTHER INFORMATION: Description of Unknown: Interleukin-4 sequence

<400> SEQUENCE: 23

Met Gly Leu Thr Ser Gln Leu Leu Pro Pro Leu Phe Phe Leu Leu Ala
1 5 10 15

Cys Ala Gly Asn Phe Val His Gly
20

<210> SEQ ID NO 24
<211> LENGTH: 37
<212> TYPE: DNA
<213> ORGANISM: Artificial Sequence
<220> FEATURE:
<223> OTHER INFORMATION: Description of Artificial Sequence: Synthetic primer

<400> SEQUENCE: 24
tgccggatcc ggcggtggcc acccagaaac gctggtg 37

<210> SEQ ID NO 25
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 25
gtctgaggat ccccaatgct taatcagtga 30

<210> SEQ ID NO 26
<211> LENGTH: 18
<212> TYPE: DNA
<213> ORGANISM: Artificial Sequence
<220> FEATURE:
<223> OTHER INFORMATION: Description of Artificial Sequence: Synthetic
primer

<400> SEQUENCE: 26
gccgttaatc cagattac 18

<210> SEQ ID NO 27
<211> LENGTH: 41
<212> TYPE: DNA
<213> ORGANISM: Artificial Sequence
<220> FEATURE:
<223> OTHER INFORMATION: Description of Artificial Sequence: Synthetic
primer
<220> FEATURE:
<221> NAME/KEY: modified_base
<222> LOCATION: (18)..(19)
<223> OTHER INFORMATION: a, c, g, t, unknown, or other
<220> FEATURE:
<221> NAME/KEY: modified_base
<222> LOCATION: (21)..(22)
<223> OTHER INFORMATION: a, c, g, t, unknown, or other

<400> SEQUENCE: 27
gtaatctgga ttaaggcnnk nnkggctata acggtctcgc t 41

<210> SEQ ID NO 28
<211> LENGTH: 18
<212> TYPE: DNA
<213> ORGANISM: Artificial Sequence
<220> FEATURE:
<223> OTHER INFORMATION: Description of Artificial Sequence: Synthetic
primer

<400> SEQUENCE: 28
gaagataatg tcagggcc 18

<210> SEQ ID NO 29
<211> LENGTH: 39
<212> TYPE: DNA
<213> ORGANISM: Artificial Sequence
<220> FEATURE:
<223> OTHER INFORMATION: Description of Artificial Sequence: Synthetic
primer
<220> FEATURE:
<221> NAME/KEY: modified_base
<222> LOCATION: (19)..(20)
<223> OTHER INFORMATION: a, c, g, t, unknown, or other

<400> SEQUENCE: 29
ggccctgaca ttatcttcnn kgcacacgac cgctttggt 39

<210> SEQ ID NO 30
<211> LENGTH: 18
<212> TYPE: DNA
<213> ORGANISM: Artificial Sequence
<220> FEATURE:
<223> OTHER INFORMATION: Description of Artificial Sequence: Synthetic
primer

<400> SEQUENCE: 30
aacagcgatc gggtaagc 18

<210> SEQ ID NO 31
<211> LENGTH: 39
<212> TYPE: DNA
<213> ORGANISM: Artificial Sequence
<220> FEATURE:
<223> OTHER INFORMATION: Description of Artificial Sequence: Synthetic primer
<220> FEATURE:
<221> NAME/KEY: modified_base
<222> LOCATION: (19)..(20)
<223> OTHER INFORMATION: a, c, g, t, unknown, or other

<400> SEQUENCE: 31
gcttacccga tcgctgttnn kgcgttatcg ctgatttat 39

<210> SEQ ID NO 32
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 32
cgggccgttg atggtcat 18

<210> SEQ ID NO 33
<211> LENGTH: 39
<212> TYPE: DNA
<213> ORGANISM: Artificial Sequence
<220> FEATURE:
<223> OTHER INFORMATION: Description of Artificial Sequence: Synthetic primer
<220> FEATURE:
<221> NAME/KEY: modified_base
<222> LOCATION: (19)..(20)
<223> OTHER INFORMATION: a, c, g, t, unknown, or other

<400> SEQUENCE: 33
atgaccatca acggcccgnn kgcatggtcc aacatcgac 39

<210> SEQ ID NO 34
<211> LENGTH: 36
<212> TYPE: DNA
<213> ORGANISM: Artificial Sequence
<220> FEATURE:
<223> OTHER INFORMATION: Description of Artificial Sequence: Synthetic primer

<400> SEQUENCE: 34
atccggacta gtaggccttt acttggtgat acgagt 36

<210> SEQ ID NO 35
<211> LENGTH: 1995
<212> TYPE: DNA
<213> ORGANISM: Escherichia coli

<400> SEQUENCE: 35
atgaaaataa aaacaggtgc acgcatcctc gcattatccg cattaacgac gatgatgttt 60
tccgcctcgg ctctcgccaa aatcgaagaa ggtaaactgg taatctggat taacggcgat 120
aaaggctata acggtctcgc tgaagtcggt aagaaattcg agaaagatac cggaattaaa 180
gtcaccgttg agcatccgga taaactggaa gagaaattcc cacaggttgc ggcaactggc 240
gatggccctg acattatctt ctgggcacac gaccgctttg gtggctacgc tcaatctggc 300
ctgttggctg aaatcacccc ggacaaagcg ttccaggaca agctgtatcc gtttacctgg 360
gatgccgtac gttacaacgg caagctgatt gcttacccga tcgctgttga agcgttatcg 420

-continued

```
ctgatttata acaaagatct gctgccgaac ccgccaaaaa cctgggaaga gatcccggcg    480

ctggataaag aactgaaagc gaaaggtaag agcgcgctga tgttcaacct gcaagaaccg    540

tacttcacct ggccgctgat tgctgctgac gggggttatg cgttcaagta tgaaaacggc    600

aagtacgaca ttaaagacgt gggcgtggat aacgctggcg cgaaagcggg tctgaccttc    660

ctggttgacc tgattaaaaa caaacacatg aatgcagaca ccgattactc catcgcagaa    720

gctgccttta ataaaggcga aacagcgatg accatcaacg gcccgtgggc atggtccaac    780

atcgacacca gcaaagtgaa ttatggtgta acggtactgc cgaccttcaa gggtcaacca    840

tccaaaccgt tcgttggcgt gctgagcgca ggtattaacg ccgccagtcc gaacaaagag    900

ctggcgaaag agttcctcga aaactatctg ctgactgatg aaggtctgga agcggttaat    960

aaagacaaac cgctgggtgc cgtagcgctg aagtcttacg aggaagagtt ggcgaaagat   1020

ccacgtaatg aagccatacc aaacgacgag cgtgacacca cgatgcctgc agcaatggca   1080

acaacgttgc gcaaactatt aactggcgaa ctacttactc tagcttcccg gcaacaatta   1140

atagactgga tggaggcgga taaagttgca ggaccacttc tgcgctcggc ccttccggct   1200

ggctggttta ttgctgataa atctggagcc ggtgagcgtg ggtctcgcgg tatcattgca   1260

gcactggggc cagatggtaa gccctcccgt atcgtagtta tctacacgac ggggagtcag   1320

gcaactatgg atgaacgaaa tagacagatc gctgagatag gtgcctcact gattaagcat   1380

tgggacaaga gccacccaga aacgctggtg aaagtaaaag atgctgaaga tcagttgggt   1440

gcacgagtgg gttacatcga actggatctc aacagcggta agatccttga gagttttcgc   1500

cccgaagaac gttttccaat gatgagcact tttaaagttc tgctatgtgg cgcggtatta   1560

tcccgtgttg acgccgggca agagcaactc ggtcgccgca tacactattc tcagaatgac   1620

ttggttgagt actcaccagt cacagaaaag catcttacgg atggcatgac agtaagagaa   1680

ttatgcagtg ctgccataac catgagtgat aacactgcgg ccaacttact tctgacaacg   1740

atcggaggac cgaaggagct aaccgctttt ttgcacaaca tgggggatca tgtaactcgc   1800

cttgatcgtt gggaaccgga actgaatgaa gccgccgcca ccatggaaaa cgcccagaaa   1860

ggtgaaatca tgccgaacat cccgcagatg tccgctttct ggtatgccgt gcgtactgcg   1920

gtgatcaacg ccgccagcgg tcgtcagact gtcgatgaag ccctgaaaga cgcgcagact   1980

cgtatcacca agtaa                                                    1995
```

<210> SEQ ID NO 36
<211> LENGTH: 664
<212> TYPE: PRT
<213> ORGANISM: Escherichia coli

<400> SEQUENCE: 36

```
Met Lys Ile Lys Thr Gly Ala Arg Ile Leu Ala Leu Ser Ala Leu Thr
  1               5                  10                  15

Thr Met Met Phe Ser Ala Ser Ala Leu Ala Lys Ile Glu Glu Gly Lys
             20                  25                  30

Leu Val Ile Trp Ile Asn Gly Asp Lys Gly Tyr Asn Gly Leu Ala Glu
         35                  40                  45

Val Gly Lys Lys Phe Glu Lys Asp Thr Gly Ile Lys Val Thr Val Glu
     50                  55                  60

His Pro Asp Lys Leu Glu Glu Lys Phe Pro Gln Val Ala Ala Thr Gly
 65                  70                  75                  80

Asp Gly Pro Asp Ile Ile Phe Trp Ala His Asp Arg Phe Gly Gly Tyr
                 85                  90                  95
```

-continued

```
Ala Gln Ser Gly Leu Leu Ala Glu Ile Thr Pro Asp Lys Ala Phe Gln
            100                 105                 110

Asp Lys Leu Tyr Pro Phe Thr Trp Asp Ala Val Arg Tyr Asn Gly Lys
        115                 120                 125

Leu Ile Ala Tyr Pro Ile Ala Val Glu Ala Leu Ser Leu Ile Tyr Asn
    130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
            180                 185                 190

Tyr Ala Phe Lys Tyr Glu Asn Gly Lys Tyr Asp Ile Lys Asp Val Gly
        195                 200                 205

Val Asp Asn Ala Gly Ala Lys Ala Gly Leu Thr Phe Leu Val Asp Leu
    210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
                245                 250                 255

Ala Trp Ser Asn Ile Asp Thr Ser Lys Val Asn Tyr Gly Val Thr Val
            260                 265                 270

Leu Pro Thr Phe Lys Gly Gln Pro Ser Lys Pro Phe Val Gly Val Leu
        275                 280                 285

Ser Ala Gly Ile Asn Ala Ala Ser Pro Asn Lys Glu Leu Ala Lys Glu
    290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
                325                 330                 335

Leu Ala Lys Asp Pro Arg Asn Glu Ala Ile Pro Asn Asp Glu Arg Asp
            340                 345                 350

Thr Thr Met Pro Ala Ala Met Ala Thr Thr Leu Arg Lys Leu Leu Thr
        355                 360                 365

Gly Glu Leu Leu Thr Leu Ala Ser Arg Gln Gln Leu Ile Asp Trp Met
    370                 375                 380

Glu Ala Asp Lys Val Ala Gly Pro Leu Leu Arg Ser Ala Leu Pro Ala
385                 390                 395                 400

Gly Trp Phe Ile Ala Asp Lys Ser Gly Ala Gly Glu Arg Gly Ser Arg
                405                 410                 415

Gly Ile Ile Ala Ala Leu Gly Pro Asp Gly Lys Pro Ser Arg Ile Val
            420                 425                 430

Val Ile Tyr Thr Thr Gly Ser Gln Ala Thr Met Asp Glu Arg Asn Arg
        435                 440                 445

Gln Ile Ala Glu Ile Gly Ala Ser Leu Ile Lys His Trp Asp Lys Ser
    450                 455                 460

His Pro Glu Thr Leu Val Lys Val Lys Asp Ala Glu Asp Gln Leu Gly
465                 470                 475                 480

Ala Arg Val Gly Tyr Ile Glu Leu Asp Leu Asn Ser Gly Lys Ile Leu
                485                 490                 495

Glu Ser Phe Arg Pro Glu Glu Arg Phe Pro Met Met Ser Thr Phe Lys
            500                 505                 510

Val Leu Leu Cys Gly Ala Val Leu Ser Arg Val Asp Ala Gly Gln Glu
        515                 520                 525
```

```
Gln Leu Gly Arg Arg Ile His Tyr Ser Gln Asn Asp Leu Val Glu Tyr
    530                 535                 540

Ser Pro Val Thr Glu Lys His Leu Thr Asp Gly Met Thr Val Arg Glu
545                 550                 555                 560

Leu Cys Ser Ala Ala Ile Thr Met Ser Asp Asn Thr Ala Ala Asn Leu
                565                 570                 575

Leu Leu Thr Thr Ile Gly Gly Pro Lys Glu Leu Thr Ala Phe Leu His
            580                 585                 590

Asn Met Gly Asp His Val Thr Arg Leu Asp Arg Trp Glu Pro Glu Leu
        595                 600                 605

Asn Glu Ala Ala Ala Thr Met Glu Asn Ala Gln Lys Gly Glu Ile Met
    610                 615                 620

Pro Asn Ile Pro Gln Met Ser Ala Phe Trp Tyr Ala Val Arg Thr Ala
625                 630                 635                 640

Val Ile Asn Ala Ala Ser Gly Arg Gln Thr Val Asp Glu Ala Leu Lys
                645                 650                 655

Asp Ala Gln Thr Arg Ile Thr Lys
            660


<210> SEQ ID NO 37
<211> LENGTH: 1989
<212> TYPE: DNA
<213> ORGANISM: Escherichia coli

<400> SEQUENCE: 37

atgaaaataa aaacaggtgc acgcatcctc gcattatccg cattaacgac gatgatgttt      60

tccgcctcgg ctctcgccaa aatcgaagaa ggtaaactgg taatctggat taacggcgat     120

aaaggctata acggtctcgc tgaagtcggt aagaaattcg agaaagatac cggaattaaa     180

gtcaccgttg agcatccgga taaactggaa gagaaattcc cacaggttgc ggcaactggc     240

gatggccctg acattatctt ctgggcacac gaccgctttg gtggctacgc tcaatctggc     300

ctgttggctg aaatcacccc ggacaaagcg ttccaggaca agctgtatcc gtttacctgg     360

gatgccgtac gttacaacgg caagctgatt gcttacccga tcgctgttga agcgttatcg     420

ctgatttata acaaagatct gctgccgaac ccgccaaaaa cctgggaaga gatcccggcg     480

ctggataaag aactgaaagc gaaaggtaag agcgcgctga tgttcaacct gcaagaaccg     540

tacttcacct ggccgctgat tgctgctgac ggggggttatg cgttcaagta tgaaaacggc     600

aagtacgaca ttaaagacgt gggcgtggat aacgctggcg cgaaagcggg tctgaccttc     660

ctggttgacc tgattaaaaa caaacacatg aatgcagaca ccgattactc catcgcagaa     720

gctgccttta ataaaggcga aacagcgatg accatcaacg gcccgtgggc atggtccaac     780

atcgacacca gcaaagtgaa ttatggtgta acggtactgc cgaccttcaa gggtcaacca     840

tccaaaccgt tcgttggcgt gctgagcgca ggtattaacg ccgccagtcc gaacaaagag     900

ctggcgaaag agttcctcga aaactatctg ctgactgatg aaggtctgga agcggttaat     960

aaagacaaac cgctgggtgc cgtagcgctg aagtcttacg aggaagagtt ggcgaaagat    1020

ccacgtgcca taccaaacga cgagcgtgac accacgatgc ctgcagcaat ggcaacaacg    1080

ttgcgcaaac tattaactgg cgaactactt actctagctt cccggcaaca attaatagac    1140

tggatggagg cggataaagt tgcaggacca cttctgcgct cggcccttcc ggctggctgg    1200

tttattgctg ataaatctgg agccggtgag cgtgggtctc gcggtatcat tgcagcactg    1260

gggccagatg gtaagccctc ccgtatcgta gttatctaca cgacggggag tcaggcaact    1320

atggatgaac gaaatagaca gatcgctgag ataggtgcct cactgattaa gcattgggac    1380
```

-continued

```
aagagccacc cagaaacgct ggtgaaagta aaagatgctg aagatcagtt gggtgcacga   1440

gtgggttaca tcgaactgga tctcaacagc ggtaagatcc ttgagagttt tcgccccgaa   1500

gaacgttttc caatgatgag cacttttaaa gttctgctat gtggcgcggt attatcccgt   1560

gttgacgccg ggcaagagca actcggtcgc cgcatacact attctcagaa tgacttggtt   1620

gagtactcac cagtcacaga aaagcatctt acggatggca tgacagtaag agaattatgc   1680

agtgctgcca taaccatgag tgataacact gcggccaact tacttctgac aacgatcgga   1740

ggaccgaagg agctaaccgc ttttttgcac aacatggggg atcatgtaac tcgccttgat   1800

cgttgggaac cggaactgaa tgaagccgcc gccaccatgg aaaacgccca gaaaggtgaa   1860

atcatgccga acatcccgca gatgtccgct ttctggtatg ccgtgcgtac tgcggtgatc   1920

aacgccgcca gcggtcgtca gactgtcgat gaagccctga aagacgcgca gactcgtatc   1980

accaagtaa                                                           1989
```

<210> SEQ ID NO 38
<211> LENGTH: 662
<212> TYPE: PRT
<213> ORGANISM: Escherichia coli

<400> SEQUENCE: 38

```
Met Lys Ile Lys Thr Gly Ala Arg Ile Leu Ala Leu Ser Ala Leu Thr
  1               5                  10                  15

Thr Met Met Phe Ser Ala Ser Ala Leu Ala Lys Ile Glu Glu Gly Lys
             20                  25                  30

Leu Val Ile Trp Ile Asn Gly Asp Lys Gly Tyr Asn Gly Leu Ala Glu
         35                  40                  45

Val Gly Lys Lys Phe Glu Lys Asp Thr Gly Ile Lys Val Thr Val Glu
     50                  55                  60

His Pro Asp Lys Leu Glu Glu Lys Phe Pro Gln Val Ala Ala Thr Gly
 65                  70                  75                  80

Asp Gly Pro Asp Ile Ile Phe Trp Ala His Asp Arg Phe Gly Gly Tyr
                 85                  90                  95

Ala Gln Ser Gly Leu Leu Ala Glu Ile Thr Pro Asp Lys Ala Phe Gln
            100                 105                 110

Asp Lys Leu Tyr Pro Phe Thr Trp Asp Ala Val Arg Tyr Asn Gly Lys
        115                 120                 125

Leu Ile Ala Tyr Pro Ile Ala Val Glu Ala Leu Ser Leu Ile Tyr Asn
    130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
            180                 185                 190

Tyr Ala Phe Lys Tyr Glu Asn Gly Lys Tyr Asp Ile Lys Asp Val Gly
        195                 200                 205

Val Asp Asn Ala Gly Ala Lys Ala Gly Leu Thr Phe Leu Val Asp Leu
    210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
                245                 250                 255

Ala Trp Ser Asn Ile Asp Thr Ser Lys Val Asn Tyr Gly Val Thr Val
            260                 265                 270
```

```
Leu Pro Thr Phe Lys Gly Gln Pro Ser Lys Pro Phe Val Gly Val Leu
        275                 280                 285

Ser Ala Gly Ile Asn Ala Ala Ser Pro Asn Lys Glu Leu Ala Lys Glu
    290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
                325                 330                 335

Leu Ala Lys Asp Pro Arg Ala Ile Pro Asn Asp Glu Arg Asp Thr Thr
            340                 345                 350

Met Pro Ala Ala Met Ala Thr Thr Leu Arg Lys Leu Leu Thr Gly Glu
        355                 360                 365

Leu Leu Thr Leu Ala Ser Arg Gln Gln Leu Ile Asp Trp Met Glu Ala
    370                 375                 380

Asp Lys Val Ala Gly Pro Leu Leu Arg Ser Ala Leu Pro Ala Gly Trp
385                 390                 395                 400

Phe Ile Ala Asp Lys Ser Gly Ala Gly Glu Arg Gly Ser Arg Gly Ile
                405                 410                 415

Ile Ala Ala Leu Gly Pro Asp Gly Lys Pro Ser Arg Ile Val Val Ile
            420                 425                 430

Tyr Thr Thr Gly Ser Gln Ala Thr Met Asp Glu Arg Asn Arg Gln Ile
        435                 440                 445

Ala Glu Ile Gly Ala Ser Leu Ile Lys His Trp Asp Lys Ser His Pro
    450                 455                 460

Glu Thr Leu Val Lys Val Lys Asp Ala Glu Asp Gln Leu Gly Ala Arg
465                 470                 475                 480

Val Gly Tyr Ile Glu Leu Asp Leu Asn Ser Gly Lys Ile Leu Glu Ser
                485                 490                 495

Phe Arg Pro Glu Glu Arg Phe Pro Met Met Ser Thr Phe Lys Val Leu
            500                 505                 510

Leu Cys Gly Ala Val Leu Ser Arg Val Asp Ala Gly Gln Glu Gln Leu
        515                 520                 525

Gly Arg Arg Ile His Tyr Ser Gln Asn Asp Leu Val Glu Tyr Ser Pro
    530                 535                 540

Val Thr Glu Lys His Leu Thr Asp Gly Met Thr Val Arg Glu Leu Cys
545                 550                 555                 560

Ser Ala Ala Ile Thr Met Ser Asp Asn Thr Ala Ala Asn Leu Leu Leu
                565                 570                 575

Thr Thr Ile Gly Gly Pro Lys Glu Leu Thr Ala Phe Leu His Asn Met
            580                 585                 590

Gly Asp His Val Thr Arg Leu Asp Arg Trp Glu Pro Glu Leu Asn Glu
        595                 600                 605

Ala Ala Ala Thr Met Glu Asn Ala Gln Lys Gly Glu Ile Met Pro Asn
    610                 615                 620

Ile Pro Gln Met Ser Ala Phe Trp Tyr Ala Val Arg Thr Ala Val Ile
625                 630                 635                 640

Asn Ala Ala Ser Gly Arg Gln Thr Val Asp Glu Ala Leu Lys Asp Ala
                645                 650                 655

Gln Thr Arg Ile Thr Lys
            660
```

<210> SEQ ID NO 39
<211> LENGTH: 1983
<212> TYPE: DNA
<213> ORGANISM: Escherichia coli -continued

<400> SEQUENCE: 39

```
atgaaaataa aaacaggtgc acgcatcctc gcattatccg cattaacgac gatgatgttt     60
tccgcctcgg ctctcgccaa aatcgaagaa ggtaaactgg taatctggat taacggcgat    120
aaaggctata acggtctcgc tgaagtcggt aagaaattcg agaaagatac cggaattaaa    180
gtcaccgttg agcatccgga taaactggaa gagaaattcc cacaggttgc ggcaactggc    240
gatggccctg acattatctt ctgggcacac gaccgctttg gtggctacgc tcaatctggc    300
ctgttggctg aaatcacccc ggacaaagcg ttccaggaca agctgtatcc gtttacctgg    360
gatgccgtac gttacaacgg caagctgatt gcttacccga tcgctgttga agcgttatcg    420
ctgatttata acaaagatct gctgccgaac ccgccaaaaa cctgggaaga gatcccggcg    480
ctggataaag aactgaaagc gaaaggtaag agcgcgctga tgttcaacct gcaagaaccg    540
tacttcacct ggccgctgat tgctgctgac gggggttatg cgttcaagta tgaaaacggc    600
aagtacgaca ttaaagacgt gggcgtggat aacgctggcg cgaaagcggg tctgaccttc    660
ctggttgacc tgattaaaaa caaacacatg aatgcagaca ccgattactc catcgcagaa    720
gctgccttta ataaaggcga aacagcgatg accatcaacg gcccgtgggc atggtccaac    780
atcgacacca gcaaagtgaa ttatggtgta acggtactgc cgaccttcaa gggtcaacca    840
tccaaaccgt tcgttggcgt gctgagcgca ggtattaacg ccgccagtcc gaacaaagag    900
ctggcgaaag agttcctcga aaactatctg ctgactgatg aaggtctgga agcggttaat    960
aaagacaaac cgctgggtgc cgtagcgctg aagtcttacg aggaagagtt ggcgaaagat   1020
ccacgtccaa acgacgagcg tgacaccacg atgcctgcag caatggcaac aacgttgcgc   1080
aaactattaa ctggcgaact acttactcta gcttcccggc aacaattaat agactggatg   1140
gaggcggata aagttgcagg accacttctg cgctcggccc ttccggctgg ctggtttatt   1200
gctgataaat ctggagccgg tgagcgtggg tctcgcggta tcattgcagc actggggcca   1260
gatggtaagc cctcccgtat cgtagttatc tacacgacgg ggagtcaggc aactatggat   1320
gaacgaaata gacagatcgc tgagataggt gcctcactga ttaagcattg ggacaagagc   1380
cacccagaaa cgctggtgaa agtaaaagat gctgaagatc agttgggtgc acgagtgggt   1440
tacatcgaac tggatctcaa cagcggtaag atccttgaga gttttcgccc cgaagaacgt   1500
tttccaatga tgagcacttt taaagttctg ctatgtggcg cggtattatc ccgtgttgac   1560
gccgggcaag agcaactcgg tcgccgcata cactattctc agaatgactt ggttgagtac   1620
tcaccagtca cagaaaagca tcttacggat ggcatgacag taagagaatt atgcagtgct   1680
gccataacca tgagtgataa cactgcggcc aacttacttc tgacaacgat cggaggaccg   1740
aaggagctaa ccgctttttt gcacaacatg ggggatcatg taactcgcct tgatcgttgg   1800
gaaccggaac tgaatgaagc cgccgccacc atggaaaacg cccagaaagg tgaaatcatg   1860
ccgaacatcc cgcagatgtc cgctttctgg tatgccgtgc gtactgcggt gatcaacgcc   1920
gccagcggtc gtcagactgt cgatgaagcc ctgaaagacg cgcagactcg tatcaccaag   1980
taa                                                                 1983
```

<210> SEQ ID NO 40
<211> LENGTH: 660
<212> TYPE: PRT
<213> ORGANISM: Escherichia coli

<400> SEQUENCE: 40

Met Lys Ile Lys Thr Gly Ala Arg Ile Leu Ala Leu Ser Ala Leu Thr
1 5 10 15

Thr Met Met Phe Ser Ala Ser Ala Leu Ala Lys Ile Glu Glu Gly Lys
20 25 30

Leu Val Ile Trp Ile Asn Gly Asp Lys Gly Tyr Asn Gly Leu Ala Glu
35 40 45

Val Gly Lys Lys Phe Glu Lys Asp Thr Gly Ile Lys Val Thr Val Glu
50 55 60

His Pro Asp Lys Leu Glu Glu Lys Phe Pro Gln Val Ala Ala Thr Gly
65 70 75 80

Asp Gly Pro Asp Ile Ile Phe Trp Ala His Asp Arg Phe Gly Gly Tyr
85 90 95

Ala Gln Ser Gly Leu Leu Ala Glu Ile Thr Pro Asp Lys Ala Phe Gln
100 105 110

Asp Lys Leu Tyr Pro Phe Thr Trp Asp Ala Val Arg Tyr Asn Gly Lys
115 120 125

Leu Ile Ala Tyr Pro Ile Ala Val Glu Ala Leu Ser Leu Ile Tyr Asn
130 135 140

Lys Asp Leu Leu Pro Asn Pro Pro Lys Thr Trp Glu Glu Ile Pro Ala
145 150 155 160

Leu Asp Lys Glu Leu Lys Ala Lys Gly Lys Ser Ala Leu Met Phe Asn
165 170 175

Leu Gln Glu Pro Tyr Phe Thr Trp Pro Leu Ile Ala Ala Asp Gly Gly
180 185 190

Tyr Ala Phe Lys Tyr Glu Asn Gly Lys Tyr Asp Ile Lys Asp Val Gly
195 200 205

Val Asp Asn Ala Gly Ala Lys Ala Gly Leu Thr Phe Leu Val Asp Leu
210 215 220

Ile Lys Asn Lys His Met Asn Ala Asp Thr Asp Tyr Ser Ile Ala Glu
225 230 235 240

Ala Ala Phe Asn Lys Gly Glu Thr Ala Met Thr Ile Asn Gly Pro Trp
245 250 255

Ala Trp Ser Asn Ile Asp Thr Ser Lys Val Asn Tyr Gly Val Thr Val
260 265 270

Leu Pro Thr Phe Lys Gly Gln Pro Ser Lys Pro Phe Val Gly Val Leu
275 280 285

Ser Ala Gly Ile Asn Ala Ala Ser Pro Asn Lys Glu Leu Ala Lys Glu
290 295 300

Phe Leu Glu Asn Tyr Leu Leu Thr Asp Glu Gly Leu Glu Ala Val Asn
305 310 315 320

Lys Asp Lys Pro Leu Gly Ala Val Ala Leu Lys Ser Tyr Glu Glu Glu
325 330 335

Leu Ala Lys Asp Pro Arg Pro Asn Asp Glu Arg Asp Thr Thr Met Pro
340 345 350

Ala Ala Met Ala Thr Thr Leu Arg Lys Leu Leu Thr Gly Glu Leu Leu
355 360 365

Thr Leu Ala Ser Arg Gln Gln Leu Ile Asp Trp Met Glu Ala Asp Lys
370 375 380

Val Ala Gly Pro Leu Leu Arg Ser Ala Leu Pro Ala Gly Trp Phe Ile
385 390 395 400

Ala Asp Lys Ser Gly Ala Gly Glu Arg Gly Ser Arg Gly Ile Ile Ala
405 410 415

-continued

```
Ala Leu Gly Pro Asp Gly Lys Pro Ser Arg Ile Val Val Ile Tyr Thr
            420                 425                 430

Thr Gly Ser Gln Ala Thr Met Asp Glu Arg Asn Arg Gln Ile Ala Glu
        435                 440                 445

Ile Gly Ala Ser Leu Ile Lys His Trp Asp Lys Ser His Pro Glu Thr
    450                 455                 460

Leu Val Lys Val Lys Asp Ala Glu Asp Gln Leu Gly Ala Arg Val Gly
465                 470                 475                 480

Tyr Ile Glu Leu Asp Leu Asn Ser Gly Lys Ile Leu Glu Ser Phe Arg
                485                 490                 495

Pro Glu Glu Arg Phe Pro Met Met Ser Thr Phe Lys Val Leu Leu Cys
            500                 505                 510

Gly Ala Val Leu Ser Arg Val Asp Ala Gly Gln Glu Gln Leu Gly Arg
        515                 520                 525

Arg Ile His Tyr Ser Gln Asn Asp Leu Val Glu Tyr Ser Pro Val Thr
    530                 535                 540

Glu Lys His Leu Thr Asp Gly Met Thr Val Arg Glu Leu Cys Ser Ala
545                 550                 555                 560

Ala Ile Thr Met Ser Asp Asn Thr Ala Ala Asn Leu Leu Leu Thr Thr
                565                 570                 575

Ile Gly Gly Pro Lys Glu Leu Thr Ala Phe Leu His Asn Met Gly Asp
            580                 585                 590

His Val Thr Arg Leu Asp Arg Trp Glu Pro Glu Leu Asn Glu Ala Ala
        595                 600                 605

Ala Thr Met Glu Asn Ala Gln Lys Gly Glu Ile Met Pro Asn Ile Pro
    610                 615                 620

Gln Met Ser Ala Phe Trp Tyr Ala Val Arg Thr Ala Val Ile Asn Ala
625                 630                 635                 640

Ala Ser Gly Arg Gln Thr Val Asp Glu Ala Leu Lys Asp Ala Gln Thr
                645                 650                 655

Arg Ile Thr Lys
            660
```

<210> SEQ ID NO 41
<211> LENGTH: 1986
<212> TYPE: DNA
<213> ORGANISM: Escherichia coli

<400> SEQUENCE: 41

```
atgaaaataa aaacaggtgc acgcatcctc gcattatccg cattaacgac gatgatgttt      60

tccgcctcgg ctctcgccaa aatcgaagaa ggtaaactgg taatctggat taacggcgat     120

aaaggctata acggtctcgc tgaagtcggt aagaaattcg agaaagatac cggaattaaa     180

gtcaccgttg agcatccgga taaactggaa gagaaattcc cacaggttgc ggcaactggc     240

gatggccctg acattatctt ctgggcacac gaccgctttg gtggctacgc tcaatctggc     300

ctgttggctg aaatcacccc ggacaaagcg ttccaggaca agctgtatcc gtttacctgg     360

gatgccgtac gttacaacgg caagctgatt gcttacccga tcgctgttga agcgttatcg     420

ctgatttata acaaagatct gctgccgaac ccgccaaaaa cctgggaaga gatcccggcg     480

ctggataaag aactgaaagc gaaaggtaag agcgcgctga tgttcaacct gcaagaaccg     540

tacttcacct ggccgctgat tgctgctgac gggggttatg cgttcaagta tgaaaacggc     600

aagtacgaca ttaaagacgt gggcgtggat aacgctggcg cgaaagcggg tctgaccttc     660

ctggttgacc tgattaaaaa caaacacatg aatgcagaca ccgattactc catcgcagaa     720
```

```
gctgccttta ataaaggcga aacagcgatg accatcaacg gcccgtgggc atggtccaac    780

atcgacacca gcaaagtgaa ttatggtgta acggtactgc cgaccttcaa gggtcaacca    840

tccaaaccgt tcgttggcgt gctgagcgca ggtattaacg ccgccagtcc gaacaaagag    900

ctggcgaaag agttcctcga aaactatctg ctgactgatg aaggtctgga agcggttaat    960

aaagacaaac cgctgggtgc cgtagcgctg aagtcttacg aggaagagtt ggcgaaagat   1020

ccacgtatac caaacgacga gcgtgacacc acgatgcctg cagcaatggc aacaacgttg   1080

cgcaaactat taactggcga actacttact ctagcttccc ggcaacaatt aatagactgg   1140

atggaggcgg ataaagttgc aggaccactt ctgcgctcgg cccttccggc tggctggttt   1200

attgctgata aatctggagc cggtgagcgt gggtctcgcg gtatcattgc agcactgggg   1260

ccagatggta agccctcccg tatcgtagtt atctacacga cggggagtca ggcaactatg   1320

gatgaacgaa atagacagat cgctgagata ggtgcctcac tgattaagca ttgggacaag   1380

agccacccag aaacgctggt gaaagtaaaa gatgctgaag atcagttggg tgcacgagtg   1440

ggttacatcg aactggatct caacagcggt aagatccttg agagttttcg ccccgaagaa   1500

cgttttccaa tgatgagcac ttttaaagtt ctgctatgtg gcgcggtatt atcccgtgtt   1560

gacgccgggc aagagcaact cggtcgccgc atacactatt ctcagaatga cttggttgag   1620

tactcaccag tcacagaaaa gcatcttacg gatggcatga cagtaagaga attatgcagt   1680

gctgccataa ccatgagtga taacactgcg gccaacttac ttctgacaac gatcggagga   1740

ccgaaggagc taaccgcttt tttgcacaac atgggggatc atgtaactcg ccttgatcgt   1800

tgggaaccgg aactgaatga agccgccgcc accatggaaa acgcccagaa aggtgaaatc   1860

atgccgaaca tcccgcagat gtccgctttc tggtatgccg tgcgtactgc ggtgatcaac   1920

gccgccagcg gtcgtcagac tgtcgatgaa gccctgaaag acgcgcagac tcgtatcacc   1980

aagtaa                                                              1986
```

<210> SEQ ID NO 42
<211> LENGTH: 661
<212> TYPE: PRT
<213> ORGANISM: Escherichia coli

<400> SEQUENCE: 42

```
Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
            20                  25                  30

Leu Val Ile Trp Ile Asn Gly Asp Lys Gly Tyr Asn Gly Leu Ala Glu
        35                  40                  45

Val Gly Lys Lys Phe Glu Lys Asp Thr Gly Ile Lys Val Thr Val Glu
    50                  55                  60

His Pro Asp Lys Leu Glu Glu Lys Phe Pro Gln Val Ala Ala Thr Gly
65                  70                  75                  80

Asp Gly Pro Asp Ile Ile Phe Trp Ala His Asp Arg Phe Gly Gly Tyr
                85                  90                  95

Ala Gln Ser Gly Leu Leu Ala Glu Ile Thr Pro Asp Lys Ala Phe Gln
            100                 105                 110

Asp Lys Leu Tyr Pro Phe Thr Trp Asp Ala Val Arg Tyr Asn Gly Lys
        115                 120                 125

Leu Ile Ala Tyr Pro Ile Ala Val Glu Ala Leu Ser Leu Ile Tyr Asn
    130                 135                 140
```

-continued

```
Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
            180                 185                 190

Tyr Ala Phe Lys Tyr Glu Asn Gly Lys Tyr Asp Ile Lys Asp Val Gly
        195                 200                 205

Val Asp Asn Ala Gly Ala Lys Ala Gly Leu Thr Phe Leu Val Asp Leu
    210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
                245                 250                 255

Ala Trp Ser Asn Ile Asp Thr Ser Lys Val Asn Tyr Gly Val Thr Val
            260                 265                 270

Leu Pro Thr Phe Lys Gly Gln Pro Ser Lys Pro Phe Val Gly Val Leu
        275                 280                 285

Ser Ala Gly Ile Asn Ala Ala Ser Pro Asn Lys Glu Leu Ala Lys Glu
    290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
                325                 330                 335

Leu Ala Lys Asp Pro Arg Ile Pro Asn Asp Glu Arg Asp Thr Thr Met
            340                 345                 350

Pro Ala Ala Met Ala Thr Thr Leu Arg Lys Leu Leu Thr Gly Glu Leu
        355                 360                 365

Leu Thr Leu Ala Ser Arg Gln Gln Leu Ile Asp Trp Met Glu Ala Asp
    370                 375                 380

Lys Val Ala Gly Pro Leu Leu Arg Ser Ala Leu Pro Ala Gly Trp Phe
385                 390                 395                 400

Ile Ala Asp Lys Ser Gly Ala Gly Glu Arg Gly Ser Arg Gly Ile Ile
                405                 410                 415

Ala Ala Leu Gly Pro Asp Gly Lys Pro Ser Arg Ile Val Val Ile Tyr
            420                 425                 430

Thr Thr Gly Ser Gln Ala Thr Met Asp Glu Arg Asn Arg Gln Ile Ala
        435                 440                 445

Glu Ile Gly Ala Ser Leu Ile Lys His Trp Asp Lys Ser His Pro Glu
    450                 455                 460

Thr Leu Val Lys Val Lys Asp Ala Glu Asp Gln Leu Gly Ala Arg Val
465                 470                 475                 480

Gly Tyr Ile Glu Leu Asp Leu Asn Ser Gly Lys Ile Leu Glu Ser Phe
                485                 490                 495

Arg Pro Glu Glu Arg Phe Pro Met Met Ser Thr Phe Lys Val Leu Leu
            500                 505                 510

Cys Gly Ala Val Leu Ser Arg Val Asp Ala Gly Gln Glu Gln Leu Gly
        515                 520                 525

Arg Arg Ile His Tyr Ser Gln Asn Asp Leu Val Glu Tyr Ser Pro Val
    530                 535                 540

Thr Glu Lys His Leu Thr Asp Gly Met Thr Val Arg Glu Leu Cys Ser
545                 550                 555                 560

Ala Ala Ile Thr Met Ser Asp Asn Thr Ala Ala Asn Leu Leu Leu Thr
                565                 570                 575
```

```
Thr Ile Gly Gly Pro Lys Glu Leu Thr Ala Phe Leu His Asn Met Gly
            580                 585                 590

Asp His Val Thr Arg Leu Asp Arg Trp Glu Pro Glu Leu Asn Glu Ala
        595                 600                 605

Ala Ala Thr Met Glu Asn Ala Gln Lys Gly Glu Ile Met Pro Asn Ile
    610                 615                 620

Pro Gln Met Ser Ala Phe Trp Tyr Ala Val Arg Thr Ala Val Ile Asn
625                 630                 635                 640

Ala Ala Ser Gly Arg Gln Thr Val Asp Glu Ala Leu Lys Asp Ala Gln
                645                 650                 655

Thr Arg Ile Thr Lys
            660


<210> SEQ ID NO 43
<211> LENGTH: 2001
<212> TYPE: DNA
<213> ORGANISM: Escherichia coli

<400> SEQUENCE: 43

atgaaaataa aaacaggtgc acgcatcctc gcattatccg cattaacgac gatgatgttt      60

tccgcctcgg ctctcgccaa aatcgaagaa ggtaaactgg taatctggat taacggcgat     120

aaaggctata acggtctcgc tgaagtcggt aagaaattcg agaaagatac cggaattaaa     180

gtcaccgttg agcatccgga taaactggaa gagaaattcc cacaggttgc ggcaactggc     240

gatggccctg acattatctt ctgggcacac gaccgctttg gtggctacgc tcaatctggc     300

ctgttggctg aaatcacccc ggacaaagcg ttccaggaca agctgtatcc gtttacctgg     360

gatgccgtac gttacaacgg caagctgatt gcttacccga tcgctgttga agcgttatcg     420

ctgatttata acaaagatct gctgccgaac ccgccaaaaa cctgggaaga gatcccggcg     480

ctggataaag aactgaaagc gaaaggtaag agcgcgctga tgttcaacct gcaagaaccg     540

tacttcacct ggccgctgat tgctgctgac ggggggttatg cgttcaagta tgaaaacggc     600

aagtacgaca ttaaagacgt gggcgtggat aacgctggcg cgaaagcggg tctgaccttc     660

ctggttaatg aagccatacc aaacgacgag cgtgacacca cgatgcctgc agcaatggca     720

acaacgttgc gcaaactatt aactggcgaa ctacttactc tagcttcccg gcaacaatta     780

atagactgga tggaggcgga taaagttgca ggaccacttc tgcgctcggc ccttccggct     840

ggctggttta ttgctgataa atctggagcc ggtgagcgtg ggtctcgcgg tatcattgca     900

gcactggggc cagatggtaa gccctcccgt atcgtagtta tctacacgac ggggagtcag     960

gcaactatgg atgaacgaaa tagacagatc gctgagatag gtgcctcact gattaagcat    1020

tgggacaaga gccacccaga aacgctggtg aaagtaaaag atgctgaaga tcagttgggt    1080

gcacgagtgg gttacatcga actggatctc aacagcggta agatccttga gagttttcgc    1140

cccgaagaac gttttccaat gatgagcact tttaaagttc tgctatgtgg cgcggtatta    1200

tcccgtgttg acgccgggca agagcaactc ggtcgccgca tacactattc tcagaatgac    1260

ttggttgagt actcaccagt cacagaaaag catcttacgg atggcatgac agtaagagaa    1320

ttatgcagtg ctgccataac catgagtgat aacactgcgg ccaacttact tctgacaacg    1380

atcggaggac cgaaggagct aaccgctttt ttgcacaaca tgggggatca tgtaactcgc    1440

cttgatcgtt gggaaccgga actgaatgaa gccgttgacc tgattaaaaa caaacacatg    1500

aatgcagaca ccgattactc catcgcagaa gctgccttta ataaaggcga aacagcgatg    1560

accatcaacg gcccgtgggc atggtccaac atcgacacca gcaaagtgaa ttatggtgta    1620
```

```
acggtactgc cgaccttcaa gggtcaacca tccaaaccgt tcgttggcgt gctgagcgca   1680

ggtattaacg ccgccagtcc gaacaaagag ctggcgaaag agttcctcga aaactatctg   1740

ctgactgatg aaggtctgga agcggttaat aaagacaaac cgctgggtgc cgtagcgctg   1800

aagtcttacg aggaagagtt ggcgaaagat ccacgtattg ccgccaccat ggaaaacgcc   1860

cagaaaggtg aaatcatgcc gaacatcccg cagatgtccg ctttctggta tgccgtgcgt   1920

actgcggtga tcaacgccgc cagcggtcgt cagactgtcg atgaagccct gaaagacgcg   1980

cagactcgta tcaccaagta a                                             2001
```

<210> SEQ ID NO 44
<211> LENGTH: 666
<212> TYPE: PRT
<213> ORGANISM: Escherichia coli

<400> SEQUENCE: 44

```
Met Lys Ile Lys Thr Gly Ala Arg Ile Leu Ala Leu Ser Ala Leu Thr
  1               5                  10                  15

Thr Met Met Phe Ser Ala Ser Ala Leu Ala Lys Ile Glu Glu Gly Lys
             20                  25                  30

Leu Val Ile Trp Ile Asn Gly Asp Lys Gly Tyr Asn Gly Leu Ala Glu
         35                  40                  45

Val Gly Lys Lys Phe Glu Lys Asp Thr Gly Ile Lys Val Thr Val Glu
     50                  55                  60

His Pro Asp Lys Leu Glu Glu Lys Phe Pro Gln Val Ala Ala Thr Gly
 65                  70                  75                  80

Asp Gly Pro Asp Ile Ile Phe Trp Ala His Asp Arg Phe Gly Gly Tyr
                 85                  90                  95

Ala Gln Ser Gly Leu Leu Ala Glu Ile Thr Pro Asp Lys Ala Phe Gln
            100                 105                 110

Asp Lys Leu Tyr Pro Phe Thr Trp Asp Ala Val Arg Tyr Asn Gly Lys
        115                 120                 125

Leu Ile Ala Tyr Pro Ile Ala Val Glu Ala Leu Ser Leu Ile Tyr Asn
    130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
            180                 185                 190

Tyr Ala Phe Lys Tyr Glu Asn Gly Lys Tyr Asp Ile Lys Asp Val Gly
        195                 200                 205

Val Asp Asn Ala Gly Ala Lys Ala Gly Leu Thr Phe Leu Val Asn Glu
    210                 215                 220

Ala Ile Pro Asn Asp Glu Arg Asp Thr Thr Met Pro Ala Ala Met Ala
225                 230                 235                 240

Thr Thr Leu Arg Lys Leu Leu Thr Gly Glu Leu Leu Thr Leu Ala Ser
                245                 250                 255

Arg Gln Gln Leu Ile Asp Trp Met Glu Ala Asp Lys Val Ala Gly Pro
            260                 265                 270

Leu Leu Arg Ser Ala Leu Pro Ala Gly Trp Phe Ile Ala Asp Lys Ser
        275                 280                 285

Gly Ala Gly Glu Arg Gly Ser Arg Gly Ile Ile Ala Ala Leu Gly Pro
    290                 295                 300
```

Asp Gly Lys Pro Ser Arg Ile Val Val Ile Tyr Thr Thr Gly Ser Gln
305 310 315 320

Ala Thr Met Asp Glu Arg Asn Arg Gln Ile Ala Glu Ile Gly Ala Ser
325 330 335

Leu Ile Lys His Trp Asp Lys Ser His Pro Glu Thr Leu Val Lys Val
340 345 350

Lys Asp Ala Glu Asp Gln Leu Gly Ala Arg Val Gly Tyr Ile Glu Leu
355 360 365

Asp Leu Asn Ser Gly Lys Ile Leu Glu Ser Phe Arg Pro Glu Glu Arg
370 375 380

Phe Pro Met Met Ser Thr Phe Lys Val Leu Leu Cys Gly Ala Val Leu
385 390 395 400

Ser Arg Val Asp Ala Gly Gln Glu Gln Leu Gly Arg Arg Ile His Tyr
405 410 415

Ser Gln Asn Asp Leu Val Glu Tyr Ser Pro Val Thr Glu Lys His Leu
420 425 430

Thr Asp Gly Met Thr Val Arg Glu Leu Cys Ser Ala Ala Ile Thr Met
435 440 445

Ser Asp Asn Thr Ala Ala Asn Leu Leu Leu Thr Thr Ile Gly Gly Pro
450 455 460

Lys Glu Leu Thr Ala Phe Leu His Asn Met Gly Asp His Val Thr Arg
465 470 475 480

Leu Asp Arg Trp Glu Pro Glu Leu Asn Glu Ala Val Asp Leu Ile Lys
485 490 495

Asn Lys His Met Asn Ala Asp Thr Asp Tyr Ser Ile Ala Glu Ala Ala
500 505 510

Phe Asn Lys Gly Glu Thr Ala Met Thr Ile Asn Gly Pro Trp Ala Trp
515 520 525

Ser Asn Ile Asp Thr Ser Lys Val Asn Tyr Gly Val Thr Val Leu Pro
530 535 540

Thr Phe Lys Gly Gln Pro Ser Lys Pro Phe Val Gly Val Leu Ser Ala
545 550 555 560

Gly Ile Asn Ala Ala Ser Pro Asn Lys Glu Leu Ala Lys Glu Phe Leu
565 570 575

Glu Asn Tyr Leu Leu Thr Asp Glu Gly Leu Glu Ala Val Asn Lys Asp
580 585 590

Lys Pro Leu Gly Ala Val Ala Leu Lys Ser Tyr Glu Glu Glu Leu Ala
595 600 605

Lys Asp Pro Arg Ile Ala Ala Thr Met Glu Asn Ala Gln Lys Gly Glu
610 615 620

Ile Met Pro Asn Ile Pro Gln Met Ser Ala Phe Trp Tyr Ala Val Arg
625 630 635 640

Thr Ala Val Ile Asn Ala Ala Ser Gly Arg Gln Thr Val Asp Glu Ala
645 650 655

Leu Lys Asp Ala Gln Thr Arg Ile Thr Lys
660 665

<210> SEQ ID NO 45
<211> LENGTH: 1989
<212> TYPE: DNA
<213> ORGANISM: Escherichia coli

<400> SEQUENCE: 45
atgaaaataa aaacaggtgc acgcatcctc gcattatccg cattaacgac gatgatgttt 60
tccgcctcgg ctctcgccaa aatcgaagaa ggtaaactgg taatctggat taacggcgat 120

-continued

```
aaaggctata acggtctcgc tgaagtcggt aagaaattcg agaaagatac cggaattaaa    180

gtcaccgttg agcatccgga taaactggaa gagaaattcc cacaggttgc ggcaactggc    240

gatggccctg acattatctt ctgggcacac gaccgctttg gtggctacgc tcaatctggc    300

ctgttggctg aaatcacccc ggacaaagcg ttccaggaca agctgtatcc gtttacctgg    360

gatgccgtac gttacaacgg caagctgatt gcttacccga tcgctgttga agcgttatcg    420

ctgatttata acaaagatct gctgccgaac ccgccaaaaa cctgggaaga gatcccggcg    480

ctggataaag aactgaaagc gaaaggtaag agcgcgctga tgttcaacct gcaagaaccg    540

tacttcacct ggccgctgat tgctgctgac gggggttatg cgttcaagta tgaaaacggc    600

aagtacgaca ttaaagacgt gggcgtggat aacgctggcg cgaaagcggg tctgaccttc    660

ctggttgacc tgattaatga agccatacca aacgacgagc gtgacaccac gatgcctgca    720

gcaatggcaa caacgttgcg caaactatta actggcgaac tacttactct agcttcccgg    780

caacaattaa tagactggat ggaggcggat aaagttgcag gaccacttct gcgctcggcc    840

cttccggctg gctggtttat tgctgataaa tctggagccg gtgagcgtgg gtctcgcggt    900

atcattgcag cactggggcc agatggtaag ccctcccgta tcgtagttat ctacacgacg    960

gggagtcagg caactatgga tgaacgaaat agacagatcg ctgagatagg tgcctcactg   1020

attaagcatt gggacaagag ccacccagaa acgctggtga aagtaaaaga tgctgaagat   1080

cagttgggtg cacgagtggg ttacatcgaa ctggatctca acagcggtaa gatccttgag   1140

agttttcgcc ccgaagaacg ttttccaatg atgagcactt ttaaagttct gctatgtggc   1200

gcggtattat cccgtgttga cgccgggcaa gagcaactcg gtcgccgcat acactattct   1260

cagaatgact tggttgagta ctcaccagtc acagaaaagc atcttacgga tggcatgaca   1320

gtaagagaat tatgcagtgc tgccataacc atgagtgata acactgcggc caacttactt   1380

ctgacaacga tcggaggacc gaaggagcta accgcttttt tgcacaacat gggggatcat   1440

gtaactcgcc ttgatcgttg ggaaccggaa ctgaatgaag ccccacatgaa tgcagacacc   1500

gattactcca tcgcagaagc tgcctttaat aaaggcgaaa cagcgatgac catcaacggc   1560

ccgtgggcat ggtccaacat cgacaccagc aaagtgaatt atggtgtaac ggtactgccg   1620

accttcaagg gtcaaccatc caaaccgttc gttggcgtgc tgagcgcagg tattaacgcc   1680

gccagtccga acaaagagct ggcgaaagag ttcctcgaaa actatctgct gactgatgaa   1740

ggtctggaag cggttaataa agacaaaccg ctgggtgccg tagcgctgaa gtcttacgag   1800

gaagagttgg cgaaagatcc acgtattgcc gccaccatgg aaaacgccca gaaaggtgaa   1860

atcatgccga acatcccgca gatgtccgct ttctggtatg ccgtgcgtac tgcggtgatc   1920

aacgccgcca gcggtcgtca gactgtcgat gaagccctga aagacgcgca gactcgtatc   1980

accaagtaa                                                           1989
```

<210> SEQ ID NO 46
<211> LENGTH: 662
<212> TYPE: PRT
<213> ORGANISM: Escherichia coli

<400> SEQUENCE: 46

```
Met Lys Ile Lys Thr Gly Ala Arg Ile Leu Ala Leu Ser Ala Leu Thr
  1               5                  10                  15

Thr Met Met Phe Ser Ala Ser Ala Leu Ala Lys Ile Glu Glu Gly Lys
             20                  25                  30

Leu Val Ile Trp Ile Asn Gly Asp Lys Gly Tyr Asn Gly Leu Ala Glu
         35                  40                  45
```

-continued

```
Val Gly Lys Lys Phe Glu Lys Asp Thr Gly Ile Lys Val Thr Val Glu
     50                  55                  60

His Pro Asp Lys Leu Glu Glu Lys Phe Pro Gln Val Ala Ala Thr Gly
 65                  70                  75                  80

Asp Gly Pro Asp Ile Ile Phe Trp Ala His Asp Arg Phe Gly Gly Tyr
                 85                  90                  95

Ala Gln Ser Gly Leu Leu Ala Glu Ile Thr Pro Asp Lys Ala Phe Gln
            100                 105                 110

Asp Lys Leu Tyr Pro Phe Thr Trp Asp Ala Val Arg Tyr Asn Gly Lys
        115                 120                 125

Leu Ile Ala Tyr Pro Ile Ala Val Glu Ala Leu Ser Leu Ile Tyr Asn
    130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
            180                 185                 190

Tyr Ala Phe Lys Tyr Glu Asn Gly Lys Tyr Asp Ile Lys Asp Val Gly
        195                 200                 205

Val Asp Asn Ala Gly Ala Lys Ala Gly Leu Thr Phe Leu Val Asp Leu
    210                 215                 220

Ile Asn Glu Ala Ile Pro Asn Asp Glu Arg Asp Thr Thr Met Pro Ala
225                 230                 235                 240

Ala Met Ala Thr Thr Leu Arg Lys Leu Leu Thr Gly Glu Leu Leu Thr
                245                 250                 255

Leu Ala Ser Arg Gln Gln Leu Ile Asp Trp Met Glu Ala Asp Lys Val
            260                 265                 270

Ala Gly Pro Leu Leu Arg Ser Ala Leu Pro Ala Gly Trp Phe Ile Ala
        275                 280                 285

Asp Lys Ser Gly Ala Gly Glu Arg Gly Ser Arg Gly Ile Ile Ala Ala
    290                 295                 300

Leu Gly Pro Asp Gly Lys Pro Ser Arg Ile Val Val Ile Tyr Thr Thr
305                 310                 315                 320

Gly Ser Gln Ala Thr Met Asp Glu Arg Asn Arg Gln Ile Ala Glu Ile
                325                 330                 335

Gly Ala Ser Leu Ile Lys His Trp Asp Lys Ser His Pro Glu Thr Leu
            340                 345                 350

Val Lys Val Lys Asp Ala Glu Asp Gln Leu Gly Ala Arg Val Gly Tyr
        355                 360                 365

Ile Glu Leu Asp Leu Asn Ser Gly Lys Ile Leu Glu Ser Phe Arg Pro
    370                 375                 380

Glu Glu Arg Phe Pro Met Met Ser Thr Phe Lys Val Leu Leu Cys Gly
385                 390                 395                 400

Ala Val Leu Ser Arg Val Asp Ala Gly Gln Glu Gln Leu Gly Arg Arg
                405                 410                 415

Ile His Tyr Ser Gln Asn Asp Leu Val Glu Tyr Ser Pro Val Thr Glu
            420                 425                 430

Lys His Leu Thr Asp Gly Met Thr Val Arg Glu Leu Cys Ser Ala Ala
        435                 440                 445

Ile Thr Met Ser Asp Asn Thr Ala Ala Asn Leu Leu Leu Thr Thr Ile
    450                 455                 460

Gly Gly Pro Lys Glu Leu Thr Ala Phe Leu His Asn Met Gly Asp His
465                 470                 475                 480
```

```
Val Thr Arg Leu Asp Arg Trp Glu Pro Glu Leu Asn Glu Ala His Met
                485                 490                 495

Asn Ala Asp Thr Asp Tyr Ser Ile Ala Glu Ala Ala Phe Asn Lys Gly
            500                 505                 510

Glu Thr Ala Met Thr Ile Asn Gly Pro Trp Ala Trp Ser Asn Ile Asp
        515                 520                 525

Thr Ser Lys Val Asn Tyr Gly Val Thr Val Leu Pro Thr Phe Lys Gly
    530                 535                 540

Gln Pro Ser Lys Pro Phe Val Gly Val Leu Ser Ala Gly Ile Asn Ala
545                 550                 555                 560

Ala Ser Pro Asn Lys Glu Leu Ala Lys Glu Phe Leu Glu Asn Tyr Leu
                565                 570                 575

Leu Thr Asp Glu Gly Leu Glu Ala Val Asn Lys Asp Lys Pro Leu Gly
            580                 585                 590

Ala Val Ala Leu Lys Ser Tyr Glu Glu Glu Leu Ala Lys Asp Pro Arg
        595                 600                 605

Ile Ala Ala Thr Met Glu Asn Ala Gln Lys Gly Glu Ile Met Pro Asn
    610                 615                 620

Ile Pro Gln Met Ser Ala Phe Trp Tyr Ala Val Arg Thr Ala Val Ile
625                 630                 635                 640

Asn Ala Ala Ser Gly Arg Gln Thr Val Asp Glu Ala Leu Lys Asp Ala
                645                 650                 655

Gln Thr Arg Ile Thr Lys
            660


<210> SEQ ID NO 47
<211> LENGTH: 1989
<212> TYPE: DNA
<213> ORGANISM: Escherichia coli

<400> SEQUENCE: 47

atgaaaataa aaacaggtgc acgcatcctc gcattatccg cattaacgac gatgatgttt      60

tccgcctcgg ctctcgccaa aatcgaagaa ggtaaactgg taatctggat taacggcgat     120

aaaggctata acggtctcgc tgaagtcggt aagaaattcg agaaagatac cggaattaaa     180

gtcaccgttg agcatccgga taaactggaa gagaaattcc cacaggttgc ggcaactggc     240

gatggccctg acattatctt ctgggcacac gaccgctttg gtggctacgc tcaatctggc     300

ctgttggctg aaatcacccc ggacaaagcg ttccaggaca agctgtatcc gtttacctgg     360

gatgccgtac gttacaacgg caagctgatt gcttacccga tcgctgttga agcgttatcg     420

ctgatttata acaaagatct gctgccgaac ccgccaaaaa cctgggaaga gatcccggcg     480

ctggataaag aactgaaagc gaaaggtaag agcgcgctga tgttcaacct gcaagaaccg     540

tacttcacct ggccgctgat tgctgctgac gggggttatg cgttcaagta tgaaaacggc     600

aagtacgaca ttaaagacgt gggcgtggat aacgctggcg cgaaagcggg tctgaccttc     660

ctggttgacc tgattaaaaa caaacacatg aatgcagaca ccgattactc catcgcagaa     720

gctgccttta ataaaggcga aacagcgatg accatcaacg gcccgtgggc atggtccaac     780

atcgacacca gcaaagtgaa ttatggtgta acggtactgc cgaccttcaa gggtcaacca     840

tccaaaccgt tcgttggcgt gctgagcgca ggtattaacg ccgccagtcc gaacaaagag     900

ctggcgaaag agttcctcga aaactatctg ctgactgatg aaggtctgga agcggttaat     960

aaagacaaac cgctgggtgc cgtagcgctg aagtcttacg aggaagagtt ggcgaaagat    1020

ccacgtaatg aagccatacc aaacgacgag cgtgacacca cgatgcctgc agcaatggca    1080
```

-continued

```
acaacgttgc gcaaactatt aactggcgaa ctacttactc tagcttcccg gcaacaatta   1140

atagactgga tggaggcgga taaagttgca ggaccacttc tgcgctcggc ccttccggct   1200

ggctggttta ttgctgataa atctggagcc ggtgagcgtg ggtctcgcgg tatcattgca   1260

gcactggggc cagatggtaa gccctcccgt atcgtagtta tctacacgac ggggagtcag   1320

gcaactatgg atgaacgaaa tagacagatc gctgagatag gtgcctcact gattaagcat   1380

tgggacaaga gccacccaga aacgctggtg aaagtaaaag atgctgaaga tcagttgggt   1440

gcacgagtgg gttacatcga actggatctc aacagcggta agatccttga gagttttcgc   1500

cccgaagaac gttttccaat gatgagcact tttaaagttc tgctatgtgg cgcggtatta   1560

tcccgtgttg acgccgggca agagcaactc ggtcgccgca tacactattc tcagaatgac   1620

ttggttgagt actcaccagt cacagaaaag catcttacgg atggcatgac agtaagagaa   1680

ttatgcagtg ctgccataac catgagtgat aacactgcgg ccaacttact tctgacaacg   1740

atcggaggac cgaaggagct aaccgctttt ttgcacaaca tgggggatca tgtaactcgc   1800

cttgatcgtt gggaaccgga actgaatgaa gccaccatgg aaaacgccca gaaaggtgaa   1860

atcatgccga acatcccgca gatgtccgct ttctggtatg ccgtgcgtac tgcggtgatc   1920

aacgccgcca gcggtcgtca gactgtcgat gaagccctga aagacgcgca gactcgtatc   1980

accaagtaa                                                           1989
```

<210> SEQ ID NO 48
<211> LENGTH: 662
<212> TYPE: PRT
<213> ORGANISM: Escherichia coli

<400> SEQUENCE: 48

```
Met Lys Ile Lys Thr Gly Ala Arg Ile Leu Ala Leu Ser Ala Leu Thr
  1               5                  10                  15

Thr Met Met Phe Ser Ala Ser Ala Leu Ala Lys Ile Glu Glu Gly Lys
             20                  25                  30

Leu Val Ile Trp Ile Asn Gly Asp Lys Gly Tyr Asn Gly Leu Ala Glu
         35                  40                  45

Val Gly Lys Lys Phe Glu Lys Asp Thr Gly Ile Lys Val Thr Val Glu
     50                  55                  60

His Pro Asp Lys Leu Glu Glu Lys Phe Pro Gln Val Ala Ala Thr Gly
 65                  70                  75                  80

Asp Gly Pro Asp Ile Ile Phe Trp Ala His Asp Arg Phe Gly Gly Tyr
                 85                  90                  95

Ala Gln Ser Gly Leu Leu Ala Glu Ile Thr Pro Asp Lys Ala Phe Gln
            100                 105                 110

Asp Lys Leu Tyr Pro Phe Thr Trp Asp Ala Val Arg Tyr Asn Gly Lys
        115                 120                 125

Leu Ile Ala Tyr Pro Ile Ala Val Glu Ala Leu Ser Leu Ile Tyr Asn
    130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
            180                 185                 190

Tyr Ala Phe Lys Tyr Glu Asn Gly Lys Tyr Asp Ile Lys Asp Val Gly
        195                 200                 205
```

-continued

```
Val Asp Asn Ala Gly Ala Lys Ala Gly Leu Thr Phe Leu Val Asp Leu
    210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
                245                 250                 255

Ala Trp Ser Asn Ile Asp Thr Ser Lys Val Asn Tyr Gly Val Thr Val
            260                 265                 270

Leu Pro Thr Phe Lys Gly Gln Pro Ser Lys Pro Phe Val Gly Val Leu
        275                 280                 285

Ser Ala Gly Ile Asn Ala Ala Ser Pro Asn Lys Glu Leu Ala Lys Glu
    290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
                325                 330                 335

Leu Ala Lys Asp Pro Arg Asn Glu Ala Ile Pro Asn Asp Glu Arg Asp
            340                 345                 350

Thr Thr Met Pro Ala Ala Met Ala Thr Thr Leu Arg Lys Leu Leu Thr
        355                 360                 365

Gly Glu Leu Leu Thr Leu Ala Ser Arg Gln Gln Leu Ile Asp Trp Met
    370                 375                 380

Glu Ala Asp Lys Val Ala Gly Pro Leu Leu Arg Ser Ala Leu Pro Ala
385                 390                 395                 400

Gly Trp Phe Ile Ala Asp Lys Ser Gly Ala Gly Glu Arg Gly Ser Arg
                405                 410                 415

Gly Ile Ile Ala Ala Leu Gly Pro Asp Gly Lys Pro Ser Arg Ile Val
            420                 425                 430

Val Ile Tyr Thr Thr Gly Ser Gln Ala Thr Met Asp Glu Arg Asn Arg
        435                 440                 445

Gln Ile Ala Glu Ile Gly Ala Ser Leu Ile Lys His Trp Asp Lys Ser
    450                 455                 460

His Pro Glu Thr Leu Val Lys Val Lys Asp Ala Glu Asp Gln Leu Gly
465                 470                 475                 480

Ala Arg Val Gly Tyr Ile Glu Leu Asp Leu Asn Ser Gly Lys Ile Leu
                485                 490                 495

Glu Ser Phe Arg Pro Glu Glu Arg Phe Pro Met Met Ser Thr Phe Lys
            500                 505                 510

Val Leu Leu Cys Gly Ala Val Leu Ser Arg Val Asp Ala Gly Gln Glu
        515                 520                 525

Gln Leu Gly Arg Arg Ile His Tyr Ser Gln Asn Asp Leu Val Glu Tyr
    530                 535                 540

Ser Pro Val Thr Glu Lys His Leu Thr Asp Gly Met Thr Val Arg Glu
545                 550                 555                 560

Leu Cys Ser Ala Ala Ile Thr Met Ser Asp Asn Thr Ala Ala Asn Leu
                565                 570                 575

Leu Leu Thr Thr Ile Gly Gly Pro Lys Glu Leu Thr Ala Phe Leu His
            580                 585                 590

Asn Met Gly Asp His Val Thr Arg Leu Asp Arg Trp Glu Pro Glu Leu
        595                 600                 605

Asn Glu Ala Thr Met Glu Asn Ala Gln Lys Gly Glu Ile Met Pro Asn
    610                 615                 620

Ile Pro Gln Met Ser Ala Phe Trp Tyr Ala Val Arg Thr Ala Val Ile
625                 630                 635                 640
```

-continued

```
Asn Ala Ala Ser Gly Arg Gln Thr Val Asp Glu Ala Leu Lys Asp Ala
                645                 650                 655

Gln Thr Arg Ile Thr Lys
            660
```

<210> SEQ ID NO 49
<211> LENGTH: 2007
<212> TYPE: DNA
<213> ORGANISM: Escherichia coli

<400> SEQUENCE: 49

```
atgaaaataa aaacaggtgc acgcatcctc gcattatccg cattaacgac gatgatgttt     60

tccgcctcgg ctctcgccaa aatcgaagaa ggtaaactgg taatctggat taacggcgat    120

aaaggctata acggtctcgc tgaagtcggt aagaaattcg agaaagatac cggaattaaa    180

gtcaccgttg agcatccgga taaactggaa gagaaattcc cacaggttgc ggcaactggc    240

gatggccctg acattatctt ctgggcacac gaccgctttg gtggctacgc tcaatctggc    300

ctgttggctg aaatcacccc ggacaaagcg ttccaggaca agctgtatcc gtttacctgg    360

gatgccgtac gttacaacgg caagctgatt gcttacccga tcgctgttga agcgttatcg    420

ctgatttata acaaagatct gctgccgaac ccgccaaaaa cctgggaaga gatcccggcg    480

ctggataaag aactgaaagc gaaaggtaag agcgcgctga tgttcaacct gcaagaaccg    540

tacttcacct ggccgctgat tgctgctgac gggggttatg cgttcaagta tgaaaacggc    600

aagtacgaca ttaaagacgt gggcgtggat aacgctggcg cgaaagcggg tctgaccttc    660

ctggttgacc tgattaaaaa caaacacatg aatgcagaca ccgattactc catcgcagaa    720

gctgccttta ataaaggcga aacagcgatg accatcaacg gcccgtgggc atggtccaac    780

atcgacacca gcaaagtgaa ttatggtgta acggtactgc cgaccttcaa gggtcaacca    840

tccaaaccgt tcgttggcgt gctgagcgca ggtattaacg ccgccagtcc gaacaaagag    900

ctggcgaaag agttcctcga aaactatctg ctgactgatg aaggtctgga agcggttaat    960

aaagacaaac cgctgggtgc cgtagcgctg aagtcttacg aggaagagtt ggcgaaagat   1020

ccacgtattg ccgccaccaa tgaagccata ccaaacgacg agcgtgacac cacgatgcct   1080

gcagcaatgg caacaacgtt gcgcaaacta ttaactggcg aactacttac tctagcttcc   1140

cggcaacaat taatagactg gatggaggcg gataaagttg caggaccact tctgcgctcg   1200

gcccttccgg ctggctggtt tattgctgat aaatctggag ccggtgagcg tgggtctcgc   1260

ggtatcattg cagcactggg gccagatggt aagccctccc gtatcgtagt tatctacacg   1320

acggggagtc aggcaactat ggatgaacga aatagacaga tcgctgagat aggtgcctca   1380

ctgattaagc attgggacaa gagccaccca gaaacgctgg tgaaagtaaa agatgctgaa   1440

gatcagttgg gtgcacgagt gggttacatc gaactggatc tcaacagcgg taagatcctt   1500

gagagttttc gccccgaaga acgttttcca atgatgagca cttttaaagt tctgctatgt   1560

ggcgcggtat tatcccgtgt tgacgccggg caagagcaac tcggtcgccg catacactat   1620

tctcagaatg acttggttga gtactcacca gtcacagaaa agcatcttac ggatggcatg   1680

acagtaagag aattatgcag tgctgccata accatgagtg ataacactgc ggccaactta   1740

cttctgacaa cgatcggagg accgaaggag ctaaccgctt ttttgcacaa catgggggat   1800

catgtaactc gccttgatcg ttgggaaccg gaactgaatg aagccgccgc caccatggaa   1860

aacgcccaga aaggtgaaat catgccgaac atcccgcaga tgtccgcttt ctggtatgcc   1920
```

-continued

```
gtgcgtactg cggtgatcaa cgccgccagc ggtcgtcaga ctgtcgatga agccctgaaa   1980

gacgcgcaga ctcgtatcac caagtaa                                       2007


<210> SEQ ID NO 50
<211> LENGTH: 668
<212> TYPE: PRT
<213> ORGANISM: Escherichia coli

<400> SEQUENCE: 50

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
            20                  25                  30

Leu Val Ile Trp Ile Asn Gly Asp Lys Gly Tyr Asn Gly Leu Ala Glu
        35                  40                  45

Val Gly Lys Lys Phe Glu Lys Asp Thr Gly Ile Lys Val Thr Val Glu
    50                  55                  60

His Pro Asp Lys Leu Glu Glu Lys Phe Pro Gln Val Ala Ala Thr Gly
65                  70                  75                  80

Asp Gly Pro Asp Ile Ile Phe Trp Ala His Asp Arg Phe Gly Gly Tyr
                85                  90                  95

Ala Gln Ser Gly Leu Leu Ala Glu Ile Thr Pro Asp Lys Ala Phe Gln
            100                 105                 110

Asp Lys Leu Tyr Pro Phe Thr Trp Asp Ala Val Arg Tyr Asn Gly Lys
        115                 120                 125

Leu Ile Ala Tyr Pro Ile Ala Val Glu Ala Leu Ser Leu Ile Tyr Asn
    130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
            180                 185                 190

Tyr Ala Phe Lys Tyr Glu Asn Gly Lys Tyr Asp Ile Lys Asp Val Gly
        195                 200                 205

Val Asp Asn Ala Gly Ala Lys Ala Gly Leu Thr Phe Leu Val Asp Leu
    210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
                245                 250                 255

Ala Trp Ser Asn Ile Asp Thr Ser Lys Val Asn Tyr Gly Val Thr Val
            260                 265                 270

Leu Pro Thr Phe Lys Gly Gln Pro Ser Lys Pro Phe Val Gly Val Leu
        275                 280                 285

Ser Ala Gly Ile Asn Ala Ala Ser Pro Asn Lys Glu Leu Ala Lys Glu
    290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
                325                 330                 335

Leu Ala Lys Asp Pro Arg Ile Ala Ala Thr Asn Glu Ala Ile Pro Asn
            340                 345                 350

Asp Glu Arg Asp Thr Thr Met Pro Ala Ala Met Ala Thr Thr Leu Arg
        355                 360                 365
```

-continued

Lys Leu Leu Thr Gly Glu Leu Leu Thr Leu Ala Ser Arg Gln Gln Leu
370 375 380

Ile Asp Trp Met Glu Ala Asp Lys Val Ala Gly Pro Leu Leu Arg Ser
385 390 395 400

Ala Leu Pro Ala Gly Trp Phe Ile Ala Asp Lys Ser Gly Ala Gly Glu
405 410 415

Arg Gly Ser Arg Gly Ile Ile Ala Ala Leu Gly Pro Asp Gly Lys Pro
420 425 430

Ser Arg Ile Val Val Ile Tyr Thr Thr Gly Ser Gln Ala Thr Met Asp
435 440 445

Glu Arg Asn Arg Gln Ile Ala Glu Ile Gly Ala Ser Leu Ile Lys His
450 455 460

Trp Asp Lys Ser His Pro Glu Thr Leu Val Lys Val Lys Asp Ala Glu
465 470 475 480

Asp Gln Leu Gly Ala Arg Val Gly Tyr Ile Glu Leu Asp Leu Asn Ser
485 490 495

Gly Lys Ile Leu Glu Ser Phe Arg Pro Glu Glu Arg Phe Pro Met Met
500 505 510

Ser Thr Phe Lys Val Leu Leu Cys Gly Ala Val Leu Ser Arg Val Asp
515 520 525

Ala Gly Gln Glu Gln Leu Gly Arg Arg Ile His Tyr Ser Gln Asn Asp
530 535 540

Leu Val Glu Tyr Ser Pro Val Thr Glu Lys His Leu Thr Asp Gly Met
545 550 555 560

Thr Val Arg Glu Leu Cys Ser Ala Ala Ile Thr Met Ser Asp Asn Thr
565 570 575

Ala Ala Asn Leu Leu Leu Thr Thr Ile Gly Gly Pro Lys Glu Leu Thr
580 585 590

Ala Phe Leu His Asn Met Gly Asp His Val Thr Arg Leu Asp Arg Trp
595 600 605

Glu Pro Glu Leu Asn Glu Ala Ala Ala Thr Met Glu Asn Ala Gln Lys
610 615 620

Gly Glu Ile Met Pro Asn Ile Pro Gln Met Ser Ala Phe Trp Tyr Ala
625 630 635 640

Val Arg Thr Ala Val Ile Asn Ala Ala Ser Gly Arg Gln Thr Val Asp
645 650 655

Glu Ala Leu Lys Asp Ala Gln Thr Arg Ile Thr Lys
660 665

<210> SEQ ID NO 51
<211> LENGTH: 1989
<212> TYPE: DNA
<213> ORGANISM: Escherichia coli

<400> SEQUENCE: 51
atgaaaataa aaacaggtgc acgcatcctc gcattatccg cattaacgac gatgatgttt 60
tccgcctcgg ctctcgccaa aatcgaagaa ggtaaactgg taatctggat taacggcgat 120
aaaggctata acggtctcgc tgaagtcggt aagaaattcg agaaagatac cggaattaaa 180
gtcaccgttg agcatccgga taaactggaa gagaaattcc cacaggttgc ggcaactggc 240
gatggccctg acattatctt ctgggcacac gaccgctttg gtggctacgc tcaatctggc 300
ctgttggctg aaatcacccc ggacaaagcg ttccaggaca agctgtatcc gtttacctgg 360
gatgccgtac gttacaacgg caagctgatt gcttacccga tcgctgttga agcgttatcg 420
ctgatttata acaaagatct gctgccgaac ccgccaaaaa cctgggaaga gatcccggcg 480

```
ctggataaag aactgaaagc gaaaggtaag agcgcgctga tgttcaacct gcaagaaccg    540
tacttcacct ggccgctgat tgctgctgac ggggggttatg cgttcaagta tgaaaacggc    600
aagtacgaca ttaaagacgt gggcgtggat aacgctggcg cgaaagcggg tctgaccttc    660
ctggttgacc tgattaaaaa caaacacatg aatgcagaca ccgattactc catcgcagaa    720
gctgccttta ataaaggcga aacagcgatg accatcaacg gcccgtgggc atggtccaac    780
atcgacacca gcaaagtgaa ttatggtgta acggtactgc cgaccttcaa gggtcaacca    840
tccaaaccgt tcgttggcgt gctgagcgca ggtattaacg ccgccagtcc gaacaaagag    900
ctggcgaaag agttcctcga aaactatctg ctgactgatg aaggtctgga agcggttaat    960
aaagacaaac cgctgggtgc cgtagcgctg aagtcttacg aggaagagtt ggcgaaagat   1020
ccacgtaatg aagccatacc aaacgacgag cgtgacacca cgatgcctgc agcaatggca   1080
acaacgttgc gcaaactatt aactggcgaa ctacttactc tagcttcccg gcaacaatta   1140
atagactgga tggaggcgga taaagttgca ggaccacttc tgcgctcggc ccttccggct   1200
ggctggttta ttgctgataa atctggagcc ggtgagcgtg ggtctcgcgg tatcattgca   1260
gcactggggc cagatggtaa gccctcccgt atcgtagtta tctacacgac ggggagtcag   1320
gcaactatgg atgaacgaaa tagacagatc gctgagatag gtgcctcact gattaagcat   1380
tgggacaaga gccacccaga aacgctggtg aaagtaaaag atgctgaaga tcagttgggt   1440
gcacgagtgg gttacatcga actggatctc aacagcggta agatccttga gagttttcgc   1500
cccgaagaac gttttccaat gatgagcact tttaaagttc tgctatgtgg cgcggtatta   1560
tcccgtgttg acgccgggca agagcaactc ggtcgccgca tacactattc tcagaatgac   1620
ttggttgagt actcaccagt cacagaaaag catcttacgg atggcatgac agtaagagaa   1680
ttatgcagtg ctgccataac catgagtgat aacactgcgg ccaacttact tctgacaacg   1740
atcggaggac cgaaggagct aaccgctttt ttgcacaaca tgggggatca tgtaactcgc   1800
cttgatcgtt gggaaccgga actgaatgaa gccaccatgg aaaacgccca gaaaggtgaa   1860
atcatgccga acatcccgca gatgtccgct ttctggtatg ccgtgcgtac tgcggtgatc   1920
aacgccgcca gcggtcgtca gactgtcgat gaagccctga aagacgcgca gactcgtatc   1980
accaagtaa                                                           1989
```

<210> SEQ ID NO 52
<211> LENGTH: 662
<212> TYPE: PRT
<213> ORGANISM: Escherichia coli

<400> SEQUENCE: 52

```
Met Lys Ile Lys Thr Gly Ala Arg Ile Leu Ala Leu Ser Ala Leu Thr
  1               5                  10                  15

Thr Met Met Phe Ser Ala Ser Ala Leu Ala Lys Ile Glu Glu Gly Lys
             20                  25                  30

Leu Val Ile Trp Ile Asn Gly Asp Lys Gly Tyr Asn Gly Leu Ala Glu
         35                  40                  45

Val Gly Lys Lys Phe Glu Lys Asp Thr Gly Ile Lys Val Thr Val Glu
     50                  55                  60

His Pro Asp Lys Leu Glu Glu Lys Phe Pro Gln Val Ala Ala Thr Gly
 65                  70                  75                  80

Asp Gly Pro Asp Ile Ile Phe Trp Ala His Asp Arg Phe Gly Gly Tyr
                 85                  90                  95

Ala Gln Ser Gly Leu Leu Ala Glu Ile Thr Pro Asp Lys Ala Phe Gln
            100                 105                 110
```

-continued

```
Asp Lys Leu Tyr Pro Phe Thr Trp Asp Ala Val Arg Tyr Asn Gly Lys
        115                 120                 125

Leu Ile Ala Tyr Pro Ile Ala Val Glu Ala Leu Ser Leu Ile Tyr Asn
    130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
            180                 185                 190

Tyr Ala Phe Lys Tyr Glu Asn Gly Lys Tyr Asp Ile Lys Asp Val Gly
        195                 200                 205

Val Asp Asn Ala Gly Ala Lys Ala Gly Leu Thr Phe Leu Val Asp Leu
    210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
                245                 250                 255

Ala Trp Ser Asn Ile Asp Thr Ser Lys Val Asn Tyr Gly Val Thr Val
            260                 265                 270

Leu Pro Thr Phe Lys Gly Gln Pro Ser Lys Pro Phe Val Gly Val Leu
        275                 280                 285

Ser Ala Gly Ile Asn Ala Ala Ser Pro Asn Lys Glu Leu Ala Lys Glu
    290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
                325                 330                 335

Leu Ala Lys Asp Pro Arg Asn Glu Ala Ile Pro Asn Asp Glu Arg Asp
            340                 345                 350

Thr Thr Met Pro Ala Ala Met Ala Thr Thr Leu Arg Lys Leu Leu Thr
        355                 360                 365

Gly Glu Leu Leu Thr Leu Ala Ser Arg Gln Gln Leu Ile Asp Trp Met
    370                 375                 380

Glu Ala Asp Lys Val Ala Gly Pro Leu Leu Arg Ser Ala Leu Pro Ala
385                 390                 395                 400

Gly Trp Phe Ile Ala Asp Lys Ser Gly Ala Gly Glu Arg Gly Ser Arg
                405                 410                 415

Gly Ile Ile Ala Ala Leu Gly Pro Asp Gly Lys Pro Ser Arg Ile Val
            420                 425                 430

Val Ile Tyr Thr Thr Gly Ser Gln Ala Thr Met Asp Glu Arg Asn Arg
        435                 440                 445

Gln Ile Ala Glu Ile Gly Ala Ser Leu Ile Lys His Trp Asp Lys Ser
    450                 455                 460

His Pro Glu Thr Leu Val Lys Val Lys Asp Ala Glu Asp Gln Leu Gly
465                 470                 475                 480

Ala Arg Val Gly Tyr Ile Glu Leu Asp Leu Asn Ser Gly Lys Ile Leu
                485                 490                 495

Glu Ser Phe Arg Pro Glu Glu Arg Phe Pro Met Met Ser Thr Phe Lys
            500                 505                 510

Val Leu Leu Cys Gly Ala Val Leu Ser Arg Val Asp Ala Gly Gln Glu
        515                 520                 525

Gln Leu Gly Arg Arg Ile His Tyr Ser Gln Asn Asp Leu Val Glu Tyr
    530                 535                 540
```

```
Ser Pro Val Thr Glu Lys His Leu Thr Asp Gly Met Thr Val Arg Glu
545                 550                 555                 560

Leu Cys Ser Ala Ala Ile Thr Met Ser Asp Asn Thr Ala Ala Asn Leu
                565                 570                 575

Leu Leu Thr Thr Ile Gly Gly Pro Lys Glu Leu Thr Ala Phe Leu His
            580                 585                 590

Asn Met Gly Asp His Val Thr Arg Leu Asp Arg Trp Glu Pro Glu Leu
        595                 600                 605

Asn Glu Ala Thr Met Glu Asn Ala Gln Lys Gly Glu Ile Met Pro Asn
    610                 615                 620

Ile Pro Gln Met Ser Ala Phe Trp Tyr Ala Val Arg Thr Ala Val Ile
625                 630                 635                 640

Asn Ala Ala Ser Gly Arg Gln Thr Val Asp Glu Ala Leu Lys Asp Ala
                645                 650                 655

Gln Thr Arg Ile Thr Lys
            660


<210> SEQ ID NO 53
<211> LENGTH: 1989
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 53

atgaaaataa aaacaggtgc acgcatcctc gcattatccg cattaacgac gatgatgttt     60

tccgcctcgg ctctcgccaa aatcgaagaa ggtaaactgg taatctggat taacggcttg    120

tttggctata acggtctcgc tgaagtcggt aagaaattcg agaaagatac cggaattaaa    180

gtcaccgttg agcatccgga taaactggaa gagaaattcc cacaggttgc ggcaactggc    240

gatggccctg acattatctt ctatgcacac gaccgctttg gtggctacgc tcaatctggc    300

ctgttggctg aaatcacccc ggacaaagcg ttccaggaca agctgtatcc gtttacctgg    360

gatgccgtac gttacaacgg caagctgatt gcttacccga tcgctgttta tgcgttatcg    420

ctgatttata acaaagatct gctgccgaac ccgccaaaaa cctgggaaga gatcccggcg    480

ctggataaag aactgaaagc gaaaggtaag agcgcgctga tgttcaacct gcaagaaccg    540

tacttcacct ggccgctgat tgctgctgac gggggttatg cgttcaagta tgaaaacggc    600

aagtacgaca ttaaagacgt gggcgtggat aacgctggcg cgaaagcggg tctgaccttc    660

ctggttgacc tgattaaaaa caaacacatg aatgcagaca ccgattactc catcgcagaa    720

gctgccttta ataaaggcga aacagcgatg accatcaacg gcccgtgggc atggtccaac    780

atcgacacca gcaaagtgaa ttatggtgta acggtactgc cgaccttcaa gggtcaacca    840

tccaaaccgt tcgttggcgt gctgagcgca ggtattaacg ccgccagtcc gaacaaagag    900

ctggcgaaag agttcctcga aaactatctg ctgactgatg aaggtctgga agcggttaat    960

aaagacaaac cgctgggtgc cgtagcgctg aagtcttacg aggaagagtt ggcgaaagat   1020

ccacgtgcca taccaaacga cgagcgtgac accacgatgc ctgcagcaat ggcaacaacg   1080

ttgcgcaaac tattaactgg cgaactactt actctagctt cccggcaaca attaatagac   1140

tggatggagg cggataaagt tgcaggacca cttctgcgct cggcccttcc ggctggctgg   1200

tttattgctg ataaatctgg agccggtgag cgtgggtctc gcggtatcat tgcagcactg   1260

gggccagatg gtaagccctc ccgtatcgta gttatctaca cgacggggag tcaggcaact   1320

atggatgaac gaaatagaca gatcgctgag ataggtgcct cactgattaa gcattgggac   1380
```

```
aagagccacc cagaaacgct ggtgaaagta aaagatgctg aagatcagtt gggtgcacga   1440

gtgggttaca tcgaactgga tctcaacagc ggtaagatcc ttgagagttt tcgccccgaa   1500

gaacgttttc caatgatgag cacttttaaa gttctgctat gtggcgcggt attatcccgt   1560

gttgacgccg ggcaagagca actcggtcgc cgcatacact attctcagaa tgacttggtt   1620

gagtactcac cagtcacaga aaagcatctt acggatggca tgacagtaag agaattatgc   1680

agtgctgcca taaccatgag tgataacact gcggccaact tacttctgac aacgatcgga   1740

ggaccgaagg agctaaccgc ttttttgcac aacatggggg atcatgtaac tcgccttgat   1800

cgttgggaac cggaactgaa tgaagccgcc gccaccatgg aaaacgccca gaaaggtgaa   1860

atcatgccga acatcccgca gatgtccgct ttctggtatg ccgtgcgtac tgcggtgatc   1920

aacgccgcca gcggtcgtca gactgtcgat gaagccctga aagacgcgca gactcgtatc   1980

accaagtaa                                                           1989
```

<210> SEQ ID NO 54
<211> LENGTH: 662
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 54

```
Met Lys Ile Lys Thr Gly Ala Arg Ile Leu Ala Leu Ser Ala Leu Thr
  1               5                  10                  15

Thr Met Met Phe Ser Ala Ser Ala Leu Ala Lys Ile Glu Glu Gly Lys
             20                  25                  30

Leu Val Ile Trp Ile Asn Gly Leu Phe Gly Tyr Asn Gly Leu Ala Glu
         35                  40                  45

Val Gly Lys Lys Phe Glu Lys Asp Thr Gly Ile Lys Val Thr Val Glu
     50                  55                  60

His Pro Asp Lys Leu Glu Glu Lys Phe Pro Gln Val Ala Ala Thr Gly
 65                  70                  75                  80

Asp Gly Pro Asp Ile Ile Phe Tyr Ala His Asp Arg Phe Gly Gly Tyr
                 85                  90                  95

Ala Gln Ser Gly Leu Leu Ala Glu Ile Thr Pro Asp Lys Ala Phe Gln
            100                 105                 110

Asp Lys Leu Tyr Pro Phe Thr Trp Asp Ala Val Arg Tyr Asn Gly Lys
        115                 120                 125

Leu Ile Ala Tyr Pro Ile Ala Val Tyr Ala Leu Ser Leu Ile Tyr Asn
    130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
            180                 185                 190

Tyr Ala Phe Lys Tyr Glu Asn Gly Lys Tyr Asp Ile Lys Asp Val Gly
        195                 200                 205

Val Asp Asn Ala Gly Ala Lys Ala Gly Leu Thr Phe Leu Val Asp Leu
    210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
                245                 250                 255
```

-continued

```
Ala Trp Ser Asn Ile Asp Thr Ser Lys Val Asn Tyr Gly Val Thr Val
            260                 265                 270

Leu Pro Thr Phe Lys Gly Gln Pro Ser Lys Pro Phe Val Gly Val Leu
        275                 280                 285

Ser Ala Gly Ile Asn Ala Ala Ser Pro Asn Lys Glu Leu Ala Lys Glu
    290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
                325                 330                 335

Leu Ala Lys Asp Pro Arg Ala Ile Pro Asn Asp Glu Arg Asp Thr Thr
            340                 345                 350

Met Pro Ala Ala Met Ala Thr Thr Leu Arg Lys Leu Leu Thr Gly Glu
        355                 360                 365

Leu Leu Thr Leu Ala Ser Arg Gln Gln Leu Ile Asp Trp Met Glu Ala
    370                 375                 380

Asp Lys Val Ala Gly Pro Leu Leu Arg Ser Ala Leu Pro Ala Gly Trp
385                 390                 395                 400

Phe Ile Ala Asp Lys Ser Gly Ala Gly Glu Arg Gly Ser Arg Gly Ile
                405                 410                 415

Ile Ala Ala Leu Gly Pro Asp Gly Lys Pro Ser Arg Ile Val Val Ile
            420                 425                 430

Tyr Thr Thr Gly Ser Gln Ala Thr Met Asp Glu Arg Asn Arg Gln Ile
        435                 440                 445

Ala Glu Ile Gly Ala Ser Leu Ile Lys His Trp Asp Lys Ser His Pro
    450                 455                 460

Glu Thr Leu Val Lys Val Lys Asp Ala Glu Asp Gln Leu Gly Ala Arg
465                 470                 475                 480

Val Gly Tyr Ile Glu Leu Asp Leu Asn Ser Gly Lys Ile Leu Glu Ser
                485                 490                 495

Phe Arg Pro Glu Glu Arg Phe Pro Met Met Ser Thr Phe Lys Val Leu
            500                 505                 510

Leu Cys Gly Ala Val Leu Ser Arg Val Asp Ala Gly Gln Glu Gln Leu
        515                 520                 525

Gly Arg Arg Ile His Tyr Ser Gln Asn Asp Leu Val Glu Tyr Ser Pro
    530                 535                 540

Val Thr Glu Lys His Leu Thr Asp Gly Met Thr Val Arg Glu Leu Cys
545                 550                 555                 560

Ser Ala Ala Ile Thr Met Ser Asp Asn Thr Ala Ala Asn Leu Leu Leu
                565                 570                 575

Thr Thr Ile Gly Gly Pro Lys Glu Leu Thr Ala Phe Leu His Asn Met
            580                 585                 590

Gly Asp His Val Thr Arg Leu Asp Arg Trp Glu Pro Glu Leu Asn Glu
        595                 600                 605

Ala Ala Ala Thr Met Glu Asn Ala Gln Lys Gly Glu Ile Met Pro Asn
    610                 615                 620

Ile Pro Gln Met Ser Ala Phe Trp Tyr Ala Val Arg Thr Ala Val Ile
625                 630                 635                 640

Asn Ala Ala Ser Gly Arg Gln Thr Val Asp Glu Ala Leu Lys Asp Ala
                645                 650                 655

Gln Thr Arg Ile Thr Lys
            660
```

-continued

<210> SEQ ID NO 55
<211> LENGTH: 662
<212> TYPE: PRT
<213> ORGANISM: Artificial Sequence
<220> FEATURE:
<223> OTHER INFORMATION: Description of Artificial Sequence: Synthetic
protein construct

<400> SEQUENCE: 55

```
Met Lys Ile Lys Thr Gly Ala Arg Ile Leu Ala Leu Ser Ala Leu Thr
  1               5                  10                  15

Thr Met Met Phe Ser Ala Ser Ala Leu Ala Lys Ile Glu Glu Gly Lys
             20                  25                  30

Leu Val Ile Trp Ile Asn Gly Leu Gln Gly Tyr Asn Gly Leu Ala Glu
         35                  40                  45

Val Gly Lys Lys Phe Glu Lys Asp Thr Gly Ile Lys Val Thr Val Glu
     50                  55                  60

His Pro Asp Lys Leu Glu Glu Lys Phe Pro Gln Val Ala Ala Thr Gly
 65                  70                  75                  80

Asp Gly Pro Asp Ile Ile Phe Tyr Ala His Asp Arg Phe Gly Gly Tyr
                 85                  90                  95

Ala Gln Ser Gly Leu Leu Ala Glu Ile Thr Pro Asp Lys Ala Phe Gln
            100                 105                 110

Asp Lys Leu Tyr Pro Phe Thr Trp Asp Ala Val Arg Tyr Asn Gly Lys
        115                 120                 125

Leu Ile Ala Tyr Pro Ile Ala Val Gln Ala Leu Ser Leu Ile Tyr Asn
    130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
            180                 185                 190

Tyr Ala Phe Lys Tyr Glu Asn Gly Lys Tyr Asp Ile Lys Asp Val Gly
        195                 200                 205

Val Asp Asn Ala Gly Ala Lys Ala Gly Leu Thr Phe Leu Val Asp Leu
    210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
                245                 250                 255

Ala Trp Ser Asn Ile Asp Thr Ser Lys Val Asn Tyr Gly Val Thr Val
            260                 265                 270

Leu Pro Thr Phe Lys Gly Gln Pro Ser Lys Pro Phe Val Gly Val Leu
        275                 280                 285

Ser Ala Gly Ile Asn Ala Ala Ser Pro Asn Lys Glu Leu Ala Lys Glu
    290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
                325                 330                 335

Leu Ala Lys Asp Pro Arg Ala Ile Pro Asn Asp Glu Arg Asp Thr Thr
            340                 345                 350

Met Pro Ala Ala Met Ala Thr Thr Leu Arg Lys Leu Leu Thr Gly Glu
        355                 360                 365
```

Leu Leu Thr Leu Ala Ser Arg Gln Gln Leu Ile Asp Trp Met Glu Ala
370 375 380

Asp Lys Val Ala Gly Pro Leu Leu Arg Ser Ala Leu Pro Ala Gly Trp
385 390 395 400

Phe Ile Ala Asp Lys Ser Gly Ala Gly Glu Arg Gly Ser Arg Gly Ile
405 410 415

Ile Ala Ala Leu Gly Pro Asp Gly Lys Pro Ser Arg Ile Val Val Ile
420 425 430

Tyr Thr Thr Gly Ser Gln Ala Thr Met Asp Glu Arg Asn Arg Gln Ile
435 440 445

Ala Glu Ile Gly Ala Ser Leu Ile Lys His Trp Asp Lys Ser His Pro
450 455 460

Glu Thr Leu Val Lys Val Lys Asp Ala Glu Asp Gln Leu Gly Ala Arg
465 470 475 480

Val Gly Tyr Ile Glu Leu Asp Leu Asn Ser Gly Lys Ile Leu Glu Ser
485 490 495

Phe Arg Pro Glu Glu Arg Phe Pro Met Met Ser Thr Phe Lys Val Leu
500 505 510

Leu Cys Gly Ala Val Leu Ser Arg Val Asp Ala Gly Gln Glu Gln Leu
515 520 525

Gly Arg Arg Ile His Tyr Ser Gln Asn Asp Leu Val Glu Tyr Ser Pro
530 535 540

Val Thr Glu Lys His Leu Thr Asp Gly Met Thr Val Arg Glu Leu Cys
545 550 555 560

Ser Ala Ala Ile Thr Met Ser Asp Asn Thr Ala Ala Asn Leu Leu Leu
565 570 575

Thr Thr Ile Gly Gly Pro Lys Glu Leu Thr Ala Phe Leu His Asn Met
580 585 590

Gly Asp His Val Thr Arg Leu Asp Arg Trp Glu Pro Glu Leu Asn Glu
595 600 605

Ala Ala Ala Thr Met Glu Asn Ala Gln Lys Gly Glu Ile Met Pro Asn
610 615 620

Ile Pro Gln Met Ser Ala Phe Trp Tyr Ala Val Arg Thr Ala Val Ile
625 630 635 640

Asn Ala Ala Ser Gly Arg Gln Thr Val Asp Glu Ala Leu Lys Asp Ala
645 650 655

Gln Thr Arg Ile Thr Lys
660

<210> SEQ ID NO 56
<211> LENGTH: 1989
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 56
atgaaaataa aaacaggtgc acgcatcctc gcattatccg cattaacgac gatgatgttt 60
tccgcctcgg ctctcgccaa aatcgaagaa ggtaaactgg taatctggat taacggcaag 120
gagggctata acggtctcgc tgaagtcggt aagaaattcg agaaagatac cggaattaaa 180
gtcaccgttg agcatccgga taaactggaa gagaaattcc cacaggttgc ggcaactggc 240
gatggccctg acattatctt ctatgcacac gaccgctttg gtggctacgc tcaatctggc 300
ctgttggctg aaatcacccc ggacaaagcg ttccaggaca agctgtatcc gtttacctgg 360

-continued

```
gatgccgtac gttacaacgg caagctgatt gcttacccga tcgctgttcg ggcgttatcg    420

ctgatttata acaaagatct gctgccgaac ccgccaaaaa cctgggaaga gatcccggcg    480

ctggataaag aactgaaagc gaaaggtaag agcgcgctga tgttcaacct gcaagaaccg    540

tacttcacct ggccgctgat tgctgctgac gggggttatg cgttcaagta tgaaaacggc    600

aagtacgaca ttaaagacgt gggcgtggat aacgctggcg cgaaagcggg tctgaccttc    660

ctggttgacc tgattaaaaa caaacacatg aatgcagaca ccgattactc catcgcagaa    720

gctgccttta ataaaggcga aacagcgatg accatcaacg gcccgtgggc atggtccaac    780

atcgacacca gcaaagtgaa ttatggtgta acggtactgc cgaccttcaa gggtcaacca    840

tccaaaccgt tcgttggcgt gctgagcgca ggtattaacg ccgccagtcc gaacaaagag    900

ctggcgaaag agttcctcga aaactatctg ctgactgatg aaggtctgga agcggttaat    960

aaagacaaac cgctgggtgc cgtagcgctg aagtcttacg aggaagagtt ggcgaaagat   1020

ccacgtgcca taccaaacga cgagcgtgac accacgatgc ctgcagcaat ggcaacaacg   1080

ttgcgcaaac tattaactgg cgaactactt actctagctt cccggcaaca attaatagac   1140

tggatggagg cggataaagt tgcaggacca cttctgcgct cggcccttcc ggctggctgg   1200

tttattgctg ataaatctgg agccggtgag cgtgggtctc gcggtatcat tgcagcactg   1260

gggccagatg gtaagccctc ccgtatcgta gttatctaca cgacggggag tcaggcaact   1320

atggatgaac gaaatagaca gatcgctgag ataggtgcct cactgattaa gcattgggac   1380

aagagccacc cagaaacgct ggtgaaagta aaagatgctg aagatcagtt gggtgcacga   1440

gtgggttaca tcgaactgga tctcaacagc ggtaagatcc ttgagagttt tcgccccgaa   1500

gaacgttttc caatgatgag cacttttaaa gttctgctat gtggcgcggt attatcccgt   1560

gttgacgccg ggcaagagca actcggtcgc cgcatacact attctcagaa tgacttggtt   1620

gagtactcac cagtcacaga aaagcatctt acggatggca tgacagtaag agaattatgc   1680

agtgctgcca taaccatgag tgataacact gcggccaact tacttctgac aacgatcgga   1740

ggaccgaagg agctaaccgc ttttttgcac aacatggggg atcatgtaac tcgccttgat   1800

cgttgggaac cggaactgaa tgaagccgcc gccaccatgg aaaacgccca gaaaggtgaa   1860

atcatgccga acatcccgca gatgtccgct ttctggtatg ccgtgcgtac tgcggtgatc   1920

aacgccgcca gcggtcgtca gactgtcgat gaagccctga aagacgcgca gactcgtatc   1980

accaagtaa                                                           1989
```

<210> SEQ ID NO 57
<211> LENGTH: 662
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 57

```
Met Lys Ile Lys Thr Gly Ala Arg Ile Leu Ala Leu Ser Ala Leu Thr
  1               5                  10                  15

Thr Met Met Phe Ser Ala Ser Ala Leu Ala Lys Ile Glu Glu Gly Lys
             20                  25                  30

Leu Val Ile Trp Ile Asn Gly Lys Glu Gly Tyr Asn Gly Leu Ala Glu
         35                  40                  45

Val Gly Lys Lys Phe Glu Lys Asp Thr Gly Ile Lys Val Thr Val Glu
     50                  55                  60
```

-continued

His Pro Asp Lys Leu Glu Glu Lys Phe Pro Gln Val Ala Ala Thr Gly
65 70 75 80

Asp Gly Pro Asp Ile Ile Phe Tyr Ala His Asp Arg Phe Gly Gly Tyr
85 90 95

Ala Gln Ser Gly Leu Leu Ala Glu Ile Thr Pro Asp Lys Ala Phe Gln
100 105 110

Asp Lys Leu Tyr Pro Phe Thr Trp Asp Ala Val Arg Tyr Asn Gly Lys
115 120 125

Leu Ile Ala Tyr Pro Ile Ala Val Arg Ala Leu Ser Leu Ile Tyr Asn
130 135 140

Lys Asp Leu Leu Pro Asn Pro Pro Lys Thr Trp Glu Glu Ile Pro Ala
145 150 155 160

Leu Asp Lys Glu Leu Lys Ala Lys Gly Lys Ser Ala Leu Met Phe Asn
165 170 175

Leu Gln Glu Pro Tyr Phe Thr Trp Pro Leu Ile Ala Ala Asp Gly Gly
180 185 190

Tyr Ala Phe Lys Tyr Glu Asn Gly Lys Tyr Asp Ile Lys Asp Val Gly
195 200 205

Val Asp Asn Ala Gly Ala Lys Ala Gly Leu Thr Phe Leu Val Asp Leu
210 215 220

Ile Lys Asn Lys His Met Asn Ala Asp Thr Asp Tyr Ser Ile Ala Glu
225 230 235 240

Ala Ala Phe Asn Lys Gly Glu Thr Ala Met Thr Ile Asn Gly Pro Trp
245 250 255

Ala Trp Ser Asn Ile Asp Thr Ser Lys Val Asn Tyr Gly Val Thr Val
260 265 270

Leu Pro Thr Phe Lys Gly Gln Pro Ser Lys Pro Phe Val Gly Val Leu
275 280 285

Ser Ala Gly Ile Asn Ala Ala Ser Pro Asn Lys Glu Leu Ala Lys Glu
290 295 300

Phe Leu Glu Asn Tyr Leu Leu Thr Asp Glu Gly Leu Glu Ala Val Asn
305 310 315 320

Lys Asp Lys Pro Leu Gly Ala Val Ala Leu Lys Ser Tyr Glu Glu Glu
325 330 335

Leu Ala Lys Asp Pro Arg Ala Ile Pro Asn Asp Glu Arg Asp Thr Thr
340 345 350

Met Pro Ala Ala Met Ala Thr Thr Leu Arg Lys Leu Leu Thr Gly Glu
355 360 365

Leu Leu Thr Leu Ala Ser Arg Gln Gln Leu Ile Asp Trp Met Glu Ala
370 375 380

Asp Lys Val Ala Gly Pro Leu Leu Arg Ser Ala Leu Pro Ala Gly Trp
385 390 395 400

Phe Ile Ala Asp Lys Ser Gly Ala Gly Glu Arg Gly Ser Arg Gly Ile
405 410 415

Ile Ala Ala Leu Gly Pro Asp Gly Lys Pro Ser Arg Ile Val Val Ile
420 425 430

Tyr Thr Thr Gly Ser Gln Ala Thr Met Asp Glu Arg Asn Arg Gln Ile
435 440 445

Ala Glu Ile Gly Ala Ser Leu Ile Lys His Trp Asp Lys Ser His Pro
450 455 460

Glu Thr Leu Val Lys Val Lys Asp Ala Glu Asp Gln Leu Gly Ala Arg
465 470 475 480

Val Gly Tyr Ile Glu Leu Asp Leu Asn Ser Gly Lys Ile Leu Glu Ser
485 490 495

-continued

Phe Arg Pro Glu Glu Arg Phe Pro Met Met Ser Thr Phe Lys Val Leu
500 505 510

Leu Cys Gly Ala Val Leu Ser Arg Val Asp Ala Gly Gln Glu Gln Leu
515 520 525

Gly Arg Arg Ile His Tyr Ser Gln Asn Asp Leu Val Glu Tyr Ser Pro
530 535 540

Val Thr Glu Lys His Leu Thr Asp Gly Met Thr Val Arg Glu Leu Cys
545 550 555 560

Ser Ala Ala Ile Thr Met Ser Asp Asn Thr Ala Ala Asn Leu Leu Leu
565 570 575

Thr Thr Ile Gly Gly Pro Lys Glu Leu Thr Ala Phe Leu His Asn Met
580 585 590

Gly Asp His Val Thr Arg Leu Asp Arg Trp Glu Pro Glu Leu Asn Glu
595 600 605

Ala Ala Ala Thr Met Glu Asn Ala Gln Lys Gly Glu Ile Met Pro Asn
610 615 620

Ile Pro Gln Met Ser Ala Phe Trp Tyr Ala Val Arg Thr Ala Val Ile
625 630 635 640

Asn Ala Ala Ser Gly Arg Gln Thr Val Asp Glu Ala Leu Lys Asp Ala
645 650 655

Gln Thr Arg Ile Thr Lys
660

<210> SEQ ID NO 58
<211> LENGTH: 1989
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 58
atgaaaataa aaacaggtgc acgcatcctc gcattatccg cattaacgac gatgatgttt 60
tccgcctcgg ctctcgccaa aatcgaagaa ggtaaactgg taatctggat taacggcttg 120
gagggctata acggtctcgc tgaagtcggt aagaaattcg agaaagatac cggaattaaa 180
gtcaccgttg agcatccgga taaactggaa gagaaattcc cacaggttgc ggcaactggc 240
gatggccctg acattatctt ctatgcacac gaccgctttg gtggctacgc tcaatctggc 300
ctgttggctg aaatcacccc ggacaaagcg ttccaggaca agctgtatcc gtttacctgg 360
gatgccgtac gttacaacgg caagctgatt gcttacccga tcgctgttcg tgcgttatcg 420
ctgatttata acaaagatct gctgccgaac ccgccaaaaa cctgggaaga gatcccggcg 480
ctggataaag aactgaaagc gaaaggtaag agcgcgctga tgttcaacct gcaagaaccg 540
tacttcacct ggccgctgat tgctgctgac gggggttatg cgttcaagta tgaaaacggc 600
aagtacgaca ttaaagacgt gggcgtggat aacgctggcg cgaaagcggg tctgaccttc 660
ctggttgacc tgattaaaaa caaacacatg aatgcagaca ccgattactc catcgcagaa 720
gctgccttta ataaaggcga aacagcgatg accatcaacg gcccgtgggc atggtccaac 780
atcgacacca gcaaagtgaa ttatggtgta acggtactgc cgaccttcaa gggtcaacca 840
tccaaaccgt tcgttggcgt gctgagcgca ggtattaacg ccgccagtcc gaacaaagag 900
ctggcgaaag agttcctcga aaactatctg ctgactgatg aaggtctgga agcggttaat 960
aaagacaaac cgctgggtgc cgtagcgctg aagtcttacg aggaagagtt ggcgaaagat 1020
ccacgtgcca taccaaacga cgagcgtgac accacgatgc ctgcagcaat ggcaacaacg 1080

```
ttgcgcaaac tattaactgg cgaactactt actctagctt cccggcaaca attaatagac   1140

tggatggagg cggataaagt tgcaggacca cttctgcgct cggcccttcc ggctggctgg   1200

tttattgctg ataaatctgg agccggtgag cgtgggtctc gcggtatcat tgcagcactg   1260

gggccagatg gtaagccctc ccgtatcgta gttatctaca cgacggggag tcaggcaact   1320

atggatgaac gaaatagaca gatcgctgag ataggtgcct cactgattaa gcattgggac   1380

aagagccacc cagaaacgct ggtgaaagta aaagatgctg aagatcagtt gggtgcacga   1440

gtgggttaca tcgaactgga tctcaacagc ggtaagatcc ttgagagttt tcgccccgaa   1500

gaacgttttc caatgatgag cacttttaaa gttctgctat gtggcgcggt attatcccgt   1560

gttgacgccg ggcaagagca actcggtcgc cgcatacact attctcagaa tgacttggtt   1620

gagtactcac cagtcacaga aaagcatctt acggatggca tgacagtaag agaattatgc   1680

agtgctgcca taaccatgag tgataacact gcggccaact tacttctgac aacgatcgga   1740

ggaccgaagg agctaaccgc ttttttgcac aacatggggg atcatgtaac tcgccttgat   1800

cgttgggaac cggaactgaa tgaagccgcc gccaccatgg aaaacgccca gaaaggtgaa   1860

atcatgccga acatcccgca gatgtccgct ttctggtatg ccgtgcgtac tgcggtgatc   1920

aacgccgcca gcggtcgtca gactgtcgat gaagccctga aagacgcgca gactcgtatc   1980

accaagtaa                                                            1989
```

<210> SEQ ID NO 59
<211> LENGTH: 662
<212> TYPE: PRT
<213> ORGANISM: Artificial Sequence
<220> FEATURE:
<223> OTHER INFORMATION: Description of Artificial Sequence: Synthetic protein construct

<400> SEQUENCE: 59

```
Met Lys Ile Lys Thr Gly Ala Arg Ile Leu Ala Leu Ser Ala Leu Thr
  1               5                  10                  15

Thr Met Met Phe Ser Ala Ser Ala Leu Ala Lys Ile Glu Glu Gly Lys
             20                  25                  30

Leu Val Ile Trp Ile Asn Gly Leu Glu Gly Tyr Asn Gly Leu Ala Glu
         35                  40                  45

Val Gly Lys Lys Phe Glu Lys Asp Thr Gly Ile Lys Val Thr Val Glu
     50                  55                  60

His Pro Asp Lys Leu Glu Glu Lys Phe Pro Gln Val Ala Ala Thr Gly
 65                  70                  75                  80

Asp Gly Pro Asp Ile Ile Phe Tyr Ala His Asp Arg Phe Gly Gly Tyr
                 85                  90                  95

Ala Gln Ser Gly Leu Leu Ala Glu Ile Thr Pro Asp Lys Ala Phe Gln
            100                 105                 110

Asp Lys Leu Tyr Pro Phe Thr Trp Asp Ala Val Arg Tyr Asn Gly Lys
        115                 120                 125

Leu Ile Ala Tyr Pro Ile Ala Val Arg Ala Leu Ser Leu Ile Tyr Asn
    130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
            180                 185                 190
```

-continued

```
Tyr Ala Phe Lys Tyr Glu Asn Gly Lys Tyr Asp Ile Lys Asp Val Gly
        195                 200                 205

Val Asp Asn Ala Gly Ala Lys Ala Gly Leu Thr Phe Leu Val Asp Leu
    210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
                245                 250                 255

Ala Trp Ser Asn Ile Asp Thr Ser Lys Val Asn Tyr Gly Val Thr Val
            260                 265                 270

Leu Pro Thr Phe Lys Gly Gln Pro Ser Lys Pro Phe Val Gly Val Leu
        275                 280                 285

Ser Ala Gly Ile Asn Ala Ala Ser Pro Asn Lys Glu Leu Ala Lys Glu
    290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
                325                 330                 335

Leu Ala Lys Asp Pro Arg Ala Ile Pro Asn Asp Glu Arg Asp Thr Thr
            340                 345                 350

Met Pro Ala Ala Met Ala Thr Thr Leu Arg Lys Leu Leu Thr Gly Glu
        355                 360                 365

Leu Leu Thr Leu Ala Ser Arg Gln Gln Leu Ile Asp Trp Met Glu Ala
    370                 375                 380

Asp Lys Val Ala Gly Pro Leu Leu Arg Ser Ala Leu Pro Ala Gly Trp
385                 390                 395                 400

Phe Ile Ala Asp Lys Ser Gly Ala Gly Glu Arg Gly Ser Arg Gly Ile
                405                 410                 415

Ile Ala Ala Leu Gly Pro Asp Gly Lys Pro Ser Arg Ile Val Val Ile
            420                 425                 430

Tyr Thr Thr Gly Ser Gln Ala Thr Met Asp Glu Arg Asn Arg Gln Ile
        435                 440                 445

Ala Glu Ile Gly Ala Ser Leu Ile Lys His Trp Asp Lys Ser His Pro
    450                 455                 460

Glu Thr Leu Val Lys Val Lys Asp Ala Glu Asp Gln Leu Gly Ala Arg
465                 470                 475                 480

Val Gly Tyr Ile Glu Leu Asp Leu Asn Ser Gly Lys Ile Leu Glu Ser
                485                 490                 495

Phe Arg Pro Glu Glu Arg Phe Pro Met Met Ser Thr Phe Lys Val Leu
            500                 505                 510

Leu Cys Gly Ala Val Leu Ser Arg Val Asp Ala Gly Gln Glu Gln Leu
        515                 520                 525

Gly Arg Arg Ile His Tyr Ser Gln Asn Asp Leu Val Glu Tyr Ser Pro
    530                 535                 540

Val Thr Glu Lys His Leu Thr Asp Gly Met Thr Val Arg Glu Leu Cys
545                 550                 555                 560

Ser Ala Ala Ile Thr Met Ser Asp Asn Thr Ala Ala Asn Leu Leu Leu
                565                 570                 575

Thr Thr Ile Gly Gly Pro Lys Glu Leu Thr Ala Phe Leu His Asn Met
            580                 585                 590

Gly Asp His Val Thr Arg Leu Asp Arg Trp Glu Pro Glu Leu Asn Glu
        595                 600                 605

Ala Ala Ala Thr Met Glu Asn Ala Gln Lys Gly Glu Ile Met Pro Asn
    610                 615                 620
```

```
Ile Pro Gln Met Ser Ala Phe Trp Tyr Ala Val Arg Thr Ala Val Ile
625                 630                 635                 640

Asn Ala Ala Ser Gly Arg Gln Thr Val Asp Glu Ala Leu Lys Asp Ala
                645                 650                 655

Gln Thr Arg Ile Thr Lys
            660


<210> SEQ ID NO 60
<211> LENGTH: 1992
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 60

atgaaaataa aaacaggtgc acgcatcctc gcattatccg cattaacgac gatgatgttt     60

tccgcctcgg ctctcgccaa aatcgaagaa ggtaaactgg taatctggat taacggcgat    120

aaaggctata acggtctcgc tgaagtcggt aagaaattcg agaaagatac cggaattaaa    180

gtcaccgttg agcatccgga taaactggaa gagaaattcc cacaggttgc ggcaactggc    240

gatggccctg acattatctt ctgggcacac gaccgctttg gtggctacgc tcaatctggc    300

ctgttggctg aaatcacccc ggacaaagcg ttccaggaca agctgtatcc gtttacctgg    360

gatgccgtac gttacaacgg caagctgatt gcttacccga tcgctgttga agcgttatcg    420

ctgatttata acaaagatct gctgccgaac ccgccaaaaa cctgggaaga gatcccggcg    480

ctggataaag aactgaaagc gaaaggtaag agcgcgctga tgttcaacct gcaagaaccg    540

tacttcacct ggccgctgat tgctgctgac gggggttatg cgttcaagta tgaaaacggc    600

aagtacgaca ttaaagacgt gggcgtggat aacgctggcg cgaaagcggg tctgaccttc    660

ctggttgacc tgattaaaaa caaacacatg aatgcagaca ccgattactc catcgcagaa    720

gctgccttta ataaaggcga aacagcgatg accatcaacg gcccgtgggc atggtccaac    780

atcgacacca gcaaagtgaa ttatggtgta acggtactgc cgaccttcaa gggtcaacca    840

tccaaaccgt tcgttggcgt gctgagcgca ggtattaacg ccgccagtcc gaacaaagag    900

ctggcgaaag agttcctcga aaactatctg ctgactgatg aaggtctgga agcggttaat    960

aaagacaaac cgctgggtgc cgtagcgctg aagtcttacg aggaagagtt ggcgaaagat   1020

ccacgctggt ttattgctga taaatctgga gccggtgagc gtgggtctcg cggtatcatt   1080

gcagcactgg ggccagatgg taagccctcc cgtatcgtag ttatctacac gacggggagt   1140

caggcaacta tggatgaacg aaatagacag atcgctgaga taggtgcctc actgattaag   1200

cattggggat ccggcggtgg ccacccagaa acgctggtga aagtaaaaga tgctgaagat   1260

cagttgggtg cacgagtggg ttacatcgaa ctggatctca acagcggtaa gatccttgag   1320

agttttcgcc ccgaagaacg ttttccaatg atgagcactt ttaaagttct gctatgtggc   1380

gcggtattat cccgtgttga cgccgggcaa gagcaactcg gtcgccgcat acactattct   1440

cagaatgact tggttgagta ctcaccagtc acagaaaagc atcttacgga tggcatgaca   1500

gtaagagaat tatgcagtgc tgccataacc atgagtgata acactgcggc caacttactt   1560

ctgacaacga tcggaggacc gaaggagcta accgcttttt tgcacaacat gggggatcat   1620

gtaactcgcc ttgatcgttg ggaaccggag ctgaatgaag ccataccaaa cgacgagcgt   1680

gacaccacga tgcctgcagc aatggcaaca acgttgcgca aactattaac tggcgaacta   1740

cttactctag cttcccggca acaattaata gactggatgg aggcggataa agttgcagga   1800
```

-continued

```
ccacttctgc gctcggccct tccggctggc tccgccacca tggaaaacgc ccagaaaggt   1860

gaaatcatgc cgaacatccc gcagatgtcc gctttctggt atgccgtgcg tactgcggtg   1920

atcaacgccg ccagcggtcg tcagactgtc gatgaagccc tgaaagacgc gcagactcgt   1980

atcaccaagt aa                                                       1992
```

<210> SEQ ID NO 61
<211> LENGTH: 663
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 61

```
Met Lys Ile Lys Thr Gly Ala Arg Ile Leu Ala Leu Ser Ala Leu Thr
  1               5                  10                  15

Thr Met Met Phe Ser Ala Ser Ala Leu Ala Lys Ile Glu Glu Gly Lys
             20                  25                  30

Leu Val Ile Trp Ile Asn Gly Asp Lys Gly Tyr Asn Gly Leu Ala Glu
         35                  40                  45

Val Gly Lys Lys Phe Glu Lys Asp Thr Gly Ile Lys Val Thr Val Glu
     50                  55                  60

His Pro Asp Lys Leu Glu Glu Lys Phe Pro Gln Val Ala Ala Thr Gly
 65                  70                  75                  80

Asp Gly Pro Asp Ile Ile Phe Trp Ala His Asp Arg Phe Gly Gly Tyr
                 85                  90                  95

Ala Gln Ser Gly Leu Leu Ala Glu Ile Thr Pro Asp Lys Ala Phe Gln
            100                 105                 110

Asp Lys Leu Tyr Pro Phe Thr Trp Asp Ala Val Arg Tyr Asn Gly Lys
        115                 120                 125

Leu Ile Ala Tyr Pro Ile Ala Val Glu Ala Leu Ser Leu Ile Tyr Asn
    130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
            180                 185                 190

Tyr Ala Phe Lys Tyr Glu Asn Gly Lys Tyr Asp Ile Lys Asp Val Gly
        195                 200                 205

Val Asp Asn Ala Gly Ala Lys Ala Gly Leu Thr Phe Leu Val Asp Leu
    210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
                245                 250                 255

Ala Trp Ser Asn Ile Asp Thr Ser Lys Val Asn Tyr Gly Val Thr Val
            260                 265                 270

Leu Pro Thr Phe Lys Gly Gln Pro Ser Lys Pro Phe Val Gly Val Leu
        275                 280                 285

Ser Ala Gly Ile Asn Ala Ala Ser Pro Asn Lys Glu Leu Ala Lys Glu
    290                 295                 300

Phe Leu Glu Asn Tyr Leu Leu Thr Asp Glu Gly Leu Glu Ala Val Asn
305                 310                 315                 320
```

-continued

```
Lys Asp Lys Pro Leu Gly Ala Val Ala Leu Lys Ser Tyr Glu Glu Glu
                325                 330                 335

Leu Ala Lys Asp Pro Arg Trp Phe Ile Ala Asp Lys Ser Gly Ala Gly
            340                 345                 350

Glu Arg Gly Ser Arg Gly Ile Ile Ala Ala Leu Gly Pro Asp Gly Lys
        355                 360                 365

Pro Ser Arg Ile Val Val Ile Tyr Thr Thr Gly Ser Gln Ala Thr Met
    370                 375                 380

Asp Glu Arg Asn Arg Gln Ile Ala Glu Ile Gly Ala Ser Leu Ile Lys
385                 390                 395                 400

His Trp Gly Ser Gly Gly Gly His Pro Glu Thr Leu Val Lys Val Lys
                405                 410                 415

Asp Ala Glu Asp Gln Leu Gly Ala Arg Val Gly Tyr Ile Glu Leu Asp
            420                 425                 430

Leu Asn Ser Gly Lys Ile Leu Glu Ser Phe Arg Pro Glu Glu Arg Phe
        435                 440                 445

Pro Met Met Ser Thr Phe Lys Val Leu Leu Cys Gly Ala Val Leu Ser
    450                 455                 460

Arg Val Asp Ala Gly Gln Glu Gln Leu Gly Arg Arg Ile His Tyr Ser
465                 470                 475                 480

Gln Asn Asp Leu Val Glu Tyr Ser Pro Val Thr Glu Lys His Leu Thr
                485                 490                 495

Asp Gly Met Thr Val Arg Glu Leu Cys Ser Ala Ala Ile Thr Met Ser
            500                 505                 510

Asp Asn Thr Ala Ala Asn Leu Leu Leu Thr Thr Ile Gly Gly Pro Lys
        515                 520                 525

Glu Leu Thr Ala Phe Leu His Asn Met Gly Asp His Val Thr Arg Leu
    530                 535                 540

Asp Arg Trp Glu Pro Glu Leu Asn Glu Ala Ile Pro Asn Asp Glu Arg
545                 550                 555                 560

Asp Thr Thr Met Pro Ala Ala Met Ala Thr Thr Leu Arg Lys Leu Leu
                565                 570                 575

Thr Gly Glu Leu Leu Thr Leu Ala Ser Arg Gln Gln Leu Ile Asp Trp
            580                 585                 590

Met Glu Ala Asp Lys Val Ala Gly Pro Leu Leu Arg Ser Ala Leu Pro
        595                 600                 605

Ala Gly Ser Ala Thr Met Glu Asn Ala Gln Lys Gly Glu Ile Met Pro
    610                 615                 620

Asn Ile Pro Gln Met Ser Ala Phe Trp Tyr Ala Val Arg Thr Ala Val
625                 630                 635                 640

Ile Asn Ala Ala Ser Gly Arg Gln Thr Val Asp Glu Ala Leu Lys Asp
                645                 650                 655

Ala Gln Thr Arg Ile Thr Lys
            660
```

<210> SEQ ID NO 62
<211> LENGTH: 1992
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 62

```
atgaaaataa aaacaggtgc acgcatcctc gcattatccg cattaacgac gatgatgttt      60

tccgcctcgg ctctcgccaa aatcgaagaa ggtaaactgg taatctggat taacggcgat     120
```

-continued

```
aaaggctata acggtctcgc tgaagtcggt aagaaattcg agaaagatac cggaattaaa    180

gtcaccgttg agcatccgga taaactggaa gagaaattcc cacaggttgc ggcaactggc    240

gatggccctg acattatctt ctgggcacac gaccgctttg gtggctacgc tcaatctggc    300

ctgttggctg aaatcacccc ggacaaagcg ttccaggaca agctgtatcc gtttacctgg    360

gatgccgtac gttacaacgg caagctgatt gcttacccga tcgctgttga agcgttatcg    420

ctgatttata acaaagatct gctgccgaac ccgccaaaaa cctgggaaga gatcccggcg    480

ctggataaag aactgaaagc gaaaggtaag agcgcgctga tgttcaacct gcaagaaccg    540

tacttcacct ggccgctgat tgctgctgac gggggttatg cgttcaagta tgaaaacggc    600

aagtacgaca ttaaagacgt gggcgtggat aacgctggcg cgaaagcggg tctgaccttc    660

ctggttgacc tgattaaaaa caaacacatg aatgcagaca ccgattactc catcgcagaa    720

gctgccttta ataaaggcga aacagcgatg accatcaacg gcccgtgggc atggtccaac    780

atcgacacca gcaaagtgaa ttatggtgta acggtactgc cgaccttcaa gggtcaacca    840

tccaaaccgt tcgttggcgt gctgagcgca ggtattaacg ccgccagtcc gaacaaagag    900

ctggcgaaag agttcctcga aaactatctg ctgactgatg aaggtctgga agcggttaat    960

aaagacaaac cgctgggtgc cgtagcgctg aagtcttacg aggaagagtt ggcgaaagat   1020

ccacgctggt ttattgctga taaatctgga gccggtgagc gtgggtctcg cggtatcatt   1080

gcagcactgg ggccagatgg taagccctcc cgtatcgtag ttatctacac gacggggagt   1140

caggcaacta tggatgaacg aaatagacag atcgctgaga taggtgcctc actgattaag   1200

cattggggat ccggcggtgg ccacccagaa acgctggtga aagtaaaaga tgctgaagat   1260

cagttgggtg cacgagtggg ttacatcgaa ctggatctca acagcggtaa gatccttgag   1320

agttttcgcc ccgaagaacg ttttccaatg atgagcactt ttaaagttct gctatgtggc   1380

gcggtattat cccgtgttga cgccgggcaa gagcaactcg gtcgccgcat acactattct   1440

cagaatgact tggttgagta ctcaccagtc acagaaaagc atcttacgga tggcatgaca   1500

gtaagagaat tatgcagtgc tgccataacc atgagtgata acactgcggc caacttactt   1560

ctgacaacga tcggaggacc gaaggagcta accgcttttt tgcacaacat gggggatcat   1620

gtaactcgcc ttgatcgttg ggaaccggag ctgaatgaag ccataccaaa cgacgagcgt   1680

gacaccacga tgcctgcagc aatggcaaca acgttgcgca aactattaac tggcgaacta   1740

cttactctag cttcccggca acaattaata gactggatgg aggcggataa agttgcagga   1800

ccacttctgc gctcggccct tccggctggc tccgccacca tggaaaacgc ccagaaaggt   1860

gaatggatgc cgaacatccc gcagatgtcc gctttctggt atgccgtgcg tactgcggtg   1920

atcaacgccg ccagcggtcg tcagactgtc gatgaagccc tgaaagacgc gcagactcgt   1980

atcaccaagt aa                                                        1992
```

<210> SEQ ID NO 63
<211> LENGTH: 663
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 63

```
Met Lys Ile Lys Thr Gly Ala Arg Ile Leu Ala Leu Ser Ala Leu Thr
  1               5                  10                  15

Thr Met Met Phe Ser Ala Ser Ala Leu Ala Lys Ile Glu Glu Gly Lys
             20                  25                  30
```

-continued

```
Leu Val Ile Trp Ile Asn Gly Asp Lys Gly Tyr Asn Gly Leu Ala Glu
        35                  40                  45

Val Gly Lys Lys Phe Glu Lys Asp Thr Gly Ile Lys Val Thr Val Glu
    50                  55                  60

His Pro Asp Lys Leu Glu Glu Lys Phe Pro Gln Val Ala Ala Thr Gly
65                  70                  75                  80

Asp Gly Pro Asp Ile Ile Phe Trp Ala His Asp Arg Phe Gly Gly Tyr
                85                  90                  95

Ala Gln Ser Gly Leu Leu Ala Glu Ile Thr Pro Asp Lys Ala Phe Gln
            100                 105                 110

Asp Lys Leu Tyr Pro Phe Thr Trp Asp Ala Val Arg Tyr Asn Gly Lys
        115                 120                 125

Leu Ile Ala Tyr Pro Ile Ala Val Glu Ala Leu Ser Leu Ile Tyr Asn
    130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
            180                 185                 190

Tyr Ala Phe Lys Tyr Glu Asn Gly Lys Tyr Asp Ile Lys Asp Val Gly
        195                 200                 205

Val Asp Asn Ala Gly Ala Lys Ala Gly Leu Thr Phe Leu Val Asp Leu
    210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
                245                 250                 255

Ala Trp Ser Asn Ile Asp Thr Ser Lys Val Asn Tyr Gly Val Thr Val
            260                 265                 270

Leu Pro Thr Phe Lys Gly Gln Pro Ser Lys Pro Phe Val Gly Val Leu
        275                 280                 285

Ser Ala Gly Ile Asn Ala Ala Ser Pro Asn Lys Glu Leu Ala Lys Glu
    290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
                325                 330                 335

Leu Ala Lys Asp Pro Arg Trp Phe Ile Ala Asp Lys Ser Gly Ala Gly
            340                 345                 350

Glu Arg Gly Ser Arg Gly Ile Ile Ala Ala Leu Gly Pro Asp Gly Lys
        355                 360                 365

Pro Ser Arg Ile Val Val Ile Tyr Thr Thr Gly Ser Gln Ala Thr Met
    370                 375                 380

Asp Glu Arg Asn Arg Gln Ile Ala Glu Ile Gly Ala Ser Leu Ile Lys
385                 390                 395                 400

His Trp Gly Ser Gly Gly Gly His Pro Glu Thr Leu Val Lys Val Lys
                405                 410                 415

Asp Ala Glu Asp Gln Leu Gly Ala Arg Val Gly Tyr Ile Glu Leu Asp
            420                 425                 430

Leu Asn Ser Gly Lys Ile Leu Glu Ser Phe Arg Pro Glu Glu Arg Phe
        435                 440                 445

Pro Met Met Ser Thr Phe Lys Val Leu Leu Cys Gly Ala Val Leu Ser
    450                 455                 460
```

```
Arg Val Asp Ala Gly Gln Glu Gln Leu Gly Arg Arg Ile His Tyr Ser
465                 470                 475                 480

Gln Asn Asp Leu Val Glu Tyr Ser Pro Val Thr Glu Lys His Leu Thr
                485                 490                 495

Asp Gly Met Thr Val Arg Glu Leu Cys Ser Ala Ala Ile Thr Met Ser
            500                 505                 510

Asp Asn Thr Ala Ala Asn Leu Leu Leu Thr Thr Ile Gly Gly Pro Lys
        515                 520                 525

Glu Leu Thr Ala Phe Leu His Asn Met Gly Asp His Val Thr Arg Leu
    530                 535                 540

Asp Arg Trp Glu Pro Glu Leu Asn Glu Ala Ile Pro Asn Asp Glu Arg
545                 550                 555                 560

Asp Thr Thr Met Pro Ala Ala Met Ala Thr Thr Leu Arg Lys Leu Leu
                565                 570                 575

Thr Gly Glu Leu Leu Thr Leu Ala Ser Arg Gln Gln Leu Ile Asp Trp
            580                 585                 590

Met Glu Ala Asp Lys Val Ala Gly Pro Leu Leu Arg Ser Ala Leu Pro
        595                 600                 605

Ala Gly Ser Ala Thr Met Glu Asn Ala Gln Lys Gly Glu Trp Met Pro
    610                 615                 620

Asn Ile Pro Gln Met Ser Ala Phe Trp Tyr Ala Val Arg Thr Ala Val
625                 630                 635                 640

Ile Asn Ala Ala Ser Gly Arg Gln Thr Val Asp Glu Ala Leu Lys Asp
                645                 650                 655

Ala Gln Thr Arg Ile Thr Lys
            660
```

```
<210> SEQ ID NO 64
<211> LENGTH: 1992
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 64

atgaaaataa aaacaggtgc acgcatcctc gcattatccg cattaacgac gatgatgttt     60

tccgcctcgg ctctcgccaa aatcgaagaa ggtaaactgg taatctggat taacggcgat    120

aaaggctata acggtctcgc tgaagtcggt aagaaattcg agaaagatac cggaattaaa    180

gtcaccgttg agcatccgga taaactggaa gagaaattcc cacaggttgc ggcaactggc    240

gatggccctg acattatctt ctgggcacac gaccgctttg gtggctacgc tcaatctggc    300

ctgttggctg aaatcacccc ggacaaagcg ttccaggaca agctgtatcc gtttacctgg    360

gattgggtac gttacaacgg caagctgatt gcttacccga tcgctgttga agcgttatcg    420

ctgatttata acaaagatct gctgccgaac ccgccaaaaa cctgggaaga gatcccggcg    480

ctggataaag aactgaaagc gaaaggtaag agcgcgctga tgttcaacct gcaagaaccg    540

tacttcacct ggccgctgat tgctgctgac gggggttatg cgttcaagta tgaaaacggc    600

aagtacgaca ttaaagacgt gggcgtggat aacgctggcg cgaaagcggg tctgaccttc    660

ctggttgacc tgattaaaaa caaacacatg aatgcagaca ccgattactc catcgcagaa    720

gctgccttta ataaaggcga aacagcgatg accatcaacg gcccgtgggc atggtccaac    780

atcgacacca gcaaagtgaa ttatggtgta acggtactgc cgaccttcaa gggtcaacca    840

tccaaaccgt tcgttggcgt gctgagcgca ggtattaacg ccgccagtcc gaacaaagag    900
```

```
ctggcgaaag agttcctcga aaactatctg ctgactgatg aaggtctgga agcggttaat    960

aaagacaaac cgctgggtgc cgtagcgctg aagtcttacg aggaagagtt ggcgaaagat   1020

ccacgctggt ttattgctga taaatctgga gccggtgagc gtgggtctcg cggtatcatt   1080

gcagcactgg ggccagatgg taagccctcc cgtatcgtag ttatctacac gacggggagt   1140

caggcaacta tggatgaacg aaatagacag atcgctgaga taggtgcctc actgattaag   1200

cattggggat ccggcggtgg ccacccagaa acgctggtga aagtaaaaga tgctgaagat   1260

cagttgggtg cacgagtggg ttacatcgaa ctggatctca acagcggtaa gatccttgag   1320

agttttcgcc ccgaagaacg ttttccaatg atgagcactt ttaaagttct gctatgtggc   1380

gcggtattat cccgtgttga cgccgggcaa gagcaactcg gtcgccgcat acactattct   1440

cagaatgact tggttgagta ctcaccagtc acagaaaagc atcttacgga tggcatgaca   1500

gtaagagaat tatgcagtgc tgccataacc atgagtgata acactgcggc caacttactt   1560

ctgacaacga tcggaggacc gaaggagcta accgcttttt tgcacaacat gggggatcat   1620

gtaactcgcc ttgatcgttg ggaaccggag ctgaatgaag ccataccaaa cgacgagcgt   1680

gacaccacga tgcctgcagc aatggcaaca acgttgcgca aactattaac tggcgaacta   1740

cttactctag cttcccggca acaattaata gactggatgg aggcggataa agttgcagga   1800

ccacttctgc gctcggccct tccggctggc tccgccacca tggaaaacgc ccagaaaggt   1860

gaatggatgc cgaacatccc gcagatgtcc gctttctggt atgccgtgcg tactgcggtg   1920

atcaacgccg ccagcggtcg tcagactgtc gatgaagccc tgaaagacgc gcagactcgt   1980

atcaccaagt aa                                                       1992
```

```
<210> SEQ ID NO 65
<211> LENGTH: 663
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 65

Met Lys Ile Lys Thr Gly Ala Arg Ile Leu Ala Leu Ser Ala Leu Thr
  1               5                  10                  15

Thr Met Met Phe Ser Ala Ser Ala Leu Ala Lys Ile Glu Glu Gly Lys
             20                  25                  30

Leu Val Ile Trp Ile Asn Gly Asp Lys Gly Tyr Asn Gly Leu Ala Glu
         35                  40                  45

Val Gly Lys Lys Phe Glu Lys Asp Thr Gly Ile Lys Val Thr Val Glu
     50                  55                  60

His Pro Asp Lys Leu Glu Glu Lys Phe Pro Gln Val Ala Ala Thr Gly
 65                  70                  75                  80

Asp Gly Pro Asp Ile Ile Phe Trp Ala His Asp Arg Phe Gly Gly Tyr
                 85                  90                  95

Ala Gln Ser Gly Leu Leu Ala Glu Ile Thr Pro Asp Lys Ala Phe Gln
            100                 105                 110

Asp Lys Leu Tyr Pro Phe Thr Trp Asp Trp Val Arg Tyr Asn Gly Lys
        115                 120                 125

Leu Ile Ala Tyr Pro Ile Ala Val Glu Ala Leu Ser Leu Ile Tyr Asn
    130                 135                 140

Lys Asp Leu Leu Pro Asn Pro Pro Lys Thr Trp Glu Glu Ile Pro Ala
145                 150                 155                 160
```

-continued

```
Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
            180                 185                 190

Tyr Ala Phe Lys Tyr Glu Asn Gly Lys Tyr Asp Ile Lys Asp Val Gly
        195                 200                 205

Val Asp Asn Ala Gly Ala Lys Ala Gly Leu Thr Phe Leu Val Asp Leu
    210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
                245                 250                 255

Ala Trp Ser Asn Ile Asp Thr Ser Lys Val Asn Tyr Gly Val Thr Val
            260                 265                 270

Leu Pro Thr Phe Lys Gly Gln Pro Ser Lys Pro Phe Val Gly Val Leu
        275                 280                 285

Ser Ala Gly Ile Asn Ala Ala Ser Pro Asn Lys Glu Leu Ala Lys Glu
    290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
                325                 330                 335

Leu Ala Lys Asp Pro Arg Trp Phe Ile Ala Asp Lys Ser Gly Ala Gly
            340                 345                 350

Glu Arg Gly Ser Arg Gly Ile Ile Ala Ala Leu Gly Pro Asp Gly Lys
        355                 360                 365

Pro Ser Arg Ile Val Val Ile Tyr Thr Thr Gly Ser Gln Ala Thr Met
    370                 375                 380

Asp Glu Arg Asn Arg Gln Ile Ala Glu Ile Gly Ala Ser Leu Ile Lys
385                 390                 395                 400

His Trp Gly Ser Gly Gly Gly His Pro Glu Thr Leu Val Lys Val Lys
                405                 410                 415

Asp Ala Glu Asp Gln Leu Gly Ala Arg Val Gly Tyr Ile Glu Leu Asp
            420                 425                 430

Leu Asn Ser Gly Lys Ile Leu Glu Ser Phe Arg Pro Glu Glu Arg Phe
        435                 440                 445

Pro Met Met Ser Thr Phe Lys Val Leu Leu Cys Gly Ala Val Leu Ser
    450                 455                 460

Arg Val Asp Ala Gly Gln Glu Gln Leu Gly Arg Arg Ile His Tyr Ser
465                 470                 475                 480

Gln Asn Asp Leu Val Glu Tyr Ser Pro Val Thr Glu Lys His Leu Thr
                485                 490                 495

Asp Gly Met Thr Val Arg Glu Leu Cys Ser Ala Ala Ile Thr Met Ser
            500                 505                 510

Asp Asn Thr Ala Ala Asn Leu Leu Leu Thr Thr Ile Gly Gly Pro Lys
        515                 520                 525

Glu Leu Thr Ala Phe Leu His Asn Met Gly Asp His Val Thr Arg Leu
    530                 535                 540

Asp Arg Trp Glu Pro Glu Leu Asn Glu Ala Ile Pro Asn Asp Glu Arg
545                 550                 555                 560

Asp Thr Thr Met Pro Ala Ala Met Ala Thr Thr Leu Arg Lys Leu Leu
                565                 570                 575

Thr Gly Glu Leu Leu Thr Leu Ala Ser Arg Gln Gln Leu Ile Asp Trp
            580                 585                 590
```

```
Met Glu Ala Asp Lys Val Ala Gly Pro Leu Leu Arg Ser Ala Leu Pro
        595                 600                 605

Ala Gly Ser Ala Thr Met Glu Asn Ala Gln Lys Gly Glu Trp Met Pro
    610                 615                 620

Asn Ile Pro Gln Met Ser Ala Phe Trp Tyr Ala Val Arg Thr Ala Val
625                 630                 635                 640

Ile Asn Ala Ala Ser Gly Arg Gln Thr Val Asp Glu Ala Leu Lys Asp
                645                 650                 655

Ala Gln Thr Arg Ile Thr Lys
            660


<210> SEQ ID NO 66
<211> LENGTH: 1989
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 66

atgaaaataa aaacaggtgc acgcatcctc gcattatccg cattaacgac gatgatgttt     60

tccgcctcgg ctctcgccaa aatcgaagaa ggtaaactgg taatctggat taacggcgat    120

aaaggctata acggtctcgc tgaagtcggt aagaaattcg agaaagatac cggaattaaa    180

gtcaccgttg agcatccgga taaactggaa gagaaattcc cacaggttgc ggcaactggc    240

gatggccctg acattatctt ctgggcacac gaccgctttg gtggctacgc tcaatctggc    300

ctgttggctg aaatcacccc ggacaaagcg ttccaggaca agctgtatcc gtttacctgg    360

gatgccgtac gttacaacgg caagctgatt gcttacccga tcgctgttga agcgttatcg    420

ctgatttata acaaagatct gctgccgaac ccgccaaaaa cctgggaaga gatcccggcg    480

ctggataaag aactgaaagc gaaaggtaag agcgcgctga tgttcaacct gcaagaaccg    540

tacttcacct ggccgctgat tgctgctgac gggcatctta cggatggcat gacagtaaga    600

gaattatgca gtgctgccat aaccatgagt gataacactg cggccaactt acttctgaca    660

acgatcggag gaccgaagga gctaaccgct tttttgcaca acatggggga tcatgtaact    720

cgccttgatc gttgggaacc ggaactgaat gaagccatac caaacgacga gcgtgacacc    780

acgatgcctg cagcaatggc aacaacgttg cgcaaactat taactggcga actacttact    840

ctagcttccc ggcaacaatt aatagactgg atggaggcgg ataaagttgc aggaccactt    900

ctgcgctcgg cccttccggc tggctggttt attgctgata aatctggagc cggtgagcgt    960

gggtctcgcg gtatcattgc agcactgggg ccagatggta agccctcccg tatcgtagtt   1020

atctacacga cggggagtca ggcaactatg gatgaacgaa atagacagat cgctgagata   1080

ggtgcctcac tgattaagca ttgggacaag agccacccag aaacgctggt gaaagtaaaa   1140

gatgctgaag atcagttggg tgcacgagtg ggttacatcg aactggatct caacagcggt   1200

aagatccttg agagttttcg ccccgaagaa cgttttccaa tgatgagcac ttttaaagtt   1260

ctgctatgtg gcgcggtatt atcccgtgtt gacgccgggc aagagcaact cggtcgccgc   1320

atacactatt ctcagaatga cttggttgag tactcaccag tcacagacgg gggttatgcg   1380

ttcaagtatg aaaacggcaa gtacgacatt aaagacgtgg gcgtggataa cgctggcgcg   1440

aaagcgggtc tgaccttcct ggttgacctg attaaaaaca aacacatgaa tgcagacacc   1500

gattactcca tcgcagaagc tgcctttaat aaaggcgaaa cagcgatgac catcaacggc   1560

ccgtgggcat ggtccaacat cgacaccagc aaagtgaatt atggtgtaac ggtactgccg   1620
```

-continued

```
accttcaagg gtcaaccatc caaaccgttc gttggcgtgc tgagcgcagg tattaacgcc   1680

gccagtccga acaaagagct ggcgaaagag ttcctcgaaa actatctgct gactgatgaa   1740

ggtctggaag cggttaataa agacaaaccg ctgggtgccg tagcgctgaa gtcttacgag   1800

gaagagttgg cgaaagatcc acgtattgcc gccaccatgg aaaacgccca gaaaggtgaa   1860

atcatgccga acatcccgca gatgtccgct ttctggtatg ccgtgcgtac tgcggtgatc   1920

aacgccgcca gcggtcgtca gactgtcgat gaagccctga aagacgcgca gactcgtatc   1980

accaagtaa                                                           1989
```

```
<210> SEQ ID NO 67
<211> LENGTH: 662
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 67

Met Lys Ile Lys Thr Gly Ala Arg Ile Leu Ala Leu Ser Ala Leu Thr
  1               5                  10                  15

Thr Met Met Phe Ser Ala Ser Ala Leu Ala Lys Ile Glu Glu Gly Lys
             20                  25                  30

Leu Val Ile Trp Ile Asn Gly Asp Lys Gly Tyr Asn Gly Leu Ala Glu
         35                  40                  45

Val Gly Lys Lys Phe Glu Lys Asp Thr Gly Ile Lys Val Thr Val Glu
     50                  55                  60

His Pro Asp Lys Leu Glu Glu Lys Phe Pro Gln Val Ala Ala Thr Gly
 65                  70                  75                  80

Asp Gly Pro Asp Ile Ile Phe Trp Ala His Asp Arg Phe Gly Gly Tyr
                 85                  90                  95

Ala Gln Ser Gly Leu Leu Ala Glu Ile Thr Pro Asp Lys Ala Phe Gln
            100                 105                 110

Asp Lys Leu Tyr Pro Phe Thr Trp Asp Ala Val Arg Tyr Asn Gly Lys
        115                 120                 125

Leu Ile Ala Tyr Pro Ile Ala Val Glu Ala Leu Ser Leu Ile Tyr Asn
    130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly His
            180                 185                 190

Leu Thr Asp Gly Met Thr Val Arg Glu Leu Cys Ser Ala Ala Ile Thr
        195                 200                 205

Met Ser Asp Asn Thr Ala Ala Asn Leu Leu Leu Thr Thr Ile Gly Gly
    210                 215                 220

Pro Lys Glu Leu Thr Ala Phe Leu His Asn Met Gly Asp His Val Thr
225                 230                 235                 240

Arg Leu Asp Arg Trp Glu Pro Glu Leu Asn Glu Ala Ile Pro Asn Asp
                245                 250                 255

Glu Arg Asp Thr Thr Met Pro Ala Ala Met Ala Thr Thr Leu Arg Lys
            260                 265                 270

Leu Leu Thr Gly Glu Leu Leu Thr Leu Ala Ser Arg Gln Gln Leu Ile
        275                 280                 285
```

-continued

```
Asp Trp Met Glu Ala Asp Lys Val Ala Gly Pro Leu Leu Arg Ser Ala
    290                 295                 300

Leu Pro Ala Gly Trp Phe Ile Ala Asp Lys Ser Gly Ala Gly Glu Arg
305                 310                 315                 320

Gly Ser Arg Gly Ile Ile Ala Ala Leu Gly Pro Asp Gly Lys Pro Ser
                325                 330                 335

Arg Ile Val Val Ile Tyr Thr Thr Gly Ser Gln Ala Thr Met Asp Glu
            340                 345                 350

Arg Asn Arg Gln Ile Ala Glu Ile Gly Ala Ser Leu Ile Lys His Trp
        355                 360                 365

Asp Lys Ser His Pro Glu Thr Leu Val Lys Val Lys Asp Ala Glu Asp
    370                 375                 380

Gln Leu Gly Ala Arg Val Gly Tyr Ile Glu Leu Asp Leu Asn Ser Gly
385                 390                 395                 400

Lys Ile Leu Glu Ser Phe Arg Pro Glu Glu Arg Phe Pro Met Met Ser
                405                 410                 415

Thr Phe Lys Val Leu Leu Cys Gly Ala Val Leu Ser Arg Val Asp Ala
            420                 425                 430

Gly Gln Glu Gln Leu Gly Arg Arg Ile His Tyr Ser Gln Asn Asp Leu
        435                 440                 445

Val Glu Tyr Ser Pro Val Thr Asp Gly Gly Tyr Ala Phe Lys Tyr Glu
    450                 455                 460

Asn Gly Lys Tyr Asp Ile Lys Asp Val Gly Val Asp Asn Ala Gly Ala
465                 470                 475                 480

Lys Ala Gly Leu Thr Phe Leu Val Asp Leu Ile Lys Asn Lys His Met
                485                 490                 495

Asn Ala Asp Thr Asp Tyr Ser Ile Ala Glu Ala Ala Phe Asn Lys Gly
            500                 505                 510

Glu Thr Ala Met Thr Ile Asn Gly Pro Trp Ala Trp Ser Asn Ile Asp
        515                 520                 525

Thr Ser Lys Val Asn Tyr Gly Val Thr Val Leu Pro Thr Phe Lys Gly
    530                 535                 540

Gln Pro Ser Lys Pro Phe Val Gly Val Leu Ser Ala Gly Ile Asn Ala
545                 550                 555                 560

Ala Ser Pro Asn Lys Glu Leu Ala Lys Glu Phe Leu Glu Asn Tyr Leu
                565                 570                 575

Leu Thr Asp Glu Gly Leu Glu Ala Val Asn Lys Asp Lys Pro Leu Gly
            580                 585                 590

Ala Val Ala Leu Lys Ser Tyr Glu Glu Glu Leu Ala Lys Asp Pro Arg
        595                 600                 605

Ile Ala Ala Thr Met Glu Asn Ala Gln Lys Gly Glu Ile Met Pro Asn
    610                 615                 620

Ile Pro Gln Met Ser Ala Phe Trp Tyr Ala Val Arg Thr Ala Val Ile
625                 630                 635                 640

Asn Ala Ala Ser Gly Arg Gln Thr Val Asp Glu Ala Leu Lys Asp Ala
                645                 650                 655

Gln Thr Arg Ile Thr Lys
            660
```

<210> SEQ ID NO 68
<211> LENGTH: 1995
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 68

```
atgaaaataa aaacaggtgc acgcatcctc gcattatccg cattaacgac gatgatgttt      60
tccgcctcgg ctctcgccaa aatcgaagaa ggtaaactgg taatctggat taacggcgat     120
aaaggctata acggtctcgc tgaagtcggt aagaaattcg agaaagatac cggaattaaa     180
gtcaccgttg agcatccgga taaactggaa gagaaattcc cacaggttgc ggcaactggc     240
gatggccctg acattatctt ctgggcacac gaccgctttg gtggctacgc tcaatctggc     300
ctgttggctg aaatcacccc ggacaaagcg ttccaggaca agctgtatcc gtttacctgg     360
gatgccgtac gttacaacgg caagctgatt gcttacccga tcgctgttga agcgttatcg     420
ctgatttata acaaagatct gctgccgaac ccgccaaaaa cctgggaaga gatcccggcg     480
ctggataaag aactgaaagc gaaaggtaag agcgcgctga tgttcaacct gcaagaaccg     540
tacttcacct ggccgctgat tgctgctgac gggcttctgc gctcggccct tccggctggc     600
tggtttattg ctgataaatc tggagccggt gagcgtgggt ctcgcggtat cattgcagca     660
ctggggccag atggtaagcc ctcccgtatc gtagttatct acacgacggg gagtcaggca     720
actatggatg aacgaaatag acagatcgct gagataggtg cctcactgat taagcattgg     780
ggatccggcg gtggccaccc agaaacgctg gtgaaagtaa aagatgctga agatcagttg     840
ggtgcacgag tgggttacat cgaactggat ctcaacagcg gtaagatcct tgagagtttt     900
cgccccgaag aacgttttcc aatgatgagc acttttaaag ttctgctatg tggcgcggta     960
ttatcccgtg ttgacgccgg gcaagagcaa ctcggtcgcc gcatacacta ttctcagaat    1020
gacttggttg agtactcacc agtcacagaa aagcatctta cggatggcat gacagtaaga    1080
gaattatgca gtgctgccat aaccatgagt gataacactg cggccaactt acttctgaca    1140
acgatcggag gaccgaagga gctaaccgct tttttgcaca acatggggga tcatgtaact    1200
cgccttgatc gttgggaacc ggagctgaat gaagccatac caaacgacga gcgtgacacc    1260
acgatgcctg cagcaatggc aacaacgttg cgcaaactat taactggcga actacttact    1320
ctagcttccc ggcaacaatt aatagactgg atggaggcgg ataaagttgc agacgggggt    1380
tatgcgttca agtatgaaaa cggcaagtac gacattaaag acgtgggcgt ggataacgct    1440
ggcgcgaaag cgggtctgac cttcctggtt gacctgatta aaaacaaaca catgaatgca    1500
gacaccgatt actccatcgc agaagctgcc tttaataaag gcgaaacagc gatgaccatc    1560
aacggcccgt gggcatggtc caacatcgac accagcaaag tgaattatgg tgtaacggta    1620
ctgccgacct tcaagggtca accatccaaa ccgttcgttg gcgtgctgag cgcaggtatt    1680
aacgccgcca gtccgaacaa agagctggcg aaagagttcc tcgaaaacta tctgctgact    1740
gatgaaggtc tggaagcggt taataaagac aaaccgctgg gtgccgtagc gctgaagtct    1800
tacgaggaag agttggcgaa agatccacgt attgccgcca ccatggaaaa cgcccagaaa    1860
ggtgaaatca tgccgaacat cccgcagatg tccgctttct ggtatgccgt gcgtactgcg    1920
gtgatcaacg ccgccagcgg tcgtcagact gtcgatgaag ccctgaaaga cgcgcagact    1980
cgtatcacca agtaa                                                     1995
```

<210> SEQ ID NO 69
<211> LENGTH: 664
<212> TYPE: PRT
<213> ORGANISM: Artificial Sequence
<220> FEATURE:
<223> OTHER INFORMATION: Description of Artificial Sequence: Synthetic
protein construct

<400> SEQUENCE: 69

Met Lys Ile Lys Thr Gly Ala Arg Ile Leu Ala Leu Ser Ala Leu Thr
1 5 10 15

Thr Met Met Phe Ser Ala Ser Ala Leu Ala Lys Ile Glu Glu Gly Lys
20 25 30

Leu Val Ile Trp Ile Asn Gly Asp Lys Gly Tyr Asn Gly Leu Ala Glu
35 40 45

Val Gly Lys Lys Phe Glu Lys Asp Thr Gly Ile Lys Val Thr Val Glu
50 55 60

His Pro Asp Lys Leu Glu Glu Lys Phe Pro Gln Val Ala Ala Thr Gly
65 70 75 80

Asp Gly Pro Asp Ile Ile Phe Trp Ala His Asp Arg Phe Gly Gly Tyr
85 90 95

Ala Gln Ser Gly Leu Leu Ala Glu Ile Thr Pro Asp Lys Ala Phe Gln
100 105 110

Asp Lys Leu Tyr Pro Phe Thr Trp Asp Ala Val Arg Tyr Asn Gly Lys
115 120 125

Leu Ile Ala Tyr Pro Ile Ala Val Glu Ala Leu Ser Leu Ile Tyr Asn
130 135 140

Lys Asp Leu Leu Pro Asn Pro Pro Lys Thr Trp Glu Glu Ile Pro Ala
145 150 155 160

Leu Asp Lys Glu Leu Lys Ala Lys Gly Lys Ser Ala Leu Met Phe Asn
165 170 175

Leu Gln Glu Pro Tyr Phe Thr Trp Pro Leu Ile Ala Ala Asp Gly Leu
180 185 190

Leu Arg Ser Ala Leu Pro Ala Gly Trp Phe Ile Ala Asp Lys Ser Gly
195 200 205

Ala Gly Glu Arg Gly Ser Arg Gly Ile Ile Ala Ala Leu Gly Pro Asp
210 215 220

Gly Lys Pro Ser Arg Ile Val Val Ile Tyr Thr Thr Gly Ser Gln Ala
225 230 235 240

Thr Met Asp Glu Arg Asn Arg Gln Ile Ala Glu Ile Gly Ala Ser Leu
245 250 255

Ile Lys His Trp Gly Ser Gly Gly Gly His Pro Glu Thr Leu Val Lys
260 265 270

Val Lys Asp Ala Glu Asp Gln Leu Gly Ala Arg Val Gly Tyr Ile Glu
275 280 285

Leu Asp Leu Asn Ser Gly Lys Ile Leu Glu Ser Phe Arg Pro Glu Glu
290 295 300

Arg Phe Pro Met Met Ser Thr Phe Lys Val Leu Leu Cys Gly Ala Val
305 310 315 320

Leu Ser Arg Val Asp Ala Gly Gln Glu Gln Leu Gly Arg Arg Ile His
325 330 335

Tyr Ser Gln Asn Asp Leu Val Glu Tyr Ser Pro Val Thr Glu Lys His
340 345 350

Leu Thr Asp Gly Met Thr Val Arg Glu Leu Cys Ser Ala Ala Ile Thr
355 360 365

Met Ser Asp Asn Thr Ala Ala Asn Leu Leu Leu Thr Thr Ile Gly Gly
370 375 380

Pro Lys Glu Leu Thr Ala Phe Leu His Asn Met Gly Asp His Val Thr
385 390 395 400

Arg Leu Asp Arg Trp Glu Pro Glu Leu Asn Glu Ala Ile Pro Asn Asp
405 410 415

```
Glu Arg Asp Thr Thr Met Pro Ala Ala Met Ala Thr Thr Leu Arg Lys
            420                 425                 430

Leu Leu Thr Gly Glu Leu Leu Thr Leu Ala Ser Arg Gln Gln Leu Ile
        435                 440                 445

Asp Trp Met Glu Ala Asp Lys Val Ala Asp Gly Gly Tyr Ala Phe Lys
    450                 455                 460

Tyr Glu Asn Gly Lys Tyr Asp Ile Lys Asp Val Gly Val Asp Asn Ala
465                 470                 475                 480

Gly Ala Lys Ala Gly Leu Thr Phe Leu Val Asp Leu Ile Lys Asn Lys
                485                 490                 495

His Met Asn Ala Asp Thr Asp Tyr Ser Ile Ala Glu Ala Ala Phe Asn
            500                 505                 510

Lys Gly Glu Thr Ala Met Thr Ile Asn Gly Pro Trp Ala Trp Ser Asn
        515                 520                 525

Ile Asp Thr Ser Lys Val Asn Tyr Gly Val Thr Val Leu Pro Thr Phe
    530                 535                 540

Lys Gly Gln Pro Ser Lys Pro Phe Val Gly Val Leu Ser Ala Gly Ile
545                 550                 555                 560

Asn Ala Ala Ser Pro Asn Lys Glu Leu Ala Lys Glu Phe Leu Glu Asn
                565                 570                 575

Tyr Leu Leu Thr Asp Glu Gly Leu Glu Ala Val Asn Lys Asp Lys Pro
            580                 585                 590

Leu Gly Ala Val Ala Leu Lys Ser Tyr Glu Glu Glu Leu Ala Lys Asp
        595                 600                 605

Pro Arg Ile Ala Ala Thr Met Glu Asn Ala Gln Lys Gly Glu Ile Met
    610                 615                 620

Pro Asn Ile Pro Gln Met Ser Ala Phe Trp Tyr Ala Val Arg Thr Ala
625                 630                 635                 640

Val Ile Asn Ala Ala Ser Gly Arg Gln Thr Val Asp Glu Ala Leu Lys
                645                 650                 655

Asp Ala Gln Thr Arg Ile Thr Lys
            660
```

<210> SEQ ID NO 70
<211> LENGTH: 2004
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 70

```
atgaaaataa aaacaggtgc acgcatcctc gcattatccg cattaacgac gatgatgttt      60

tccgcctcgg ctctcgccaa aatcgaagaa ggtaaactgg taatctggat taacggcgat     120

aaaggctata acggtctcgc tgaagtcggt aagaaattcg agaaagatac cggaattaaa     180

gtcaccgttg agcatccgga taaactggaa gagaaattcc cacaggttgc ggcaactggc     240

gatggccctg acattatctt ctgggcacac gaccgctttg gtggctacgc tcaatctggc     300

ctgttggctg aaatcacccc ggacaaagcg ttccaggaca agctgtatcc gtttacctgg     360

gatgccgtac gttacaacgg caagctgatt gcttacccga tcgctgttga agcgttatcg     420

ctgatttata acaaagatct gctgccgaac ccgccaaaaa cctgggaaga gatcccggcg     480

ctggataaag aactgaaagc gaaaggtaag agcgcgctga tgttcaacct gcaagaaccg     540

tacttcacct ggccgctgat tgctgctgac gggaatgaag ccataccaaa cgacgagcgt     600

gacaccacga tgcctgcagc aatggcaaca acgttgcgca aactattaac tggcgaacta     660
```

-continued

```
cttactctag cttcccggca acaattaata gactggatgg aggcggataa agttgcagga    720

ccacttctgc gctcggccct tccggctggc tggtttattg ctgataaatc tggagccggt    780

gagcgtgggt ctcgcggtat cattgcagca ctggggccag atggtaagcc ctcccgtatc    840

gtagttatct acacgacggg gagtcaggca actatggatg aacgaaatag acagatcgct    900

gagataggtg cctcactgat taagcattgg gacaagagcc acccagaaac gctggtgaaa    960

gtaaaagatg ctgaagatca gttgggtgca cgagtgggtt acatcgaact ggatctcaac   1020

agcggtaaga tccttgagag ttttcgcccc gaagaacgtt ttccaatgat gagcactttt   1080

aaagttctgc tatgtggcgc ggtattatcc cgtgttgacg ccgggcaaga gcaactcggt   1140

cgccgcatac actattctca gaatgacttg gttgagtact caccagtcac agaaaagcat   1200

cttacggatg gcatgacagt aagagaatta tgcagtgctg ccataaccat gagtgataac   1260

actgcggcca acttacttct gacaacgatc ggaggaccga aggagctaac cgcttttttg   1320

cacaacatgg gggatcatgt aactcgcctt gatcgttggg aaccggaact gaatgaagcc   1380

gacgggggtt atgcgttcaa gtatgaaaac ggcaagtacg acattaaaga cgtgggcgtg   1440

gataacgctg gcgcgaaagc gggtctgacc ttcctggttg acctgattaa aaacaaacac   1500

atgaatgcag acaccgatta ctccatcgca gaagctgcct ttaataaagg cgaaacagcg   1560

atgaccatca acggcccgtg ggcatggtcc aacatcgaca ccagcaaagt gaattatggt   1620

gtaacggtac tgccgacctt caagggtcaa ccatccaaac cgttcgttgg cgtgctgagc   1680

gcaggtatta acgccgccag tccgaacaaa gagctggcga aagagttcct cgaaaactat   1740

ctgctgactg atgaaggtct ggaagcggtt aataaagaca aaccgctggg tgccgtagcg   1800

ctgaagtctt acgaggaaga gttggcgaaa gatccacgta ttgccgccac catggaaaac   1860

gcccagaaag gtgaaatcat gccgaacatc ccgcagatgt ccgctttctg gtatgccgtg   1920

cgtactgcgg tgatcaacgc cgccagcggt cgtcagactg tcgatgaagc cctgaaagac   1980

gcgcagactc gtatcaccaa gtaa                                          2004
```

```
<210> SEQ ID NO 71
<211> LENGTH: 667
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 71

Met Lys Ile Lys Thr Gly Ala Arg Ile Leu Ala Leu Ser Ala Leu Thr
  1               5                  10                  15

Thr Met Met Phe Ser Ala Ser Ala Leu Ala Lys Ile Glu Glu Gly Lys
             20                  25                  30

Leu Val Ile Trp Ile Asn Gly Asp Lys Gly Tyr Asn Gly Leu Ala Glu
         35                  40                  45

Val Gly Lys Lys Phe Glu Lys Asp Thr Gly Ile Lys Val Thr Val Glu
     50                  55                  60

His Pro Asp Lys Leu Glu Glu Lys Phe Pro Gln Val Ala Ala Thr Gly
 65                  70                  75                  80

Asp Gly Pro Asp Ile Ile Phe Trp Ala His Asp Arg Phe Gly Gly Tyr
                 85                  90                  95

Ala Gln Ser Gly Leu Leu Ala Glu Ile Thr Pro Asp Lys Ala Phe Gln
            100                 105                 110

Asp Lys Leu Tyr Pro Phe Thr Trp Asp Ala Val Arg Tyr Asn Gly Lys
        115                 120                 125
```

-continued

```
Leu Ile Ala Tyr Pro Ile Ala Val Glu Ala Leu Ser Leu Ile Tyr Asn
    130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Asn
            180                 185                 190

Glu Ala Ile Pro Asn Asp Glu Arg Asp Thr Thr Met Pro Ala Ala Met
        195                 200                 205

Ala Thr Thr Leu Arg Lys Leu Leu Thr Gly Glu Leu Leu Thr Leu Ala
    210                 215                 220

Ser Arg Gln Gln Leu Ile Asp Trp Met Glu Ala Asp Lys Val Ala Gly
225                 230                 235                 240

Pro Leu Leu Arg Ser Ala Leu Pro Ala Gly Trp Phe Ile Ala Asp Lys
                245                 250                 255

Ser Gly Ala Gly Glu Arg Gly Ser Arg Gly Ile Ile Ala Ala Leu Gly
            260                 265                 270

Pro Asp Gly Lys Pro Ser Arg Ile Val Val Ile Tyr Thr Thr Gly Ser
        275                 280                 285

Gln Ala Thr Met Asp Glu Arg Asn Arg Gln Ile Ala Glu Ile Gly Ala
    290                 295                 300

Ser Leu Ile Lys His Trp Asp Lys Ser His Pro Glu Thr Leu Val Lys
305                 310                 315                 320

Val Lys Asp Ala Glu Asp Gln Leu Gly Ala Arg Val Gly Tyr Ile Glu
                325                 330                 335

Leu Asp Leu Asn Ser Gly Lys Ile Leu Glu Ser Phe Arg Pro Glu Glu
            340                 345                 350

Arg Phe Pro Met Met Ser Thr Phe Lys Val Leu Leu Cys Gly Ala Val
        355                 360                 365

Leu Ser Arg Val Asp Ala Gly Gln Glu Gln Leu Gly Arg Arg Ile His
    370                 375                 380

Tyr Ser Gln Asn Asp Leu Val Glu Tyr Ser Pro Val Thr Glu Lys His
385                 390                 395                 400

Leu Thr Asp Gly Met Thr Val Arg Glu Leu Cys Ser Ala Ala Ile Thr
                405                 410                 415

Met Ser Asp Asn Thr Ala Ala Asn Leu Leu Leu Thr Thr Ile Gly Gly
            420                 425                 430

Pro Lys Glu Leu Thr Ala Phe Leu His Asn Met Gly Asp His Val Thr
        435                 440                 445

Arg Leu Asp Arg Trp Glu Pro Glu Leu Asn Glu Ala Asp Gly Gly Tyr
    450                 455                 460

Ala Phe Lys Tyr Glu Asn Gly Lys Tyr Asp Ile Lys Asp Val Gly Val
465                 470                 475                 480

Asp Asn Ala Gly Ala Lys Ala Gly Leu Thr Phe Leu Val Asp Leu Ile
                485                 490                 495

Lys Asn Lys His Met Asn Ala Asp Thr Asp Tyr Ser Ile Ala Glu Ala
            500                 505                 510

Ala Phe Asn Lys Gly Glu Thr Ala Met Thr Ile Asn Gly Pro Trp Ala
        515                 520                 525

Trp Ser Asn Ile Asp Thr Ser Lys Val Asn Tyr Gly Val Thr Val Leu
    530                 535                 540

Pro Thr Phe Lys Gly Gln Pro Ser Lys Pro Phe Val Gly Val Leu Ser
545                 550                 555                 560
```

-continued

```
Ala Gly Ile Asn Ala Ala Ser Pro Asn Lys Glu Leu Ala Lys Glu Phe
                565                 570                 575

Leu Glu Asn Tyr Leu Leu Thr Asp Glu Gly Leu Glu Ala Val Asn Lys
            580                 585                 590

Asp Lys Pro Leu Gly Ala Val Ala Leu Lys Ser Tyr Glu Glu Glu Leu
        595                 600                 605

Ala Lys Asp Pro Arg Ile Ala Ala Thr Met Glu Asn Ala Gln Lys Gly
    610                 615                 620

Glu Ile Met Pro Asn Ile Pro Gln Met Ser Ala Phe Trp Tyr Ala Val
625                 630                 635                 640

Arg Thr Ala Val Ile Asn Ala Ala Ser Gly Arg Gln Thr Val Asp Glu
                645                 650                 655

Ala Leu Lys Asp Ala Gln Thr Arg Ile Thr Lys
            660                 665
```

<210> SEQ ID NO 72
<211> LENGTH: 2001
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 72

```
atgaaaataa aaacaggtgc acgcatcctc gcattatccg cattaacgac gatgatgttt     60

tccgcctcgg ctctcgccaa aatcgaagaa ggtaaactgg taatctggat taacggcgat    120

aaaggctata acggtctcgc tgaagtcggt aagaaattcg agaaagatac cggaattaaa    180

gtcaccgttg agcatccgga taaactggaa gagaaattcc cacaggttgc ggcaactggc    240

gatggccctg acattatctt ctgggcacac gaccgctttg gtggctacgc tcaatctggc    300

ctgttggctg aaatcacccc ggacaaagcg ttccaggaca agctgtatcc gtttacctgg    360

gatgccgtac gttacaacgg caagctgatt gcttacccga tcgctgttga agcgttatcg    420

ctgatttata acaaagatct gctgccgaac ccgccaaaaa cctgggaaga gatcccggcg    480

ctggataaag aactgaaagc gaaaggtaag agcgcgctga tgttcaacct gcaagaaccg    540

tacttcacct ggccgctgat tgctgctgac gggggttatg cgttcaagta tgaaaacggc    600

aagtacgaca ttaaagacgt gggcgtggat aacgctggcg cgaaagcggg tctgaccttc    660

ctggttgacc tgattaaaaa caaacacatg aatgcagaca ccgattactc catcgcagaa    720

gctgccttta ataaaggcga aacagcgatg accatcaacg gcccgtgggc atggtccaac    780

atcgacacca gcaaagtgaa ttatggtgta acggtactgc cgaccttcaa gggtcaacca    840

tccaaaccgt tcgttggcgt gctgagcgca ggtattaacg ccgccagtcc gaacaaagag    900

ctggcgaaag agttcctcga aaactatctg ctgactgatg aaggtctgga agcggttaat    960

aaagacaaac cgctgggtgc cgtagcgctg aagtcttacg aggaagagtt ggcgaaagat   1020

ccacgtattg ccgccaccat ggaaaacgcc cagaaaggtg aaatcatgcc gaacatcccg   1080

cagatgtccg ctttctggta tgccgtgcgt actgcggtga tcaacgccgc cagcggtcgt   1140

cagactgtcg atgaagccct gaaagacgcg cagactcgta tcaccaaggg catgacagta   1200

agagaattat gcagtgctgc cataaccatg agtgataaca ctgcggccaa cttacttctg   1260

acaacgatcg gaggaccgaa ggagctaacc gcttttttgc acaacatggg ggatcatgta   1320

actcgccttg atcgttggga accggagctg aatgaagcca taccaaacga cgagcgtgac   1380

accacgatgc ctgcagcaat ggcaacaacg ttgcgcaaac tattaactgg cgaactactt   1440
```

```
actctagctt cccggcaaca attaatagac tggatggagg cggataaagt tgcaggacca   1500

cttctgcgct cggcccttcc ggctggctgg tttattgctg ataaatctgg agccggtgag   1560

cgtgggtctc gcggtatcat tgcagcactg gggccagatg gtaagccctc ccgtatcgta   1620

gttatctaca cgacggggag tcaggcaact atggatgaac gaaatagaca gatcgctgag   1680

ataggtgcct cactgattaa gcattgggga tccggcggtg gccacccaga aacgctggtg   1740

aaagtaaaag atgctgaaga tcagttgggt gcacgagtgg gttacatcga actggatctc   1800

aacagcggta agatccttga gagttttcgc cccgaagaac gttttccaat gatgagcact   1860

tttaaagttc tgctatgtgg cgcggtatta tcccgtgttg acgccgggca agagcaactc   1920

ggtcgccgca tacactattc tcagaatgac ttggttgagt actcaccagt cacagaaaag   1980

catcttacgg atggcaagtg a                                              2001
```

<210> SEQ ID NO 73
<211> LENGTH: 666
<212> TYPE: PRT
<213> ORGANISM: Artificial Sequence
<220> FEATURE:
<223> OTHER INFORMATION: Description of Artificial Sequence: Synthetic protein construct

<400> SEQUENCE: 73

```
Met Lys Ile Lys Thr Gly Ala Arg Ile Leu Ala Leu Ser Ala Leu Thr
  1               5                  10                  15

Thr Met Met Phe Ser Ala Ser Ala Leu Ala Lys Ile Glu Glu Gly Lys
             20                  25                  30

Leu Val Ile Trp Ile Asn Gly Asp Lys Gly Tyr Asn Gly Leu Ala Glu
         35                  40                  45

Val Gly Lys Lys Phe Glu Lys Asp Thr Gly Ile Lys Val Thr Val Glu
     50                  55                  60

His Pro Asp Lys Leu Glu Glu Lys Phe Pro Gln Val Ala Ala Thr Gly
 65                  70                  75                  80

Asp Gly Pro Asp Ile Ile Phe Trp Ala His Asp Arg Phe Gly Gly Tyr
                 85                  90                  95

Ala Gln Ser Gly Leu Leu Ala Glu Ile Thr Pro Asp Lys Ala Phe Gln
            100                 105                 110

Asp Lys Leu Tyr Pro Phe Thr Trp Asp Ala Val Arg Tyr Asn Gly Lys
        115                 120                 125

Leu Ile Ala Tyr Pro Ile Ala Val Glu Ala Leu Ser Leu Ile Tyr Asn
    130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
            180                 185                 190

Tyr Ala Phe Lys Tyr Glu Asn Gly Lys Tyr Asp Ile Lys Asp Val Gly
        195                 200                 205

Val Asp Asn Ala Gly Ala Lys Ala Gly Leu Thr Phe Leu Val Asp Leu
    210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
                245                 250                 255
```

-continued

```
Ala Trp Ser Asn Ile Asp Thr Ser Lys Val Asn Tyr Gly Val Thr Val
            260                 265                 270

Leu Pro Thr Phe Lys Gly Gln Pro Ser Lys Pro Phe Val Gly Val Leu
        275                 280                 285

Ser Ala Gly Ile Asn Ala Ala Ser Pro Asn Lys Glu Leu Ala Lys Glu
    290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
                325                 330                 335

Leu Ala Lys Asp Pro Arg Ile Ala Ala Thr Met Glu Asn Ala Gln Lys
            340                 345                 350

Gly Glu Ile Met Pro Asn Ile Pro Gln Met Ser Ala Phe Trp Tyr Ala
        355                 360                 365

Val Arg Thr Ala Val Ile Asn Ala Ala Ser Gly Arg Gln Thr Val Asp
    370                 375                 380

Glu Ala Leu Lys Asp Ala Gln Thr Arg Ile Thr Lys Gly Met Thr Val
385                 390                 395                 400

Arg Glu Leu Cys Ser Ala Ala Ile Thr Met Ser Asp Asn Thr Ala Ala
                405                 410                 415

Asn Leu Leu Leu Thr Thr Ile Gly Gly Pro Lys Glu Leu Thr Ala Phe
            420                 425                 430

Leu His Asn Met Gly Asp His Val Thr Arg Leu Asp Arg Trp Glu Pro
        435                 440                 445

Glu Leu Asn Glu Ala Ile Pro Asn Asp Glu Arg Asp Thr Thr Met Pro
    450                 455                 460

Ala Ala Met Ala Thr Thr Leu Arg Lys Leu Leu Thr Gly Glu Leu Leu
465                 470                 475                 480

Thr Leu Ala Ser Arg Gln Gln Leu Ile Asp Trp Met Glu Ala Asp Lys
                485                 490                 495

Val Ala Gly Pro Leu Leu Arg Ser Ala Leu Pro Ala Gly Trp Phe Ile
            500                 505                 510

Ala Asp Lys Ser Gly Ala Gly Glu Arg Gly Ser Arg Gly Ile Ile Ala
        515                 520                 525

Ala Leu Gly Pro Asp Gly Lys Pro Ser Arg Ile Val Val Ile Tyr Thr
    530                 535                 540

Thr Gly Ser Gln Ala Thr Met Asp Glu Arg Asn Arg Gln Ile Ala Glu
545                 550                 555                 560

Ile Gly Ala Ser Leu Ile Lys His Trp Gly Ser Gly Gly Gly His Pro
                565                 570                 575

Glu Thr Leu Val Lys Val Lys Asp Ala Glu Asp Gln Leu Gly Ala Arg
            580                 585                 590

Val Gly Tyr Ile Glu Leu Asp Leu Asn Ser Gly Lys Ile Leu Glu Ser
        595                 600                 605

Phe Arg Pro Glu Glu Arg Phe Pro Met Met Ser Thr Phe Lys Val Leu
    610                 615                 620

Leu Cys Gly Ala Val Leu Ser Arg Val Asp Ala Gly Gln Glu Gln Leu
625                 630                 635                 640

Gly Arg Arg Ile His Tyr Ser Gln Asn Asp Leu Val Glu Tyr Ser Pro
                645                 650                 655

Val Thr Glu Lys His Leu Thr Asp Gly Lys
            660                 665
```

<210> SEQ ID NO 74
<211> LENGTH: 2010
<212> TYPE: DNA
<213> ORGANISM: Artificial Sequence
<220> FEATURE:
<223> OTHER INFORMATION: Description of Artificial Sequence: Synthetic
nucleotide construct

<400> SEQUENCE: 74

```
atgaaaataa aaacaggtgc acgcatcctc gcattatccg cattaacgac gatgatgttt     60
tccgcctcgg ctctcgccaa aatcgaagaa ggtaaactgg taatctggat taacggcgat    120
aaaggctata acggtctcgc tgaagtcggt aagaaattcg agaaagatac cggaattaaa    180
gtcaccgttg agcatccgga taaactggaa gagaaattcc cacaggttgc ggcaactggc    240
gatggccctg acattatctt ctgggcacac gaccgctttg gtggctacgc tcaatctggc    300
ctgttggctg aaatcacccc ggacaaagcg ttccaggaca agctgtatcc gtttacctgg    360
gatgccgtac gttacaacgg caagctgatt gcttacccga tcgctgttga agcgttatcg    420
ctgatttata acaaagatct gctgccgaac ccgccaaaaa cctgggaaga gatcccggcg    480
ctggataaag aactgaaagc gaaaggtaag agcgcgctga tgttcaacct gcaagaaccg    540
tacttcacct ggccgctgat tgctgctgac ggggggttatg cgttcaagta tgaaaacggc    600
aagtacgaca ttaaagacgt gggcgtggat aacgctggcg cgaaagcggg tctgaccttc    660
ctggttgacc tgattaaaaa caaacacatg aatgcagaca ccgattactc catcgcagaa    720
gctgccttta ataaaggcga aacagcgatg accatcaacg gcccgtgggc atggtccaac    780
atcgacacca gcaaagtgaa ttatggtgta acggtactgc cgaccttcaa gggtcaacca    840
tccaaaccgt tcgttggcgt gctgagcgca ggtattaacg ccgccagtcc gaacaaagag    900
ctggcgaaag agttcctcga aaactatctg ctgactgatg aaggtctgga agcggttaat    960
aaagacaaac cgctgggtgc cgtagcgctg aagtcttacg aggaagagtt ggcgaaagat   1020
ccacgtattg ccgccaccat ggaaaacgcc cagaaaggtg aaatcatgcc gaacatcccg   1080
cagatgtccg ctttctggta tgccgtgcgt actgcggtga tcaacgccgc cagcggtcgt   1140
cagactgtcg atgaagccct gaaagacgcg cagactcgta tcaccaaggg catgacagta   1200
agagaattat gcagtgctgc cataaccatg agtgataaca ctgcggccaa cttacttctg   1260
acaacgatcg gaggaccgaa ggagctaacc gcttttttgc acaacatggg ggatcatgta   1320
actcgccttg atcgttggga accggagctg aatgaagcca taccaaacga cgagcgtgac   1380
accacgatgc ctgcagcaat ggcaacaacg ttgcgcaaac tattaactgg cgaactactt   1440
actctagctt cccggcaaca attaatagac tggatggagg cggataaagt tgcaggacca   1500
cttctgcgct cggcccttcc ggctggctgg tttattgctg ataaatctgg agccggtgag   1560
cgtgggtctc gcggtatcat tgcagcactg gggccagatg gtaagccctc ccgtatcgta   1620
gttatctaca cgacggggag tcaggcaact atggatgaac gaaatagaca gatcgctgag   1680
ataggtgcct cactgattaa gcattgggga tccggcggtg gccacccaga aacgctggtg   1740
aaagtaaaag atgctgaaga tcagttgggt gcacgagtgg gttacatcga actggatctc   1800
aacagcggta agatccttga gagttttcgc cccgaagaac gttttccaat gatgagcact   1860
tttaaagttc tgctatgtgg cgcggtatta tcccgtgttg acgccgggca agagcaactc   1920
ggtcgccgca tacactattc tcagaatgac ttggttgagt actcaccagt cacagaaaag   1980
catcttacgg aagtgaagag cactagttag                                    2010
```

<210> SEQ ID NO 75
<211> LENGTH: 669
<212> TYPE: PRT
<213> ORGANISM: Artificial Sequence
<220> FEATURE:
<223> OTHER INFORMATION: Description of Artificial Sequence: Synthetic
protein construct

<400> SEQUENCE: 75

```
Met Lys Ile Lys Thr Gly Ala Arg Ile Leu Ala Leu Ser Ala Leu Thr
  1               5                  10                  15

Thr Met Met Phe Ser Ala Ser Ala Leu Ala Lys Ile Glu Glu Gly Lys
             20                  25                  30

Leu Val Ile Trp Ile Asn Gly Asp Lys Gly Tyr Asn Gly Leu Ala Glu
         35                  40                  45

Val Gly Lys Lys Phe Glu Lys Asp Thr Gly Ile Lys Val Thr Val Glu
     50                  55                  60

His Pro Asp Lys Leu Glu Glu Lys Phe Pro Gln Val Ala Ala Thr Gly
 65                  70                  75                  80

Asp Gly Pro Asp Ile Ile Phe Trp Ala His Asp Arg Phe Gly Gly Tyr
                 85                  90                  95

Ala Gln Ser Gly Leu Leu Ala Glu Ile Thr Pro Asp Lys Ala Phe Gln
            100                 105                 110

Asp Lys Leu Tyr Pro Phe Thr Trp Asp Ala Val Arg Tyr Asn Gly Lys
        115                 120                 125

Leu Ile Ala Tyr Pro Ile Ala Val Glu Ala Leu Ser Leu Ile Tyr Asn
    130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
            180                 185                 190

Tyr Ala Phe Lys Tyr Glu Asn Gly Lys Tyr Asp Ile Lys Asp Val Gly
        195                 200                 205

Val Asp Asn Ala Gly Ala Lys Ala Gly Leu Thr Phe Leu Val Asp Leu
    210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
                245                 250                 255

Ala Trp Ser Asn Ile Asp Thr Ser Lys Val Asn Tyr Gly Val Thr Val
            260                 265                 270

Leu Pro Thr Phe Lys Gly Gln Pro Ser Lys Pro Phe Val Gly Val Leu
        275                 280                 285

Ser Ala Gly Ile Asn Ala Ala Ser Pro Asn Lys Glu Leu Ala Lys Glu
    290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
                325                 330                 335

Leu Ala Lys Asp Pro Arg Ile Ala Ala Thr Met Glu Asn Ala Gln Lys
            340                 345                 350

Gly Glu Ile Met Pro Asn Ile Pro Gln Met Ser Ala Phe Trp Tyr Ala
        355                 360                 365
```

```
Val Arg Thr Ala Val Ile Asn Ala Ala Ser Gly Arg Gln Thr Val Asp
    370                 375                 380

Glu Ala Leu Lys Asp Ala Gln Thr Arg Ile Thr Lys Gly Met Thr Val
385                 390                 395                 400

Arg Glu Leu Cys Ser Ala Ala Ile Thr Met Ser Asp Asn Thr Ala Ala
                405                 410                 415

Asn Leu Leu Leu Thr Thr Ile Gly Gly Pro Lys Glu Leu Thr Ala Phe
            420                 425                 430

Leu His Asn Met Gly Asp His Val Thr Arg Leu Asp Arg Trp Glu Pro
        435                 440                 445

Glu Leu Asn Glu Ala Ile Pro Asn Asp Glu Arg Asp Thr Thr Met Pro
    450                 455                 460

Ala Ala Met Ala Thr Thr Leu Arg Lys Leu Leu Thr Gly Glu Leu Leu
465                 470                 475                 480

Thr Leu Ala Ser Arg Gln Gln Leu Ile Asp Trp Met Glu Ala Asp Lys
                485                 490                 495

Val Ala Gly Pro Leu Leu Arg Ser Ala Leu Pro Ala Gly Trp Phe Ile
            500                 505                 510

Ala Asp Lys Ser Gly Ala Gly Glu Arg Gly Ser Arg Gly Ile Ile Ala
        515                 520                 525

Ala Leu Gly Pro Asp Gly Lys Pro Ser Arg Ile Val Val Ile Tyr Thr
    530                 535                 540

Thr Gly Ser Gln Ala Thr Met Asp Glu Arg Asn Arg Gln Ile Ala Glu
545                 550                 555                 560

Ile Gly Ala Ser Leu Ile Lys His Trp Gly Ser Gly Gly Gly His Pro
                565                 570                 575

Glu Thr Leu Val Lys Val Lys Asp Ala Glu Asp Gln Leu Gly Ala Arg
            580                 585                 590

Val Gly Tyr Ile Glu Leu Asp Leu Asn Ser Gly Lys Ile Leu Glu Ser
        595                 600                 605

Phe Arg Pro Glu Glu Arg Phe Pro Met Met Ser Thr Phe Lys Val Leu
    610                 615                 620

Leu Cys Gly Ala Val Leu Ser Arg Val Asp Ala Gly Gln Glu Gln Leu
625                 630                 635                 640

Gly Arg Arg Ile His Tyr Ser Gln Asn Asp Leu Val Glu Tyr Ser Pro
                645                 650                 655

Val Thr Glu Lys His Leu Thr Glu Val Lys Ser Thr Ser
            660                 665
```

<210> SEQ ID NO 76
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 76

```
ggaccaggat ccatgaaaat aaaaacaggt                                    30
```

<210> SEQ ID NO 77
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 77

Gly Gly Ser Gly His His His His His His His His His
1 5 10

<210> SEQ ID NO 78
<211> LENGTH: 26
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 78
gctcttctca cccagaaacg ctggtg 26

<210> SEQ ID NO 79
<211> LENGTH: 35
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 79
ctgattaagc attgggacaa gagccactga agaga 35

<210> SEQ ID NO 80
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 80
cacccagaaa cgctggtg 18

<210> SEQ ID NO 81
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 81
ctgattaagc attgggacaa gagc 24

<210> SEQ ID NO 82
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 82
gtggctcttg tcccaatgct taatcag 27

<210> SEQ ID NO 83
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 83
caccagcgtt tctgg 15

<210> SEQ ID NO 84
<211> LENGTH: 42
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 84
ctgattaagc attgggacaa gagccaccca gaaacgctgg tg 42

<210> SEQ ID NO 85
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 85
ggatccggcg gtggccaccc agaaacgctg gtg 33

<210> SEQ ID NO 86
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 86
ctgattaagc attggggatc c 21

<210> SEQ ID NO 87
<211> LENGTH: 32
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 87
gatccggcgg tggccaccca gaaacgctgg tg 32

<210> SEQ ID NO 88
<211> LENGTH: 16
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 88
ctgattaagc attggg 16

<210> SEQ ID NO 89
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 89
gatccccaat gcttaatcag 20

<210> SEQ ID NO 90
<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 90
caccagcgtt tctgggtggc caccgccg 28

<210> SEQ ID NO 91
<211> LENGTH: 48
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 91
ctgattaagc attggggatc cggcggtggc cacccagaaa cgctggtg 48

<210> SEQ ID NO 92
<211> LENGTH: 59
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 92
ctgattgctg ctgacgggtg aagagcgctc gaggctcttc cgacgggggt tatgcgttc 59

<210> SEQ ID NO 93
<211> LENGTH: 15
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 93
ctgattgctg ctgac 15

<210> SEQ ID NO 94
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 94
gacgggggtt atgcgttc 18

<210> SEQ ID NO 95
<211> LENGTH: 15
<212> TYPE: DNA
<213> ORGANISM: Artificial Sequence
<220> FEATURE:
<223> OTHER INFORMATION: Description of Artificial Sequence: Synthetic
oligonucleotide -continued

```
<400> SEQUENCE: 95

gaacgcataa ccccc                                                        15


<210> SEQ ID NO 96
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96

cccgtcagca gcaatcag                                                     18


<210> SEQ ID NO 97
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97

ctgattgctg ctgacggg                                                     18


<210> SEQ ID NO 98
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98

ctgatcgcta ggagacggcg a                                                 21


<210> SEQ ID NO 99
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 99

His His His His His His
  1               5
```